(12) United States Patent
Stone et al.

(10) Patent No.: US 7,822,483 B2
(45) Date of Patent: Oct. 26, 2010

(54) ELECTRICAL AND ACTIVATION FIELD MODELS FOR CONFIGURING STIMULATION THERAPY

(75) Inventors: Richard T. Stone, Minneapolis, MN (US); Warren W. Ball, Coon Rapids, MN (US); Carl D. Wahlstrand, Columbia Heights, MN (US); Steven M. Goetz, Brooklyn Center, MN (US); Lynn M. Otten, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 876 days.

(21) Appl. No.: 11/591,299

(22) Filed: Oct. 31, 2006

(65) Prior Publication Data
US 2007/0203546 A1    Aug. 30, 2007

Related U.S. Application Data

(60) Provisional application No. 60/776,454, filed on Feb. 24, 2006, provisional application No. 60/785,255, filed on Mar. 23, 2006.

(51) Int. Cl.
*A61N 1/00* (2006.01)
(52) U.S. Cl. ....................... 607/116
(58) Field of Classification Search ................. 607/116, 607/59; 600/407, 378; 345/664
See application file for complete search history.

(56) References Cited

U.S. PATENT DOCUMENTS

| | | | |
|---|---|---|---|
| 4,328,809 A | 5/1982 | Hirschowitz et al. |
| 4,735,204 A | 4/1988 | Sussman et al. |
| 4,793,353 A | 12/1988 | Borkan |
| 5,370,672 A | 12/1994 | Fowler et al. |
| 5,443,486 A | 8/1995 | Hrdlicka et al. |

(Continued)

FOREIGN PATENT DOCUMENTS

EP    0811395    12/1997

(Continued)

OTHER PUBLICATIONS

Notification of Transmittal of the International Preliminary Report on Patentablity for patent application No. PCT/US2007/002021, mailed Mar. 28, 2008, (8 pages).

(Continued)

*Primary Examiner*—George Manuel
*Assistant Examiner*—Robert N Wieland
(74) *Attorney, Agent, or Firm*—Shumaker & Sieffert, P.A.

(57) ABSTRACT

The disclosure describes a method and system that generates an electrical field model of defined stimulation therapy and displays the electrical field model to a user via a user interface. The electrical field model is generated based upon a patient anatomy and stimulation parameters to illustrate which areas of a patient anatomical region will be covered by the electrical field during therapy. In addition, a neuron model may be applied to the electrical field model to generate an activation field model. The activation field model indicates which neurons will be activated by the electrical field in the anatomical region. These field models may be used by a clinician to determine effective therapy prior to stimulation delivery. In particular, the field models may be beneficial when programming non axi-symmetric, or three-dimensional (3D), leads which allow greater flexibility in creating stimulation fields.

33 Claims, 76 Drawing Sheets

U.S. PATENT DOCUMENTS

| | | | |
|---|---|---|---|
| 5,626,629 | A | 5/1997 | Faltys et al. |
| 5,643,330 | A | 7/1997 | Holsheimer et al. |
| 5,724,985 | A | 3/1998 | Snell et al. |
| 5,740,037 | A | 4/1998 | McCann et al. |
| 5,769,875 | A | 6/1998 | Peckham |
| 5,776,171 | A | 7/1998 | Peckham |
| 5,893,883 | A | 4/1999 | Torgerson et al. |
| 5,895,416 | A | 4/1999 | Barreras et al. |
| 5,938,690 | A | 8/1999 | Law et al. |
| 5,954,758 | A | 9/1999 | Peckham |
| 5,983,140 | A | 11/1999 | Smith et al. |
| 6,004,276 | A | 12/1999 | Wright et al. |
| 6,026,328 | A | 2/2000 | Peckham |
| 6,027,456 | A | 2/2000 | Feler et al. |
| 6,052,624 | A | 4/2000 | Mann |
| 6,077,223 | A | 6/2000 | Satherley |
| 6,099,479 | A | 8/2000 | Christopherson et al. |
| 6,106,464 | A | 8/2000 | Bass et al. |
| 6,120,467 | A | 9/2000 | Scallhorn |
| 6,163,725 | A | 12/2000 | Peckham |
| 6,208,894 | B1 | 3/2001 | Schulman et al. |
| 6,249,703 | B1 | 6/2001 | Stanton et al. |
| 6,289,247 | B1 | 9/2001 | Faltys et al. |
| 6,308,102 | B1 | 10/2001 | Sieracki et al. |
| 6,358,245 | B1 | 3/2002 | Edwards et al. |
| 6,381,496 | B1 | 4/2002 | Meadows et al. |
| 6,393,325 | B1 | 5/2002 | Mann et al. |
| 6,542,773 | B2 | 4/2003 | Dupree et al. |
| 6,609,032 | B1 | 8/2003 | Woods et al. |
| 6,659,968 | B1 | 12/2003 | McClure |
| 6,748,276 | B1 | 6/2004 | Daignault, Jr. et al. |
| 7,033,326 | B1 | 4/2006 | Pianca et al. |
| 7,035,690 | B2 | 4/2006 | Goetz |
| 7,065,412 | B2 | 6/2006 | Swoyer et al. |
| 7,184,837 | B2 | 2/2007 | Goetz |
| 7,252,090 | B2 | 8/2007 | Goetz |
| 7,266,412 | B2 | 9/2007 | Stypulkowski |
| 2001/0007950 | A1 | 7/2001 | North et al. |
| 2001/0031919 | A1 | 10/2001 | Strommer et al. |
| 2002/0072785 | A1 | 6/2002 | Nelson et al. |
| 2002/0095098 | A1 | 7/2002 | Marinello |
| 2002/0103512 | A1 | 8/2002 | Echauz et al. |
| 2002/0116036 | A1* | 8/2002 | Daignault et al. ............ 607/59 |
| 2002/0120188 | A1 | 8/2002 | Brock et al. |
| 2003/0040291 | A1 | 2/2003 | Brewer |
| 2003/0158587 | A1 | 8/2003 | Esteller et al. |
| 2003/0171789 | A1 | 9/2003 | Malek et al. |
| 2003/0174066 | A1 | 9/2003 | Goetz et al. |
| 2003/0174069 | A1 | 9/2003 | Goetz et al. |
| 2003/0176906 | A1 | 9/2003 | Lee |
| 2004/0034394 | A1 | 2/2004 | Woods et al. |
| 2004/0059395 | A1 | 3/2004 | North et al. |
| 2004/0098063 | A1 | 5/2004 | Goetz |
| 2005/0070781 | A1 | 3/2005 | Dawant et al. |
| 2005/0267347 | A1* | 12/2005 | Oster ......................... 600/378 |
| 2006/0017749 | A1* | 1/2006 | McIntyre et al. ............ 345/664 |
| 2006/0020297 | A1 | 1/2006 | Gerber et al. |
| 2006/0094951 | A1 | 5/2006 | Dean et al. |
| 2006/0155333 | A1 | 7/2006 | Goetz |
| 2006/0229687 | A1 | 10/2006 | Goetz et al. |
| 2007/0055322 | A1 | 3/2007 | Forsberg et al. |
| 2007/0129770 | A1 | 6/2007 | Younis |
| 2008/0097195 | A1 | 4/2008 | Urquhart et al. |
| 2008/0215125 | A1 | 9/2008 | Farah et al. |

FOREIGN PATENT DOCUMENTS

| | | |
|---|---|---|
| EP | 1134003 | 9/2001 |
| EP | 0939661 B1 | 8/2002 |
| WO | WO 92/17240 | 10/1992 |
| WO | WO 98/43701 | 10/1998 |
| WO | WO 99/56820 | 11/1999 |
| WO | WO 00/02623 | 1/2000 |
| WO | WO 01/39831 | 6/2001 |
| WO | WO 01/43818 | 6/2001 |
| WO | WO 01/47411 | 7/2001 |
| WO | WO 01/80732 | 11/2001 |
| WO | WO 01/83028 | 11/2001 |
| WO | WO 01/93952 | 12/2001 |
| WO | WO 03/077995 | 9/2003 |

OTHER PUBLICATIONS

Notification of Transmittal of the International Preliminary Report on Patentablity for patent application No. PCT/US2007/002048, mailed Apr. 16, 2008, (7 pages).

Notification of Transmittal of the International Preliminary Report on Patentablity for patent application No. PCT/US2007/002019, mailed Apr. 16, 2008, (5 pages).

Notification of Transmittal of the International Preliminary Report on Patentablity for corresponding patent application No. PCT/US2007/002047, mailed Apr. 18, 2008, (8 pages).

Notification of Transmittal of the International Preliminary Report on Patentablity for patent application No. PCT/US2007/001810, mailed Apr. 4, 2008, (8 pages).

Notification of Transmittal of the International Preliminary Report on Patentablity for patent application No. PCT/US2007/001811, mailed Apr. 16, 2008, (5 pages).

Notification of Transmittal of the International Preliminary Report on Patentablity for patent application No. PCT/US2007/001808, mailed Apr. 18, 2008, (5 pages).

Notification of Transmittal of the International Preliminary Report on Patentablity for patent application No. PCT/US2007/001807, mailed Apr. 18, 2008, (5 pages).

Notification of Transmittal of the International Preliminary Report on Patentablity for patent application No. PCT/US2007/002049, mailed Apr. 9, 2008, (7 pages).

Notification of Transmittal of the International Preliminary Report on Patentablity for patent application No. PCT/US2007/002022, mailed Mar. 7, 2008, (9 pages).

Honeywell Inc. Systems and Research Division Research Department, "Experimental Evaluation of Symbolic and Pictorial Displays for Submarine Control," U.S. Dept. of Commerce Nat'l Technical Info. Service, Sep. 1965, 120 pages.

Advanced Neuromodulation Systems Renew Neurostimulation Systems User's Guide, Oct. 1997 (52 pages).

Advanced Neuromodulation Systems PainDoc® Operator's Manual, 2002 (59 pages).

Medtronic Memorymod® Model 7459 Software Programming Guide for Synergy™ and Itrel® 3 Neurostimulation Systems, 1999 (211 pgs.).

International Search Report from PCT Application Serial No. PCT/US03/35883 dated Apr. 14, 2004 (3 pages).

Office Action for U.S. Appl. No. 11/371,868, mailed May 2, 2008, 12 pages.

U.S. Appl. No. 11/371,868, entitled "Human-Implantable Neurostimulator User Interface Having Multiple Levels of Abstraction", filed Mar. 9, 2006, Steven M. Goetz.

Notification of Transmittal of the International Search Report and the Written Opinion of the International Searching Authority for patent application No. PCT/US2007/002021, filed Jan. 24, 2007, (9 pages).

Notification of Transmittal of the International Search Report and the Written Opinion of the International Searching Authority for patent application No. PCT/US2007/002048, filed Jan. 24, 2007, (9 pages).

Notification of Transmittal of the International Search Report and the Written Opinion of the International Searching Authority for patent application No. PCT/US2007/002019, filed Jan. 24, 2007, (9 pages).

Notification of Transmittal of the International Search Report and the Written Opinion of the International Searching Authority for corresponding patent application No. PCT/US2007/002047, filed Jan. 24, 2007, (9 pages).

Notification of Transmittal of the International Search Report and the Written Opinion of the International Searching Authority for patent application No. PCT/US2007/001810, filed Jan. 24, 2007, (9 pages).

Final Office Action for U.S. Appl. No. 11/591,281, mailed Aug. 25, 2009, 13 pages.
Responsive Amendment for U.S. Appl. No. 11/591,281, filed Oct. 22, 2009, 18 pages.
Final Office Action for U.S. Appl. No. 11/591,193, mailed Oct. 6, 2009, 8 pages.
Office Action for U.S. Appl. No. 11/591,176, dated Apr. 6, 2009, 11 pages.
Office Action for U.S. Appl. No. 11/591,281, dated Apr. 6, 2009, 12 pages.
Office Action for U.S. Appl. No. 11/591,178, dated Apr. 6, 2009, 13 pages.
Office Action for U.S. Appl. No. 11/591,193, dated Apr. 6, 2009, 9 pages.
Office Action for U.S. Appl. No. 11/591,188, dated Apr. 6, 2009, 9 pages.
Office Action for U.S. Appl. No. 11/591,280, dated Apr. 6, 2009, 9 pages.
Office Action for U.S. Appl. No. 11/591,170, dated Mar. 20, 2009, 7 pages.
Office Action for U.S. Appl. No. 11/591,189, dated Apr. 6, 2009, 11 pages.
Office Action for U.S. Appl. No. 11/591,187, dated Apr. 6, 2009, 12 pages.
European Office Action for European Application No. 07 709 862.2-2305, dated Feb. 19, 2009, 2 pages.
Response to European Office Action for European Application No. 07 709 862.2-2305, dated Jun. 29, 2009, 6 pages.
European Office Action for European Application No. 07 717 004.1-2305, dated Feb. 18, 2009, 2 pages.
Response to European Office Action for European Application No. 07 717 004.1-2305, dated Jun. 29, 2009, 6 pages.
European Office Action for European Application No. 07 749 226.2-2305, dated Feb. 18, 2009, 2 pages.
Response to European Office Action for European Application No. 07 749 226.2-2305, dated Jun. 29, 2009, 6 pages.
European Office Action for European Application No. 07 716 942.3-2305, dated Feb. 18, 2009, 2 pages.
Response to European Office Action for European Application No. 07 716 942.3-2305, dated Jun. 17, 2009, 6 pages.
Responsive Amendment for U.S. Appl. No. 11/591,176, filed Jun. 30, 2009, 13 pages.
Responsive Amendment for U.S. Appl. No. 11/591,281, filed Jun. 18, 2009, 18 pages.
Responsive Amendment for U.S. Appl. No. 11/591,178, filed Jun. 30, 2009, 21 pages.
Responsive Amendment for U.S. Appl. No. 11/591,193, filed Jun. 18, 2009, 15 pages.
Responsive Amendment for U.S. Appl. No. 11/591,188, filed Jun. 12, 2009, 10 pages.
Responsive Amendment for U.S. Appl. No. 11/591,280, filed Jun. 30, 2009, 21 pages.
Response for U.S. Appl. No. 11/591,170, filed May 12, 2009, 8 pages.
Responsive Amendment for U.S. Appl. No. 11/591,189, filed Jun. 30, 2009, 20 pages.
Responsive Amendment for U.S. Appl. No. 11/591,187, filed Jul. 1, 2009, 23 pages.
Responsive Amendment for U.S. Appl. No. 11/371,868, filed Aug. 19, 2008, 13 pages.
Office Action for U.S. Appl. No. 11/371,868, dated Nov. 28, 2008, 8 pages.
Response for U.S. Appl. No. 11/371,868, filed Jan. 27, 2009, 5 pages.
Advisory Action for U.S. Appl. No. 11/371,868, dated Feb. 25, 2009, 3 pages.
Responsive Amendment for U.S. Appl. No. 11/371,868, filed Apr. 28, 2009, 14 pages.
Office Action for U.S. Appl. No. 11/591,176, mailed Nov. 17, 2009, 17 pages.
Office Action for U.S. Appl. No. 11/591,281, mailed Dec. 29, 2009, 13 pages.
Office Action for U.S. Appl. No. 11/591,178, mailed Nov. 2, 2009, 12 pages.
Final Office Action for U.S. Appl. No. 11/591,188, mailed Oct. 29, 2009, 8 pages.
Final Office Action for U.S. Appl. No. 11/591,280, mailed Oct. 30, 2009, 8 pages.
Advisory Action for U.S. Appl. No. 11/591,280, mailed Jan. 7, 2010, 3 pages.
Final Office Action for U.S. Appl. No. 11/591,187, mailed Nov. 20, 2009, 8 pages.
Responsive Amendement for U.S. Appl. No. 11/591,193, filed Dec. 2, 2009, 14 pages.
Advisory Action for U.S. Appl. No. 11/591,188, mailed Jan. 15, 2010, 4 pages.
Response to Final Office Action for U.S. Appl. No. 11/591,187, filed Jan. 19, 2010, 8 pages.
Response to Office Action dated Nov. 17, 2009, from U.S. Appl. No. 11/591,176, filed Mar. 17, 2010, 14 pp.
Response to Office Action dated Dec. 29, 2009, from U.S. Appl. No. 11/591,281, filed Mar. 25, 2009, 18 pp.
Response to Office Action dated Nov. 2, 2009, from U.S. Appl. No. 11/591,178, filed Jan. 29, 2010, 8 pp.
Advisory Action from U.S. Appl. No. 11/591,193, dated Feb. 5, 2010, 3 pp.
Response to Advisory Action dated Feb. 5, 2010, from U.S. Appl. No. 11/591,193, filed Mar. 2, 2010, 13 pp.
Response to Office Action dated Oct. 29, 2009, from U.S. Appl. No. 11/591,188, filed Jan. 28, 2010, 17 pp.
Response to Office Action dated Oct. 30, 2009, from U.S. Appl. No. 11/591,280, filed Jan. 26, 2010, 14 pp.
Response to Office Action dated Nov. 20, 2009, and Advisory Action dated Feb. 5, 2010, from U.S. Appl. No. 11/591,187, filed Feb. 17, 2010, 19 pp.
Office Action from U.S. Appl. No. 11/591,178, dated Mar. 22, 2010, 17 pp.
Office Action from U.S. Appl. No. 11/591,188, dated Feb. 22, 2010, 11 pp.
Office Action from U.S. Appl. No. 11/591,280, dated Feb. 23, 2010, 11 pp.
Response to Office Action dated Apr. 15, 2010, from U.S. Appl. No. 11/591,193, filed Jul. 15, 2010, 10 pp.
Final Office Action for U.S. Appl. No. 11/591,281, mailed Jun. 24, 2010, 12 pages.
Response to final Office Action for U.S. Appl. No. 11/591,281, filed Aug. 20, 2010. 17 pages.
Advisory Action for U.S. Appl. No. 11/591,281, mailed Sep. 1, 2010, 3 pages.
Final Office Action for U.S. Appl. No. 11/591,176, mailed Jun. 25, 2010, 12 pages.
Final Office Action for U.S. Appl. No. 11/591,188, mailed Aug. 6, 2010, 8 pages.

* cited by examiner

ELECTRICAL AND ACTIVATION FIELD MODELS FOR CONFIGURING STIMULATION THERAPY

This application claims the benefit of U.S. provisional application No. 60/776,454, filed Feb. 24, 2006, and U.S. provisional application No. 60/785,255, filed Mar. 23, 2006. The entire content of both provisional applications is incorporated herein by reference.

TECHNICAL FIELD

The invention relates to medical devices and, more particularly, to user interfaces for configuring electrical stimulation therapy.

BACKGROUND

Implantable electrical stimulators may be used to deliver electrical stimulation therapy to patients to treat a variety of symptoms or conditions such as chronic pain, tremor, Parkinson's disease, epilepsy, urinary or fecal incontinence, sexual dysfunction, obesity, or gastroparesis. In general, an implantable stimulator delivers neurostimulation therapy in the form of electrical pulses. An implantable stimulator may deliver neurostimulation therapy via one or more leads that include electrodes located proximate to target tissues of the brain, the spinal cord, pelvic nerves, peripheral nerves, or the stomach of a patient. Hence, stimulation may be used in different therapeutic applications, such as deep brain stimulation (DBS), spinal cord stimulation (SCS), pelvic stimulation, gastric stimulation, or peripheral nerve stimulation. Stimulation also may be used for muscle stimulation, e.g., functional electrical stimulation (FES) to promote muscle movement or prevent atrophy.

In general, a clinician selects values for a number of programmable parameters in order to define the electrical stimulation therapy to be delivered by the implantable stimulator to a patient. For example, the clinician ordinarily selects a combination of electrodes carried by one or more implantable leads, and assigns polarities to the selected electrodes. In addition, the clinician selects an amplitude, which may be a current or voltage amplitude, a pulse width and a pulse rate for stimulation pulses to be delivered to the patient. A group of parameters, including electrode combination, electrode polarity, amplitude, pulse width and pulse rate, may be referred to as a program in the sense that they drive the neurostimulation therapy to be delivered to the patient. In some applications, an implantable stimulator may deliver stimulation therapy according to multiple programs either simultaneously or on a time-interleaved, overlapping or non-overlapping, basis.

The process of selecting electrode combinations and other parameters can be time consuming, and may require a great deal of trial and error before a therapeutic program is discovered. The "best" program may be a program that best balances greater clinical efficacy and minimal side effects experienced by the patient. In addition, some programs may consume less power during therapy. The clinician typically needs to test a large number of possible electrode combinations within the electrode set implanted in the patient, in order to identify an optimal combination of electrodes and associated polarities. As mentioned previously, an electrode combination is a selected subset of one or more electrodes located on one or more implantable leads coupled to an implantable neurostimulator. As a portion of the overall parameter selection process, the process of selecting electrodes and the polarities of the electrodes can be particularly time-consuming and tedious.

The clinician may test electrode combinations by manually specifying combinations based on intuition or some idiosyncratic methodology. The clinician may then record notes on the efficacy and side effects of each combination after delivery of stimulation via that combination. In some cases, efficacy can be observed immediately within the clinic. For example, spinal cord stimulation may produce parasthesia and side effects that can be observed by the clinician based on patient feedback. In other cases, side effects and efficacy may not be apparent until a program has been applied for an extended period of time, as is sometimes the case in deep brain stimulation. Upon receipt of patient feedback and/or observation of symptoms by the clinician, the clinician is able to compare and select from the tested programs.

In order to improve the efficacy of neurostimulation therapy, electrical stimulators have grown in capability and complexity. Modern neurostimulators tend to have larger numbers of electrode combinations, larger parameter ranges, and the ability to simultaneously deliver multiple therapy configurations by interleaving stimulation pulses in time. Although these factors increase the clinician's ability to adjust therapy for a particular patient or disease state, the burden involved in optimizing the device parameters has similarly increased. Unfortunately, fixed reimbursement schedules and scarce clinic time present challenges to effective programming of neurostimulator therapy.

Existing lead sets include axial leads carrying ring electrodes disposed at different axial positions, and so-called "paddle" leads carrying planar arrays of electrodes. Selection of electrode combinations within an axial lead, a paddle lead, or among two or more different leads presents a challenge to the clinician. The emergence of more complex lead array geometries presents still further challenges. The design of the user interface used to program the implantable neurostimulator, in the form of either a clinician programmer or patient programmer, has a great impact on the ability to efficiently define and select efficacious stimulation programs.

SUMMARY

The disclosure describes a method and system that generates an electrical field model of defined stimulation therapy and displays the electrical field model to a user via a user interface. The electrical field model is generated based upon a patient anatomy and stimulation parameters to illustrate which areas of a patient anatomical region will be covered by an electrical field during therapy. In addition, a neuron model may be applied to the electrical field model to generate an activation field model. The activation field model indicates which neurons will be activated by the electrical field in the anatomical region. In particular, the field models may be beneficial when programming non axi-symmetric, or three-dimensional (3D), leads which have a complex electrode array geometry and allow greater flexibility in creating stimulation fields. The techniques may be applied to a programming interface associated with a clinician programmer, a patient programmer, or both.

The electrical field model and activation field model may be used by a clinician to determine effective therapy prior to stimulation delivery. One of the field models may be displayed to the clinician within a two-dimensional or three-dimensional anatomical region of the patient to estimate the exact structures that will be affected by the therapy. The clinician may then modify the field model to alter the stimulation therapy, if necessary, to effectively treat the patient's condition or avoid side effects.

A complex electrode array geometry generally refers to an arrangement of stimulation electrodes at multiple non-planar or non-coaxial positions, in contrast to simple electrode array geometries in which the electrodes share a common plane or a common axis. An example of a simple electrode array geometry is an array of ring electrodes distributed at different axial positions along the length of a lead. Another example of a simple electrode array geometry is a planar array of electrodes on a paddle lead.

An example of a complex electrode array geometry, in accordance with this disclosure, is an array of electrodes positioned at different axial positions along the length of a lead, as well as at different angular positions about the periphery, e.g., circumference, of the lead. In some embodiments, the electrodes in the complex array geometry may appear similar to non-contiguous, arc-like segments of a conventional ring electrode. A lead with a complex electrode array geometry may include multiple "rings" of such electrode segments. Each ring is disposed at a different axial position. Each electrode segment within a given ring is disposed at a different angular position. The lead may be cylindrical or have a circular cross-section of varying diameter. Another example of a complex electrode array geometry is an array of electrodes positioned on multiple planes or faces of a lead. As an illustration, arrays of electrodes may be positioned on opposite planes of a paddle lead or multiple faces of a lead having a polygonal cross-section.

An electrode combination is a selected subset of one or more electrodes located on one or more implantable leads coupled to an implantable stimulator. The electrode combination also refers to the polarities of the electrodes in the selected subset. The electrode combination, electrode polarities, amplitude, pulse width and pulse rate together define a program for delivery of electrical stimulation therapy by an implantable stimulator via an implantable lead or leads.

In some cases, a lead icon representing the implanted lead is displayed to show the clinician where the lead is relative to one or more anatomical regions of the atlas or patient. Electrodes mounted at different axial and angular positions of an implanted lead may allow the clinician to provide a more directional stimulation field to more effectively stimulate a target nerve site, reduce side affects, or compensate for inaccurate lead placement.

The task of effectively configuring electrical stimulation therapy increases substantially as geometries and capabilities of stimulation leads become more complex. In particular, leads with complex electrode array geometries present the difficult task of orienting the position of lead electrodes to anatomical structures of the patient in a manner intuitive to the clinician. Allowing the clinician to partially or completely disregard the electrode locations and focus on selecting the structures that need to be stimulated to treat the patient may decrease clinician time and confusion in configuring the electrical stimulation and increase therapy efficacy. Based upon the selected structures, the system may automatically generate the best stimulation parameters for therapy.

The disclosure describes multiple embodiments of a user interface designed to allow the clinician to effectively program delivery of stimulation from leads having complex electrode array geometries. The user interface may use a two-dimensional or three-dimensional user interface to display the anatomical region of the patient and either the electrical field model or activation field model to the clinician. When programming a complex electrode array geometry, viewing one of the field models prior to delivery of therapy may reduce the trial and error most common with conventional programming methods.

The techniques described herein may be used during a test or evaluation mode to select different electrode combinations in an effort to identify efficacious electrode combinations. Additionally, the techniques may be used to select different electrode combinations associated with different stimulation programs during an operational mode, either directly or by selection of programs including such electrode combinations. For example, the techniques and associated user interfaces may be implemented in a clinician programmer used by a clinician to program a stimulator, in a patient programmer used by a patient to program or control a stimulator, or in an external stimulator including both pulse generation and programming functionality.

In one embodiment, the disclosure provides a method that includes receiving a patient anatomy data set that describes at least one characteristic of patient tissue proximate to an electrical stimulation lead implanted within a patient, receiving user input that defines stimulation parameter values, generating a stimulation field model that represents where the electrical current will propagate from the electrical stimulation lead based upon the patient anatomy data set and stimulation parameter values, and displaying the stimulation field model on a representation of an anatomical region of the patient.

In another embodiment, the disclosure provides a system that includes a communications module that receives a patient anatomy data set that describes at least one characteristic of patient tissue proximate to an electrical stimulation lead implanted within a patient, a user interface that receives user input that defines stimulation parameter values, and a processor. The processor generates a stimulation field model that represents where the electrical current will propagate from the electrical stimulation lead based upon the patient anatomy data set and stimulation parameter values, and displays the stimulation field model on a representation of an anatomical region of the patient via the user interface.

In an additional embodiment, the disclosure provides a computer-readable medium that includes instructions that cause a processor to receive a patient anatomy data set that describes at least one characteristic of patient tissue proximate to an electrical stimulation lead implanted within a patient, receive user input that defines stimulation parameter values, generate a stimulation field model that represents where the electrical current will propagate from the electrical stimulation lead based upon the patient anatomy data set and stimulation parameter values, and display the stimulation field model on a representation of an anatomical region of the patient.

In another embodiment, the disclosure provides a method comprising receiving a patient anatomy data set that describes at least one characteristic of patient neural tissue proximate to an electrical stimulation lead implanted within a patient, receiving user input that defines stimulation parameter values, generating an activation field model indicates which neural structures of the patient are activated by applying the stimulation field model to the anatomical region of the patient based on the patient anatomy data set and stimulation parameter values, and displaying the activation field model over the anatomical region.

In another embodiment, the disclosure provides a system comprising a communications module that receives a patient anatomy data set that describes at least one characteristic of patient neural tissue proximate to an electrical stimulation lead implanted within a patient, a user interface that receives user input that defines stimulation parameter values, and a processor. The processor generates an activation field model that indicates which neural structures of the patient are activated by applying the stimulation field model to the anatomical region of the patient based on the patient anatomy data set and stimulation parameter values, and displays the activation field model on a representation of an anatomical region of the patient via the user interface.

In another embodiment, the disclosure provides a computer-readable medium comprising instructions that cause a processor to receive a patient anatomy data set that describes at least one characteristic of patient neural tissue proximate to an electrical stimulation lead implanted within a patient, receive user input that defines stimulation parameter values; generate an activation field model indicates which neural structures of the patient are activated by applying the stimulation field model to the anatomical region of the patient based on the patient anatomy data set and stimulation parameter values, and display the activation field model over the anatomical region.

In various embodiments, the disclosure may provide one or more advantages. Presenting an electrical field model to the user may help the user to visualize which structures of the patient anatomical region will be covered by the electrical field. Further, allowing the user view which neurons will be activated in an activation field model may reduce the time required to optimize the stimulation therapy. In addition, either field model may be displayed in a two-dimensional or three-dimensional format within the anatomical region of interest.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
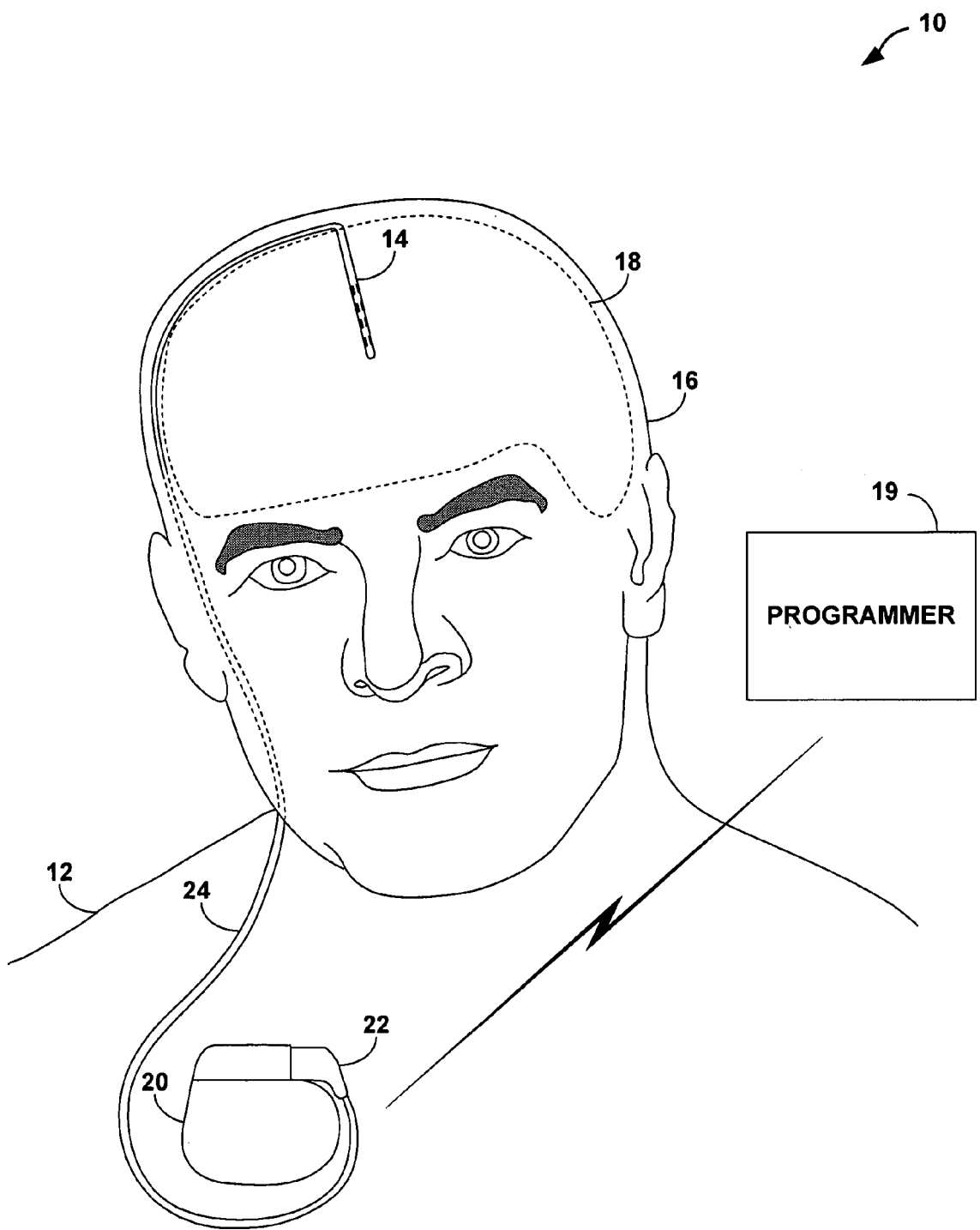
FIG. 1 is a conceptual diagram illustrating an example stimulation system with a stimulation lead implanted in the brain of a patient.

Electrical stimulation therapy may provide relief to a patient from many conditions. However, the stimulation therapy efficacy is contingent on a clinician correctly configuring, or programming, the stimulation parameters in a manner that provides therapy to the patient while minimizing side-effects produced from the stimulation. Due to physiological diversity, condition differences, and inaccuracies in stimulation lead placement, the parameters may vary greatly between patients. Therefore, the clinician must individually program stimulation parameters for each patient. This programming process continues throughout the therapy as patient needs change.

Implanting stimulation leads with complex electrode array geometries introduces more complex programming challenges for the clinician. Although leads with complex electrode array geometries provide greater flexibility in defining a stimulation field to provide therapy, the clinician must identify effective electrodes, electrode polarity, current and voltage amplitudes, pulse widths, and pulse frequencies of each electrode combination. Clinicians may prefer to focus on stimulating a particular anatomical structure or target tissue of the patient, which becomes difficult when facing potentially millions of programming options presented by a complex electrode array geometry.

A complex electrode array geometry generally refers to an arrangement of stimulation electrodes at multiple non-planar or non-coaxial positions, in contrast to simple electrode array geometries in which the electrodes share a common plane or a common axis. An example of a simple electrode array geometry is an array of ring electrodes distributed at different axial positions along the length of a lead. Another example of a simple electrode array geometry is a planar array of electrodes on a paddle lead.

An example of a complex electrode array geometry, in accordance with this disclosure, is an array of electrodes positioned at different axial positions along the length of a lead, as well as at different angular positions about the circumference of the lead. In some embodiments, the electrodes in the complex array geometry may appear similar to non-contiguous, arc-like segments of a conventional ring electrode. A lead with a complex electrode array geometry may include multiple rings of electrode segments. Each ring is disposed at a different axial position. Each electrode segment within a given ring is disposed at a different angular position. The lead may be cylindrical or have a circular cross-section of varying diameter.

Another example of a complex electrode array geometry is an array of electrodes positioned on multiple planes or faces of a lead. As an illustration, arrays of electrodes may be positioned on opposite planes of a paddle lead or multiple faces of a lead having a polygonal cross-section in a plane transverse to the longitudinal axis of the lead. As further examples, electrodes may be arranged at different axial and angular positions on leads defining spherical, hemispherical or generally rounded surfaces. Leads with complex electrode array geometries may have a defined shape or be at least partially conformable to an anatomical structure. In some embodiments, electrodes may be arc sections conforming to the overall lead geometry. In addition, the electrodes may also be recessed within the lead.

An electrode combination is a selected subset of one or more electrodes located on one or more implantable leads coupled to an implantable stimulator. The electrode combination also refers to the polarities of the electrode segments in the selected subset. The electrode combination, electrode polarities, amplitude, pulse width and pulse rate together define a program for delivery of electrical stimulation therapy by an implantable stimulator via an implantable lead or leads. By selecting particular electrode combinations, a physician can target particular anatomic structures. By selecting values for amplitude, pulse width and pulse rate, the physician can attempt to optimize the electrical therapy delivered to the patient via the selected electrode combination or combinations.

As stimulation is moved from one electrode to another electrode around the periphery, e.g., circumference, of a lead, the stimulation may affect entirely different anatomical structures. For this reason, providing the clinician with an interface that shows the electrodes in relation the anatomical regions of the patient may be beneficial to effective and efficient programming. Displaying the anatomy of the patient to the clinician may allow the clinician to focus on configuring a stimulation field such that it is applied to targeted tissue, instead of manually manipulating electrodes of a lead to conform to the anatomical structures of the patient. Once desired stimulation field is "marked" on an anatomical region of the patient, a system may automatically generate the required stimulation parameters needed to approximate the defined stimulation field requested by the clinician. The stimulator then applies the stimulation parameters to produce the field within the patient.

In accordance with this disclosure, a user interface facilitates electrical stimulation programming by allowing a clinician to define and manipulate a stimulation field within anatomical regions representing the anatomical structures of the patient using a "field view." The stimulation field may be shown in conjunction with a representation of the implanted lead, e.g., a lead icon; and the field and lead representations may be shown in relation the anatomical structures.

The resulting user interface may provide a programming environment that promotes delivering therapy instead of programming individual stimulation parameters of each electrode. However, an electrode view that permits programming of individual parameters and electrodes may be provided on a selective basis.

The user interface may include two or more two dimensional (2D) views of anatomical regions of the patient, or a 3D representation of the anatomical regions. One or more stimulation fields are displayed on the anatomical regions, and the clinician may adjust or manipulate the stimulation fields to reach the target one or more anatomical regions.

The user interface may be applied to any type electrical stimulation lead. Even programming a lead with one electrode, or an array of electrodes in one plane (2D), may become less demanding of clinic resources and result in greater quality of patient therapy when compared to trial and error programming techniques that focus on manual selection of electrodes instead of the stimulation field that the electrodes produce.

To select electrode combinations within a complex lead array geometry, in accordance with this disclosure, a user interface permits a user to view electrodes from different perspectives relative to the lead. For example, the user interface may provide one or more axial perspectives of a lead and a cross-sectional perspective of the lead in a plane transverse to a longitudinal axis of the lead. For DBS applications, examples of multiple perspectives include views of coronal, sagittal and horizontal planes of the brain and the lead implanted within the brain.

As an alternative or in addition to defining and manipulating a stimulation field to program the electrical stimulation therapy, the user may program the stimulation therapy by selecting the appropriate structure of the anatomical region to stimulate. For example, the system may provide the user with an atlas, or reference anatomical region of a reference anatomy, that the user may use to select structures to stimulate. Alternatively, the system may provide the user with a morphed atlas that combines the reference anatomical region with a specific patient anatomical region. This morphed atlas may allow the user to view known structures while correlating the known structures to the specific patient anatomical region.

The system may determine the stimulation parameters for stimulation based upon the selected structures from the morphed atlas. In this manner, programming the stimulation parameters may be more efficient for a clinician by reducing or eliminating the need to manually program the stimulation parameters.

In other embodiments, the system may show the user the tissue that will be affected by the electrical stimulation as defined by the user. The system may create a stimulation template set defining stimulation parameters that best matches the stimulation field defined by the user. The template set may be shown to the user in relation to the desired stimulation field to illustrate the tissue that will be stimulated by the system. The stimulation template set may be created from many stimulation templates stored within the system and used to simplify the process of generating stimulation parameters that fit the desired stimulation field.

Alternatively, the system may illustrate an electrical field over the anatomical region to illustrate the estimated tissue that will be affected by the defined stimulation field. The electrical field may be estimated by modeling the tissue around the complex electrode array geometry, and determining the propagation of the electrical field. The system may use the electrical field to determine stimulation parameters, and the user may desire to view the electrical field to review which structures of the anatomical region will be affected by the electrical field of the therapy. In addition to the electrical field, the system may apply a neuron model to the electrical field and use the resulting activation model to determine which tissues within the electrical field will be activated by the stimulation. The activation model may be provided to the user such that the user can accurately review which structures of the anatomical region will be activated by the stimulation. The activation model may allow a user to avoid stimulation of unwanted structures, and confirm that desired structures are stimulated.

FIG. 1 is a conceptual diagram illustrating an example stimulation system with a stimulation lead implanted in the brain of a patient. As shown in FIG. 1, stimulation system 10 includes implantable medical device (IMD) 20, lead plug 22, lead wire 24 and lead 14 implanted within patient 12. Specifically, lead 14 enters through cranium 16 and is implanted within brain 18 to deliver deep brain stimulation (DBS). One or more electrodes of lead 14 provides electrical pulses to surrounding anatomical regions of brain 18 in a therapy that may alleviate a condition of patient 12. In some embodiments, more than one lead 14 may be implanted within brain 18 of patient 12 to stimulate multiple anatomical regions of the brain. As shown in FIG. 1, system 10 may also include a programmer 19, which may be a handheld device, portable computer, or workstation that provides a user interface to a clinician. The clinician interacts with the user interface to program stimulation parameters.

DBS may be used to treat dysfunctional neuronal activity in the brain which manifests as diseases or disorders such as Huntington's Disease, Parkinson's Disease, or movement disorders. The exact reasons why electrical stimulation therapy is capable of treating such conditions of the brain is unknown, but symptoms of these disease can be lessened or eliminated with stimulation therapy. Certain anatomical regions of brain 18 are responsible for producing the symptoms of such brain disorders. For example, stimulating an anatomical region, such as the Substantia Nigra, in brain 18 may reduce the number and magnitude of tremors experienced by patient 12. Other anatomical regions may include the subthalamic nucleus, globus pallidus interna, ventral intermediate, and zona inserta. Anatomical regions such as these are targeted by the clinician during lead 14 implantation. In other words, the clinician attempts to position the lead as close to these regions as possible.

While DBS may successfully reduce symptoms of some neurological diseases, the stimulation commonly causes unwanted side effects as well. Side effects may include incontinence, tingling, loss of balance, paralysis, slurred speech, loss of memory, and many other neurological problems. Side effects may be mild to severe; however, most side effects are reversible when stimulation is stopped. DBS may cause one or more side effects by inadvertently providing electrical stimulation pulses to anatomical regions near the targeted anatomical region. For this reason, the clinician typically programs the stimulation parameters in order to balance effective therapy and minimal side effects.

Typical DBS leads include one or more electrodes placed along the longitudinal axis of the lead, such as lead 14. Each electrode is typically a ring electrode that resides along the entire circumference of the lead. Therefore, electrical current from the ring electrodes propagates in all directions from the active electrode. The resulting stimulation field reaches anatomical regions of brain 18 within a certain distance in all directions. The stimulation field may reach the target anatomical region, but the stimulation field may also affect non-target anatomical regions and produce unwanted side effects. Implanting a lead with a complex electrode array geometry may help to customize the stimulation field and provide improved therapy while decreasing side effects. In this manner, specific electrodes of the complex electrode array geometry may be selected to produce a stimulation field at desired portions of the circumference instead of always producing a stimulation field around the entire circumference of the lead. Also, the complex electrode array geometry may require a three dimensional method for a clinician to define which electrodes to use.

Lead 14 has a complex electrode array geometry in the preferred embodiment, but the lead may also include one or more single ring electrodes along the longitudinal axis in other embodiments. For example, the disclosure may be applicable to leads having all ring electrodes, or one or more ring electrodes in combination with electrodes at different axial positions and angular positions around the circumference of the lead. As an example, lead 14 includes a plurality of electrodes positioned at different axial positions along the longitudinal axis of the lead and a plurality of electrodes positioned at different angular positions around the circumference of the lead (which may be referred to as segmented electrodes). In this manner, electrodes may be selected along the longitudinal axis of lead 14 and along the circumference of the lead. Activating selective electrodes of lead 14 can produce customizable stimulation fields that may be directed to a particular side of lead 14 in order to isolate the stimulation field around the target anatomical region of brain 18.

Producing irregular stimulation fields with a lead 14 with a complex electrode geometry not only allows system 10 to more effectively treat certain anatomical regions of brain 18, but the system can also reduce or eliminate side effects from more spherical stimulation fields produced by a conventional array of ring electrodes. The center of the stimulation field may be moved away from lead 14 to avoid unwanted stimulation or compensate for inaccurately placed leads. If leads migrate within brain 18 slightly, a customizable stimulation field may provide a longer duration of effective therapy as stimulation needs of patient 12 change.

Programming lead 14 is more involved and complex when compared to traditional leads because of the increased number of possible electrode combinations and resulting stimulation fields. Effective programming may be difficult for the clinician if the clinician is required to systematically select each electrode of lead 14 in order to find the electrode combinations that provide therapy and minimal side effects. While the clinician may still desire the ability to manually select certain general areas of electrodes of lead 14, e.g., the group of circumferential electrodes at one level or length of the lead, programming time may be reduced if the clinician uses a user interface that enables the clinician to define a stimulation field and automatically generate the stimulation parameters that would produce the stimulation field in patient 12.

The user interface of programmer 19 displays a representation of the anatomical regions of patient 12, specifically anatomical regions of brain 18. The 3D space of the anatomical regions may be displayed as multiple 2D views or one 3D visualization environment. Lead 14 may also be represented on the display of the user interface, positioned according to the actual implantation location by the clinician or directly from an image taken of the lead within brain 18.

The clinician interacts with the user interface to manually select and program certain electrodes of lead 14, select an electrode level of the lead and adjust the resulting stimulation field with the anatomical regions as guides, or defining one or more stimulation fields only affect anatomical regions of interest. Once the clinician has defined the one or more stimulation fields, system 10 automatically generates the stimulation parameters associated with each of the stimulation fields and transmits the parameters to IMD 20.

System 10 may provide the clinician with additional tools that allow the clinician to accurately program the complex electrode array geometry of lead 14 for therapy. These tools may include creating and displaying a stimulation template set that corresponds to the stimulation field defined by the clinician. The stimulation template set may indicate to the clinician the actual stimulation that will occur based upon the stimulation field. Alternatively, system 10 may provide an electrical field or activation field to the clinician that illustrates the exact structures of the anatomical region that will be affected by the stimulation field. The electrical field may be indicative of the electrical propagation through the tissue surrounding lead 14, while the activation field may be indicative of the actual neurons within the electrical field that are activated by the therapy. Further, instead of or in addition to defining a stimulation field over an anatomical region of the patient, system 10 may provide a reference anatomical region of a reference anatomy, or an atlas, that allows the clinician to directly select the structures of the atlas that are targeted for therapy. The atlas may be mapped to the anatomical region of the patient anatomy or morphed together with the patient specific imaging to create a morphed atlas that indicates where each structure of the patient specific imaging resides. System 10 may then generate stimulation parameters to stimulate the selected structures. These alternative aspects of system 10 will be described in detail below.

Because clinicians are more familiar with physiology and anatomy than the operation and programming of stimulation parameters, clinicians may spend much less time configuring therapy for patient 12 by choosing what structures of the anatomical region should be stimulated. In some cases, system 10 may even indicate which structures the clinician has selected through the use of a pop-up bubble or structure list. Alternatively, the clinician may be able to select one or more specific outcomes from a list, e.g., outcome selection input, where the outcome is a common result of stimulation to one or more structures of patient 12. Less clinician programming time with the user interface may result in a greater number of patients receiving effective therapy with potentially less side effects from time induced clinician mistakes.

The user interface provided in many different embodiments may allow a clinician to define a stimulation field which is used to generate stimulation parameters for IMD 20 and lead 14. A first embodiment may utilize 2D views, or sections, of the anatomical regions of brain 18. The clinician may place a lead icon over the anatomical regions in each 2D view to represent the actual location of implanted lead 14. Once the lead icon is present, the clinician may select an electrode level and adjust the stimulation field position and magnitude by switching between different 2D views. Example 2D views may include coronal, sagittal, and axial slices of brain 18.

Another embodiment is similar to the first embodiment in that multiple 2D views are provided to the clinician to represent the 3D anatomical regions. The clinician defines, with an outline for example, one or more stimulation fields on three 2D views of the anatomical regions of patient 12. A 3D stimulation field volume is therefore defined by the 2D outlines and programmer 19 automatically generates appropriate stimulation parameters to at least approximate the defined field. The clinician may adjust the stimulation field by reviewing the 2D views and moving the outline. The outline may be established automatically by the programmer or the clinician may draw the outline using a stylus and touchscreen or other input media.

Further embodiments of system 10 allow the user to define a stimulation field on each of multiple 2D views in accordance to which structures of the anatomical region should be stimulated. System 10 then creates a stimulation template set that best fits the defined stimulation field. The stimulation template set that best fits the stimulation field may be presented to the clinician via the user interface over the defined stimulation field. If the clinician is not satisfied with the stimulation template set that is provided, the clinician may change the stimulation field until a template set is acceptable.

Other embodiments of system 10 provide an atlas to the clinician to reduce the difficulty of finding the desired structure to stimulate. In this case, the clinician may select the desired structure by selecting the structure from a simple drop down menu or from a graphical representation of the atlas. The atlas may be overlaid with the anatomical region of the patient anatomy for easy identification of structures of the patient. Alternatively, system 10 may generate a morphed atlas based upon the atlas and the patient anatomical region. Essentially, the locations of structures in the atlas are mapped to the patient anatomical region for selection.

Further embodiments of system 10 provide an electrical field model or an activation field model to the clinician over the anatomical region to indicate which structures will actually be affected by the defined stimulation. After defining the stimulation field and viewing the resulting electrical field or activation field, the clinician may be able to increase or decrease the amplitude to adjust the model according to what structures need to be stimulated by lead 14.

An additional embodiment utilizes a 3D visualization environment that enables the clinician to view a 3D representation of anatomical regions of brain 18. The clinician places a 3D stimulation field within the anatomical regions and manipulates the shape, size, and placement of the 3D stimulation field to stimulation the target anatomical regions. The clinician may rotate and zoom the view to see exactly what anatomical regions the stimulation field will reach. A 3D lead icon may be present to show the clinician how the stimulation field relates to the position of implanted lead 14.

The 3D visualization environment may also incorporate an atlas, a morphed atlas, a stimulation template set, an electrical field model, or an activation model to assist the clinician in programming the stimulation therapy. The 3D environment allows the physician to rotate and zoom in on any portion of the 3D anatomical region represented in the 3D environment. The clinician can easily see which structures will be stimulated according to the defined stimulation field and which structures will be left unaffected. The 3D environment may reduce the amount of time the clinician must spend to initially program the stimulation therapy and optimize the therapy.

Other embodiments of the user interface are also contemplated, such as combinations of elements of the three embodiments described briefly above. For example, the clinician may select an electrode level of a lead icon in the 3D environment and manipulate the stimulation field provided by the electrodes of that electrode level. Some embodiments may begin with 2D views of the 3D anatomical regions and generate a 3D view of the defined stimulation field within the anatomical structures. In any embodiment, the user interface may restrict clinician defined stimulation fields based upon the stimulation abilities of IMD 20 and lead 14. For example, the clinician may not make the stimulation field larger when the voltage cannot be increased or no more electrodes are available in the direction of the stimulation field. Additionally, the user interface may restrict the clinician from applying the stimulation field to an anatomical region or structure specifically banned from stimulation. Stimulation of these areas may severely alter the physiology of patient 12 and cause detrimental side effects or irreversible side effects.

The stimulation field defined by the clinician using a user interface described herein is associated with certain stimulation parameter values. Programmer 19 automatically generates the stimulation parameters required by the stimulation field and wirelessly transmits the parameters to IMD 20. The parameters may also be saved on programmer 19 for review at a later time. In some cases, programmer 19 may not be capable of generating stimulation parameters that can produce the defined stimulation field within brain 18. Programmer 19 may display an error message to the clinician alerting the clinician to adjust the stimulation field. Programmer 19 may also display a reason why the stimulation field cannot be provided, such as the field is too large or an electrode is malfunctioning and cannot be used. Other errors may also be displayed to the clinician.

Generally, the user interface is not used to provide real-time programming to IMD 20. The clinician will use the user interface to define stimulation fields, and programmer 19 automatically generates the stimulation parameters when the clinician has determined the stimulation field is ready for therapy. In this manner, stimulation therapy perceived by patient 12 does not change at the same time the clinician changes the stimulation field. However, the user interface could be used as such in a real-time programming environment to provide immediate feedback to the clinician. In this manner, System 10 may also include multiple leads 14 or electrodes on leads of other shapes and sizes. The user interface may allow the clinician to program each lead simultaneously or require the clinician to program each lead separately. In some DBS patients, two leads 14 are implanted at symmetrical locations within brain 18 for bilateral stimulation. In particular, a first lead is placed in the right hemisphere of brain 18 and a second lead is placed at the same location within the left hemisphere of the brain. Programmer 19 may allow the clinician to create a stimulation field for the first lead and create a mirrored stimulation field for the second lead. The clinician may be able to make fine adjustment to either stimulation field do accommodate the slight anatomical region differences between the left and right hemispheres.

While lead 14 is described for use in DBS applications throughout this disclosure as an example, lead 14, or other leads, may be implanted at any other location within patient 12. For example, lead 14 may be implanted near the spinal cord, pudendal nerve, sacral nerve, or any other nervous or muscle tissue that may be stimulated. The user interface described herein may be used to program the stimulation parameters of any type of stimulation therapy. In the case of pelvic nerves, defining a stimulation field may allow the clinician to stimulate multiple desired nerves without placing multiple leads deep into patient 12 and adjacent to sensitive nerve tissue. Therapy may also be changed if leads migrate to new locations within the tissue or patient 12 no longer perceives therapeutic effects of the stimulation.

Figure 2A:
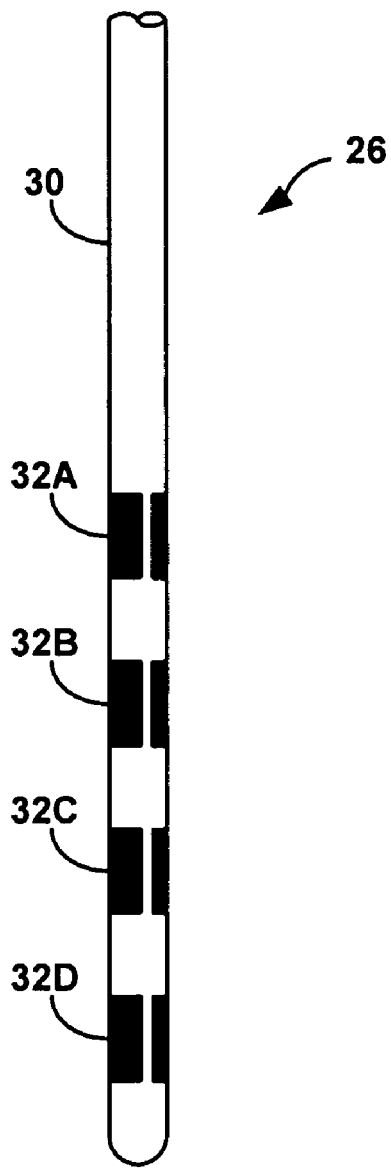
FIGS. 2A and 2B are conceptual diagrams illustrating two different implantable stimulation leads.
Figure 2B:
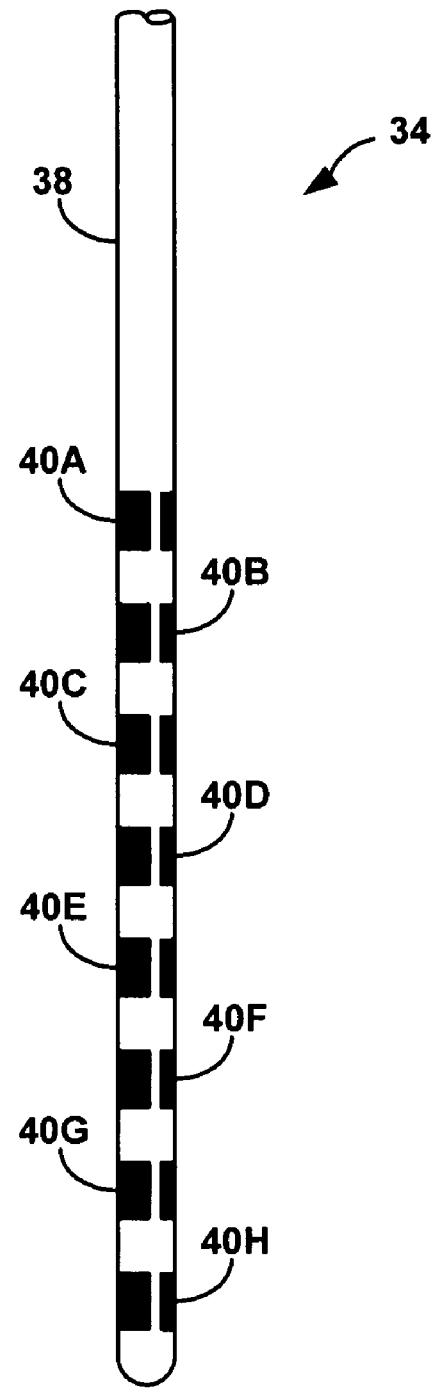

FIGS. 2A and 2B are conceptual diagrams illustrating two different implantable stimulation leads. Leads 26 and 34 are embodiments of lead 14 shown in FIG. 1. As shown in FIG. 2A, lead 26 includes four electrode levels 32 (includes levels 32A-32D) mounted at various lengths of lead housing 30. Lead 26 is inserted into through cranium 16 to a target position within brain 18.

Lead 26 is implanted within brain 18 at a location determined by the clinician to be near an anatomical region to be stimulated. Electrode levels 32A, 32B, 32C, and 32D are equally spaced along the axial length of lead housing 30 at different axial positions. Each electrode level 32 may have two or more electrodes located at different angular positions around the circumference of lead housing 30. Electrodes of one circumferential location may be lined up on an axis parallel to the longitudinal axis of lead 26. Alternatively, electrodes of different electrode levels may be staggered around the circumference of lead housing 30. In addition, lead 26 or 34 may include asymmetrical electrode locations around the circumference of each lead or electrodes of the same level that have different sizes. These electrodes may include semi-circular electrodes that may or may not be circumferentially aligned between electrode levels.

Lead housing 30 may include a radiopaque stripe (not shown) along the outside of the lead housing. The radiopaque stripe corresponds to a certain circumferential location that allows lead 26 to the imaged when implanted in patient 12. Using the images of patient 12, the clinician can use the radiopaque stripe as a marker for the exact orientation of lead 26 within the brain of patient 12. Orientation of lead 26 may be needed to easily program the stimulation parameters by generating the correct electrode configuration to match the stimulation field defined by the clinician. In other embodiments, a marking mechanism other than a radiopaque stripe may be used to identify the orientation of lead 14. These marking mechanisms may include something similar to a tab, detent, or other structure on the outside of lead housing 30. In some embodiments, the clinician may note the position of markings along lead wire 24 during implantation to determine the orientation of lead 14 within patient 12.

FIG. 2B illustrates lead 34 that includes more electrode levels than lead 26. Similar to lead 26, lead 34 is inserted though a burr hole in cranium 16 to a target location within brain 18. Lead 34 includes lead housing 38. Eight electrode levels 40 (40A-40H) are located at the distal end of lead 34. Each electrode level 40 is evenly spaced from the adjacent electrode level and includes one or more electrodes. In a preferred embodiment, each electrode level 40 includes four electrodes distributed around the circumference of lead housing 38. Therefore, lead 34 includes 32 electrodes in a preferred embodiment. Each electrode may be substantially rectangular in shape. Alternatively, the individual electrodes may have alternative shapes, e.g., circular, oval, triangular, or the like.

In alternative embodiments, electrode levels 32 or 40 are not evenly spaced along the longitudinal axis of the respective leads 26 and 34. For example, electrode levels 32C and 32D may be spaced approximately 3 millimeters (mm) apart while electrodes 32A and 32B are 10 mm apart. Variable spaced electrode levels may be useful in reaching target anatomical regions deep within brain 18 while avoiding potentially dangerous anatomical regions. Further, the electrodes in adjacent levels need not be aligned in the direction as the longitudinal axis of the lead, and instead may be oriented diagonally with respect to the longitudinal axis.

Leads 26 and 34 are substantially rigid to prevent the implanted lead from varying from the expected lead shape. Leads 26 or 34 may be substantially cylindrical in shape. In other embodiments, leads 26 or 34 may be shaped differently than a cylinder. For example, the leads may include one or more curves to reach target anatomical regions of brain 18. In some embodiments, leads 26 or 34 may be similar to a flat paddle lead or a conformable lead shaped for patient 12. Also, in other embodiments, leads 26 and 34 may any of a variety of different polygonal cross sections taken transverse to the longitudinal axis of the lead.

Lead housings 30 and 38 may continue directly into lead wire 24. A retention device may be used to squeeze the lead and shape it to approximately a 90 degree angle as it exits cranium 16. In some embodiments, lead housing 30 or 38 may include a right angle connector that allows lead 26 and 34 to be inserted into cranium 16 via a burr hole cap. In embodiments of system 10 including two or more leads 14, two or more leads may be connected to a common lead wire 24. In this case, a connector at the surface of cranium 16 may couple each lead 14 to lead wire 24.

Figure 3A:
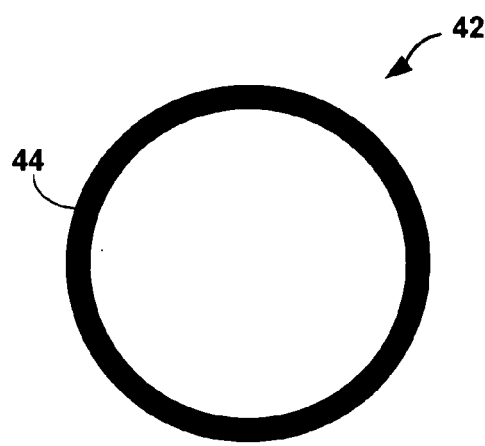
FIGS. 3A-3D are cross-sections of example stimulation leads having one or more electrodes around the circumference of the lead.

FIGS. 3A-3D are transverse cross-sections of example stimulation leads having one or more electrodes around the circumference of the lead. As shown in FIGS. 3A-3D, one electrode level, such as one of electrode levels 32 and 40 of leads 26 and 34, respectively, are shown to include one or more circumferential electrodes. FIG. 3A shows electrode level 42 that includes circumferential electrode 44. Circumferential electrode 44 encircles the entire circumference of electrode level 42. Circumferential electrode 44 may be utilized as a cathode or anode as configured by the user interface.

Figure 3B:
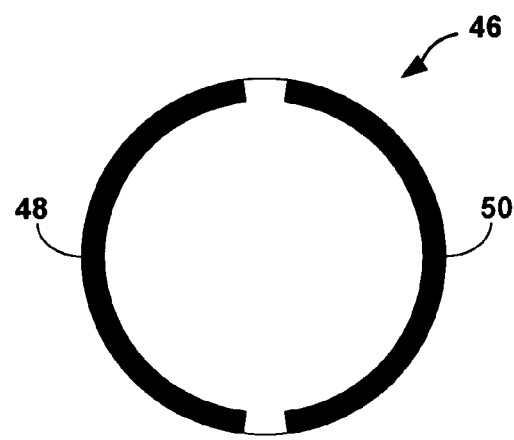

FIG. 3B shows electrode level 46 which includes two electrodes 48 and 50. Each electrode 48 and 50 wraps approximately 170 degrees around the circumference of electrode level 46. Spaces of approximately 10 degrees are located between electrodes 48 and 50 to prevent inadvertent coupling of electrical current between the electrodes. Each electrode 48 and 50 may be programmed to act as an anode or cathode.

Figure 3C:
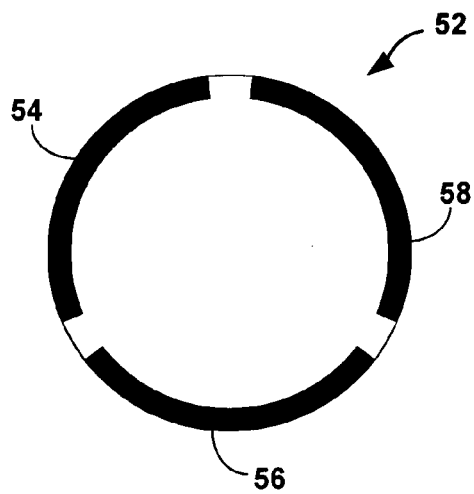

FIG. 3C shows electrode level 52 which includes three equally sized electrodes 54, 56 and 58. Each electrode 54, 56 and 58 encompass approximately 110 degrees of the circumference of electrode level 52. Similar to electrode level 46, spaces of approximately 10 degrees separate electrodes 54, 56 and 58. Electrodes 54, 56 and 58 may be independently programmed as an anode or cathode for stimulation.

Figure 3D:
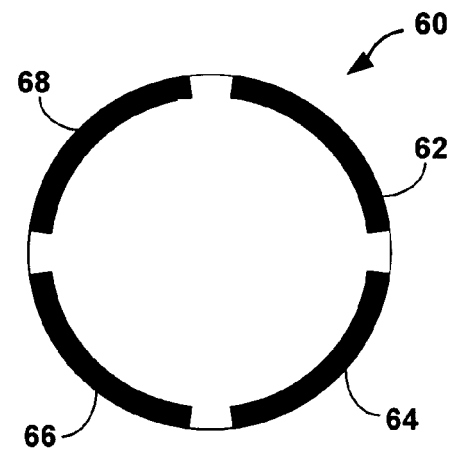

FIG. 3D shows electrode level 60 which includes four electrodes 62, 64, 66 and 68. Each electrode 62-68 covers approximately 80 degrees of the circumference with approximately 10 degrees of insulation space between adjacent electrodes. In other embodiments, up to ten or more electrodes may be included within an electrode level. In alternative embodiments, consecutive electrode levels of lead 14 may include a variety of electrode levels 42, 46, 52 or 60. For example, lead 14 may include electrode levels that alternate between electrode levels 52 and 60 depicted in FIGS. 3C and 3D. In this manner, various stimulation field shapes may be produced within brain 18 of patient 12. Further the above-described sizes of electrodes within an electrode level are merely examples, and the invention is not limited to the example electrode sizes.

Also, the insulation space, or non-electrode surface area, may be of any size. Generally, the insulation space is between approximately 1 degree and approximately 20 degrees. More specifically, the insulation space may be between approximately 5 and approximately 15 degrees. Smaller insulation spaces may allow a greater volume of tissue to be stimulated. In alternative embodiments, electrode size may be varied around the circumference of an electrode level. In addition, insulation spaces may vary in size as well. Such asymmetrical electrode levels may be used in leads implanted at tissues needing certain shaped stimulation fields.

Figure 4:
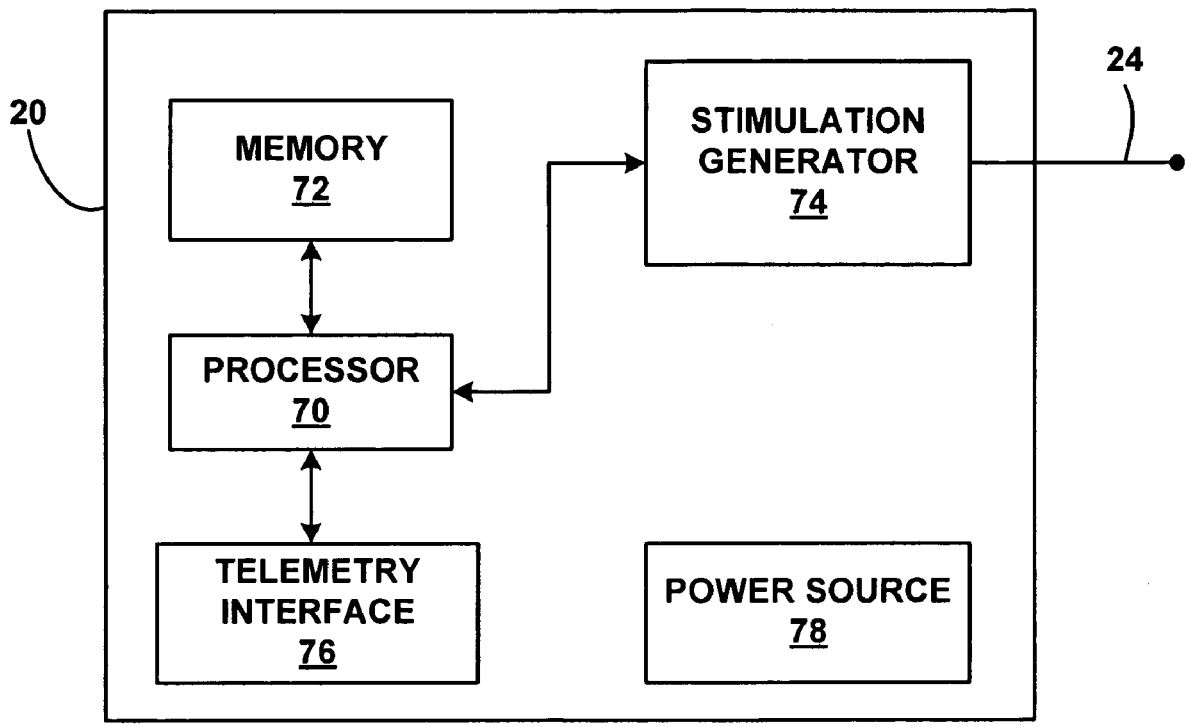
FIG. 4 is a functional block diagram of an example implantable medical device that generates electrical stimulation pulses.

FIG. 4 is a functional block diagram of an example implantable medical device that generates electrical stimulation signals. FIG. 4 illustrates components of IMD 20, which can be utilized by any of the IMD embodiments described herein. In the example of FIG. 4, IMD 20 includes a processor 70, memory 72, stimulation generator 74, telemetry interface 76, and power source 78. As shown in FIG. 4, stimulation generator 74 is coupled to lead wire 24 (which includes lead 14). Alternatively, stimulation generator 74 may be coupled to a different number of leads as needed to provide stimulation therapy to patient 12.

Processor 70 controls stimulation generator 74 to deliver electrical stimulation therapy according to programs generated by a user interface and stored in memory 72 and/or received from programmer 19 via telemetry interface 76. As an example, a new program received from programmer 19 may modify the electrode configuration and amplitude of stimulation. Processor 70 may communicate with stimulation generator 74 to change the electrode configuration used during the therapy and modify the amplitude of stimulation. Processor 70 may then store these values in memory 72 to continue providing stimulation according to the new program. Processor 70 may stop the previous program before starting the new stimulation program as received from programmer 19. In some embodiments, amplitude of the stimulation signal may be ramped down or ramped up as a program is being turned off or turned on. In this manner, no abrupt stimulation changes may be perceived by patient 12. A ramp up of the new program may provide patient 12 time to stop stimulation if the new program is uncomfortable or even painful.

Processor 70 may comprise any one or more of a microprocessor, digital signal processor (DSP), application specific integrated circuit (ASIC), field-programmable gate array (FPGA), or other digital logic circuitry. Memory 72 stores instructions for execution by processor 70, e.g., instructions that when executed by processor 70 cause the processor and IMD to provide the functionality ascribed to them herein, as well as stimulation programs. Memory 72 may include any one or more of a random access memory (RAM), read-only memory (ROM), electronically-erasable programmable ROM (EEPROM), flash memory, or the like.

Stimulation generator 74 may provide stimulation in the form of pulses to patient 12. Alternatively, stimulation generator 74 may provide therapy in the form of some continuous signal such as a sine wave or other non-pulse therapy. Stimulation parameters for each stimulation program may include electrode configuration, current or voltage amplitude, pulse width, pulse rate, or duty cycle. Other parameters may be used depending on the therapy to be provided to patient 12. Stimulation generator 74 may independently utilize any circumferential electrodes 32 or 40 or leads 26 and 34, respectively. In this manner, stimulation generator 74 may be utilized to deliver stimulation via numerous different electrode configurations to provide therapy for a wide variety of patient conditions. In addition, stimulation generator 74 may test the functionality of electrodes on lead 14. Based upon the impedance testing, specific electrodes may be removed from possible use in therapy when the test indicates that the impedance is above or below normal operating limits.

Telemetry interface 76 may include circuitry known in the art for facilitating wireless telemetry, e.g., via radio frequency (RF) communication or proximal inductive interaction with similar circuitry within external programmer 19. Power source 78 delivers operating power to the components of IMD 20. Power source 78 may include a battery and a power generation circuit to produce the operating power. In some embodiments, the battery may be rechargeable to allow extended operation. Recharging may be accomplished through proximal inductive interaction between an external charger and an inductive charging coil within IMD 20. In other embodiments, non-rechargeable batteries may be used. As a further alternative, an external power supply could transcutaneously power IMD 20 whenever stimulation is needed or desired.

Figure 5:
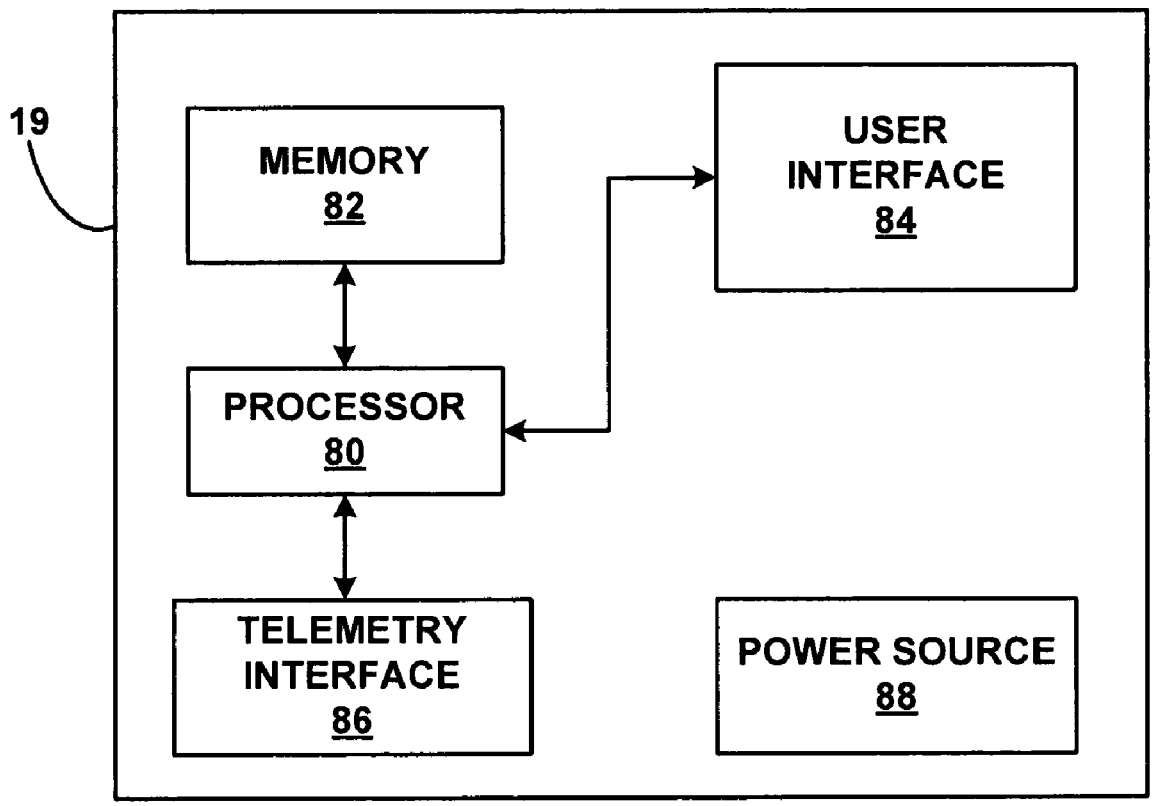
FIG. 5 is a functional block diagram of an example programmer.

FIG. 5 is a functional block diagram of an example programmer. As shown in FIG. 5, external programmer 19 includes processor 80, memory 82, user interface 84, telemetry interface 86, and power source 88. Programmer 19 may be used to present anatomical regions to the user via user interface 84, select stimulation programs, generate new stimulation programs with stimulation fields, and transmit the new programs to IMD 20. As described herein, programmer 19 may allow a clinician to define stimulation fields and generate appropriate stimulation parameters. For example, as described herein processor 80 may store stimulation parameters as one or more programs in memory 82. Processor 80 may send programs to IMD 20 via telemetry interface 86 to control stimulation automatically and/or as directed by the user.

Programmer 19 may be one of a clinician programmer or a patient programmer in some embodiments, i.e., the programmer may be configured for use depending on the intended user. A clinician programmer may include more functionality than the patient programmer. For example, a clinician programmer may include a more featured user interface, allow a clinician to download usage and status information from IMD 20, and allow a clinician to control aspects of the IMD not accessible by a patient programmer embodiment of programmer 19.

A user, either a clinician or patient 12, may interact with processor 80 through user interface 84. Any of the user interface embodiments described herein may be embodiments of user interface 84, such as user interfaces 90, 314, 380, 456, 554, 600, 652, 730, 798, 850, 876, 916, 964, 1072, 1114, 1162, 1198. User interface 84 may include a display, such as a liquid crystal display (LCD), light-emitting diode (LED) display, or other screen, to show information related to stimulation therapy, and buttons or a pad to provide input to programmer 19. In embodiments where user interface 84 requires a 3D environment, the user interface may support 3D environments such as a holographic display, a stereoscopic display, an autostereoscopic display, a head-mounted 3D display, or any other display that is capable of presenting a 3D image to the user. Buttons may include an on/off switch, plus and minus buttons to zoom in or out or navigate through options, a select button to pick or store an input, and pointing device, i.e. a mouse, trackball, pointstick or stylus. Other input devices may be a wheel to scroll through options or a touch pad to move a pointing device on the display. In some embodiments, the display may be a touch screen that enables the user to select options directly from the display screen.

As described, the display may be more involved for the 3D user interface 189. In this case, programmer 19 may be a workstation within a laboratory, clinic room, or surgical room. The clinician may need to immerse within the display to fully utilize the functionality of the user interface. In some cases, programmer 19 may be a hand held device for all features except the 3D environment when the 3D environment necessitates a larger system. However, programmer 19 may still be integrated with or communicate with the 3D environment to simplify system 10 for the user.

Processor 80 processes instructions from memory 82 and may store user input received through user interface 84 into the memory when appropriate for the current therapy. In addition, processor 80 provides and supports any of the functionality described herein with respect to each embodiment of user interface 84. Processor 80 may comprise any one or more of a microprocessor, digital signal processor (DSP), application specific integrated circuit (ASIC), field-programmable gate array (FPGA), or other digital logic circuitry.

Memory 82 may include instructions for operating user interface 84, telemetry interface 86 and managing power source 88. Memory 82 also includes instructions for generating stimulation fields and stimulation parameters from the stimulation fields. These instructions may include a set of equations needed to characterize brain tissue and interpret stimulation field dimensions. Memory 82 may include any one or more of a random access memory (RAM), read-only memory (ROM), electronically-erasable programmable ROM (EEPROM), flash memory, or the like. Processor 80 may comprise any one or more of a microprocessor, digital signal processor (DSP), application specific integrated circuit (ASIC), field-programmable gate array (FPGA), or other digital logic circuitry.

Memory 82 may store program instructions that, when executed by processor 80, cause the processor and programmer 19 to provide the functionality ascribed to them herein. For example, memory 82 may include a plurality of stimulation templates that are used by processor 80 to create a stimulation template set. Memory 82 may also include instructions for generating stimulation parameters based upon the defined stimulation field. In addition, instructions that allow processor 80 to create electrical field models and activation field models may be stored within memory 82. An atlas or reference anatomical region may also be stored in memory 82 for presentation to the clinician. In some embodiments, memory 82 does not contain instructions for all functionality for the user interfaces and programming of stimulation parameters as described herein. In this case, memory 82 may only hold the necessary instructions for the specific embodiment that the user desires. Memory 82 may be reformatted with different sets of instructions when needed.

Wireless telemetry in programmer 19 may be accomplished by radio frequency (RF) communication or proximal inductive interaction of programmer 19 with IMD 20. This wireless communication is possible through the use of telemetry interface 86. Accordingly, telemetry interface 86 may include circuitry known in the art for such communication.

Power source 88 delivers operating power to the components of programmer 19. Power source 88 may include a battery and a power generation circuit to produce the operating power. In some embodiments, the battery may be rechargeable to allow extended operation. Recharging may be accomplished through proximal inductive interaction, or electrical contact with circuitry of a base or recharging station. In other embodiments, primary batteries may be used. In addition, programmer 19 may be directly coupled to an alternating current source, such would be the case with a stationary workstation for 3D visualization environments.

Figure 6:
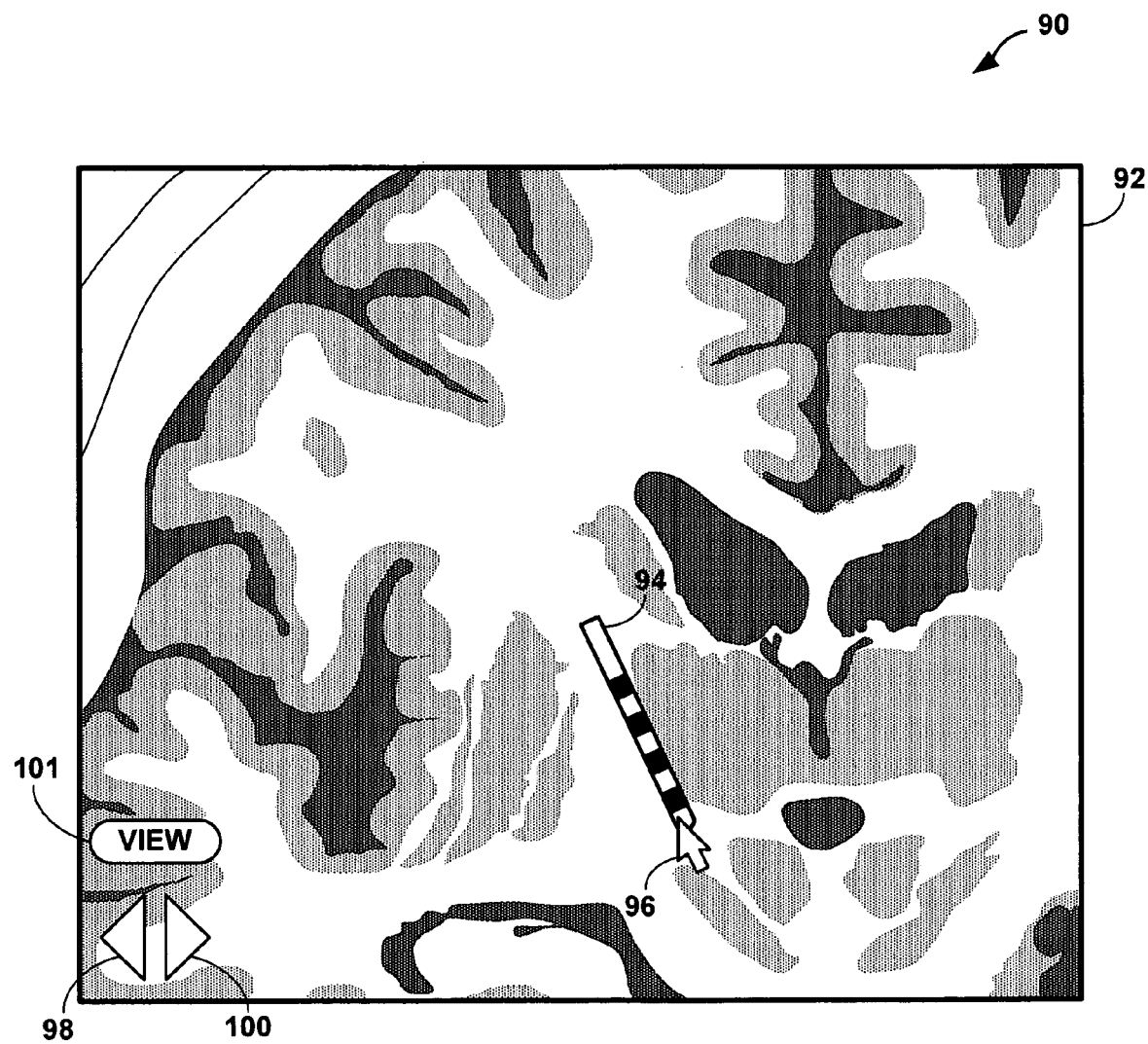
FIG. 6 is an example screen shot of a lead icon placed on a coronal view of brain tissue.

FIGS. 6-13 describe an example embodiment of the user interface for programming stimulation therapy. FIG. 6 is an example screen shot of a lead icon placed on a coronal view of brain tissue. As shown in FIG. 6, a representation of anatomical regions of brain 18 is displayed by user interface 90. Programmer 19 displays coronal view 92 to the clinician, which is a front-back vertical section of brain 18. Coronal view 92 may be an actual image of brain 18 produced with magnetic resonance imaging (MRI), computed tomography (CT), or another imaging modality. These images are used to produce the anatomical regions needed to help the clinician program the stimulation parameters.

Coronal view 92 is a 2D coronal slice of brain 18. Differently shaded portions of coronal view 92 indicate varying densities of tissue within brain 18. Darker portions indicate less dense tissue. For example, the darkest portion of coronal view 92 is indicative of spaces within brain 18 that contain cerebral spinal fluid (CSF). White portions of brain 18 indicate dense tissue and more neurons. The clinician may be able to recognize target anatomical regions by viewing coronal view 92. It should be noted that coronal view 92 is only an example, and actual images may include a wider range of shades and higher image resolution. Coronal view 92 provides a first perspective of the lead and the anatomical region in which the lead is implanted.

Coronal view 92 includes lead icon 94, pointer 96, previous arrow 98 and next arrow 100. The clinician uses pointer 96 to drag lead icon 94 into position on top of the anatomical regions to duplicate the position of lead 14 within brain 18. Programmer 19 may initially orient the clinician to the middle depth of the coronal view 92 or another depth that the programmer automatically selects based upon they type of therapy, implant location, or some other simple indication of location. However, the clinician may use arrows 98 and 100 to move to another coronal depth where lead 14 is implanted in brain 18.

Pointer 96 may be controlled with a mouse and buttons, a track-ball, touch-pad, or other movement input device. In addition, programmer 19 may include a touch screen to enable the clinician to use a stylus to click on the touch screen and drag lead icon 94 into position. Pointer 96 may also be used to rotate lead icon 94 within coronal view 92 to correctly orient the lead icon according to the actual position of lead 14 within brain 18. In other embodiments, the clinician may first select the type of lead implanted within patient 12 and select the correctly scaled size of lead icon 94 to correspond with the anatomical regions of coronal view 92.

The clinician may zoom in to or out of coronal view 92 for a larger view of anatomical regions of the coronal view. In addition, the clinician may move coronal view 92 up, down, left, or right to view a greater portion of brain 18. Input mechanisms for adjusting coronal view 92 may be located on programmer 19 or directly within user interface 92.

While the clinician may manually position lead icon 94 within coronal view 92, user interface 90 may automatically position lead icon 94 based upon stereotactic data generated before lead 14 implantation is performed. A stereotactic frame may be placed on cranium 16 to specifically locate areas of brain 18. In addition, this stereotactic information may be used to provide coordinates of the exact location of lead 14 implantation. In other embodiments, brain 18 may be imaged after implantation of lead 14 such that the lead is identifiable on coronal view 92. The clinician may point to and identify electrodes of lead 14 in the image to allow programmer 19 to reconstruct the correct position of the lead. In some cases, programmer 19 may automatically identify lead 14 and place lead icon 94 correctly within the anatomical region without any input from the clinician.

Once lead icon 94 is correctly placed on coronal view 92, the clinician may move to the next view of user interface 90 by selecting view button 101 to cycle through available orthogonal views. Coronal view 92 is only one 2D representation of brain 18. Two more 2D views of brain 18 may be used to correctly orient lead icon 94 according to the implant orientation of lead 14, including another axial view from the sagittal perspective and a cross-sectional view from the horizontal perspective.

Figure 7:
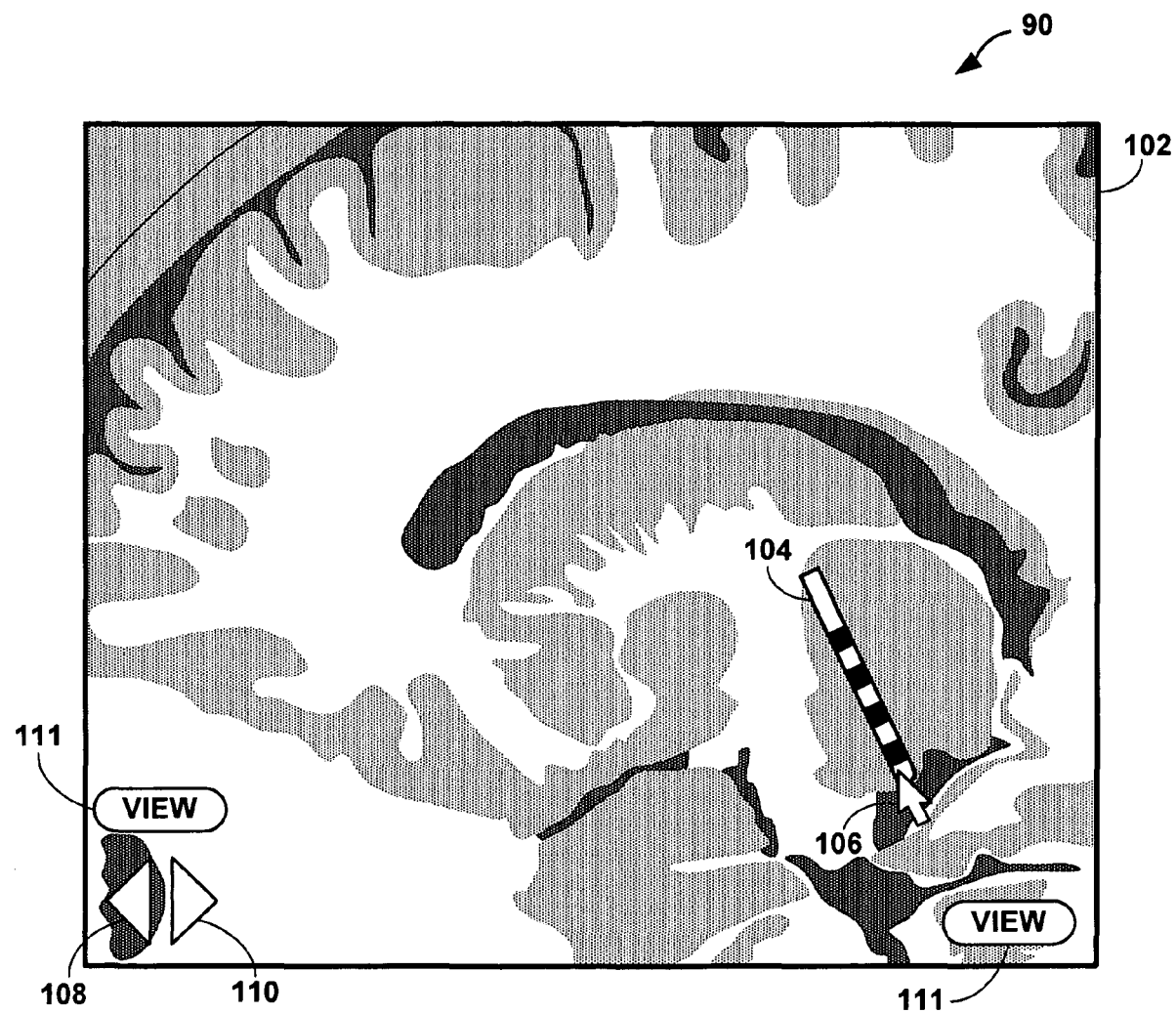
FIG. 7 is an example screen shot of a lead icon placed on a sagittal view of brain tissue.

FIG. 7 is an example screen shot of a lead placed on a sagittal view of brain tissue. As shown in FIG. 7, user interface 90 includes sagittal view 102 of brain 18. The anatomical regions represented in sagittal view 102 may be generated with the same imaging data used for coronal view 92 in FIG. 6. Sagittal view 102 also includes lead icon 104, pointer 106, previous arrow 108 and next arrow 110, similar to lead icon 94, pointer 96, previous arrow 98 and next arrow 100 FIG. 6. The clinician may zoom in and out of sagittal view 102 and move the view to the left, right, up and down.

The initial placement of lead icon 104 corresponds to the position determined in coronal view 92 of FIG. 6. The clinician uses pointer 106 to drag lead icon 104 into its correct place among the represented anatomical regions. The clinician may also rotate lead icon 104 if necessary to match the orientation of lead 14 implanted within patient 12. Programmer 19 may initially orient the clinician to the depth of sagittal view 102 that corresponds to the initial placement of lead icon 94 in view 92. However, the clinician may use arrows 108 and 110 to move to another sagittal depth where lead 14 is implanted in brain 18.

In the example of Parkinson's disease, stimulation therapy is generally directed to an anatomical region of brain 18 identified as the Substantia Nigra (SN). Simulation of the SN is generally regarded as a mechanism to reduce the motor tremors associated with Parkinson's disease. The clinician uses sagittal view 102, and coronal view 92, to locate lead icon 14 near the SN because lead 14 is implanted near the SN. Stimulation of adjacent non-target anatomical regions of brain 18 may produce side effects in patient 12. In some embodiments, the clinician may target the Subthalamic Nucleus, instead of or in addition to the Substantia Nigra.

Similar to coronal view 92, lead icon 104 may be automatically placed in the proper position of sagittal view 102 or the actual location of lead 14 may be shown to allow a user to correct the orientation of lead icon 104. Once lead icon 104 is correctly positioned, the clinician may move to an axial view (or another previous view such as sagittal or coronal) by pressing view button 111 to finish orienting lead icon 104 within user interface 90.

Figure 8:
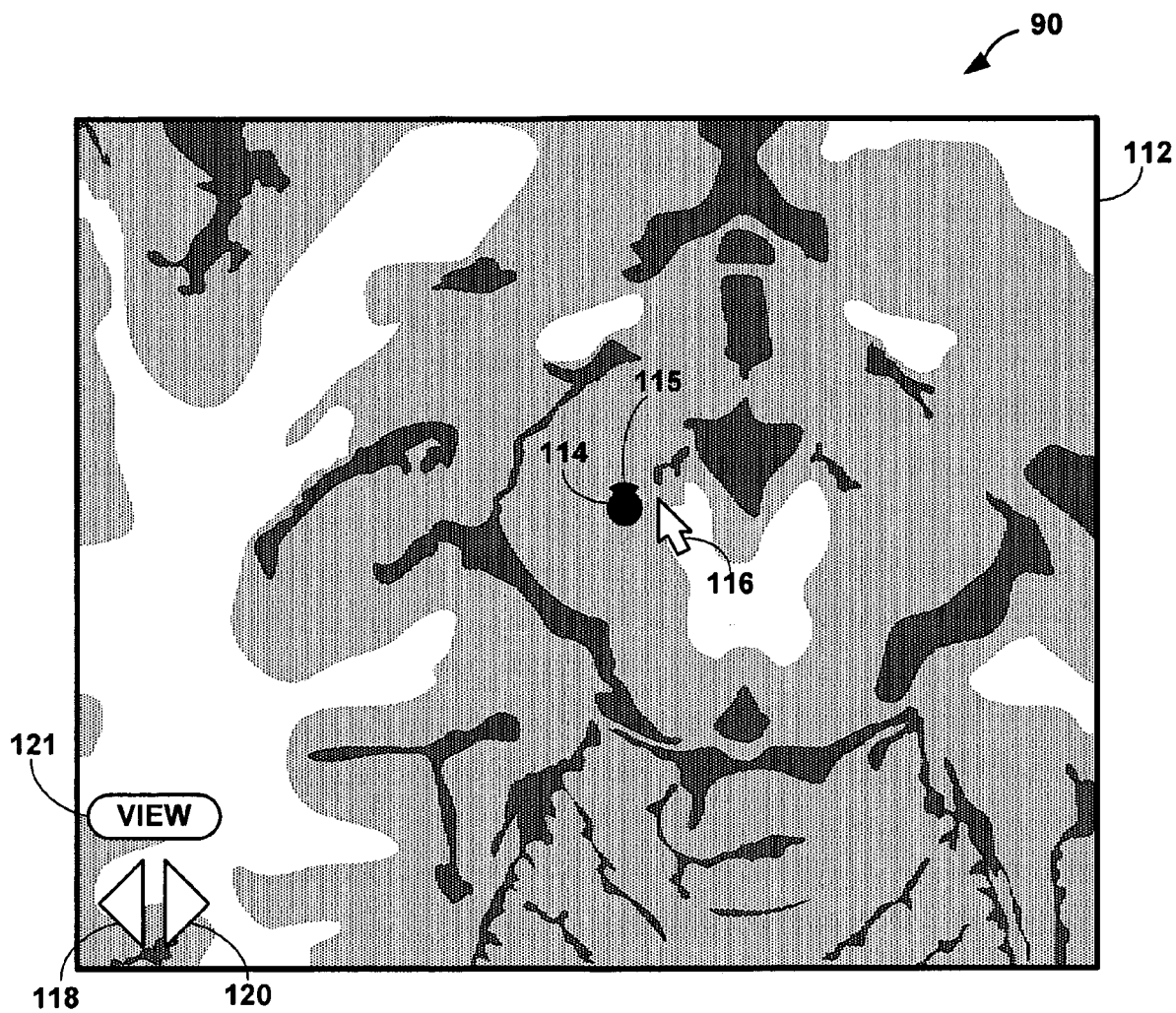
FIG. 8 is an example screen shot of a lead icon placed on an axial view of brain tissue.

FIG. 8 is an example screen shot of a lead placed on an axial view of brain tissue. As shown in FIG. 8, user interface 90 provides axial view 112. Axial view 112 displays pointer 116, lead icon 114, previous arrow 118 and next arrow 120. The initial position of lead icon 114 is determined by the positioning of lead icons 94 and 104 in FIGS. 6 and 7. The clinician uses pointer 116 to rotate lead icon 114 such that the lead icon is correctly oriented in the circumferential direction according to implanted lead 14. Programmer 19 may initially orient lead icon 114 to the axial depth of axial view 112. However, the clinician may use arrows 118 and 120 to move to another coronal depth where lead 14 is implanted in brain 18.

Lead icon 114 includes stripe 115 extending from the lead icon that corresponds to a radiopaque stripe or other marker on lead 14. The clinician matches the stripe location to match lead 14 orientation such that stimulation parameters, including electrode configurations, are correct. Once the rotation of lead icon top 114 is complete, the lead icon is correctly positioned within user interface 90. The stripe aids the user in maintaining a sense of spatial relationship between the lead and the anatomical structure.

In some embodiments, lead 14 may not actually be completely perpendicular with axial view 112. Even though the orientation of lead icons 94, 104 and 114 and lead 14 may not be perfectly matched, the generally matched orientations may be sufficiently accurate to effectively program stimulation therapy. In other embodiments, axial view 112 may display lead icon 114 as a slightly oblique view of that illustrated in FIG. 8 to match the actual placement of lead 14 within brain 18.

After correctly orienting lead icons 94, 104 and 114 within user interface 90, the clinician may define stimulation fields that can be transposed from the user interface to IMD 20. At any time during the programming process, the clinician may return to re-position lead icons 94, 104, or 114 if the placement is not accurate. The clinician may select view button 121 to cycle through the other views. In some embodiments, programmer 19 may display one or more of coronal view 92, sagittal view 102, or axial views 102 at the same time to allow the clinician to simultaneously position lead icons 94, 104 and 114 and continue programming therapy. In alternative embodiments, the correct placement of lead icon 94 may not lie within one of the coronal view 92, sagittal view 102, or axial view 102. Instead, lead icon 94 may lie within an oblique view, e.g., a view in a plane not parallel to one of the aforementioned orthogonal views. In this case, the clinician may be able to request that programmer 19 generate and present the oblique view with or without lead icon 94 to facilitate stimulation programming. In addition, programmer 19 may be able to display other orthogonal views to the oblique view, wherein the oblique or orthogonal view allows the clinician to view down the central axis of lead icon 94.

Figure 9:
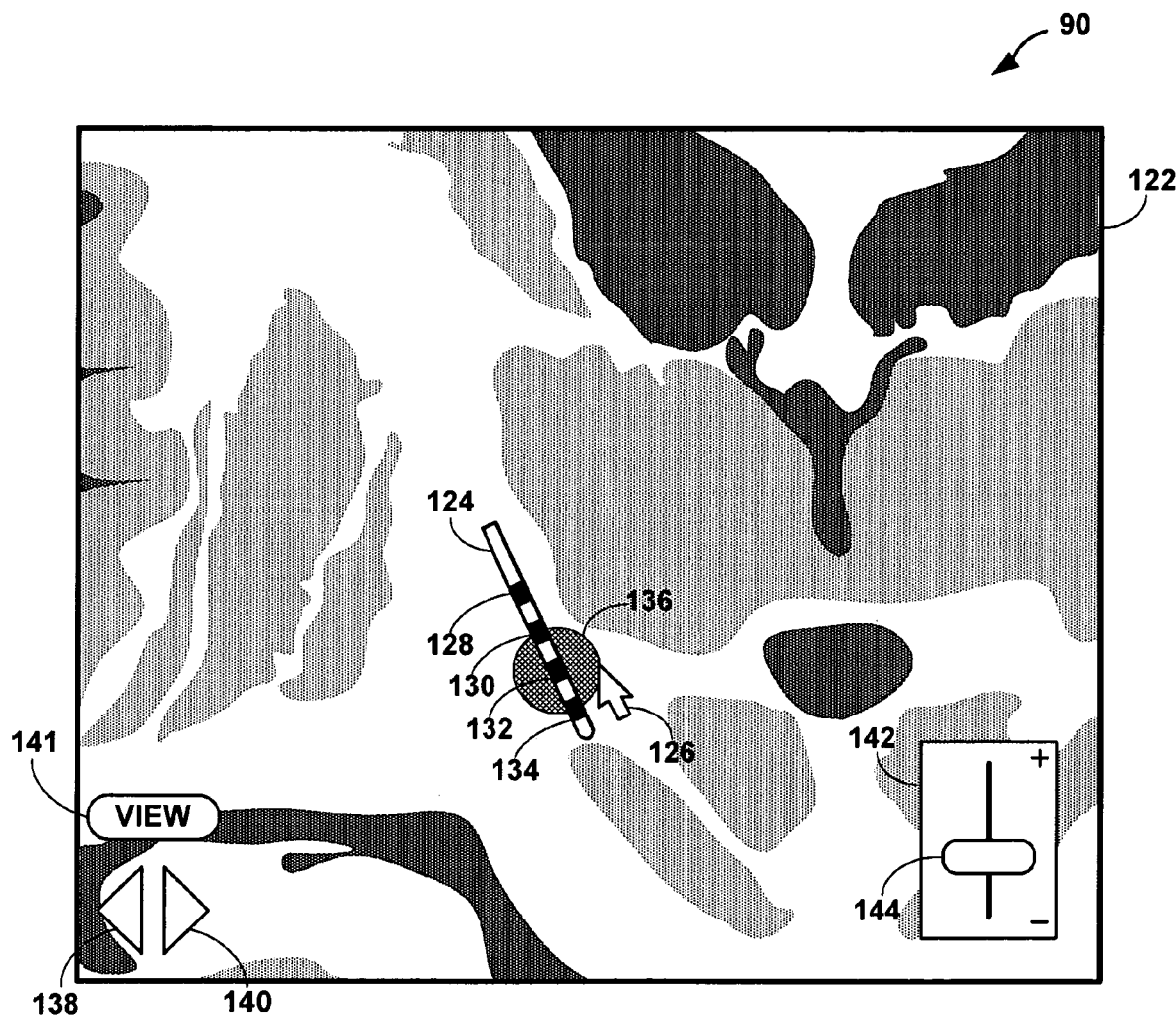
FIG. 9 is an example screen shot of stimulation field selection on a coronal view of brain tissue.

FIG. 9 is an example screen shot of stimulation field selection on a coronal view of brain tissue. As shown in FIG. 9, field view 122 of user interface 90 allows the clinician to select and adjust one or more stimulation fields. Field view 122 includes lead icon 124, pointer 126, stimulation field 136, fine control 142, control slide 144, previous arrow 138, and next arrow 140. Lead icon 124 is similar to lead icon 94 of FIG. 6, but the clinician may user pointer 126 to select one of electrode levels 128, 130, 132 or 134 to place a stimulation field over the selected electrode level. An electrode level may have one or more electrodes around the circumference of lead icon 124, e.g., a complex electrode array geometry. All circumferential electrodes of the selected electrode level are initially activated for programming. Generally, the clinician attempts to place stimulation field 136 over the anatomical regions targeted for stimulation therapy while avoiding anatomical regions that may initiate unwanted side effects. In some embodiments, stimulation field 136 may be a representation of an electrical field, current density, voltage gradient, or neuron activation, applied to a generic human tissue or the anatomy of patient 12. In addition, the clinician may be able to switch between any of these representations when desired.

The clinician selected electrode level 132 and stimulation field 136 shows the anatomical region that would be stimulated with the electrode level. The clinician may use pointer 126 to drag stimulation field 136 to a smaller or larger size that corresponds to a lower or higher voltage or current amplitude. For example, the user may click on a border, or perimeter of the field, and then drag the border to expand or contract the field. This adjustment is the coarse control of the size of stimulation field 136. The clinician may use pointer 126 to move control slide 144 up to slightly increase the size of stimulation field 136 or down to slightly decrease the size of stimulation field 136. In some embodiments, the actual voltage or current amplitude associated with stimulation field 136 is displayed on field view 122 as the field changes.

When a user clicks on the field border and drags it, the entire field may be expanded in two dimensions in equal proportions. Alternatively, the field may expand only in the direction in which the user drags the field. For example, horizontal dragging of the field perimeter to enlarge the field may result in overall enlargement of the field, keeping the vertical to horizontal aspect ratio constant. Alternatively, horizontal dragging may result only in horizontal expansion, leaving the vertical dimension constant. The application of a constant or varying aspect ratio may be specified by a user as a user preference. Alternatively, the programmer may provide different aspect ratio modes on a selective basis for expansion and shrinkage of the field. Programmer 19 may limit the rate of movement of stimulation field 136. In other words, stimulation field 136 may only be moved a certain number of steps per second within user interface 136, or any other user interface that allows the clinician to drag the stimulation field. This rate movement limit may prevent unnecessary calculations or ensure patient comfort in real-time changing of stimulation parameters with modifications of stimulation field 136.

The initial size of stimulation field 136 may be determined by a minimal threshold voltage previously determined effective in brain 18. In other embodiments, the initial stimulation field size may be small to allow the clinician to safely increase the size of stimulation field 136. The size of stimulation field 136 may be limited by a volume parameter or a maximum voltage limit previously defined by user interface 90. The limit may be associated with capabilities of IMD 20 or safe voltage or current levels. Once the size of stimulation field 136 is met, the clinician may no longer be able to drag the size of the stimulation field away from lead icon 124.

Stimulation field 136 may grow or split in size if the clinician selects more than one electrode level 128, 130, 132 or 134. For example, the clinician may select electrode levels 92 and 86 to generate stimulation fields associated with each electrode level. The clinician may also move stimulation field 136 along the length of lead icon 124 and user interface may automatically select which electrode levels to activate to produce the stimulation field on field view 122. The clinician may also move to other depths or slices of coronal view 122 with arrows 138 and 140. The clinician may continue to adjust the stimulation therapy on an axial view or other view by selecting view button 141 to cycle through other orthogonal views.

Figure 10:
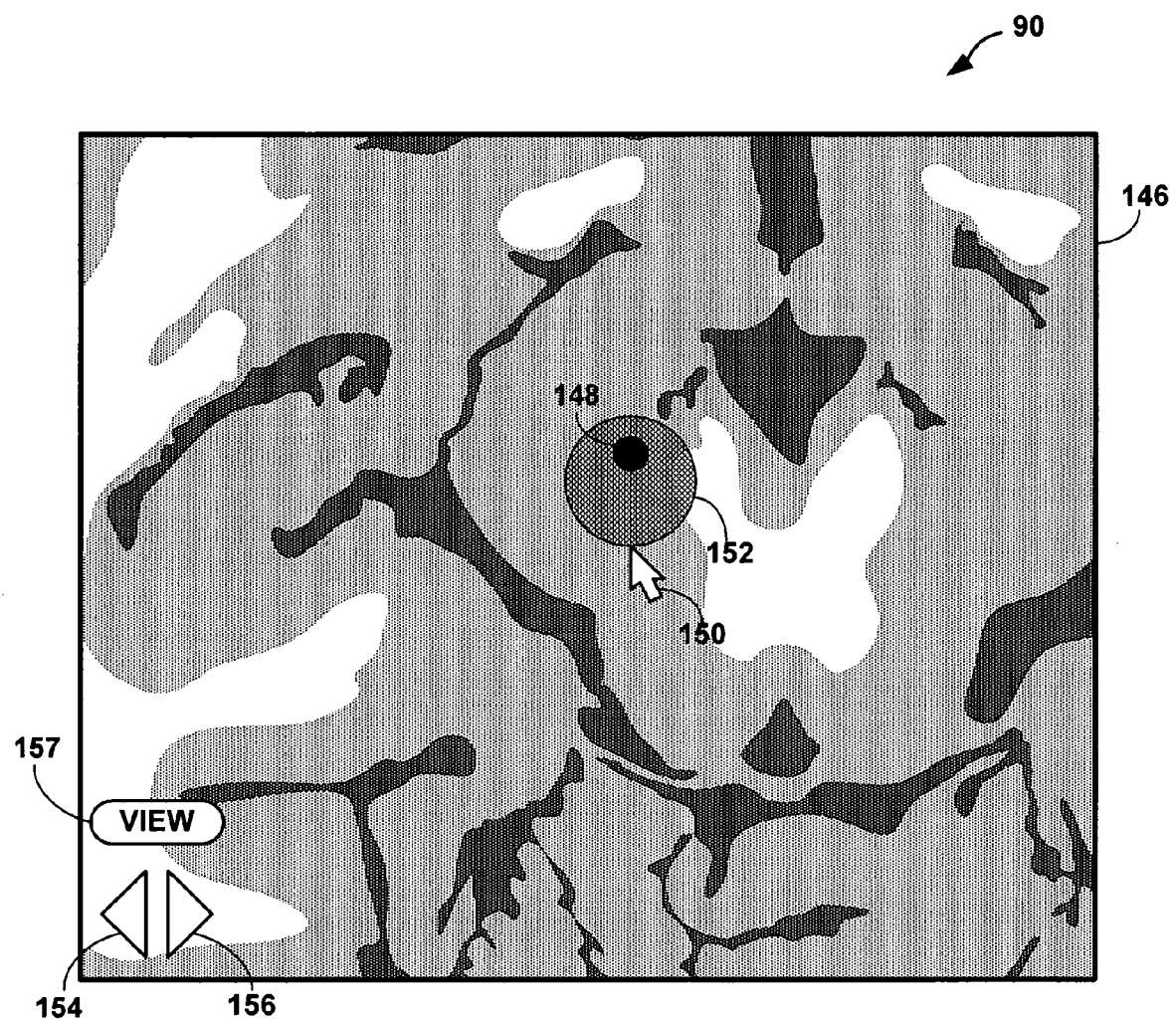
FIG. 10 is an example screen shot of stimulation field adjustment on an axial view of brain tissue.

FIG. 10 is an example screen shot of stimulation field adjustment on an axial view of brain tissue. As shown in FIG. 10, user interface 90 includes adjust view 146 and lead icon 148 (similar to lead icon 114). The size and location of stimulation field 152 on the axial view of brain tissue indicates the anatomical regions that would receive electrical stimulation. The user may use pointer 150 to drag the position of stimulation field 152 and increase or decrease the size of the stimulation field.

Dragging stimulation field 152 away from the center of lead icon 148, e.g., offsetting or directing the stimulation field in a radial direction from the lead icon, would require that the multiple electrodes of an electrode level have different voltage or current amplitudes. In FIG. 10, electrodes on the side of lead icon 148 with the greater portion of stimulation field 152 must generate a greater voltage or current amplitude than electrodes on the opposite side of lead icon 148. Limitations of electrode locations, voltage or current capabilities, or physiological safe guards may limit the clinician of moving stimulation field 152 to certain locations of adjust view 146. In some embodiments, the clinician may use pointer 150 to modify stimulation field 152 shape to a non-circular shape such as an ellipse or curved field. In some embodiments, user interface 90 may present an error message to the clinician if stimulation field 152 cannot be supported by system 10.

The clinician moves stimulation field 152 in adjust view 146 to create the most effective stimulation therapy program. The clinician uses the anatomical regions represented by user interface 90 to focus electrical stimulation to target anatomical regions and avoid side effects from the stimulation of surrounding tissue. Specifically, this trade-off between maximum therapeutic effects and minimal side effects is how patient 12 may evaluate the success of the stimulation therapy.

The clinician may continue to evaluate other electrode levels by selecting previous arrow 154 and returning to field view 122. Alternatively, the clinician may use arrows 154 and 156 to move to other axial depths and view other cross-sections of the volumetric stimulation field partially defined by stimulation field 152. The clinician may also return to other views by selecting view button 157. Once the clinician is satisfied with the orientation of the stimulation field, the clinician may press a "generate" or "apply" button on programmer 19 or provided by user interface that causes programmer 19 to generate a program of the stimulation parameters necessary to produce the stimulation field in patient 12. The clinician may generate multiple programs for patient 12 to evaluate during the course of therapy. In some cases, patient 12 may prefer one program over another depending on the activity of the patient. The programs are transmitted from programmer 19 to IMD 20 for therapy to begin.

In some embodiments, adjust view 146 may include a control that allows the clinician to scroll through various axial depths of the anatomical regions. In this manner, the clinician may identify the shape of the stimulation field at various locations along the longitudinal length of lead icon 124 of FIG. 9. In other embodiments, adjust view 146 may include a depth chart to show the clinician where the 2D axial view is in relation to the lead icon 124. In systems that include more than one lead 14 implanted within patient 12, user interface 90 may provide lead representations of two or more of the leads instead of just a single side and cross-sectional view of one lead.

Figure 11:
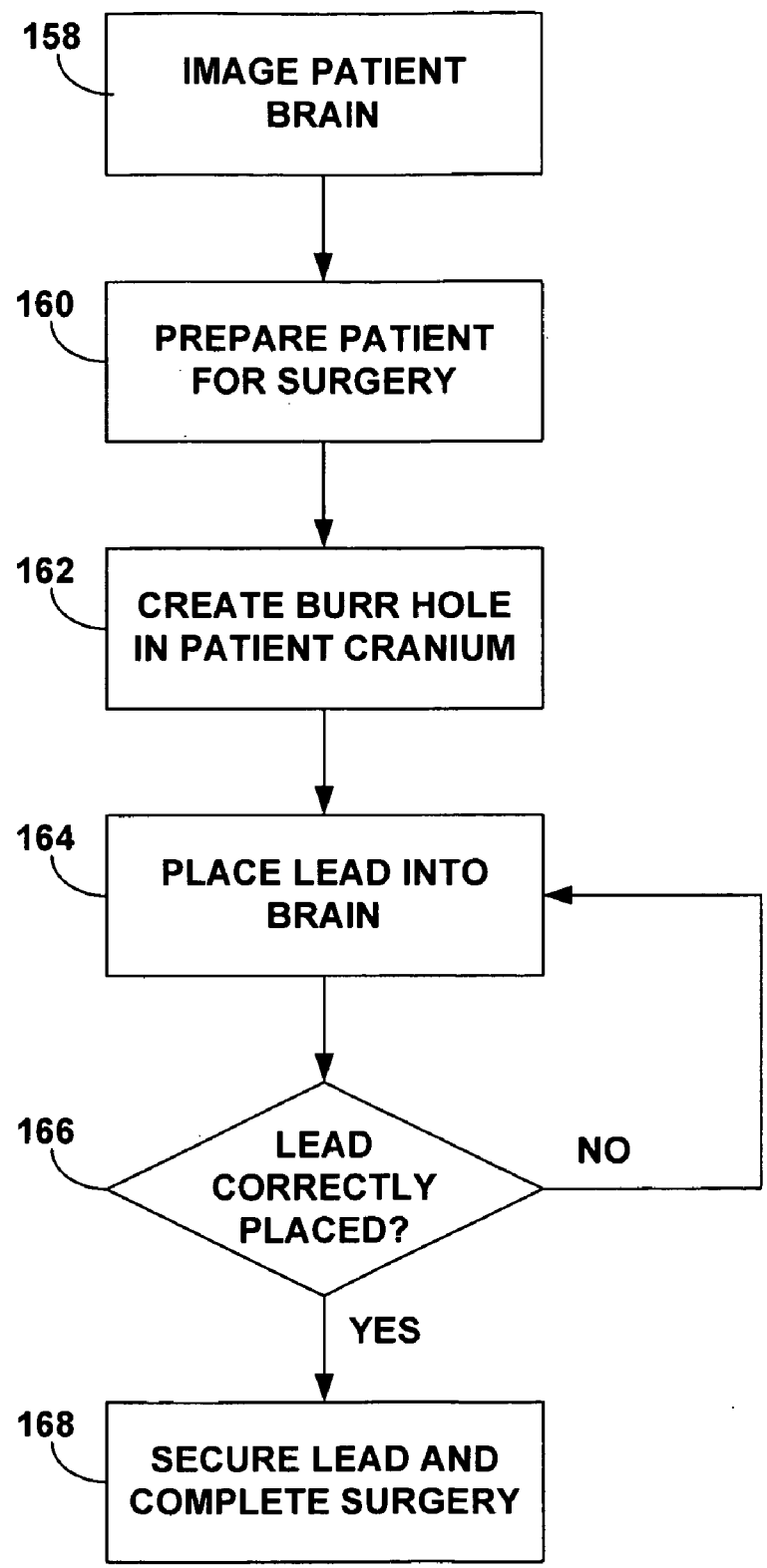
FIG. 11 is a flow diagram illustrating an example technique for implanting a stimulation lead in a brain of a patient.

FIG. 11 is a flow diagram illustrating an example technique for implanting a stimulation lead in a brain of a patient. As shown in FIG. 11, patient 12 is imaged using an MRI or CT scanner. In particular, brain 18 is scanned to create the representation of anatomical regions (158). Either shortly after or several days later, patient 12 is prepared for surgery and implantation of lead 14 (160). Preparation may include generating stereotactic information with a stereotactic frame attached to cranium 18. The implant site may also be precisely located and images of brain 18 reviewed to identify any abnormalities of brain 18.

Once in surgery, the clinician creates a burr hole in cranium 16 of patient 12 (162). The clinician inserts lead 14 into brain 18 and places the lead near the target anatomical regions (164). The clinician next tests if lead 14 is correctly placed in brain 18 (166). The clinician may use micro recordings or patient feedback to identify results from small electrical stimulation of brain 18. If lead 14 is not correctly placed, the clinician may reposition lead 14 (164). If lead 14 is correctly placed in brain 18, the clinician secures lead 14 within brain 18 and reattaches patient 12 scalp (168). The clinician may also tunnel lead wire 24 to IMD 20 and implant the IMD.

In some embodiments, lead 14 may be implanted in a different manner. For example, lead 14 may be implanted with a robotic assistant using a map of brain 18 to increase the accuracy of lead placement. In other embodiments, more leads may be implanted within brain 18 for stimulation therapy as well.

Figure 12:
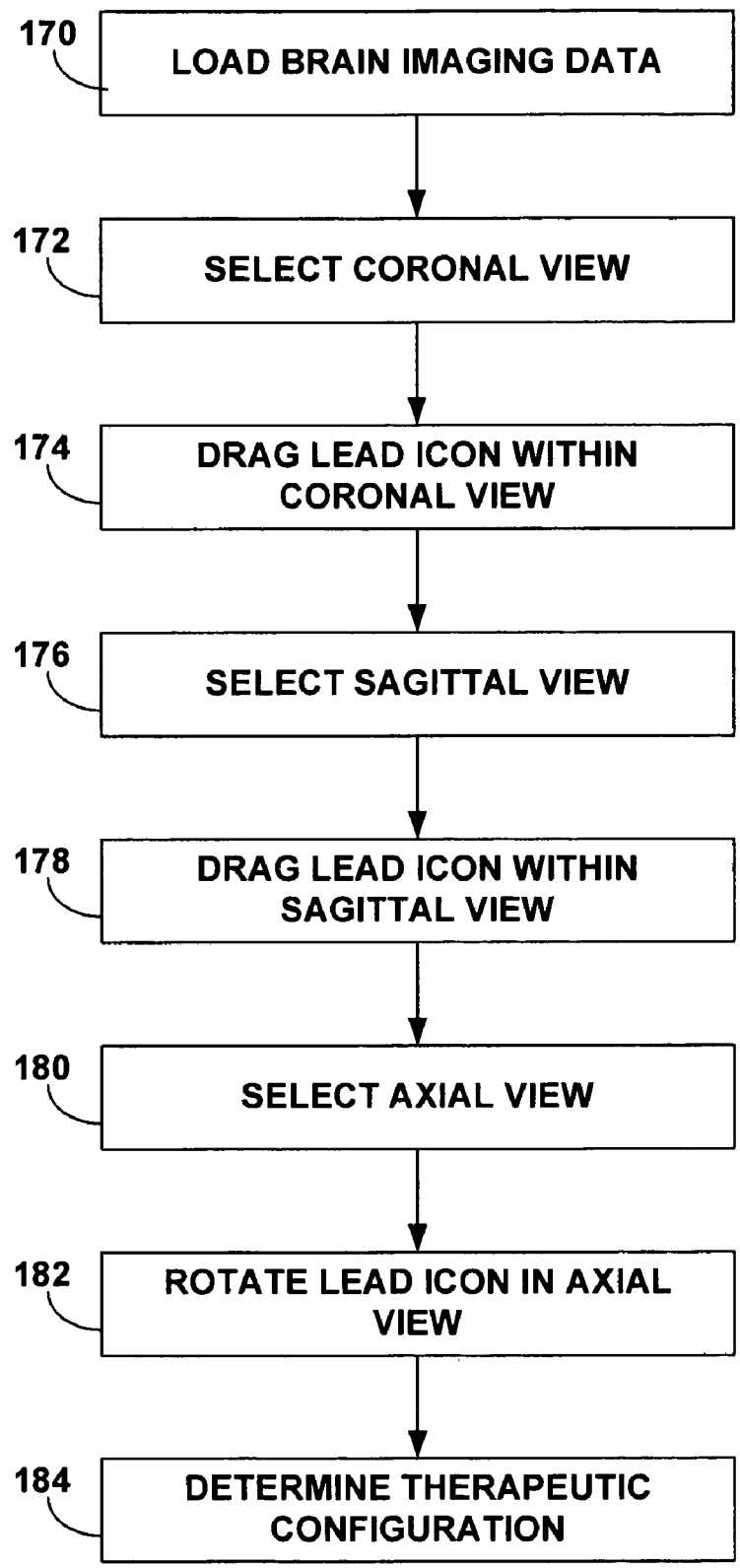
FIG. 12 is a flow diagram illustrating an example technique for positioning a lead icon over anatomical regions of a patient.

FIG. 12 is a flow diagram illustrating an example technique for positioning a lead icon over anatomical regions of a patient. More particularly, the clinician places lead icons 94, 104, 114 within respective views to correspond to the correct location of lead 14 within brain 18. The clinician enters the brain imaging data into user interface 90 (170). The clinician selects the coronal view (172) and drags lead icon 94 to the appropriate location within the coronal view (174). Next, the clinician selects the sagittal view (176) and drags lead icon 104 to the correct location within the anatomical regions represented within the sagittal view (178).

The clinician next selects the axial view (180) and rotates the lead icon 114 to correctly orient the stripe of the lead icon within brain 18 (182). Once lead icon 114 is correctly placed, the clinician proceeds to determine the therapeutic configuration of the stimulation parameters (184). In other embodiments, lead icons 94, 104 and 114 may be automatically placed in user interface 90 based on an image taken post-implant, and the clinician may review the placement to look for placement errors. The order of lead icon placement may be switched in some embodiments as well.

Figure 13:
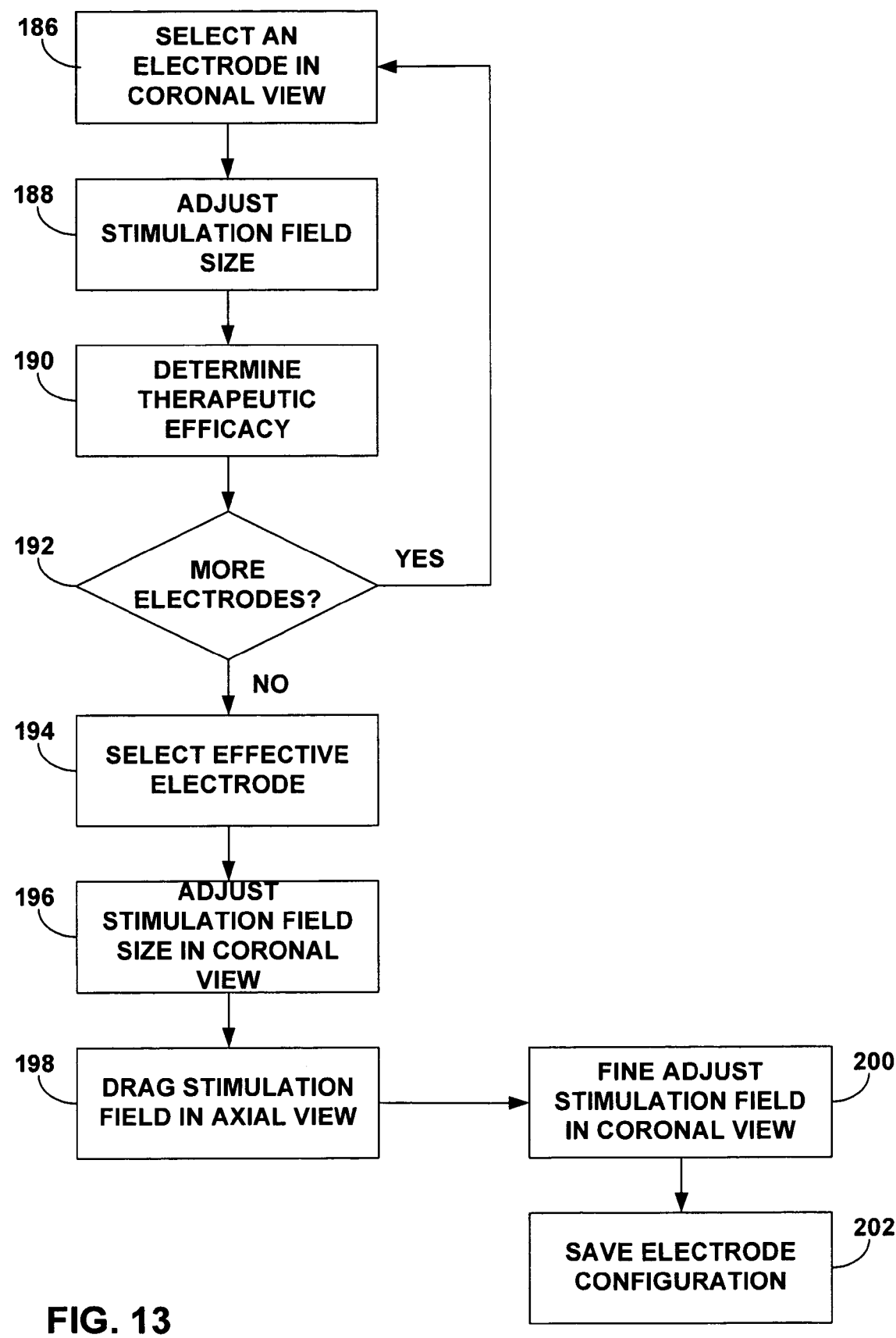
FIG. 13 is a flow diagram illustrating an example technique for adjusting the stimulation field for stimulation therapy.

FIG. 13 is a flow diagram illustrating an example technique for adjusting the stimulation field for stimulation therapy. As shown in FIG. 13, the clinician begins by selecting an electrode level in field view 122 of user interface 90 (186). All electrodes, i.e., electrodes at different angular positions around the lead circumference, in the electrode level are active. The clinician adjusts the stimulation field 136 size (188) and proceeds to test the stimulation field on patient 12 to determine the therapeutic effect, if any (190). If there are more electrode levels to try (192), the clinician repeats this process by selecting another electrode level and testing it on patient 12.

If there are no more electrode levels to test, the clinician selects the most effective electrode level (194) and adjusts the stimulation field size again in field view 122 (196). The clinician next drags the stimulation field in adjust view 146 to minimize side effects and maximize the therapy (198). The clinician may return to field view 122 and fine adjust the stimulation field (200). In some embodiments, the clinician may adjust the simulation field in any of sagittal, coronal, or axial field views as desired by the clinician. In other embodiments, user interface 90 may require that the clinician enters each of the sagittal, coronal, and axial field views at least once before adjustment of the stimulation can be completed. Once the stimulation field is adjusted to produce effective therapy, the clinician saves the electrode configuration and other stimulation parameters as a stimulation program and transmits the program to IMD 20 (202). In some embodiments, the clinician may repeat the programming procedure with user interface 90 to create multiple stimulation programs. The clinician may also reprogram the therapy at any time.

Programmer 19 uses the information received via user interface 90 to automatically generate stimulation parameters according to the stimulation field defined by the clinician. The user interface determines the dimensions of the stimulation field to create a 3D vector field identifying the distances from lead 14 that stimulation may reach. Programmer 19 uses the 3D vector field with an equation approximating electrical current propagation within brain 18 tissue. The resulting data determines the electrode combination, voltage and current amplitudes, pulse rates, and pulse widths needed for reproducing the stimulation field within patient 12. In other embodiments, programmer 19 interprets density of tissue in the imaging data to more precisely approximate the stimulation parameters.

FIGS. 14A-14F are conceptual diagrams illustrating different stimulation fields produced by combinations of electrodes from the complex electrode array geometry. As shown in FIGS. 14A-14F, the potential stimulation fields along the length of lead 204 are shown, where lead 206 is an embodiment of lead 14. Stimulation fields are shown along only one side of lead 206; however, similar stimulation fields may be produced between other electrodes around the circumference of lead 206. The stimulation fields may be similar to a stimulation template for that electrode configuration, where a stimulation template is a predetermined stimulation volume that is defined by a set of stimulation parameters. As mentioned previously, a stimulation template may be a volumetric stimulation field defined by stimulation parameters. Programmer 19 may include a certain number of stimulation templates that are used to automatically generate stimulation parameters that best fit a user defined stimulation field. In addition to the stimulation fields shown with lead 206, reversing the polarity of the electrodes that produce each stimulation field may result in a similar stimulation field, but have a different therapeutic effect on patient 12.

Figure 14A:
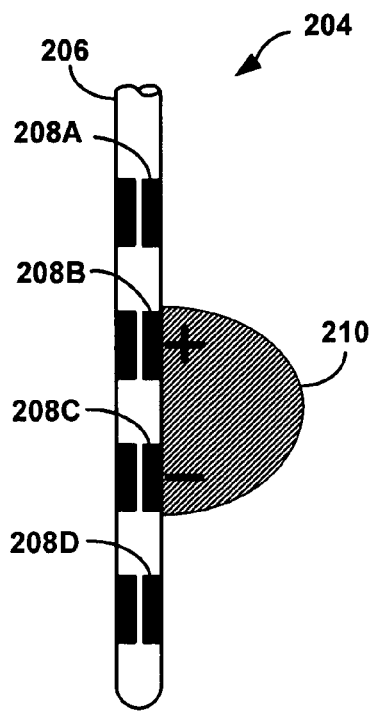
FIGS. 14A-14F are conceptual diagrams illustrating different stimulation fields produced by combinations of electrodes from a complex electrode array geometry.
Figure 14B:
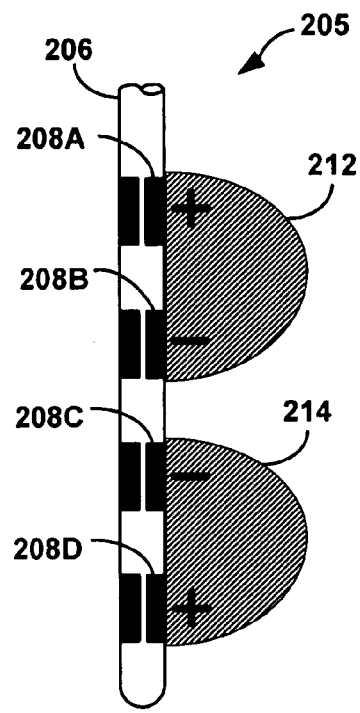

FIG. 14A illustrates electrode configuration 204 providing one stimulation field 210 that is formed from designating electrode 208A as the anode and electrode 208C as the cathode. Stimulation field 210 could be similarly produced by any other adjacent electrode pair, such as electrodes 208A and 208B. FIG. 14B illustrates electrode configuration 205 that includes stimulation fields 212 and 214. Stimulation field 212 is produced by electrode 208A as an anode and electrode 208B as a cathode. Stimulation field 214 is produced by electrode 208C as a cathode and electrode 208D as an anode. Electrode configuration 205 may be used when different structures of the anatomical region are desired to be stimulated.

Figure 14C:
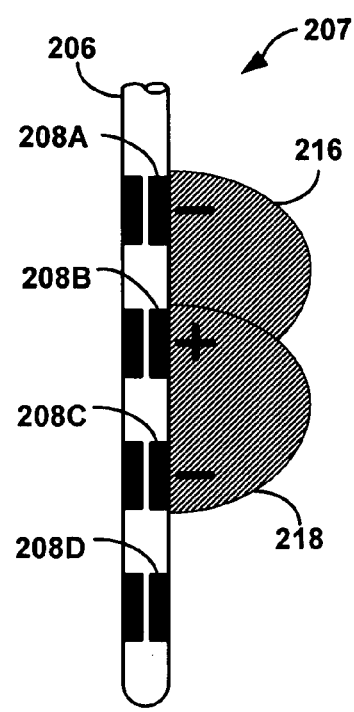
Figure 14D:
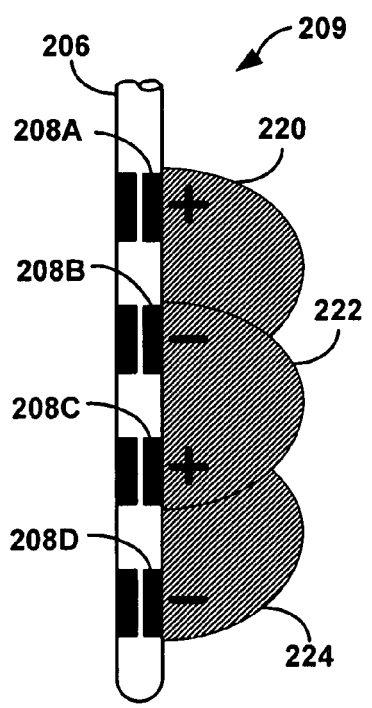

FIGS. 14C and 14D illustrate larger stimulation fields that are produced from overlapping smaller stimulation fields. FIG. 14C presents electrode configuration 207 that includes stimulation fields 216 and 218. Stimulation fields 16 and 17 are created by anode electrode 208B and cathode electrodes 208A and 208C. FIG. 14D presents electrode configuration 209 that includes stimulation fields 220, 222 and 224. Stimulation field 220 is produced by electrodes 208A and 208B, stimulation field 222 is produced by electrodes 208B and 208C, and stimulation field 224 is produced by electrodes 208C and 208D. Polarity of collective electrodes 208 may be altered while maintaining the stimulation fields of electrode configuration 209.

Figure 14E:
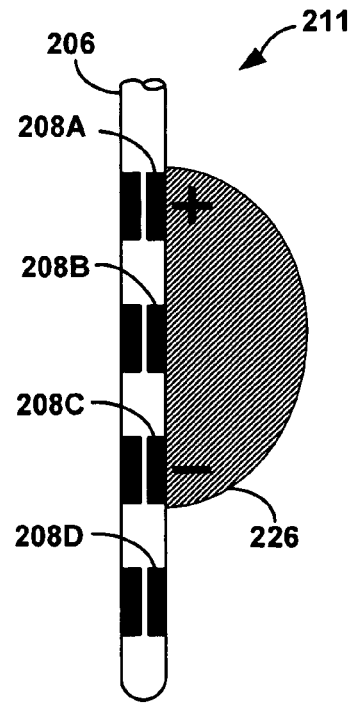
Figure 14F:
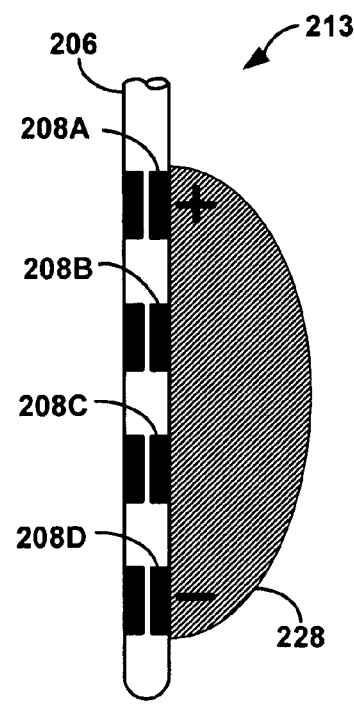

FIGS. 14E and 14F provide examples of stimulation fields that span over inactivated electrodes. FIG. 14E illustrates electrode configuration 211 of electrodes 208A and 208C that produce stimulation field 226. Stimulation field 226 covers electrode 208B without activating the electrode. Activating electrode 208B as an anode or cathode may affect the shape of stimulation field 226. FIG. 14F illustrates electrode configuration 213 of active electrodes 208A and 208B. Stimulation field 228 overlaps inactive electrodes 208B and 208C. The polarity of either electrode configurations 211 or 213 may be changed without modifying the shape of the corresponding stimulation field; however, the tissue treated by these stimulation fields may be affected differently.

FIGS. 15A-15D are conceptual diagrams illustrating possible cross-sections of stimulation templates for electrodes of two adjacent levels of a complex electrode array geometry. A stimulation template is a predetermined volumetric stimulation field that programmer 19 can use to match to a desired stimulation field from the clinician. Each stimulation template may be based upon any one or combination of modeled data, experimental data, or analytical calculations prior to being stored in programmer 19. Cross-sections of example stimulation templates are provided to illustrate possible fields around the circumference of implanted lead 14. FIGS. 15A-15D illustrate possible cross-sections of stimulation templates of an electrode of one electrode level paired to another electrode at another electrode level at the same circumferential position. Even through only cross-sections of stimulation templates are shown, they will be referred to as a stimulation template for simplicity. When creating a stimulation template set to provide stimulation therapy, system 10 may use such stimulation templates to create the stimulation template set. If only one electrode template is chosen, at least one other electrode above or below the selected electrode must also be used to create the stimulation template. In other embodiments, similar stimulation templates may be created for complex electrode array geometries having more or less than four electrodes in a given electrode level. The stimulation template may not indicate the exact shape of the resulting stimulation field, as the tissue adjacent to the electrode may affect the propagation of the electrical stimulation. In alternative embodiments, programmer 19 may only store one volumetric stimulation template per electrode combination and scale each template as needed to the size of the stimulation field. In other words, programmer 19 may adjust the current or voltage amplitude to increase or decrease the volumetric stimulation template to best fit the stimulation field.

While generally bipolar electrode combinations are described herein, volumetric stimulation templates may include unipolar electrodes. Unipolar electrodes may be anodes or cathodes that are combined with an electrode to complete the circuit that is located on the housing of stimulator 12 or some other location not on lead 14. Unipolar electrodes may allow for increased flexibility in programming effective therapy.

Figure 15A:
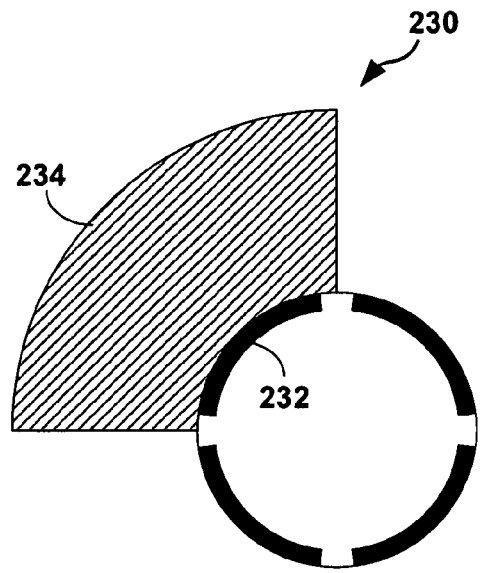
FIGS. 15A-15D are conceptual diagrams illustrating possible stimulation templates for each electrode of a complex electrode array geometry.
Figure 15B:
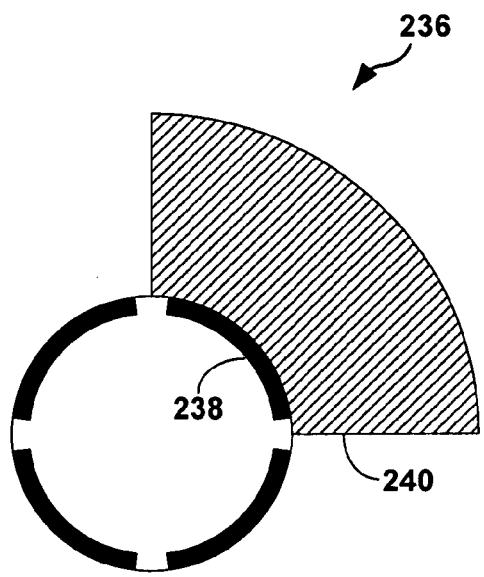
Figure 15C:
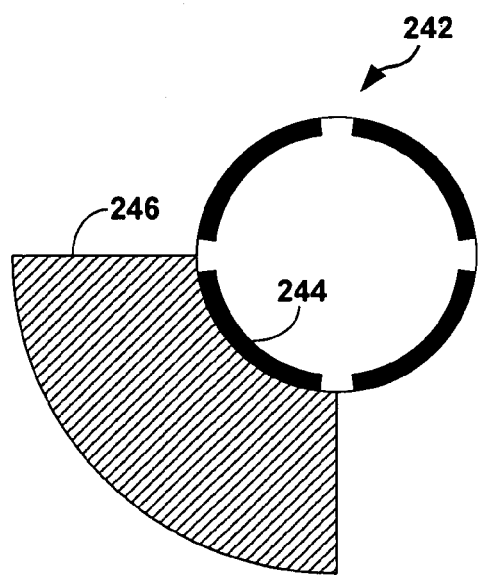
Figure 15D:
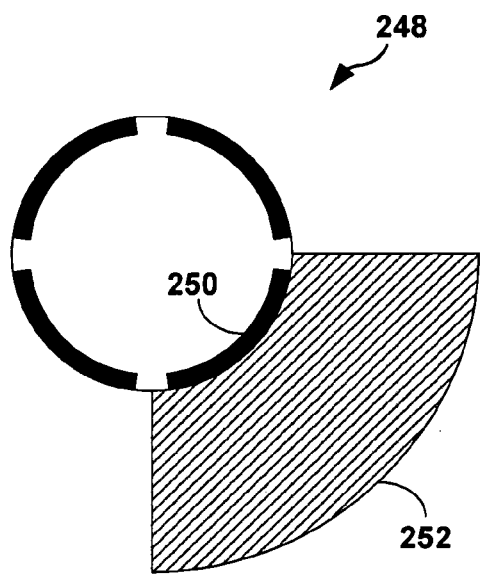

FIG. 15A shows electrode 232 and corresponding cross-section of idealized stimulation field 234 that is included in template 230. FIG. 15B shows electrode 238 and corresponding cross-section of idealized stimulation field 240 that is included in stimulation template 236. FIG. 15C includes stimulation template 242 which includes electrode 244 and corresponding cross-section of idealized stimulation field 246 adjacent to the electrode. FIG. 15D indicates that stimulation template 248 includes electrode 250 and corresponding cross-section of idealized stimulation field 252. The actual shape of each stimulation template may vary depending upon the surrounding tissue to the implanted lead. However, system 10 may use the idealized stimulation templates as approximate stimulation templates for the purpose of matching the best template to the user defined stimulation field. For all stimulation templates, system 10 may be able to adjust the current amplitude or voltage amplitude to alter the size of the stimulation field provided by the stimulation template to cover the desired stimulation field identified by the clinician. In addition, system 10 may combine any of the stimulation templates 230, 236, 242 and 248 to stimulate tissue at certain locations around the lead. In some embodiments, polarity of an electrode of a stimulation template may be changed to accommodate the combine stimulation templates, or stimulation template set.

Figure 16:
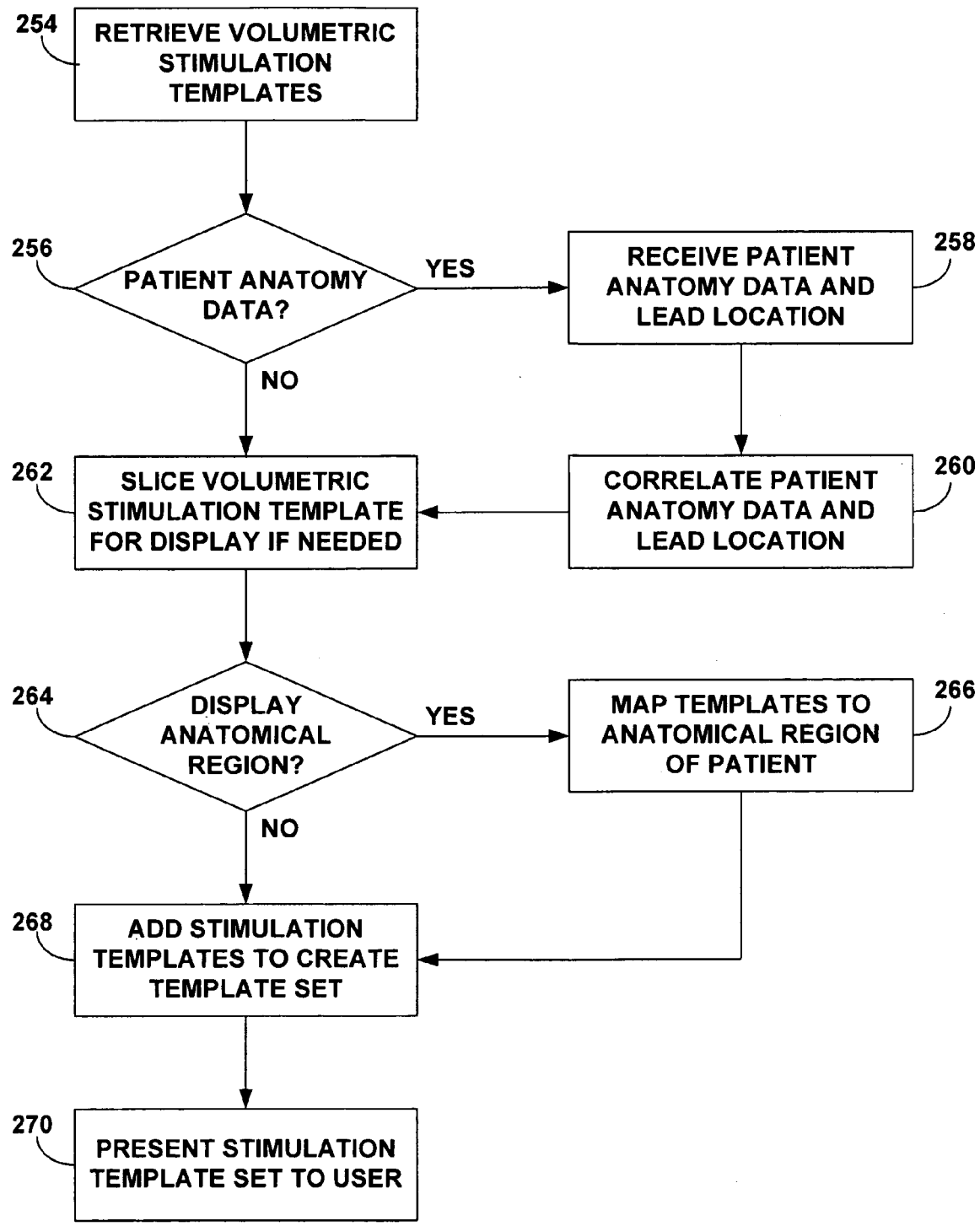
FIG. 16 is a flow diagram illustrating an example technique for creating a template set according to the electrode configuration selected by the user.

FIG. 16 is a flow diagram illustrating an example technique for creating a template set from volumetric stimulation templates stored in programmer 19. As shown in FIG. 16, system 10 may use stimulation templates stored within programmer 19 to create a stimulation template set that defines the stimulation therapy for patient 12. Once programmer 19 has received stimulation field input from the clinician, processor 80 of programmer 19 retrieves volumetric stimulation templates from memory 82 that best correlate to the stimulation field input from the clinician (254). Each stimulation template may be stored as a volumetric stimulation template and compared to the stimulation field input by processor 80. In some cases, processor 80 may use an iterative process to find the best one or more stimulation templates that fit the stimulation field input, e.g., step-by-step narrowing of templates according to most important variables first and less important variables next. In other embodiments, processor 80 may use a point field in which each template is labeled with the points the template includes. The template, or templates, with points most closely matching the stimulation field input may be selected. Storing volumetric stimulation templates may effectively reduce the time needed to find a stimulation template by limiting possible templates to only those capable of being created by the complex electrode array geometry. If template small sections or 2D slices were employed, constructing a viable volumetric template that can be produced by the complex electrode array geometry may be time consuming or computation intensive.

If the clinician has loaded patient anatomy data for the anatomical region (256), processor 80 receives the patient anatomy data and data indicating the location of the one or more leads implanted within brain 18 (258). The patient anatomy data may be information created by an imaging modality such as magnetic resonance imaging (MRI), computed tomography (CT), or positron emission tomography (PET). The patient anatomy set may be used as a "map" of the patient anatomical structure. The location of the lead may be determined by stereotactic techniques or a post-implant image of the lead with respect to the anatomy. Processor 80 next correlates the patient anatomy data to the lead location in order to create a single coordinate system (260). Next, processor 80 slices the volumetric stimulation template to create a cross-section that can be displayed in accordance with the stimulation field input from the clinician (262). If there is no patient anatomy data (256), processor 80 proceeds directly to slice the volumetric stimulation template as needed. Since the patient anatomy data set may only be used to display the stimulation field and template over the anatomical region of the patient, some embodiments may display the template and stimulation field without the patient anatomy data.

Processor 80 next determines if the anatomical region should be displayed on user interface 84. If there is no anatomical region to be displayed, processor 80 will directly add the necessary stimulation templates, if there are more than one needed, to create the "best fit" stimulation template set to treat patient 12, e.g., the stimulation template set that best matches the desired stimulation field as indicated by the clinician. If the anatomical region is to be displayed to the clinician, processor 80 maps the stimulation templates to the patient anatomical region (266) and adds the templates together to create the stimulation template set (268). Processor 80 presents the stimulation template set to the user for review and verification (270). If there is an anatomical region to display to the clinician in addition to the stimulation template set, user interface 84 will display the stimulation template set over the associated areas of the anatomical region.

Each stimulation template may be stored as a set of equations that govern the template. For example, variables of the template equations may be stimulation parameters such as voltage amplitude, current amplitude, pulse rate, pulse width, or frequency. A clinician may change proposed stimulation parameters by modifying the stimulation field input or directly change the size of the stimulation template on user interface 84. Changes in the stimulation field input will affect the size or selection of the stimulation template set, and changes in the size of the stimulation template will affect the stimulation parameters. Other variables may include physical parameters such as electrode size, shape, and curvature. In less complicated embodiments, each electrode may have a predefined number of possible templates that are defined by predetermined stimulation parameters. In this manner, processor 80 selects the template that best fits defined stimulation field from the clinician, compiles each template, and creates the stimulation template set. In some embodiments, system 10 may store and process stimulation templates differently. For example, the clinician may even search memory 82 for possible templates to manually create a stimulation template set or adjust a previously created stimulation template set.

Figure 17A:
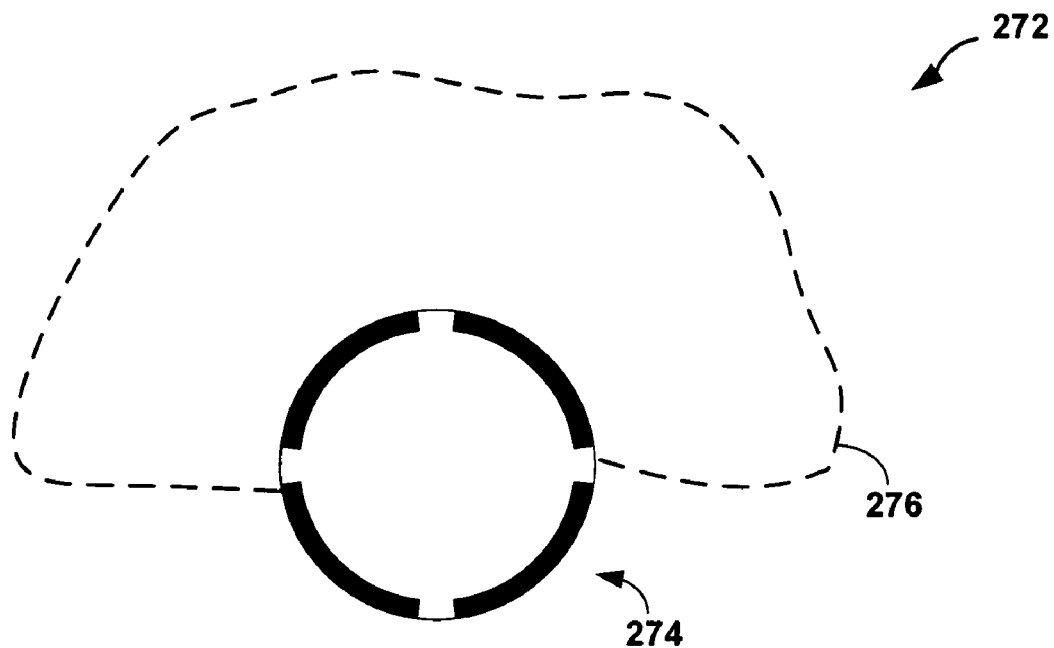
FIGS. 17A and 17B are conceptual diagrams illustrating a template set that does not target any tissue outside of a defined stimulation area.
Figure 17B:
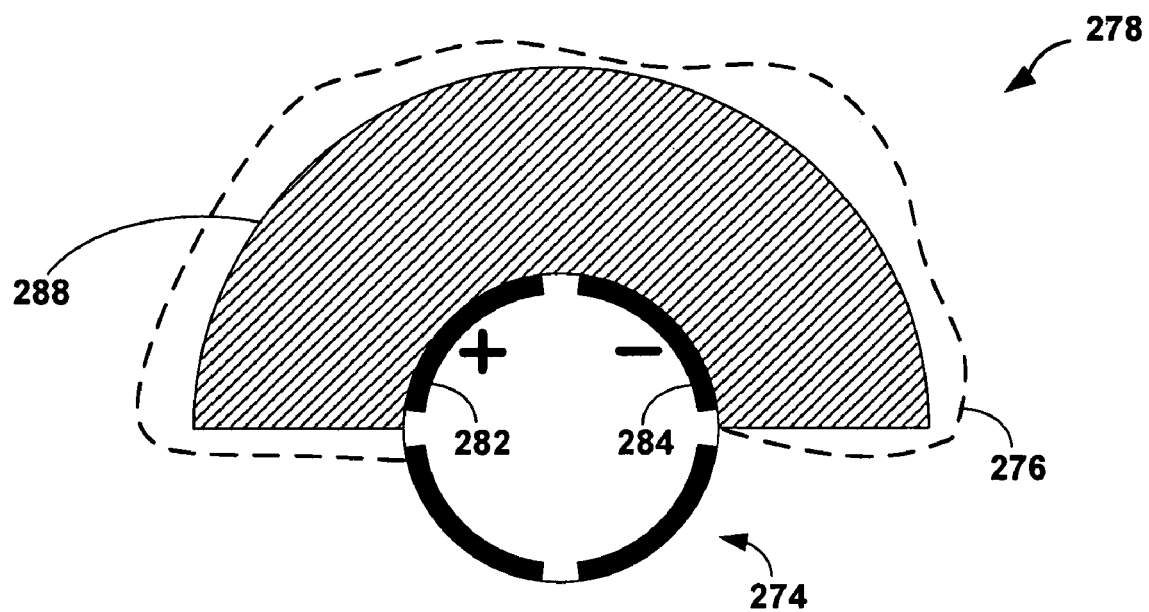

FIGS. 17A and 17B are conceptual diagrams illustrating a template set that does not target any tissue outside of a defined stimulation area. As shown in FIG. 17A, the clinician has defined stimulation field 276 in relation to one level of lead 274 in view 272. Stimulation field 276 outlines the area of an anatomical region (not shown) that the clinician desires to stimulate. FIG. 17B illustrates stimulation template set 288 in view 278 that processor 80 creates according to stimulation field 276. In the example of FIG. 17B, the processor creates the stimulation template set with the highest priority of not affecting areas of the anatomical region outside of stimulation field 276. The next highest priority for processor 80 is to create a stimulation template set 288 that affects as much of the area within the stimulation field area as possible. Template set 288 is created by an anode electrode 282 and cathode electrode 284 of lead 274. While a larger template set 288 may be able to stimulate more of the area within stimulation field 286, the additional stimulated tissue may cause unwanted side effects to patient 12. The clinician may use the similar process for each level of lead 274 to treat other areas of the anatomical region along the length of the lead. In some embodiments, the priorities of when to avoid non-target tissue, cover non-target tissue, or some combination of covered target and non-target tissue may be variable based upon the type of stimulation therapy or user adjustable.

Figure 18A:
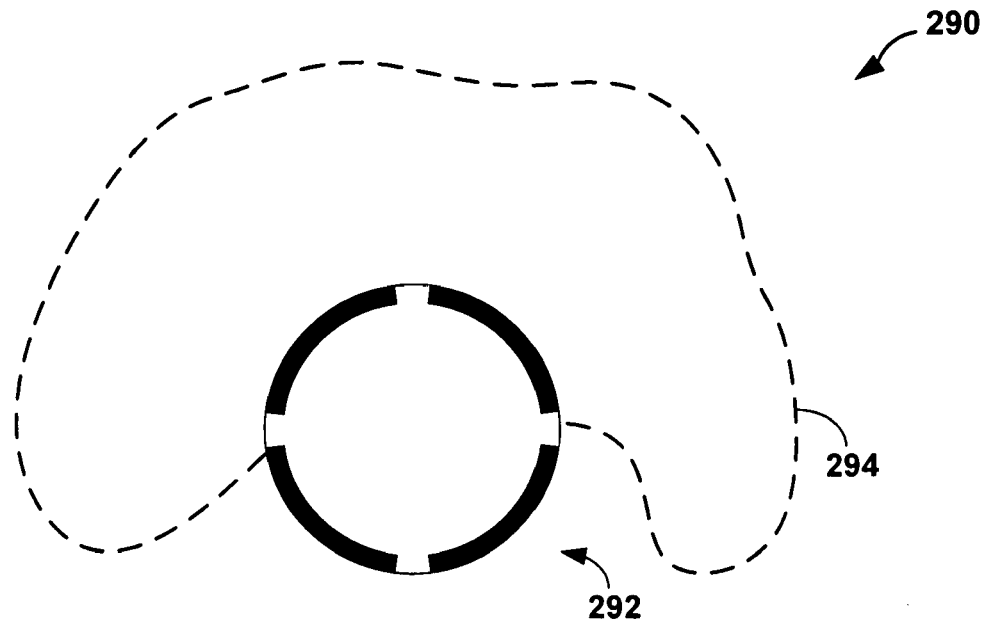
FIGS. 18A and 18B are conceptual diagrams illustrating a template set that targets all tissue within a defined stimulation area.
Figure 18B:
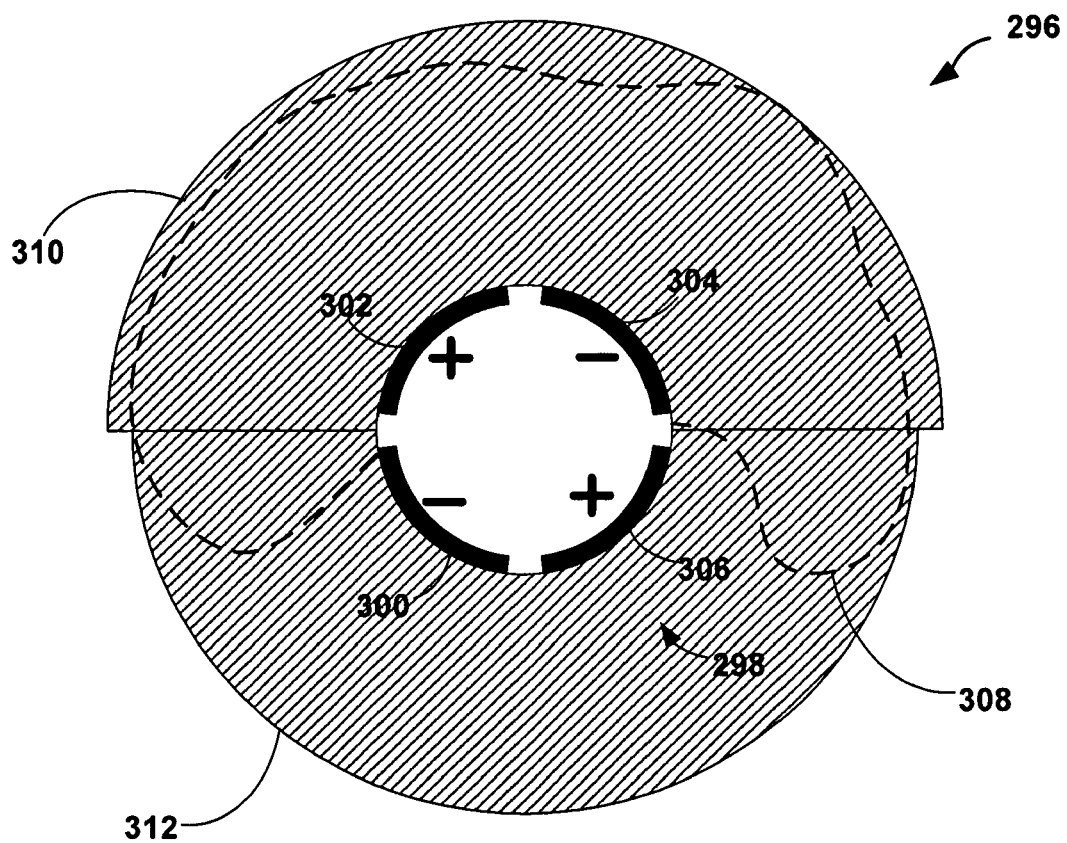

FIGS. 18A and 18B are conceptual diagrams illustrating a template set that targets all tissue within a defined stimulation area. As shown in FIG. 18A, the clinician has defined stimulation field 294 in relation to one level of lead 292 in view 290. Stimulation field 294 outlines the area of an anatomical region (not shown) that the clinician desires to stimulate. FIG. 18B illustrates stimulation templates 310 and 312 that processor 80 creates according to stimulation field 294. In the example of FIG. 17B, the processor creates the stimulation template set with the highest priority of stimulating all tissue areas within stimulation field 308. Next, processor 80 attempts to stimulate the least amount of tissue outside of stimulation field 308. This method of creating template sets may cause side effects to patient 12 with the benefit of possibly treating the entire patient condition. Template 310 is created by an anode electrode 302 and cathode electrode 304 of lead 298. Template 312 is created by an anode electrode 306 and cathode electrode 308 of lead 298. Templates 310 and 312 together create the stimulation template set for therapy, but only a cross-section of the volumetric stimulation template is displayed. In addition, templates 310 and 312 are only idealized estimations of the actual stimulation field produced within patient 12. However, this estimation may be adequate to aid the clinician in programming the stimulation therapy of a complex electrode array geometry. The clinician may use the similar process for each level of lead 292 or 298 to treat other areas of the anatomical region along the length of the lead.

Figure 19:
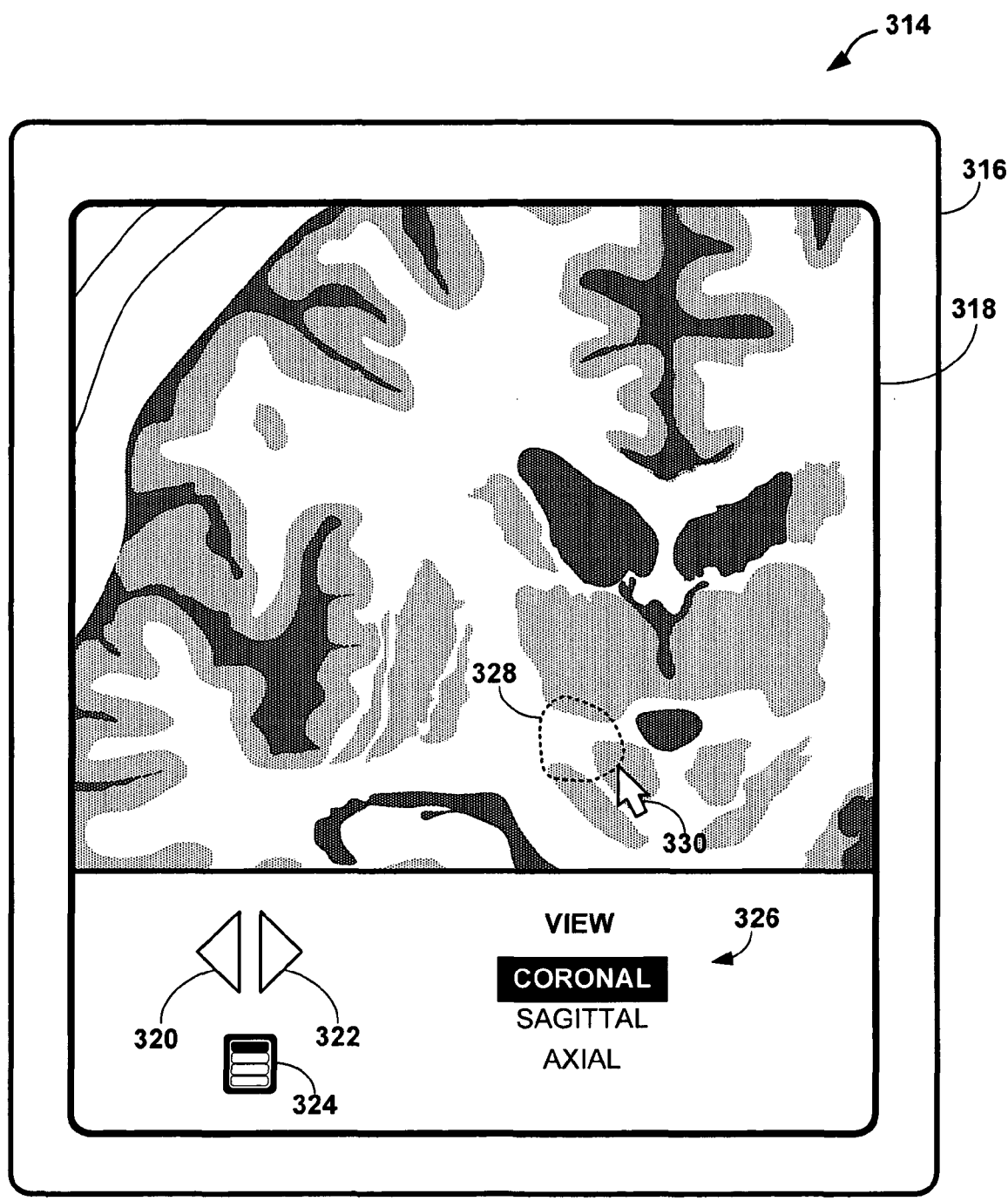
FIG. 19 is an example screen shot of an outline of a stimulation field placed on a coronal view of brain tissue.

FIGS. 19-22 are illustrative of another embodiment of this disclosure intended to allow physicians to focus on patient anatomy. FIGS. 19-22 may generate stimulation parameters according to predetermined stimulation equations, stored stimulation templates, or another method of generating parameters based upon the defined stimulation field. FIG. 19 is an example screen shot of an outline of a stimulation field placed on a coronal view of brain tissue. As shown in FIG. 19, user interface 314 is displayed on programmer 316, which may be substantially similar to programmer 19 described above with reference to FIG. 5. User interface 314 includes coronal view 318 of brain 18. Also shown on coronal view 318 are pointer 330, stimulation field 328, previous arrow 320, next arrow 322, menu 324, and view indicator 326. Stimulation field 328 is a cross-sectional view of volumetric stimulation field, which is further defined in other orthogonal views. Coronal view 318 is a 2D slice of a 3D image of brain 18. White areas indicate dense neuronal tissue while dark areas indicate generally fluid filled area, where the fluid is CSF.

The clinician begins by examining the anatomical regions displayed in coronal view 318. The clinician identifies the target anatomical regions that should be stimulated to treat patient 12. In the example of Parkinson's disease, the clinician identifies the SN and other structures of brain 18. The clinician moves pointer 330 to create an outline defining the outer edges of the stimulation field. While a representation of lead 14 is not shown on coronal view 318, other embodiments may show a lead icon for a starting point.

The clinician may zoom in or out of an area of coronal view 318. In addition, the clinician may move coronal view right, left, up or down to isolated areas of interest. Zoom may be of interest to the clinician when outlining the target anatomical region in order to fine tune the resulting stimulation field. Programmer may set limit boundaries to the outline that the clinician may generate. These limit boundaries may be shown on coronal view 318. In some embodiments, user interface 314 may allow the clinician to move up or down to view cross-section coronal views in other depths of brain 18 using arrows 320 and 322. This movement through 2D slices may allow the clinician to identify each area of stimulation field 328 throughout the 3D stimulation field represented by user interface 314.

The clinician may select menu 324 to view or change preferences of user interface 314. For example, preferences may be appearance preferences such as brightness or contrast of the display of programmer 316. Alternatively, the clinician may select the manner in which programmer 316 determines the stimulation parameters based upon stimulation field 330 when the clinician has completed defining the stimulation field and stimulation parameters can be generated. Pressing menu 324 may bring up a pop-up window that includes the menu choices for the clinician. View indicator 326 allows the user to change to a different 2D view of the anatomical region, such as sagittal or axial views. "Coronal" is highlighted to indicate that the current view is a coronal section of brain 18. Previous arrow 320 and next arrow 322 may allow the clinician to move between slices of adjacent depths of brain 18 and the stimulation field 328 in relation to the anatomical region of the other depths.

In some embodiments, user interface 314 may include a wand tool, e.g., a virtual automatic selection based upon one selected point, that the clinician can use to select an area. Then, all pixels of that same shade of color may be outlined or highlighted. In this manner, the physician may select all anatomical regions of the same density which may be indicative of an entire target region. The clinician may define the range of pixel shade, e.g., allowable variability in tissue density, with one selection. The clinician may then modify the automatically selected area to provide greater flexibility in stimulation field selection. Alternatively, the clinician may manually modify the outlined area after using the wand tool.

The benefit to the clinician outlining desired areas includes allowing the clinician to focus on the anatomy and physiology of patient 12 instead of manipulating an implanted device. The clinician is an expert at understanding the anatomy and physiology of patient 12, but may not be as adept at understanding then the effect of different combinations of stimulation parameters on the stimulation delivered by an IMD. Consequently, automatically generating stimulation parameters according to the desired stimulation area may increase therapy efficacy and decrease programming time.

In other embodiments, user interface 314 may allow the clinician to use a stylus or finger on a touch screen to define the stimulation field and outline. In alternative embodiments, user interface 314 may identify and label certain anatomical regions to help guide the clinician in quickly orienting the stimulation field to brain 18 of patient 12.

Figure 20:
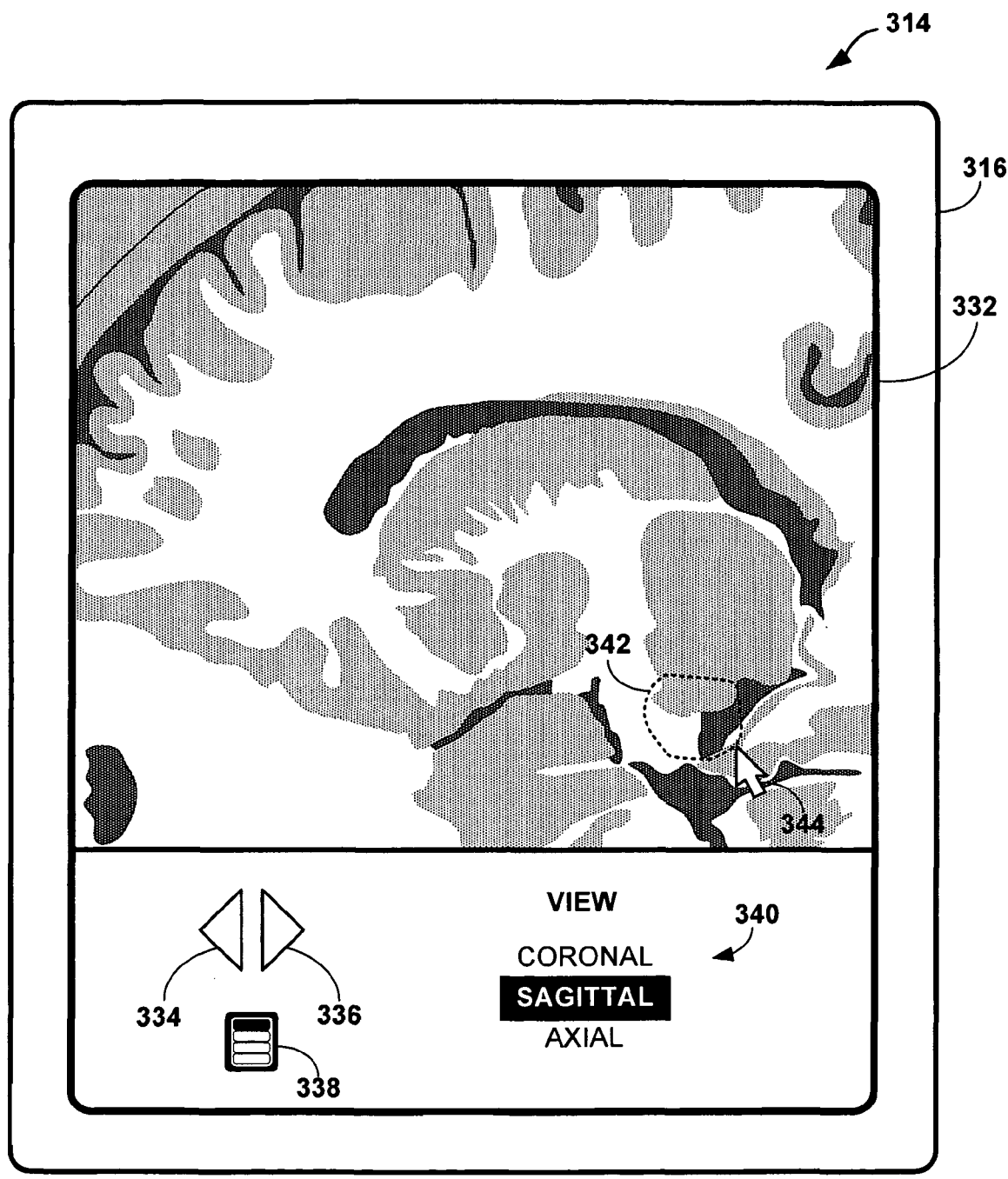
FIG. 20 is an example screen shot of an outline of a stimulation field placed on a sagittal view of brain tissue.

FIG. 20 is an example screen shot of an outline of a stimulation field placed on a sagittal view of brain tissue. Since the defined stimulation field is three dimensional, the clinician must outline the stimulation field on three 2D views, rather than just the coronal view of FIG. 19. As shown in FIG. 20, the clinician uses pointer 344 to create stimulation field 342 within sagittal view 332 of user interface 314. Stimulation field 342 defines the structures of the anatomical region that the clinician desires to stimulate. Stimulation field 342 is also a cross-sectional view of volumetric stimulation field, which is further defined by other orthogonal views, such as the cross-section stimulation field 328 of coronal view 318. Previous arrow 334 and next arrow 336 may be used to move to other slices of the sagittal plane of the anatomical region, while menu 338 may be selected and used similar to menu 324. View indicator 340 also highlights the word "Sagittal" to remind the clinician which plane of the anatomical region the clinician is viewing. Similar to FIG. 19, the clinician may zoom in and out of sagittal view 332 and move the view to display different areas within the current slice of the sagittal plane. Additionally, the clinician may use a wand tool to select a range of pixel shades to quickly select anatomical regions that will be included in the stimulation field.

Figure 21:
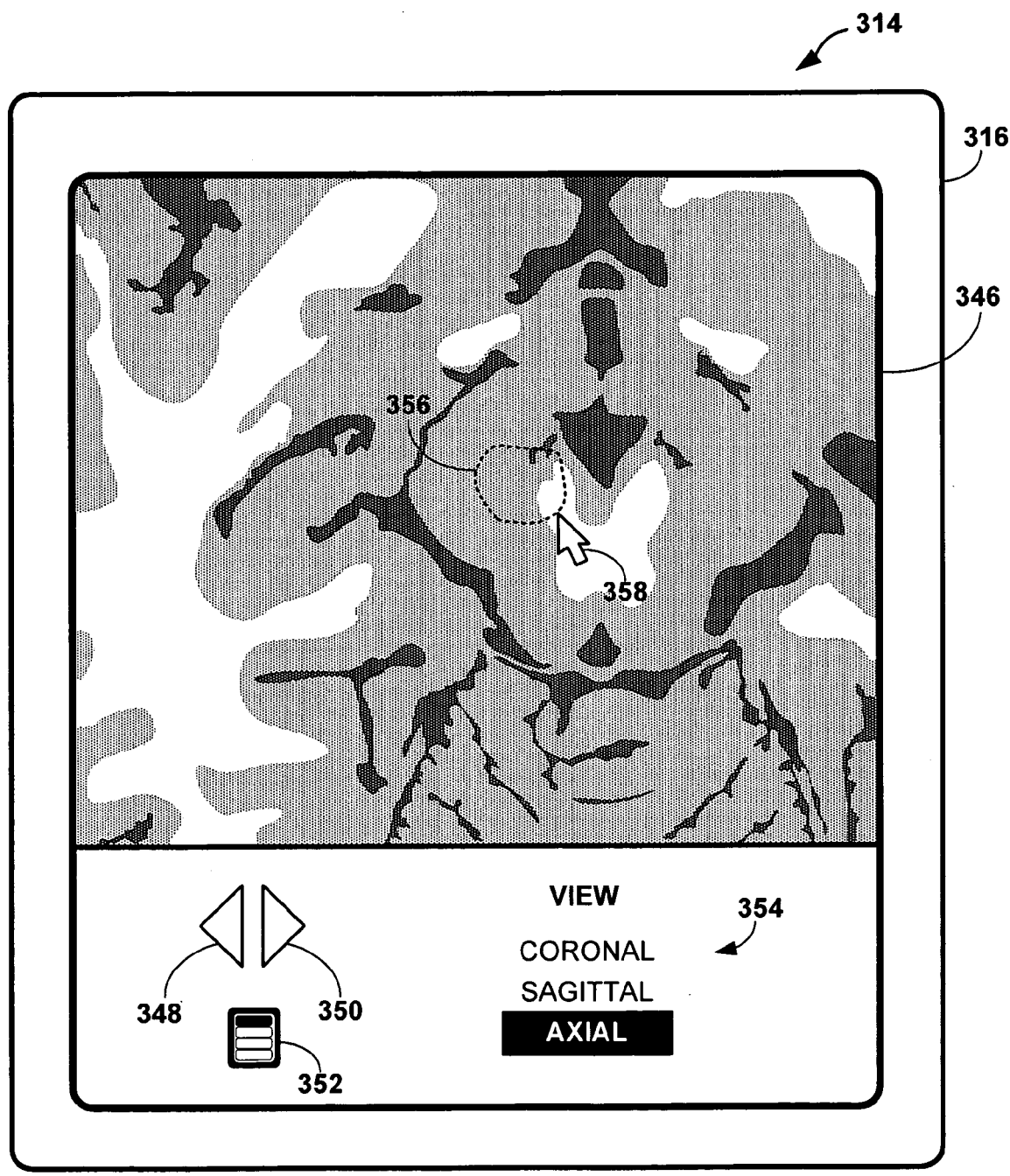
FIG. 21 is an example screen shot of an outline of a stimulation field placed on an axial view of brain tissue.

FIG. 21 is an example screen shot of an outline of a stimulation field placed on an axial view of brain tissue. As shown in FIG. 21, user interface 314 is provided by programmer 316 and includes axial view 346 that displays pointer 358, stimulation field 356, previous arrow 348 and next arrow 350. Simulation field 356 is a cross-section of the volumetric stimulation field defined in views 318 and 322. User interface 314 also includes view indicator 354. Similar to coronal view 318 and sagittal view 332, the clinician uses pointer 358 to create an outline of stimulation field 356 around target structures of the anatomical region.

The clinician may make adjustments to stimulation field 356 in axial view 346 or using previous arrow 348 and next arrow 350 to step up or down in axial slices of brain 18. The clinician may also go back and forth between views 318, 332 and 346 to make fine adjustments to the stimulation field defined by the outlines in the three orthogonal views. Similar to FIGS. 19 and 21, the clinician may zoom in and out of axial view 346, as well as move the view to the right, left, up and down of the anatomical region. The clinician may also use a wand tool to select similar pixels in the same area.

Once all stimulation fields 328, 342 and 356 are complete, the clinician may have programmer 316 automatically generate stimulation parameters associated to the 3D stimulation field defined by stimulation fields 328, 342 and 356. The clinician may test the stimulation field on patient 12 and adjust the stimulation parameters, if necessary. In other embodiments, stimulation fields 328, 342 and 356 are not all defined from separate outlines. For example, once stimulation field 328 is defined, programmer 316 may display a line that indicates the different orthogonal view to aid the clinician in creating stimulation field 342, both of which are cross-sections of the volumetric stimulation field actually produced in therapy. Alternatively, programmer 316 may use stimulation field 328 to estimate an initial volumetric stimulation field which determines the starting point for stimulation field 342 that the clinician modifies. In any case, the order in which the clinician accesses views 318, 332, and 346 to create stimulation fields 328, 342, and 356 may be changed by the clinician or alternative instructions stored in memory 82 programmer 316.

User interface 314 may include limits to the shape and size of the outline from the clinician. In some embodiments, processor 80 may use stimulation templates to generate the stimulation parameters requested by the stimulation field, as described previously. In other embodiments, stimulation parameter equations may be used to determine the appropriate stimulation parameters that will satisfy the stimulation field. In the case where stimulation parameters cannot create an identical match to the defined stimulation field, user interface 314 may provide a percent under or over indication to the clinician that indicates the error of the best fit stimulation field. User interface 314 allows the clinician to focus on structures of the anatomical region without worrying about the exact position of lead 14 within brain 18. Processor 80 will compare the position of the stimulation field to the actual lead position. If the defined stimulation field cannot be satisfied because it is out of range of lead 14, a warning message may be delivered to the clinician via user interface 314. Otherwise, processor 80 will determine parameters for delivery of stimulation via lead 14 that will approximately result in the stimulation field defined by the clinician using the user interface.

Figure 22:
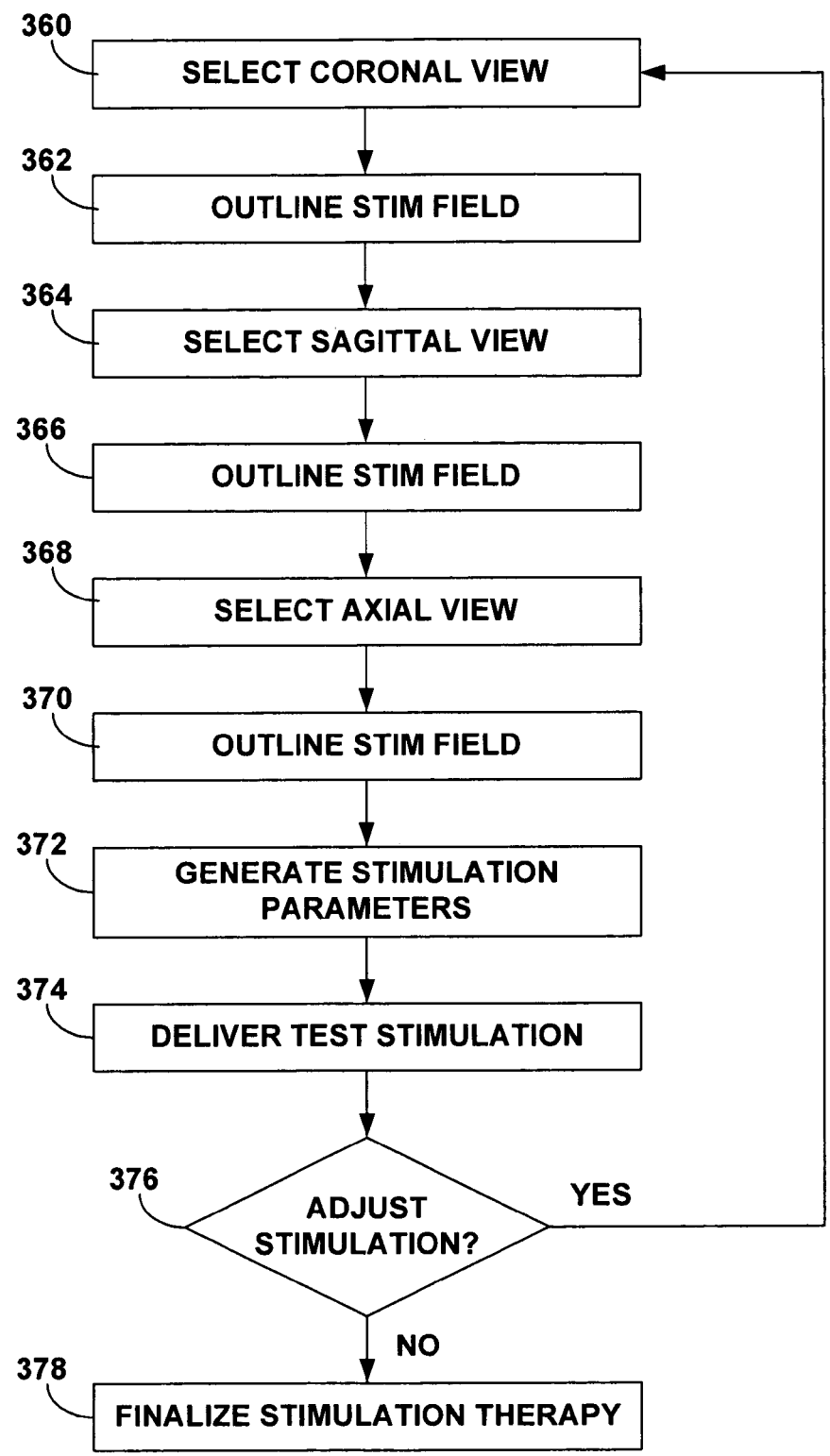
FIG. 22 is a flow diagram illustrating an example technique for defining a stimulation field over an anatomical region without reference to an implanted lead.

FIG. 22 is a flow diagram illustrating an example technique for defining a 3D stimulation field over an anatomical region without reference to an implanted lead. While user interface 314 does not provide a lead icon to the user when defining the stimulation field, other embodiments may provide the lead icon as a reference to the origination of stimulation therapy. As shown in FIG. 22, the clinician begins programming by selecting coronal view 318 (360) and outlining a 2D cross-section of the stimulation field in the coronal view (362). Next, the clinician selects sagittal view 332 (364) and outlines the 2D cross-section of the stimulation field in that view (366). The clinician continues to define the stimulation field by selecting axial view 346 (368) and outlining the 2D cross-section of the stimulation field in that view (370). The clinician instructs programmer 19 to automatically generate stimulation parameters corresponding to the 3D stimulation field defined by the 2D stimulation fields drawn in each of the three views, and the programmer transmits the parameters to IMD 20 (372).

The clinician delivers test stimulation with the generated stimulation parameters (374). If the clinician desires to adjust the stimulation therapy (376), the clinician repeats the process by selecting coronal view 318 (360). If the stimulation does not need to be adjusted, the clinician finalizes the stimulation therapy and sets IMD 20 to continue stimulation therapy (378).

In some embodiments, the clinician may continue to generate more stimulation fields to produce multiple stimulation programs for patient 12 to evaluate at home. Since programming may become easier than manually selecting parameters, using user interface 314 may allow the clinician to spend more time producing multiple therapy programs.

Figure 23:
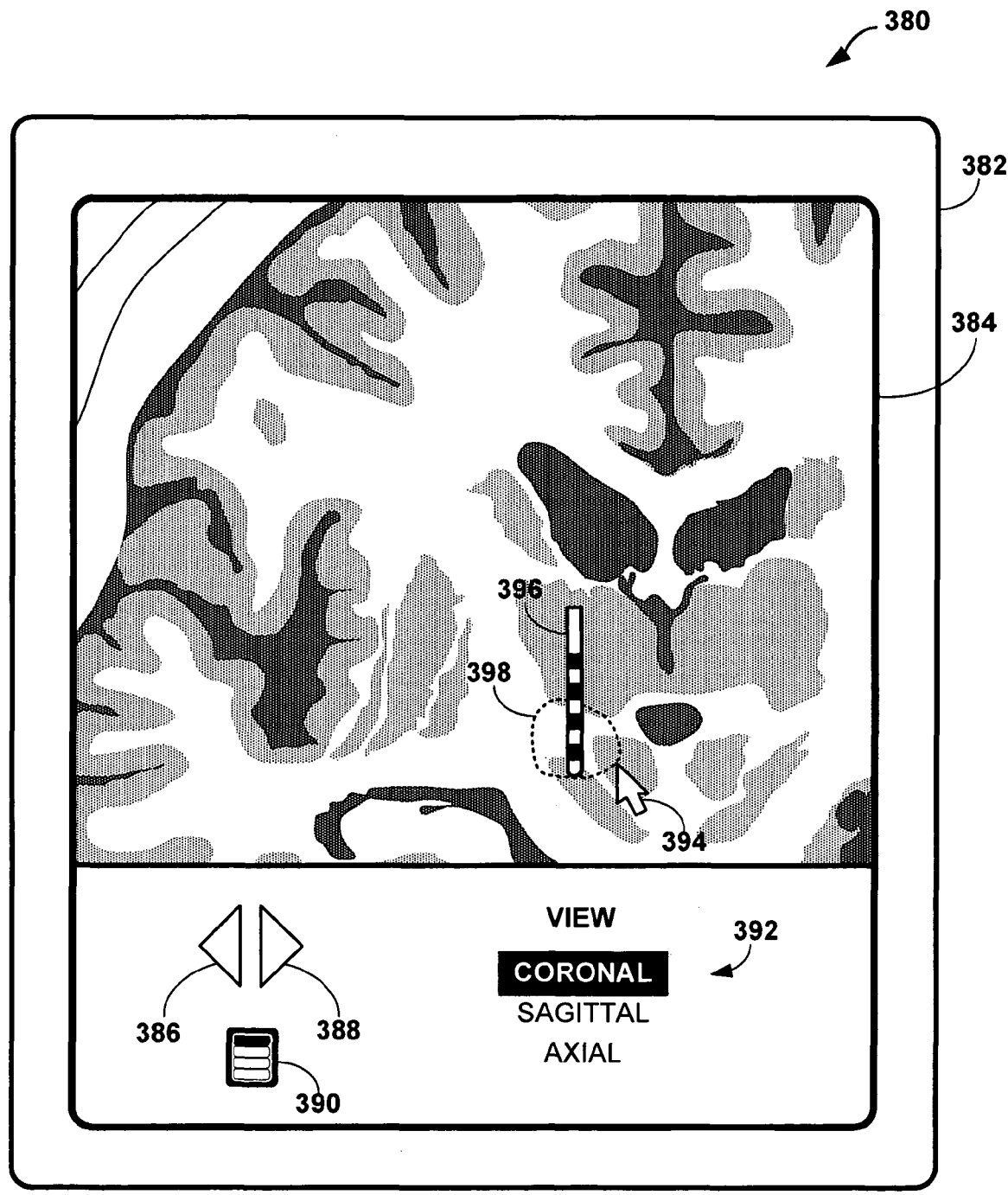
FIG. 23 is an example screen shot of an outline of a stimulation field placed around a lead icon on a coronal view of brain tissue.

FIGS. 23-27 are illustrative of another embodiment of this disclosure intended to allow physicians to define a stimulation field with respect to a lead icon within the anatomical region. FIG. 23 is an example screen shot of an outline of a stimulation field placed around a lead icon on a coronal view of brain tissue. As shown in FIG. 23, user interface 380 is displayed on programmer 382, which may be substantially similar to programmer 19. User interface 380 includes coronal view 384 of brain 18. Also shown on coronal view 384 are pointer 394, lead icon 396, stimulation field 398, previous arrow 386, next arrow 388, menu 390, and view indicator 392. Stimulation field 384 is a cross-section of a volumetric stimulation field further defined in other sagittal and axial orthogonal views. Coronal view 384 is a 2D slice of a 3D image of brain 18. White areas indicate dense neuronal tissue while dark areas indicate generally fluid filled area, where the fluid is CSF.

The clinician begins by examining the anatomical regions displayed in coronal view 384. The clinician identifies the target anatomical regions that should be stimulated to treat patient 12. In the example of Parkinson's disease, the clinician identifies the SN and other structures of brain 18. The clinician moves pointer 394 to create an outline defining the outer edges of the stimulation field 398. Lead icon 396 is a representation of lead 14. Lead icon 396 location may be determined by the clinician moving the lead icon to the appropriate place according to the implantation in the manner discussed above. However, lead icon 396 may be automatically placed if the anatomical region is imaged with the lead implanted, as also discussed above.

The clinician uses pointer 394 to create the outline of stimulation field 398, using lead icon 396 and the anatomical region as guidelines. The clinician may use lead icon 396 to define stimulation field 398 to correspond to the location of the electrodes of the lead icon. In this manner, the clinician may be able to stimulate the appropriate structures of the anatomical region and use desired electrode levels to do so. In some embodiments, lead icon 396 may only show the location of lead 14 and not provide the electrode level details of lead icon 396.

The clinician may zoom in or out of an area of coronal view 384. In addition, the clinician may move coronal view right, left, up or down to isolated areas of interest within the plane. Zoom may be of interest to the clinician when outlining the target anatomical region in order to fine tune the resulting stimulation field. Programmer 80 may set limit boundaries to the outline that the clinician may generate. These limit boundaries may be shown on coronal view 384. In some embodiments, user interface 380 may allow the clinician to move up or down to view cross-section coronal views in other depths of brain 18 with arrows 386 and 388. This movement through 2D slices may allow the clinician to identify each area of stimulation field 398 throughout the 3D stimulation field represented by user interface 380.

The clinician may select menu 390 to perform any of the operations discussed above with respect to menus 324, 338, or 352 of user interface 314. View indicator 392 allows the user to change to a different 2D view of the anatomical region, such as sagittal or axial views. "Coronal" is highlighted to indicate that the current view is a coronal section of brain 18. Previous arrow 386 and next arrow 388 may allow the clinician to move between slices of adjacent depths of brain 18 and the stimulation field 398 in relation to the anatomical region of the other depths.

In some embodiments, user interface 380 may include a wand tool that the clinician can use to select an area. Then, all pixels of that same shade of color are outlined or highlighted. In this manner, the physician may select all anatomical regions of the same density which may be indicative of an entire target region. The clinician may define the range of pixels selected at one click. In addition, the clinician may manually modify the outlined area after using the wand tool.

The benefit to the clinician outlining desired areas includes allowing the clinician to focus on the anatomy and physiology of patient 12 instead of manipulating an implanted device. In other embodiments, user interface 380 may allow the clinician to use a stylus or finger on a touch screen to define the stimulation field and outline. In alternative embodiments, user interface 380 may identify and label certain anatomical regions to help guide the clinician in quickly orienting the stimulation field to brain 18 of patient 12.

Figure 24:
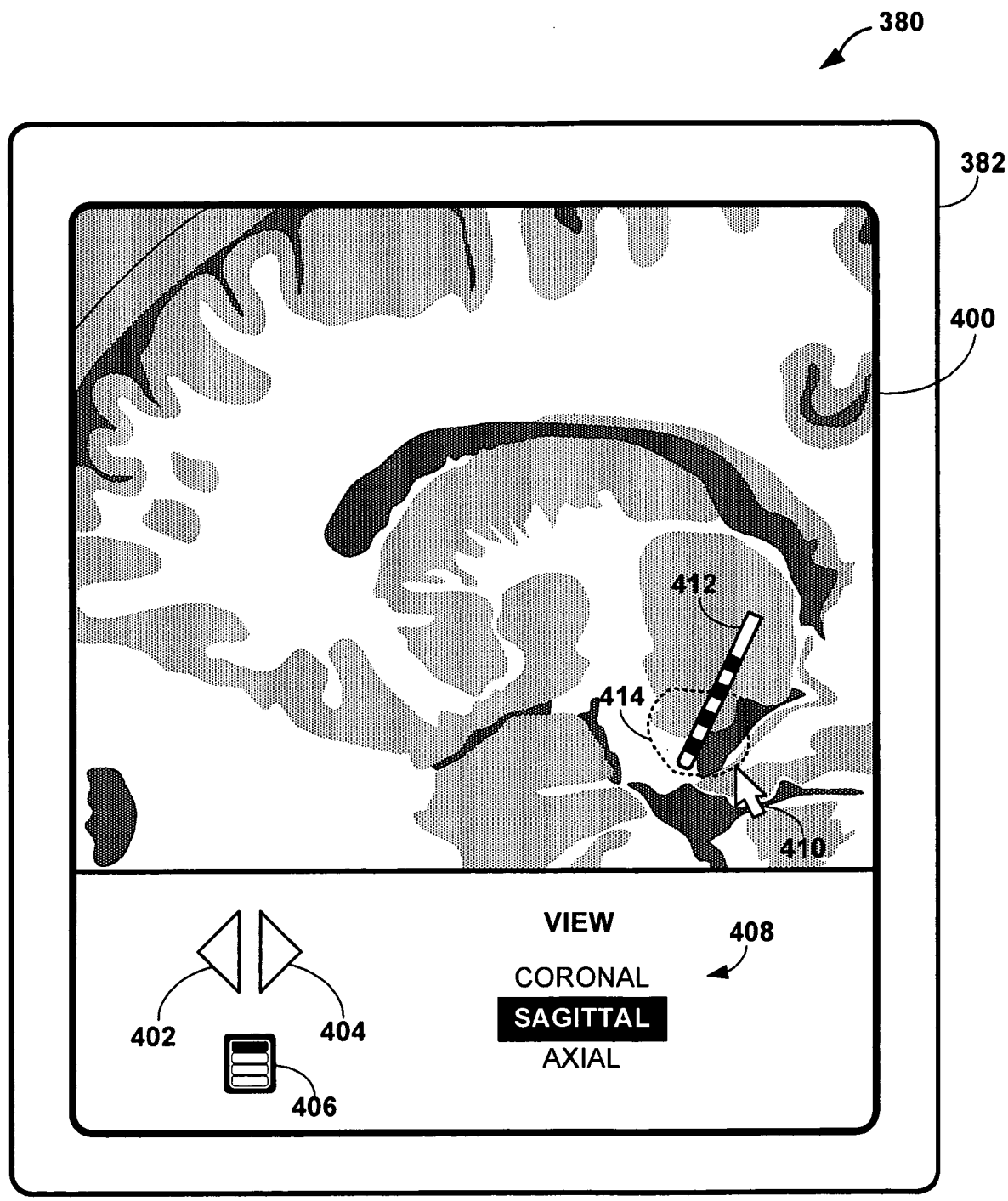
FIG. 24 is an example screen shot of an outline of a stimulation field placed around a lead icon on a sagittal view of brain tissue.

FIG. 24 is an example screen shot of an outline of a stimulation field placed around a lead icon on a sagittal view of brain tissue. Since the defined stimulation field is three dimensional, the clinician must outline the stimulation field on three 2D views, rather than just the coronal view 384 of FIG. 23. As shown in FIG. 24, the clinician uses pointer 410 to create stimulation field 414 around lead icon 412 within sagittal view 400 of user interface 380. Stimulation field 414 encompasses the structures of the anatomical region that the clinician desires to stimulate and is a cross-section of the volumetric stimulation field defined by cross-sectional stimulation fields 398 and 430 in other orthogonal views. In some embodiments, programmer 382 may display a dotted line to indicate to the clinician where the previous cross-section stimulation field 398 was defined. In other embodiments, programmer 382 estimates the volumetric stimulation field from only one cross-section, e.g., stimulation field 398, and presents the estimation to the clinician as stimulation field 414 which the clinician may alter as desired. Previous arrow 402 and next arrow 404 may be used to move within other slices of the sagittal place of the anatomical region, while menu 406 may be selected and used similar to menu 390. View indicator 408 also highlights the Word "Sagittal" to remind the clinician which plane of the anatomical region the clinician is viewing. Similar to FIG. 23, the clinician may zoom in and out of sagittal view 400 and move the view around the display. Additionally, the clinician may use a wand tool to select a range of pixel shades to quickly select anatomical regions that will be included in the stimulation field.

Similar to FIG. 23, lead icon 412 is a representation of lead 14. Lead icon 412 location may be determined by the clinician moving the lead icon to the appropriate place according to the implantation. In addition, the clinician may rotate lead icon 412 to correctly position the lead icon within the anatomical region. However, lead icon 396 may be automatically placed if the anatomical region is imaged with the lead implanted.

Figure 25:
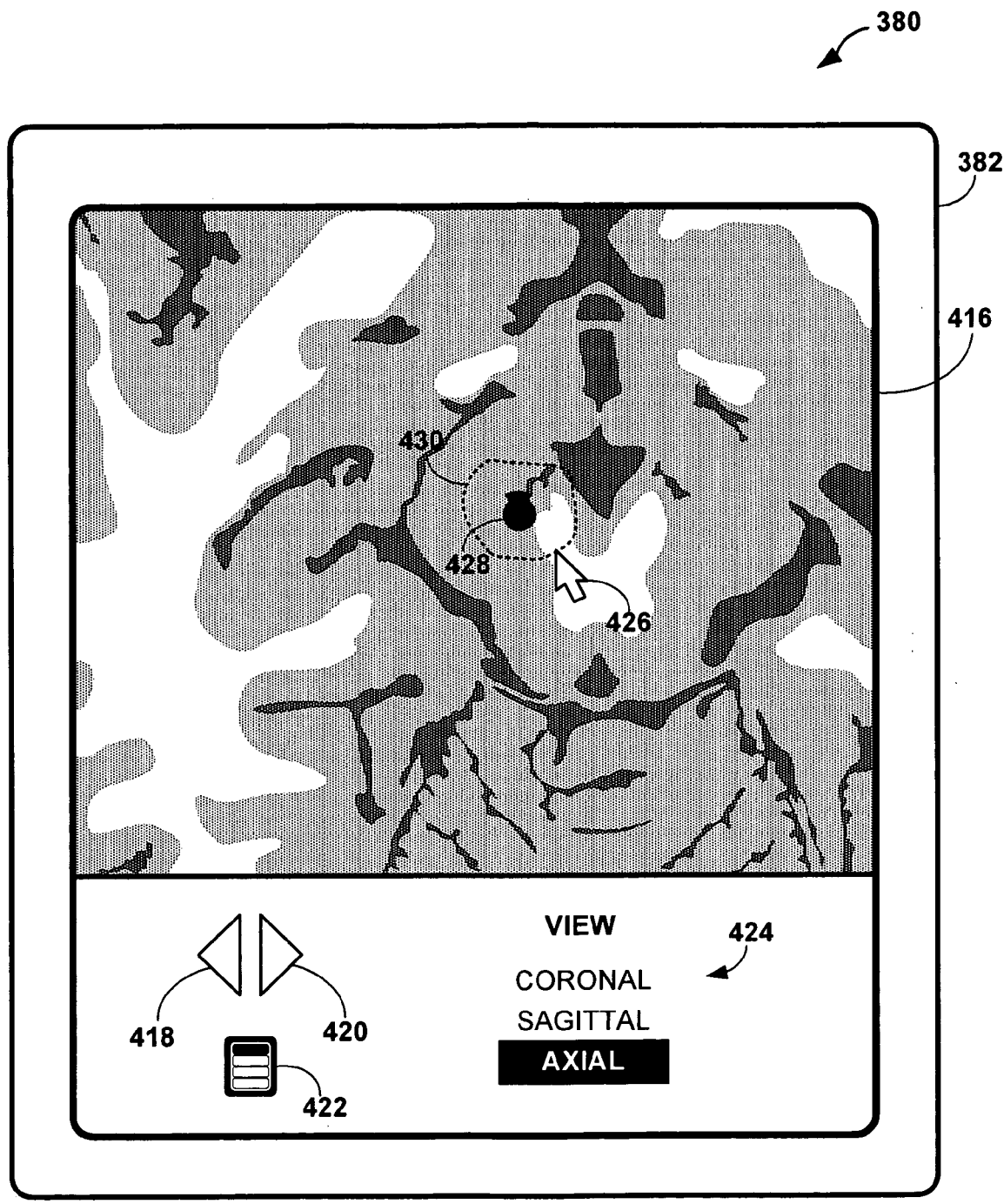
FIG. 25 is an example screen shot of an outline of a stimulation field placed around a lead icon on an axial view of brain tissue.

FIG. 25 is an example screen shot of an outline of a stimulation field placed around a lead icon on an axial view of brain tissue. As shown in FIG. 25, user interface 380 is provided by programmer 382 and includes axial view 416 that displays pointer 426, stimulation field 430, previous arrow 418 and next arrow 420. Stimulation field 430 is a cross-section of the volumetric stimulation field defined in coronal and sagittal views 384 and 400. User interface 380 also includes view indicator 424. Similar to coronal view 384 and sagittal view 400, the clinician uses pointer 426 to create an outline of stimulation field 430 around target structures of the anatomical region and lead icon 428. Similar to FIGS. 23 and 24, lead icon 428 is placed in the correct position within the anatomical region according to the implanted lead 14 position. While lead icon 428 indicates that lead 14 is positioned orthogonal to axial view 416, the actual position of lead 14 may be tilted.

The clinician may make adjustments to stimulation field 430 in axial view 416 or using previous arrow 418 and next arrow 420 to step up or down in axial slices of brain 18. The clinician may also go back and forth between views 384, 400 and 416 to make fine adjustments to the stimulation field defined by the one or more outlines in each of the three orthogonal views. Similar to FIGS. 23 and 24, the clinician may zoom in and out of axial view 416, as well as move the view to the right, left, up and down of the anatomical region. The clinician may also use a wand tool to select similar pixels in the same area.

Once all stimulation fields 398, 414 and 430 are complete, the clinician may have user interface 380 automatically generate stimulation parameters associated to the 3D stimulation field defined by stimulation fields 398, 414 and 430. The clinician may test the stimulation field on patient 12 and adjust the stimulation accordingly. Programmer 382 may provide limits to the shape and size of the outline from the clinician. In some embodiments, processor 80 may use stimulation templates to generate the stimulation parameters required to approximately reproduce the defined stimulation field, as described previously. In other embodiments, stimulation parameter equations may be used to determine the appropriate stimulation parameters that will satisfy the defined 3D stimulation field.

Figure 26:
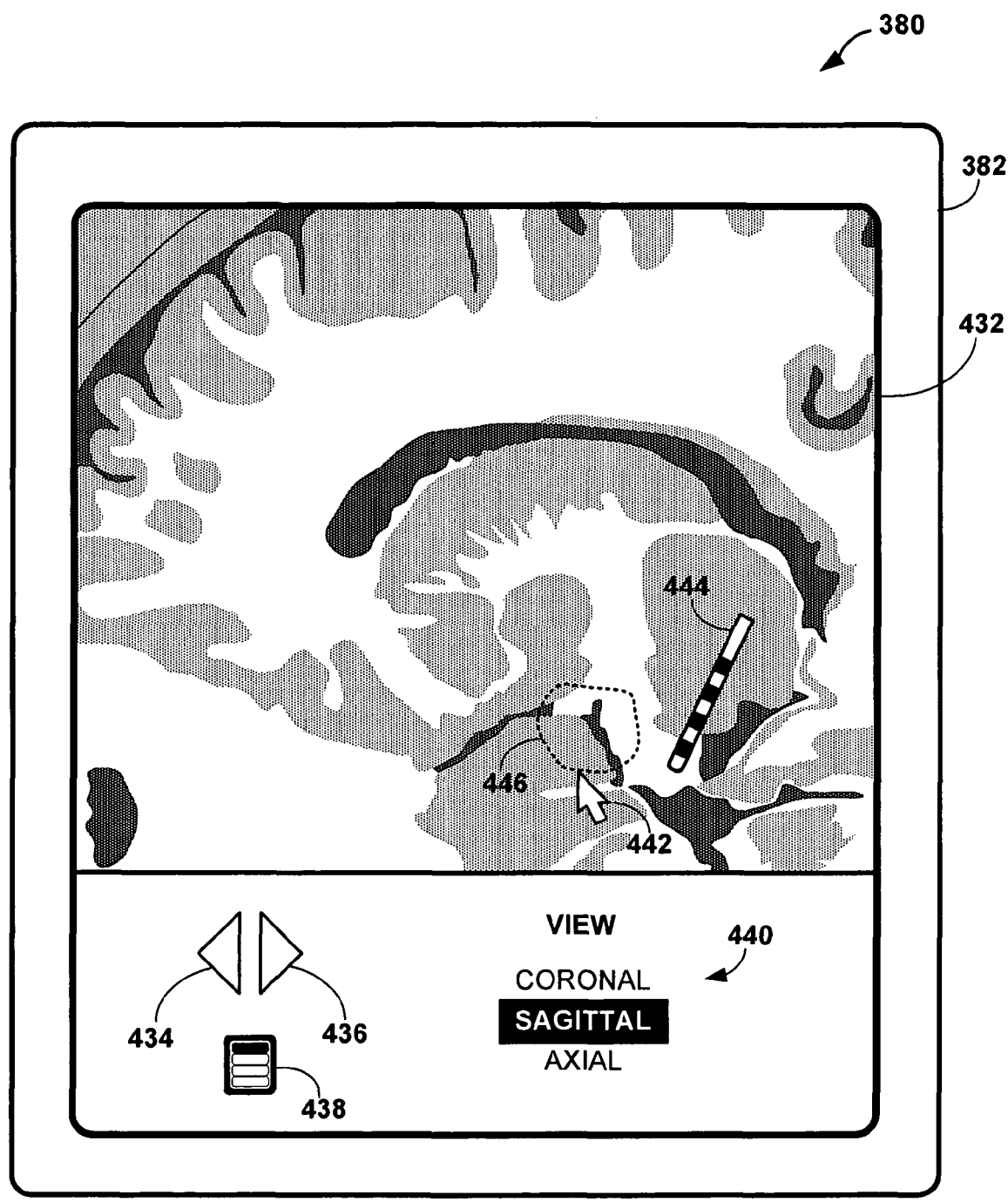
FIG. 26 is an example screen shot of an outline of a stimulation field placed away from a lead icon on a sagittal view of brain tissue.
Figure 27:
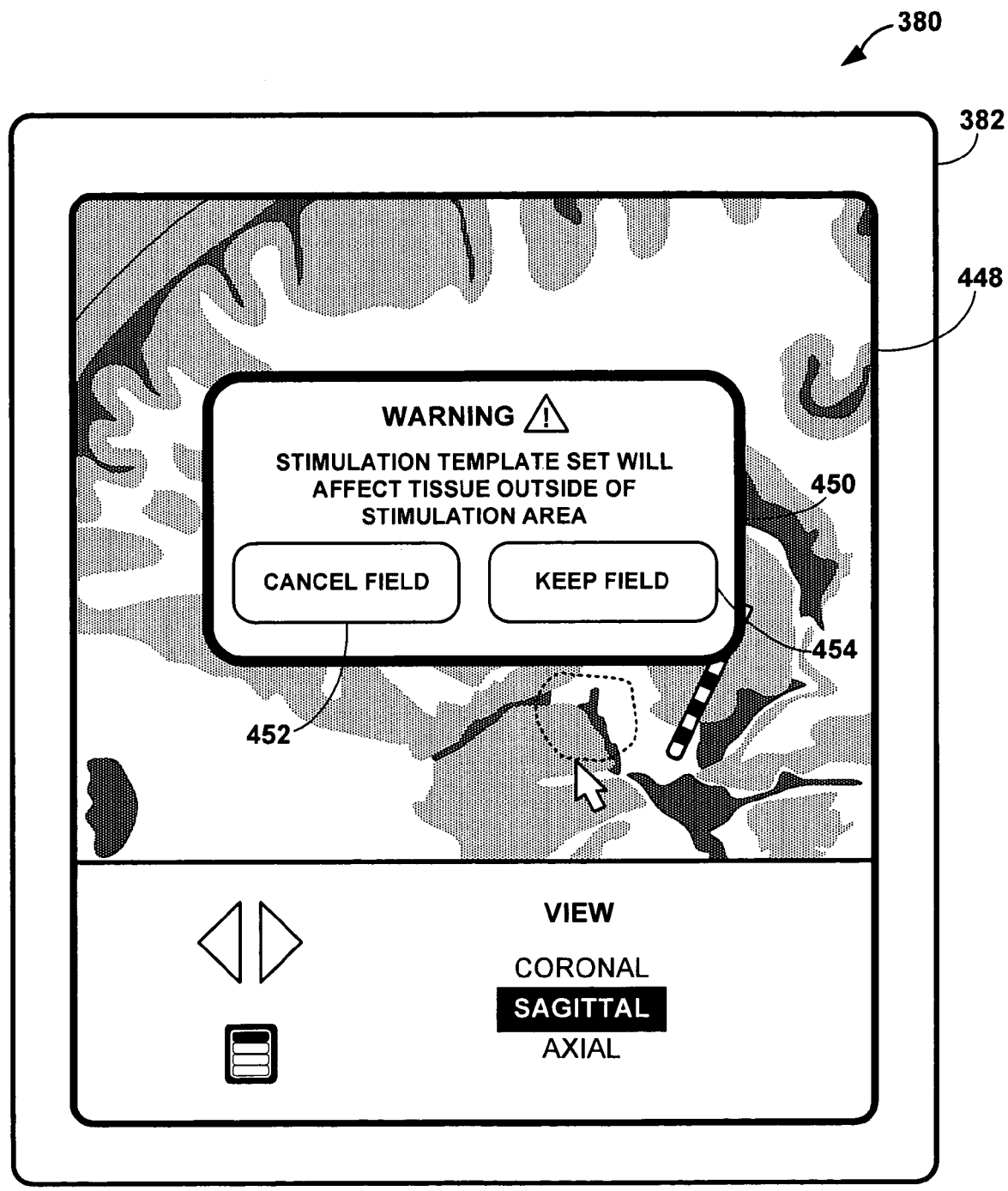
FIG. 27 is an example screen shot of a warning message regarding the best template set available for a stimulation field on a sagittal view of brain tissue.

FIG. 26 is an example screen shot of an outline of a stimulation field placed away from a lead icon on a sagittal view of brain tissue. As shown in FIG. 26, user interface 380 presents sagittal view 432 to the clinician with programmer 382. Similar to FIG. 24, previous arrow 434, next arrow 436, menu 438, and view indicator 440 are also provided to the clinician. Lead icon 444 represents the correct location of lead 14 implanted within patient 12. Using pointer 442, the clinician has outlined cross-sectional stimulation field 446 to cover the desired structures of the anatomical region. However, stimulation field 446 and the corresponding volumetric stimulation field does not overlap with any portion of lead icon 444. Therefore, any stimulation therapy will affect tissue outside of stimulation field 446 between the stimulation field and implanted lead 14. The clinician may be able to program the therapy in this manner, depending on the preferences stored within memory 82 of programmer 382. FIG. 27 indicates what may happen if a clinician creates a stimulation field such as stimulation field 446.

FIG. 27 is an example screen shot of a warning message regarding the best template set available for a stimulation field on a sagittal view of brain tissue. As shown in FIG. 27, user interface 380 provides sagittal view 448 on programmer 382. In this embodiment, system 10 uses stimulation templates to automatically generate stimulation parameters according to the stimulation field. However, according to FIG. 26, the clinician has defined a stimulation field 446 that does not overlap with lead icon 444. Therefore, warning box 450 is presented to the clinician. Warning box 450 indicates that the best fit stimulation template set will affect tissue of patient 12 that resides outside of the defined stimulation area 446. The clinician may select cancel button 452 to remove stimulation field 446 and re-define a stimulation field. Alternatively, the clinician may select keep button 454 to disregard the warning and proceed with the currently defined stimulation area 446.

In some embodiments, a similar message may be presented to the clinician without the use of stimulation templates, i.e., in embodiments in which stimulation parameters are automatically generated from the stimulation field defined by the clinician using any of the techniques described herein. In other embodiments, warning box 450 may provide a selection to the clinician that allows programmer 382 to suggest an alternative stimulation field that incorporates the currently selected stimulation field and areas adjacent to the lead. Warning box 450 may also be applied to user interface 314 of FIGS. 19-21.

Figure 28:
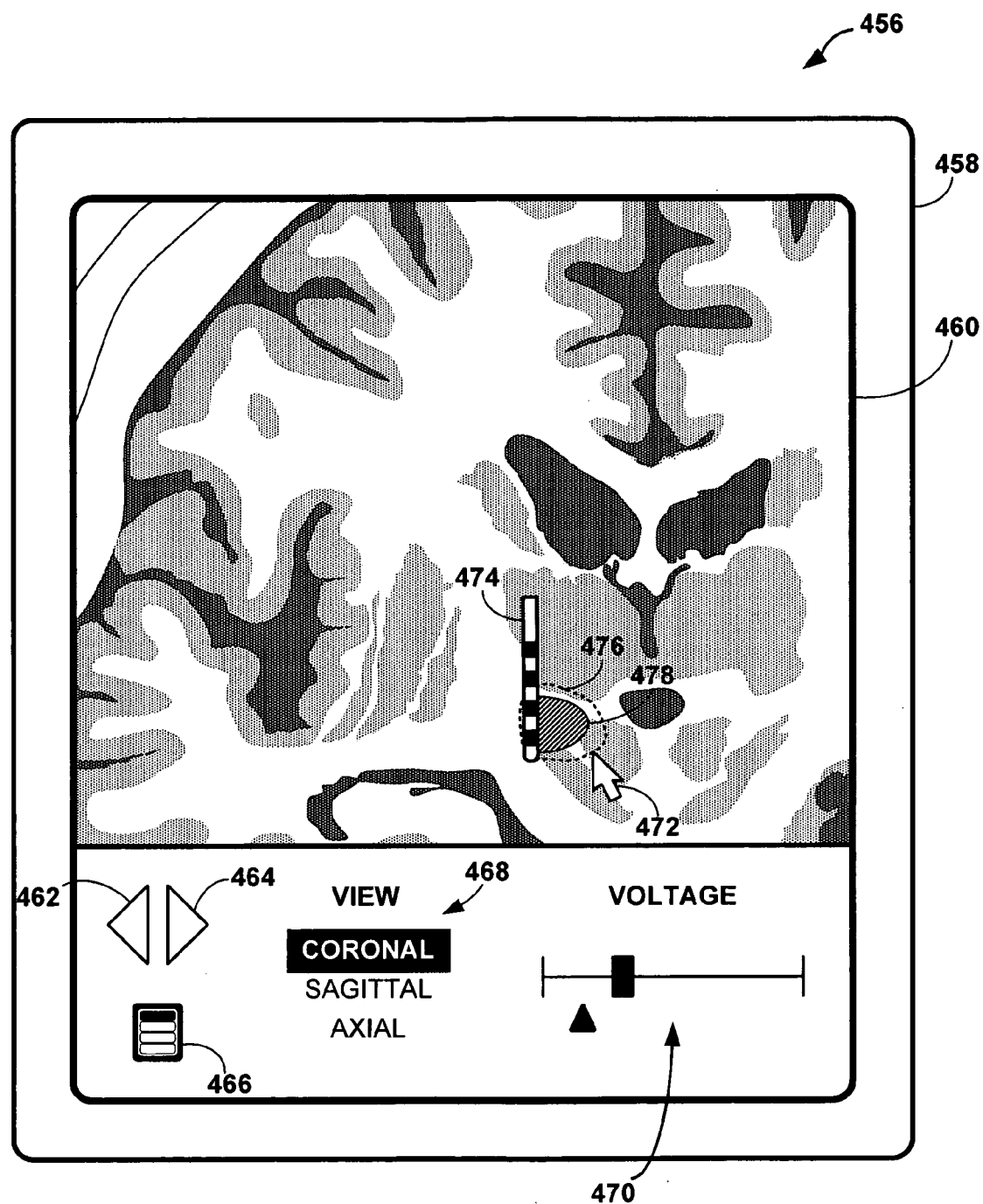
FIG. 28 is an example screen shot of an outline of a stimulation field and corresponding template set on a coronal view of brain tissue.

FIGS. 28-32 illustrate user interfaces which provide 2D views of an anatomical region overlaid with a stimulation field and corresponding best fit stimulation template set. FIG. 28 is an example screen shot of an outline of a stimulation field and corresponding template set on a coronal view of brain tissue. Programmer 458 presents coronal view 460 of an anatomical region of brain 18 to the clinician via user interface 456. Programmer 458 may be substantially similar to programmer 19. User interface 456 also includes previous arrow 462, next arrow 464, menu 466, view indicator 468, and voltage slider 470. Lead icon 474 represents the location of lead 14 implanted within patient 12. The clinician uses pointer 472 to define stimulation field 476. Programmer 458 creates a stimulation template set 478 that best fits stimulation field 496. Stimulation field 476 and stimulation template set 478 are each cross-sectional views of a volumetric stimulation field and a volumetric stimulation template, respectively. After the clinician has only defined one cross-section of the volumetric stimulation field, programmer 458 may estimate the volume and modify the estimation with further input from the clinician in other orthogonal views.

Figure 29:
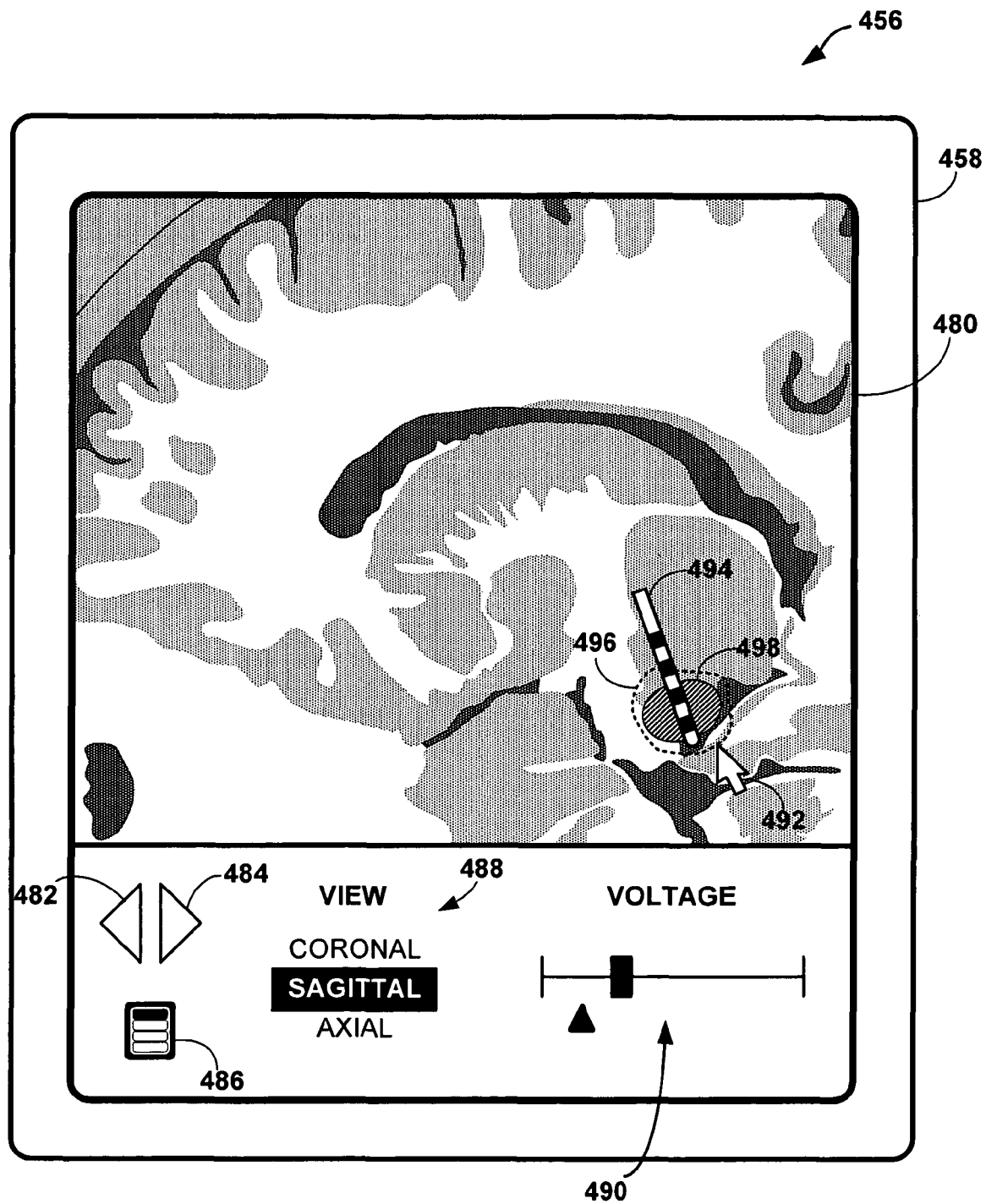
FIG. 29 is an example screen shot of an outline of a stimulation field and corresponding template set on a sagittal view of brain tissue.
Figure 30:
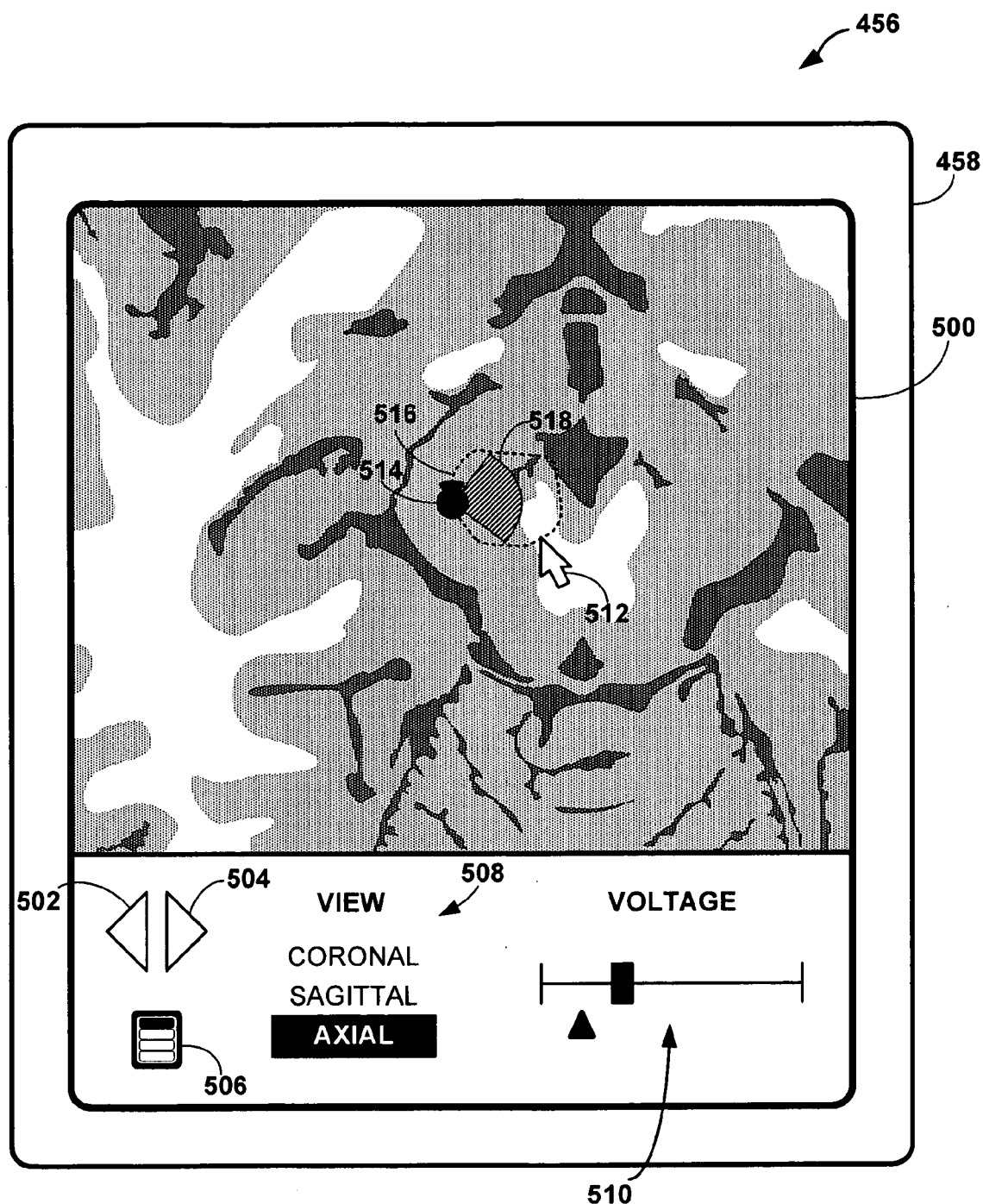
FIG. 30 is an example screen shot of an outline of a stimulation field and corresponding template set on an axial view of brain tissue.

In the example of FIGS. 28-30, stimulation template sets are selected by programmer 458, e.g., processor 80, to best fit the stimulation field, such as stimulation field 476. Processor 80 is governed by instructions stored in memory 82 which may indicate that a stimulation template set should cover as much area within stimulation field 476 without affecting any area of the anatomical region outside of the stimulation field. In this manner, all portions of a desired structure may not be treated by the electrical stimulation. However, unwanted side effects that could occur from stimulation affecting areas outside of stimulation field 476 may be less likely. As discussed above, in other examples, processor 80 may be governed by instructions stored in memory 82 that define how the stimulation template set must correlate to the stimulation field. In some cases, the instructions may cause the processor to select a stimulation template set that covers as much of the stimulation field without covering tissue outside of the stimulation area. In other cases, the instructions may cause processor 80 to select a stimulation template set that at least covers all of the stimulation field.

Voltage slider 470 may be used by the clinician to increase or decrease the overall size of stimulation field 476 from the origin of lead icon 474. Voltage slider 470 is an analog adjustment mechanism and may also be in the form of an adjustment knob instead of the slider. As the size of stimulation field 476 changes, the resulting best fit stimulation template set 478 may change, e.g., processor 80 may create a better fitting template set. In other embodiments, a new stimulation template set that fits the changes stimulation field 476 may only be provided if the user enters menu 466 to request programmer 458 try to identify a new stimulation template set. In addition, the clinician may view other coronal slices of the anatomical region by selecting previous button 462 or next button 464 that move to a different depth of the anatomical region. In some embodiments, programmer 458 may extrapolate stimulation field 476 and stimulation template 478 into other coronal slices of the anatomical regions if the clinician changes the slice. In other embodiments, lead icon 474 may be present in other slices, but stimulation field 476, stimulation template 468, or both, may not be present until the clinician defines the stimulation in at least one more orthogonal view so that programmer 458 can generate the volumetric stimulation field and template.

FIG. 29 is an example screen shot of an outline of a stimulation field and corresponding template set on a sagittal view of brain tissue. As shown in FIG. 29, user interface 456 presents sagittal view 480 of an anatomical region of brain 18 to the clinician via programmer 458. User interface 456 also includes previous arrow 482, next arrow 484, menu 486, view indicator 488, and voltage slider 490. Lead icon 494 represents the location of lead 14 implanted within patient 12. The clinician uses pointer 492 to outline and define stimulation field 496. Stimulation field 496 is a cross-section of a volumetric stimulation field defined by multiple orthogonal views. Programmer 458 continues to display the sagittal view of template 478 if that template remains the best fit to stimulation field 498. Otherwise, programmer 458 will generate a new stimulation template set that is a best fit for the volumetric stimulation field defined by stimulation fields 476 and 496. In some embodiments, the clinician may reference stimulation field 476 from coronal view 460 by a dotted line indicating the orthogonal 2D stimulation field 476. In other embodiments, stimulation field 496 may already be present in sagittal view 480 if programmer 458 estimates the volumetric stimulation field based upon the input in FIG. 28. In this case, the clinician may simply adjust the presented stimulation field to create stimulation field 496 as shown. These processes of defining the volumetric stimulation field may be used when viewing coronal, sagittal, and axial views in any order, not only the example order described herein.

The clinician may change the size of stimulation field 496 using voltage slider 490. Voltage slider 490 is an analog adjustment mechanism and may also be in the form of an adjustment knob instead of the slider. The modified stimulation field 496 size may accommodate a different stimulation template set 498 that best fits the defined stimulation field. In addition, the clinician may move stimulation field 496 with pointer 492 to another location in sagittal view 480. As in FIG. 28, the clinician may view different depth slices of the anatomical region by selecting previous arrow 482 or next arrow 484.

FIG. 30 is an example screen shot of an outline of a stimulation field and corresponding template set on an axial view of brain tissue. As shown in FIG. 29, user interface 456 presents axial view 500 of an anatomical region of brain 18 to the clinician via programmer 458. User interface 456 also includes previous arrow 502, next arrow 504, menu 506, view indicator 508, and voltage slider 510. Lead icon 514 represents the location of lead 14 implanted within patient 12. Stimulation field 516 is already displayed on axial view 500 and is a cross-section of the volumetric stimulation field defined by stimulation fields 476 and 496 of FIGS. 28 and 29, if they are defined first. However, the clinician may use pointer 512 to alter the shape or size of stimulation field 516. Programmer 458 creates a stimulation template set 518 that best fits stimulation field 516. In other embodiments, the clinician may have selected to begin defining the volumetric stimulation field in axial view 500; therefore, there stimulation field 516 may not be already displayed on the axial view.

The clinician may change the size of stimulation field 516 using voltage slider 510. Voltage slider 510 is an analog adjustment mechanism and may also be in the form of an adjustment knob instead of the slider. The modified stimulation field 516 size may accommodate a different stimulation template set 518 that best fits the defined stimulation field. In addition, the clinician may move stimulation field 516 with pointer 512 to another location in axial view 500. As in FIG. 28, the clinician may view different depth slices of the anatomical region by selecting previous arrow 502 or next arrow 504.

Figure 31:
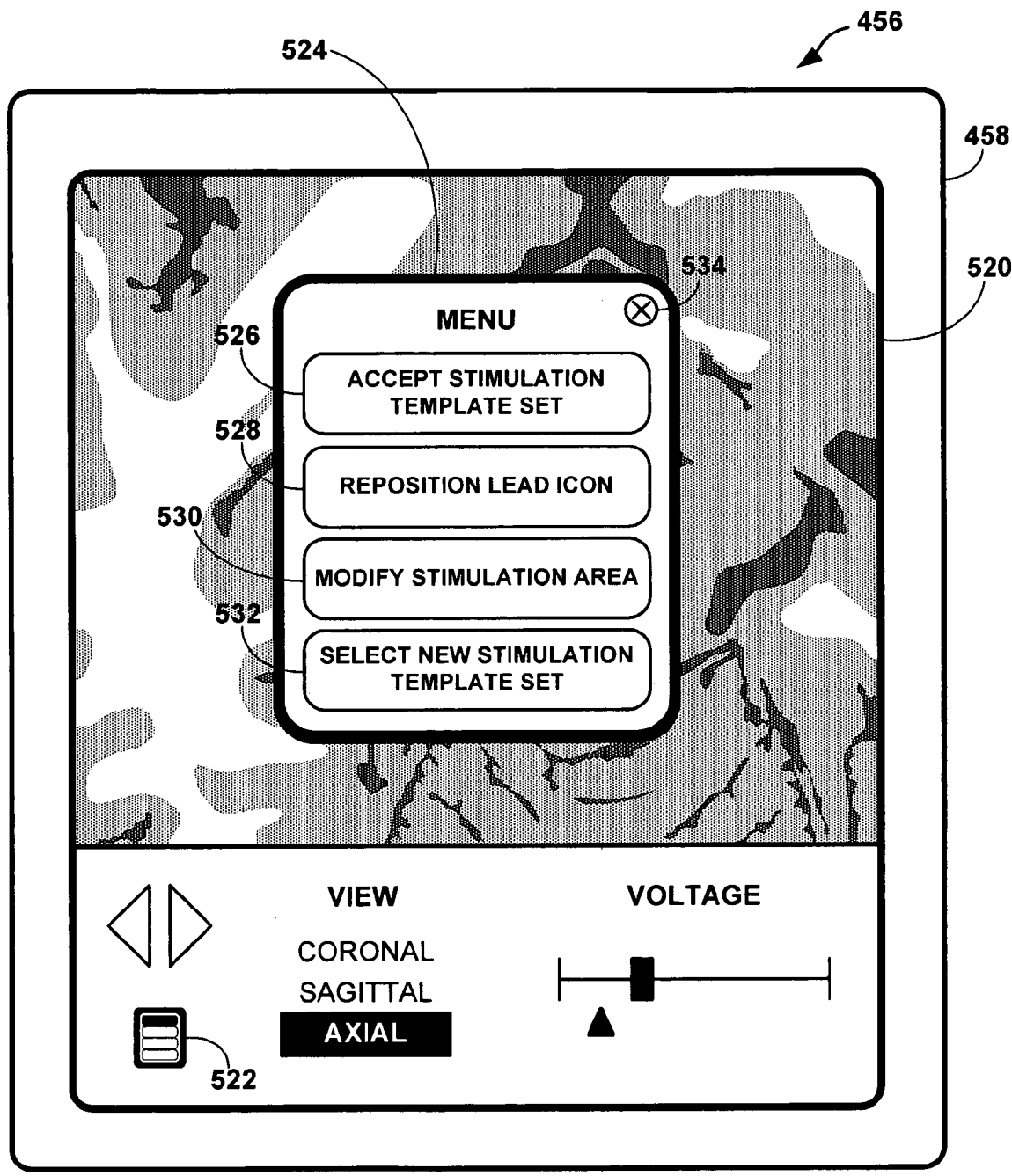
FIG. 31 is an example screen shot of a menu window for template sets over a sagittal view of brain tissue.

FIG. 31 is an example screen shot of a menu window for template sets over a sagittal view of brain tissue. User interface 456 includes menu box 524, which may be accessed from menu 522, which may be substantially similar to any of menus 466, 486 or 506. Menus 466, 486 and 506 have similar functionality, and are numbered differently to reflect that they are present in different views of user interface 456. Menu box 524 provides options for the clinician such as accept button 526, reposition button 528, modify button 530, and template button 532. The clinician may select any of buttons 526, 528, 530 and 532 when the clinician desires that function. The clinician may also select exit button 534 to close menu box 524. Alternative embodiments of menu button 524 may include more or less buttons that perform similar tasks related to programming the stimulation therapy.

Figure 32:
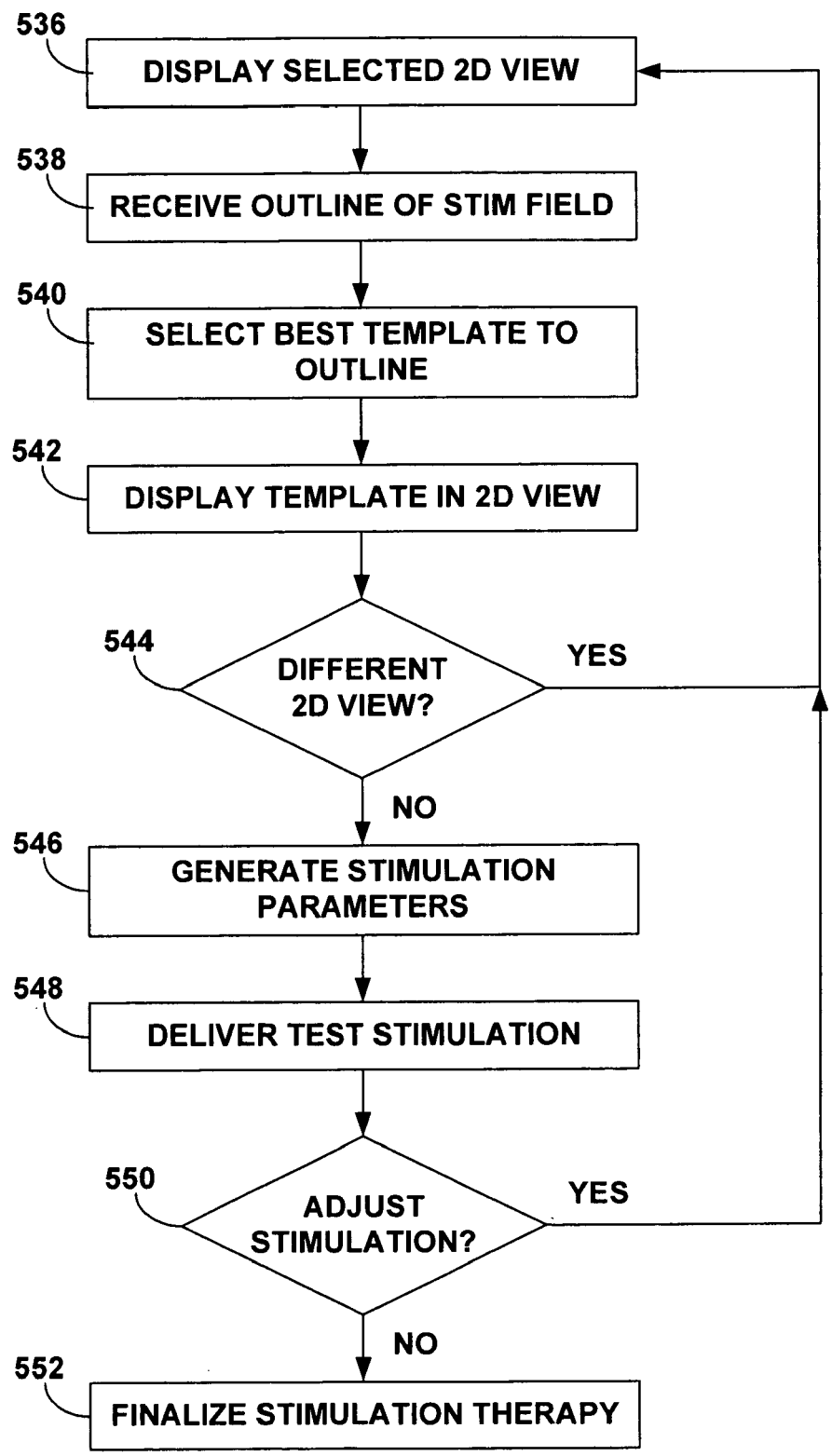
FIG. 32 is a flow diagram illustrating an example technique for creating a stimulation template set based upon received stimulation fields defined by the user.

FIG. 32 is a flow diagram illustrating an example technique for creating a stimulation template set based upon received stimulation fields defined by the user. As shown in FIG. 32, user interface 456 begins by displaying the first default 2D view of the anatomical region, e.g., a coronal view, or the 2D view selected by the clinician (536). User interface 456 next receives the outline of a stimulation field from the clinician (538) and selects the best initial template set that fits the stimulation field currently defined by the clinician (540). User interface then displays the stimulation template set with the stimulation field in the selected 2D view (542). If the user selects another 2D view (544), user interface 456 displays the newly selected 2D view (536). After multiple stimulation fields have been defined in different orthogonal views, the volumetric stimulation field becomes more accurate to reflect the desired therapy of the clinician.

If the user does not select a different 2D view (544), user interface 456 will generate stimulation parameters according to the stimulation template set that best fits the stimulation field (546). Programmer 458 will transmit the stimulation parameters to IMD 20 and deliver test stimulation with the stimulation parameters (548). If the clinician desires to adjust the stimulation therapy (550), user interface will again display a selected or default 2D view of the anatomical region (536). If the clinician does not need to make any therapy adjustments, system 10 will finalize the stimulation therapy for chronic use (552).

In some embodiments, test stimulation may be provided to patient 12 in real time as the clinician defines new stimulation fields. This manner of testing therapy may take less time for the clinician to find an appropriate therapy. In other embodiments, programmer 458 may not need to generate stimulation parameters after the stimulation template set has been selected because the stimulation template set may already include stimulation parameters as needed by IMD 20 to provide the therapy.

Figure 33:
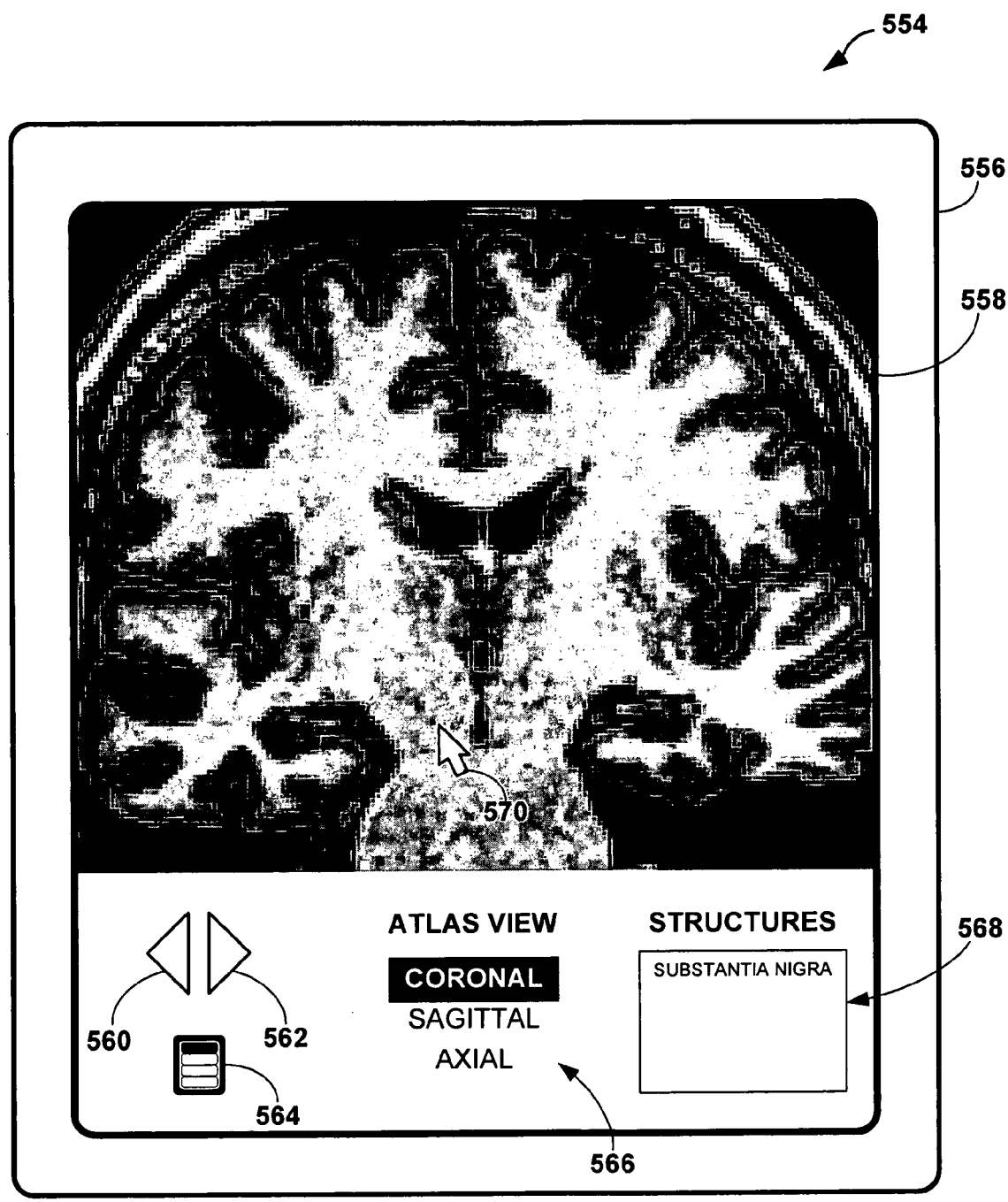
FIG. 33 is an example screen shot of a coronal view of reference anatomy brain tissue to aid the user in selecting a structure of the anatomy to stimulate.

FIGS. 33-38 illustrate user interfaces that provide an atlas to a clinician for selecting structures of an anatomical region to stimulate. FIG. 33 is an example screen shot of a coronal view of reference anatomy brain tissue to aid the user in selecting a structure of the anatomy to stimulate. As shown in FIG. 33, user interface 554 presents coronal view 558 of an atlas to the clinician via programmer 556. Programmer 556 is an embodiment of programmer 19. User interface 554 also includes previous arrow 560, next arrow 562, menu 564, view indicator 566, and structure box 568. Pointer 570 is used by the clinician, or another user, to select a structure of the anatomical region represented in coronal view 558 to program stimulation therapy.

Coronal view 558 presents an atlas, where the atlas is a reference anatomical region of a reference anatomy. The atlas may be represented in the form of a drawing or actual image from an imaging modality such as magnetic resonance imaging (MRI), computer-aided tomography (CT), or other similar imaging technique. The reference anatomy may be an anatomy different from patient 12 anatomy. Specific structures of the reference anatomy may be identified and their locations within the reference anatomy determined to create an atlas. The atlas may be stored in memory 82. While the atlas of coronal view 558 is mostly likely slightly different from the patient anatomical region of patient 12 anatomy, the structure locations may be close enough to generate stimulation parameters based upon the atlas. In this manner, the clinician may not need to recognize each structure of patient 12. Instead, the clinician may only need to select the structure that is recognizable in the atlas. The clinician may use pointer 570 to select a specific structure of the atlas, at which time the structure name is displayed in structure box 568. In the example of FIG. 33, the substantia nigra has been identified in the atlas, and programmer 556 will map that structure of the atlas to the location of lead 14 in brain 18.

User interface 554 may also allow the clinician to view other 2D sections of the atlas by using previous arrow 560 and next arrow 562 to move to other depths of the atlas. Since structures may be located throughout the volume of the 3D atlas, the clinician may need to move to other slices of the atlas to find a structure of interest. In some embodiments, user interface 554 may include a search input that allows the clinician to type in a structure name to move directly to the correct depth of the atlas.

Programmer 556 generates stimulation parameters based upon the location of the one or more selected structures to the location of lead 14. In some embodiments, generating stimulation parameters may include selection of stimulation templates and creation of a stimulation template set based on the selected structures. In any case, the atlas allows the clinician to quickly select the most appropriate structure that needs to be stimulated to treat the condition of patient 12.

Figure 34:
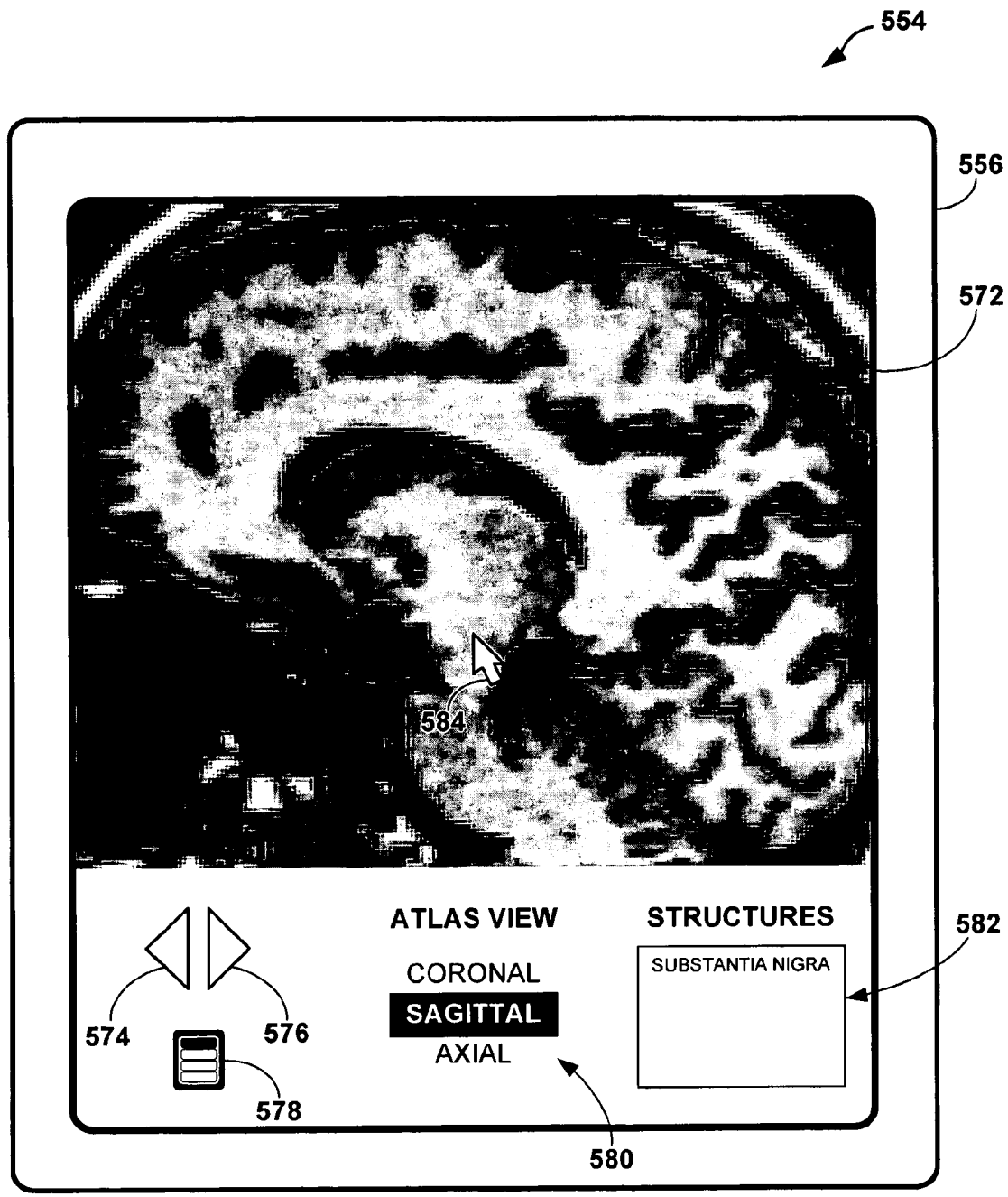
FIG. 34 is an example screen shot of a sagittal view of reference anatomy brain tissue to aid the user in selecting a structure of the anatomy to stimulate.

FIG. 34 is an example screen shot of a sagittal view of reference anatomy brain tissue to aid the user in selecting a structure of the anatomy to stimulate. As shown in FIG. 34, user interface 554 presents sagittal view 572 of an atlas to the clinician via programmer 556. User interface 554 also includes previous arrow 574, next arrow 576, menu 578, view indicator 580, and structure box 582. Pointer 584 is used by the clinician, or another user, to select a structure of the atlas represented in sagittal view 572 to program stimulation therapy, similar to FIG. 33.

Previous arrow 574 and next arrow 576 allow the clinician to move to other depths of the atlas for sagittal view 572.

Since structures may be located throughout the volume of the 3D atlas, the clinician may need to move to other slices of the atlas to find a structure of interest. In some embodiments, user interface 554 may include a search input that allows the clinician to type in a structure name to move directly to the correct depth of the atlas in the sagittal plane. In some embodiments, the clinician may not need to access sagittal view 572 because the desired structure may be found in coronal view 558.

Figure 35:
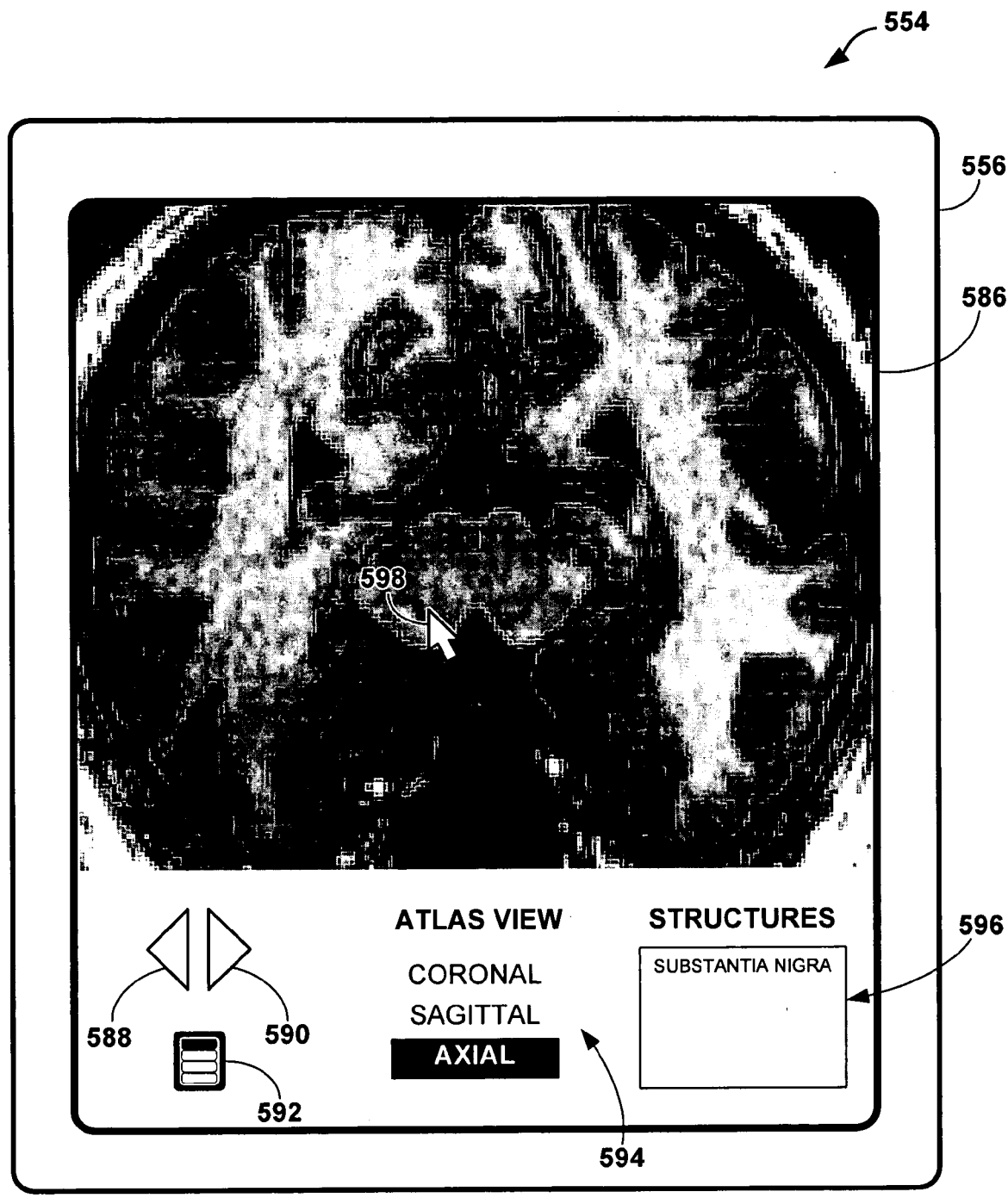
FIG. 35 is an example screen shot of an axial view of reference anatomy brain tissue to aid the user in selecting a structure of the anatomy to stimulate.

FIG. 35 is an example screen shot of an axial view of reference anatomy brain tissue to aid the user in selecting a structure of the anatomy such that parameters for stimulation of patient 12 may be automatically determined based on the selected structure. As shown in FIG. 35, user interface 554 presents axial view 586 of an atlas to the clinician via programmer 556. User interface 554 also includes previous arrow 588, next arrow 590, menu 592, view indicator 594, and structure box 596. Pointer 598 is used by the clinician, or another user, to select a structure of the atlas represented in sagittal view 572 to program stimulation therapy, similar to FIGS. 33 and 34. In some embodiments, the clinician may not need to access axial view 586 because the desired structure may be found in coronal view 558 or sagittal view 572.

Previous arrow 588 and next arrow 590 allow the clinician to move to other depths of the atlas for axial view 586. Since structures may be located throughout the volume of the 3D atlas, the clinician may need to move to other slices of the atlas to find a structure of interest. In some embodiments, user interface 554 may include a search input that allows the clinician to type in a structure name to move directly to the correct depth of the atlas in the sagittal plane.

In some embodiments of user interface 554, the user interface may highlight the selected one or more structures once the clinician has made the selection in the atlas. This graphical representation of the selected structures may allow the clinician to review the structures for accuracy in where stimulation therapy should occur. Alternatively, the atlas may show areas of atlas where stimulation therapy should be avoided to prevent unwanted side-effects. The highlighted structures may allow the clinician to make sure that no overlaps occur between the selected structures and areas where stimulation should be avoided.

Figure 36:
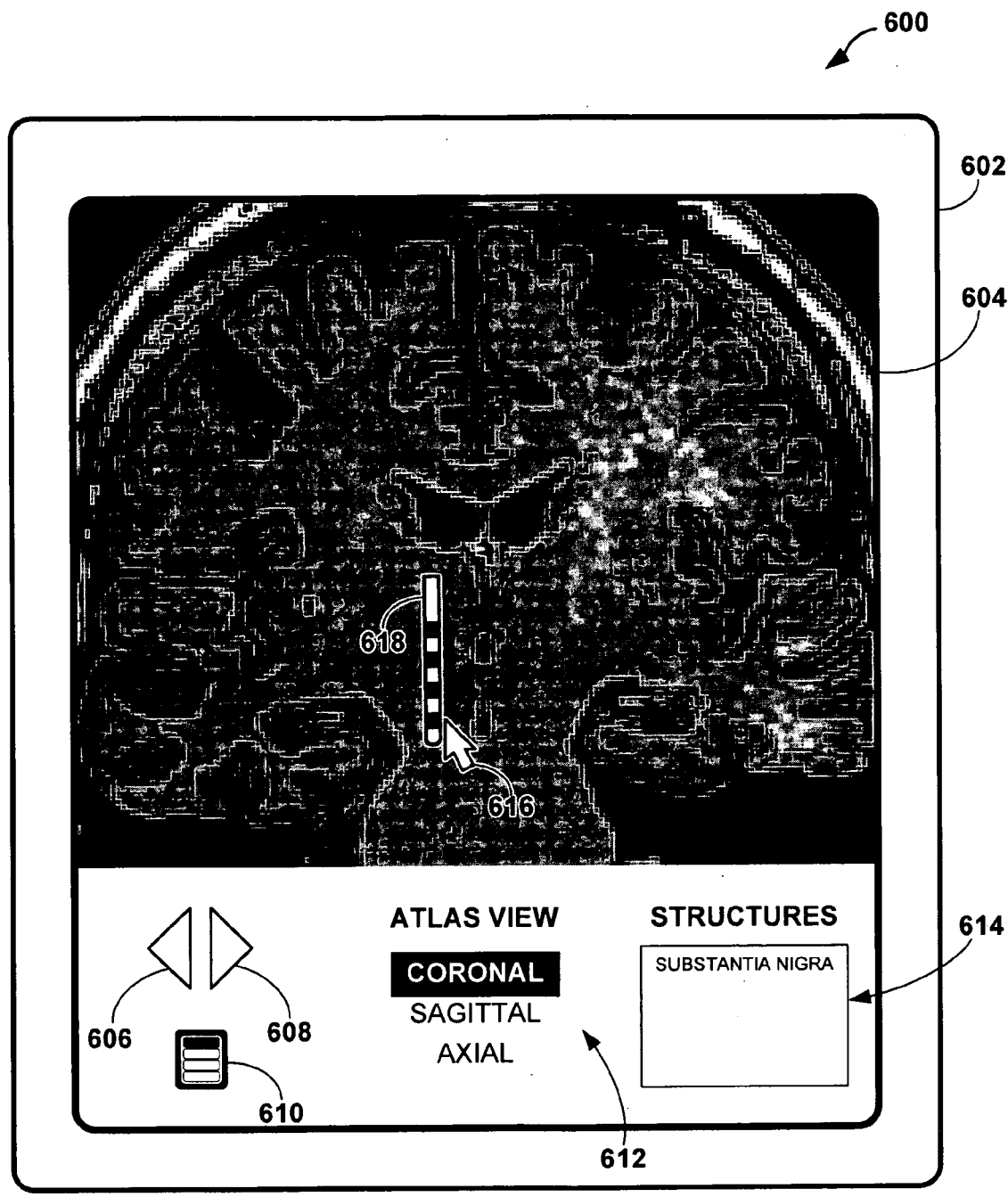
FIG. 36 is an example screen shot of a coronal view of reference anatomy brain tissue with the lead icon to aid the user in selecting a structure of the anatomy to stimulate.

FIG. 36 is an example screen shot of a coronal view of reference anatomy brain tissue with the lead icon to aid the user in selecting a structure of the anatomy such that parameters for stimulation of patient 12 may be automatically determined based on the selected structure. As shown in FIG. 36, user interface 600 presents coronal view 604 of an atlas of to the clinician via programmer 602. Programmer 602 is an embodiment of programmer 19. User interface 600 also includes previous arrow 606, next arrow 608, menu 610, view indicator 612, and structure box 614. Pointer 616 is used by the clinician, or another user, to select a structure of the anatomical region represented in coronal view 604 to program stimulation therapy. FIG. 36 is substantially similar to FIG. 33, except that lead icon 618 is provided in user interface 600 to represent the implant location of lead 14.

The clinician may place lead icon 618 into coronal view 604 of the atlas according to the implantation location within patient 12. In alternative embodiments, system 10 may automatically enter the correct lead icon 618 location according to coordinates provided by the clinician, a surgeon, or an image of lead 14 within patient 12. The clinician may prefer to use lead icon 618 location within the atlas as a reference location to select the appropriate structures. Based on the location of lead icon 618 and the selected structures within the atlas, programmer 602 may be able to automatically determine parameters for delivery of stimulation from lead 14 to patient 12.

Figure 37:
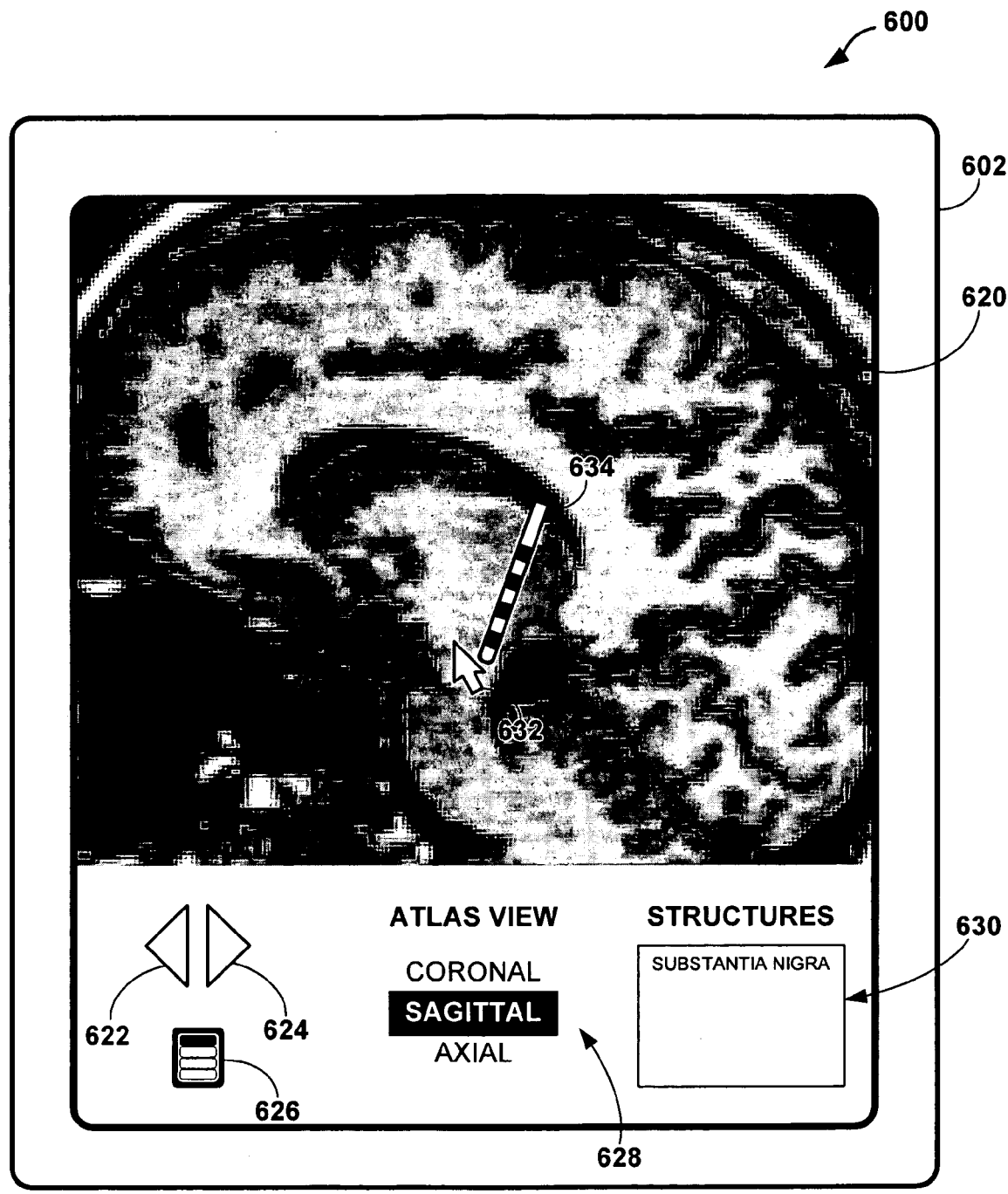
FIG. 37 is an example screen shot of a sagittal view of reference anatomy brain tissue with the lead icon to aid the user in selecting a structure of the anatomy to stimulate.

FIG. 37 is an example screen shot of a sagittal view of reference anatomy brain tissue with the lead icon to aid the user in selecting a structure of the anatomy to stimulate. As shown in FIG. 37, user interface 600 presents sagittal view 620 of an atlas to the clinician via programmer 602. User interface 600 also includes previous arrow 622, next arrow 624, menu 626, view indicator 628, and structure box 630. Pointer 632 is used by the clinician, or another user, to select a structure of the atlas represented in sagittal view 620 to program stimulation therapy. FIG. 37 is substantially similar to FIG. 34, except that lead icon 634 is provided in user interface 600 to represent the implant location of lead 14 for reference to the clinician. The clinician may adjust the location of lead icon 634 in coronal view 620 of the atlas according to the implantation location within patient 12. Similar to FIG. 36, the clinician may prefer to use lead icon 634 location within the atlas as a reference location to select the appropriate structures for generating stimulation parameters.

Figure 38:
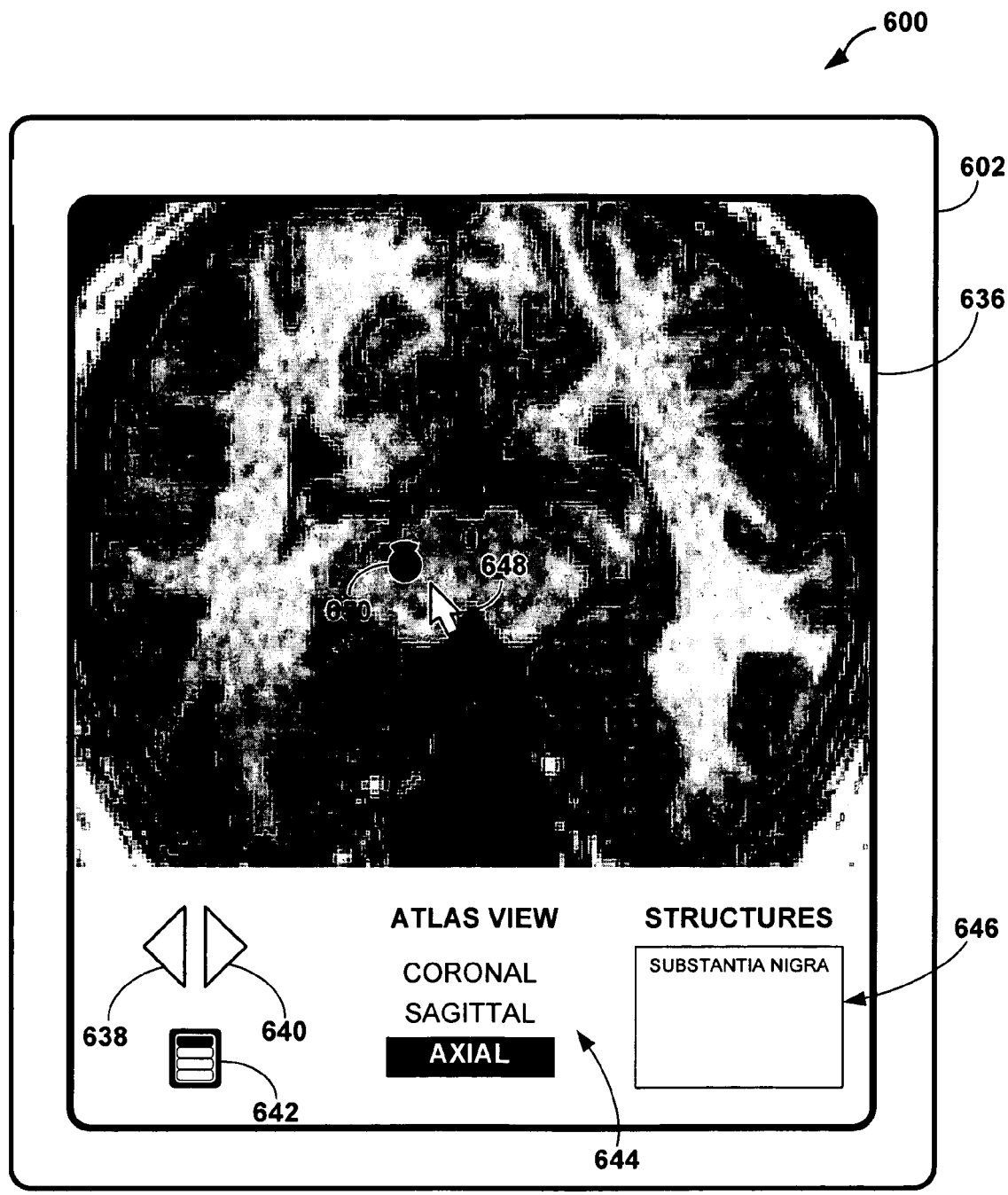
FIG. 38 is an example screen shot of an axial view of reference anatomy brain tissue to with the lead icon aid the user in selecting a structure of the anatomy to stimulate.

FIG. 38 is an example screen shot of an axial view of reference anatomy brain tissue with a lead icon to aid the user in selecting a structure of the anatomy to stimulate. As shown in FIG. 38, user interface 600 presents axial view 636 of an atlas to the clinician via programmer 602. User interface 600 also includes previous arrow 638, next arrow 640, menu 642, view indicator 644, and structure box 646. Pointer 648 is used by the clinician, or another user, to select a structure of the atlas represented in coronal view 604 or sagittal view 620 to program stimulation therapy, similar to FIG. 35. FIG. 38 is substantially similar to FIG. 35, except that lead icon 650 is provided in user interface 600 to represent the implant location of lead 14 for reference to the clinician. The clinician may adjust the location of lead icon 650 in axial view 636 of the atlas according to the implantation location within patient 12. Similar to FIG. 36, the clinician may prefer to use lead icon 350 location within the atlas as a reference location to select the appropriate structures for generating stimulation parameters.

Figure 39:
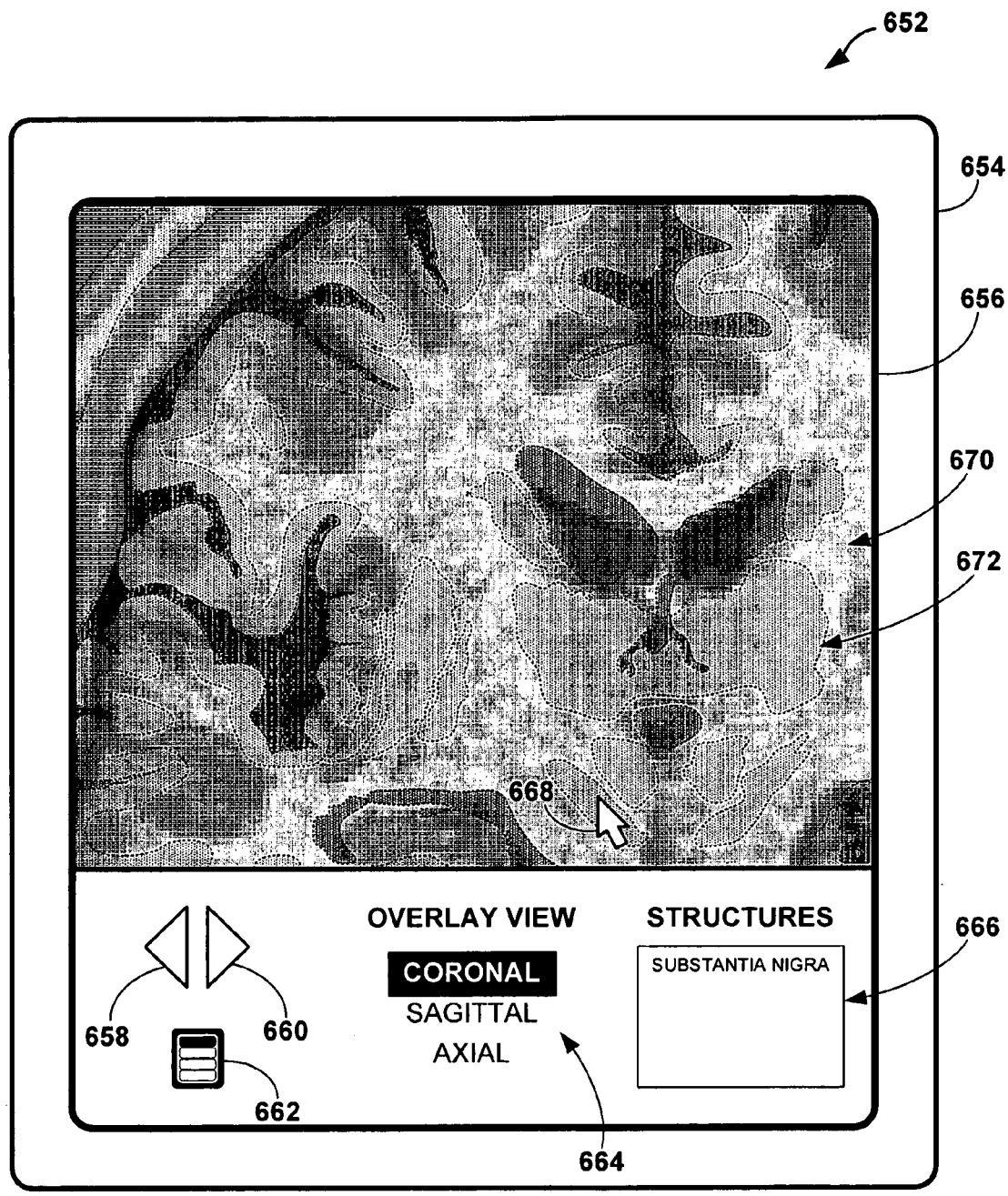
FIG. 39 is an example screen shot of a coronal view of reference anatomy brain tissue overlaid over a coronal view of the patient anatomy to aid the user in selecting a structure of the patient anatomy to stimulate.
Figure 40:
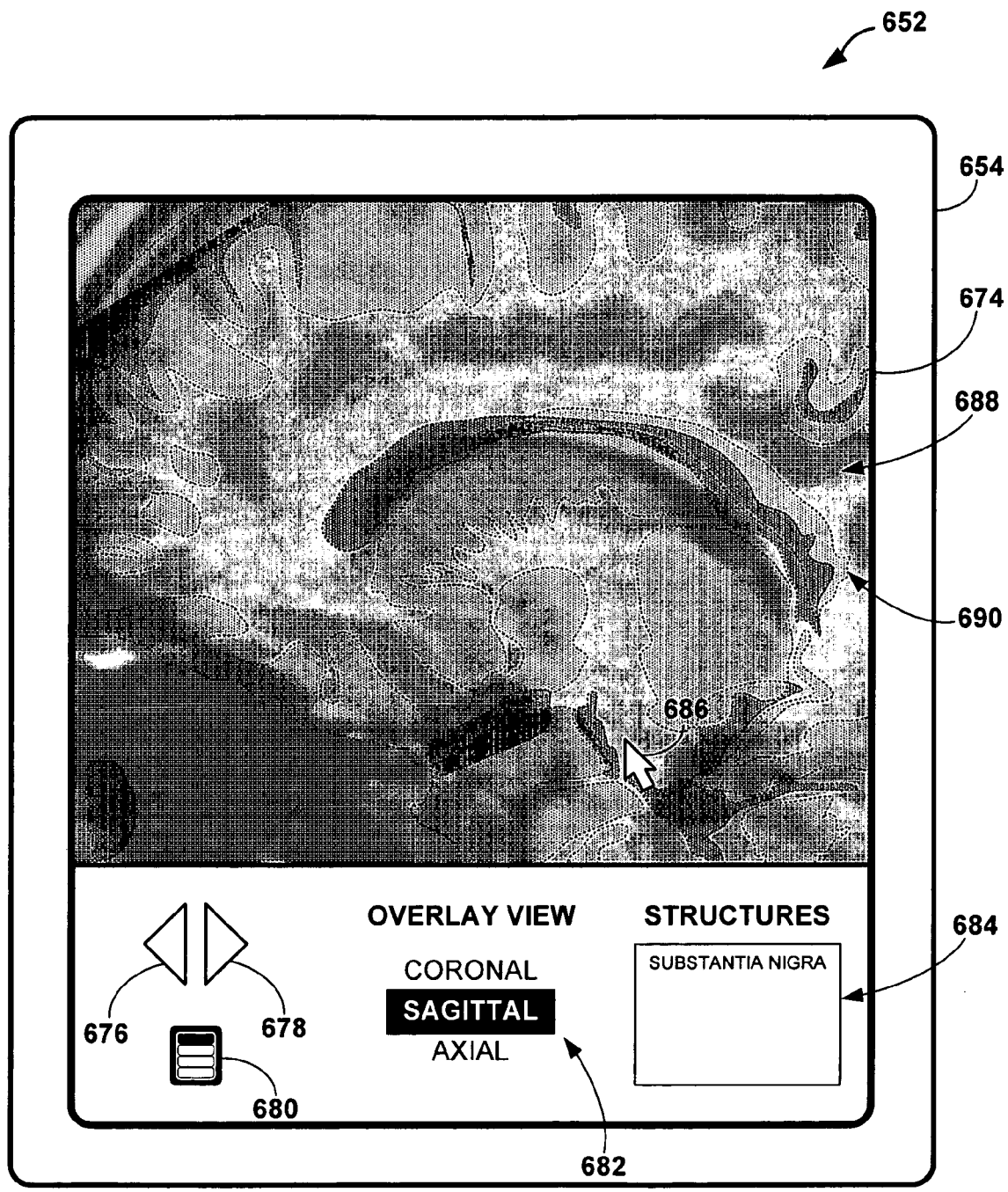
FIG. 40 is an example screen shot of a sagittal view of reference anatomy brain tissue overlaid over a sagittal view of the patient anatomy to aid the user in selecting a structure of the patient anatomy to stimulate.
Figure 41:
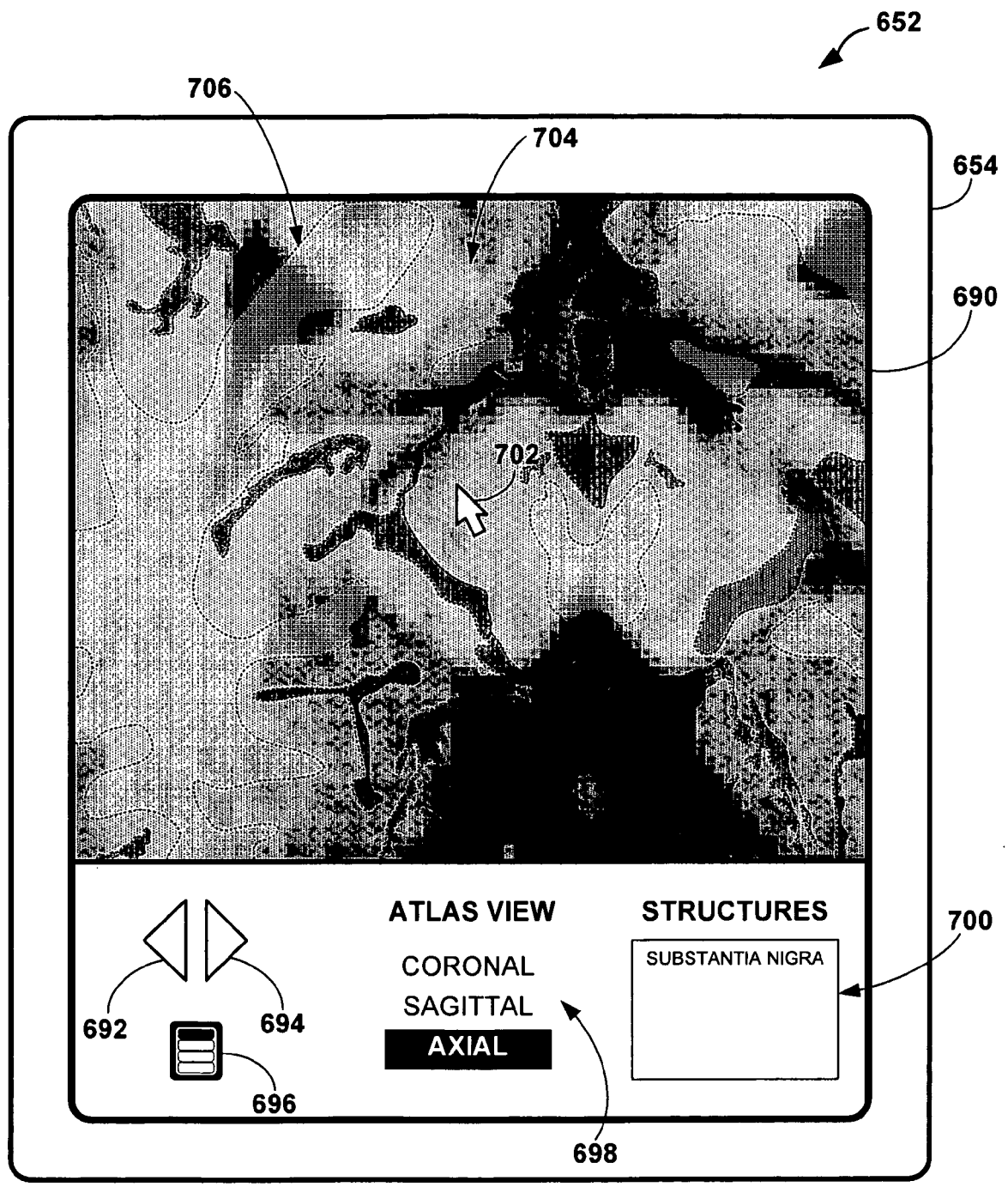
FIG. 41 is an example screen shot of an axial view of reference anatomy brain tissue overlaid over an axial view of the patient anatomy to aid the user in selecting a structure of the patient anatomy to stimulate.

FIGS. 39-41 illustrate a user interface which includes an atlas overlaid with a patient anatomical region (shown in the examples via dotted lines and shading) that allows a clinician to select a structure for stimulation. In other embodiments, the atlas may be computer generated images while the patient anatomy is an actual CT image. Alternatively, both the atlas and patient anatomy are CT images or some other imaging modality which are separated by coloration, shading, or some other visual distinction. Furthermore, while not necessary, the clinician may be able to search different slices of each 2D view in order to locate specific anatomical structures in the atlas and patient anatomical region. FIG. 39 is an example screen shot of a coronal view of reference anatomy brain tissue overlaid over a coronal view of the patient anatomy to aid the user in selecting a structure of the anatomy to stimulate. As shown in FIG. 39, programmer 654 presents coronal view 656 of an atlas 670 and a coronal view 656 of a patient anatomical region 672 to the clinician via user interface 652. Programmer 654 may be substantially similar to programmer 19. User interface 652 also includes previous arrow 658, next arrow 660, menu 662, view indicator 664, and structure box 666. Pointer 668 is used by the clinician, or another user, to select a structure of atlas 670 represented in coronal view 656 to program stimulation therapy. FIG. 39 is substantially similar to FIG. 33, except that patient anatomical region 672 is provided over atlas 670 to allow the clinician to view both the atlas and actual anatomy of patient 12 at the same time.

The clinician may select structures directly from the locations within atlas 670. Patient anatomical region 672 is scaled to atlas 670 and provided to indicate to the clinician where the actual structure of patient 12 is located in relation to the atlas. In cases where atlas 670 closely mirrors the anatomy of patient 12, overlaying patient anatomical region 672 may not be necessary for programming stimulation therapy. However, adding patient anatomical region 672 may be beneficial to the clinician in correctly treating patient 12 while avoiding problematic areas of brain 18 that may induce side-effects. Patient anatomical region 672 may be partially transparent so that atlas 670 may be readily viewable by the clinician or other user.

In some embodiments, user interface 652 may allow the clinician to toggle between viewing only atlas 670 or patient anatomical region 672 for clarity. Menu 662 may allow the clinician to select the transparency of patient anatomical region 672 according to their preference. In alternative embodiments, user interface may also present a lead icon in coronal view 656, similar to FIG. 36. The lead icon may be placed within patient anatomical region 672 to accurately show the clinician from where stimulation therapy will be originating in patient 12.

FIG. 40 is an example screen shot of a sagittal view of reference anatomy brain tissue overlaid over a sagittal view of the patient anatomy to aid the user in selecting a structure of the patient anatomy to stimulate. As shown in FIG. 40, user interface 652 presents sagittal view 674 of an atlas 688 and a patient anatomical region 690 to the clinician via programmer 654. User interface 652 also includes previous arrow 676, next arrow 679, menu 680, view indicator 682, and structure box 684. Pointer 686 is used by the clinician, or another user, to select a structure of atlas 688 represented in sagittal view 674 to program stimulation therapy. FIG. 40 is substantially similar to FIG. 34, except that patient anatomical region 690 is provided over atlas 688 to allow the clinician to view both the atlas and actual anatomy of patient 12 at the same time. As in FIG. 39, patient anatomical region 690 is at least partially transparent so that atlas 688 can be seen as well. The clinician may also use previous arrow 676 and next arrow 678 to move between slices at different depths than is shown in sagittal view 674.

FIG. 41 is an example screen shot of an axial view of reference anatomy brain tissue overlaid over an axial view of the patient anatomy to aid the user in selecting a structure of the patient anatomy to stimulate. As shown in FIG. 41, programmer 654 presents axial view 690 of an atlas 704 and a patient anatomical region 706 to the clinician via user interface 652. User interface 652 also includes previous arrow 692, next arrow 694, menu 696, view indicator 698, and structure box 700. Pointer 702 is used by the clinician, or another user, to select a structure of atlas 704 represented in axial view 690 to program stimulation therapy. FIG. 41 is substantially similar to FIG. 35, except that patient anatomical region 706 is provided over atlas 704 to allow the clinician to view both the atlas and actual anatomy of patient 12 at the same time. As in FIG. 39, patient anatomical region 706 is at least partially transparent so that atlas 704 can be seen as well. The clinician may also use previous arrow 692 and next arrow 694 to move between slices at different depths than is shown in axial view 690. Once the clinician is satisfied with the selected structures, the clinician can use menu 696 to request that programmer 654 generate stimulation parameters based upon the selected structures. In other embodiments, user interface 652 may provide a separate button to generate the stimulation parameters.

Figure 42:
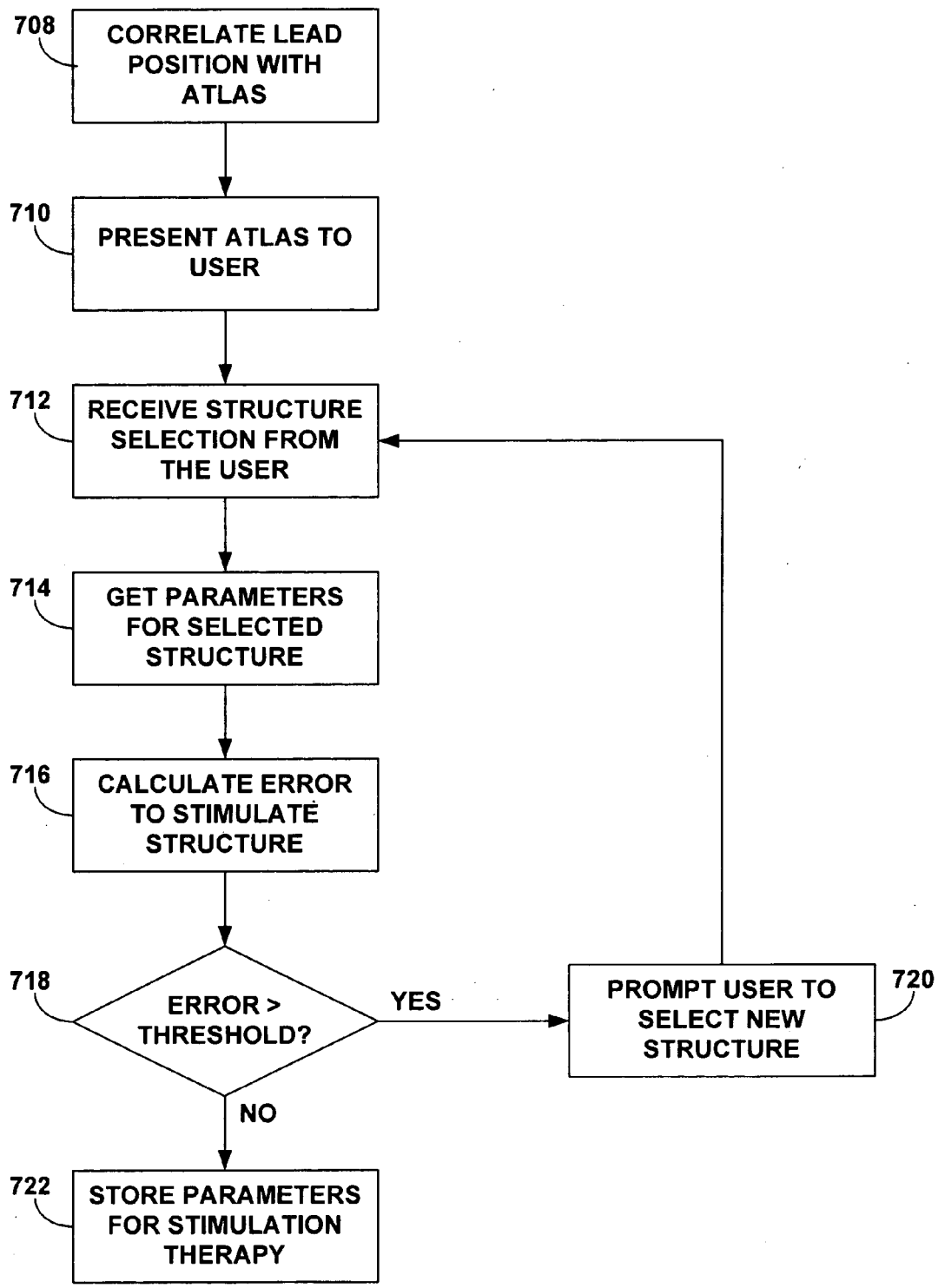
FIG. 42 is a flow diagram illustrating an example technique for receiving stimulation input from a user using the reference anatomy.

FIG. 42 is a flow diagram illustrating an example technique for receiving stimulation input from a user using the reference anatomy, or atlas. FIG. 42 may correspond to the process of programming the stimulation therapy illustrated in any examples if FIGS. 33-41. However, user interface 554 of FIGS. 33-35 will be used as an example. The method begins when programmer 556 correlates the actual lead 14 position within patient 12 to the coordinates of the atlas (708). User interface 556 then presents the atlas to the clinician (710) and receives the structure selection from the clinician after the clinician has viewed the various 2D views of the atlas (712). Processor 80 of programmer 558 next generates stimulation parameters for the selected one or more structures in accordance with the location of lead 14 relative to the structures selected (714). Processor 80 also calculates an error for the stimulation therapy to the structures that are to be treated (716). Calculating the error may involve identifying the extent to which structures other than the selected structure must be stimulation in order for an IMD to deliver stimulation from lead to the selected structures. Processor 80 may calculate the error as a volume of extraneous tissue stimulated. Processor 80 may apply a weighting factor to the error based on the likelihood that stimulation of the particular extraneous tissue will result in side effects. If the error is greater than a predetermined threshold (718), user interface 558 prompts the clinician to select a new structure that may have a lower error (720). Then, user interface 556 again receives structure selection from the clinician (712).

If the error is smaller than the predetermined threshold, programmer 558 may store the stimulation parameters and initiate the transfer of the stimulation parameters to IMD 20. Calculating the error may reduce the frequency and magnitude of side-effects that may be produced from stimulation therapy affecting non-target structures. In addition, calculating the error may reduce the number of ineffective stimulation parameters tried that do not fully treat the structure of concern. In either case, the error calculation may improve therapy efficacy and reduce clinician programming trial and error.

Figure 43:
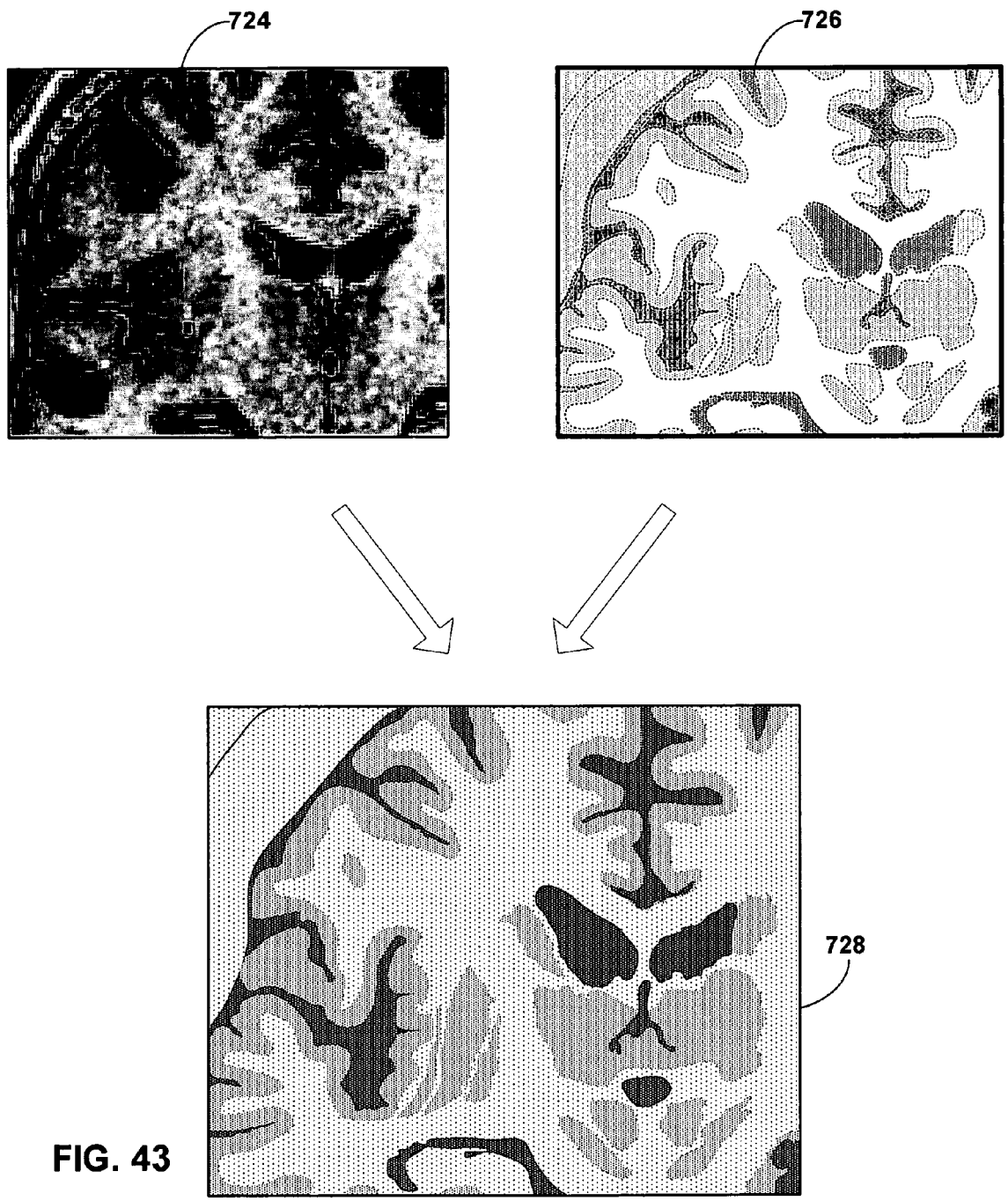
FIG. 43 is an illustration that shows how the reference anatomy may be combined with the patient anatomy to result in a morphed atlas for programming the stimulation therapy.

FIG. 43 is an illustration that shows how the reference anatomy may be combined with the patient anatomy to result in a morphed atlas for programming the stimulation therapy. Atlas 724 is shown as a CT image while patient anatomical region 726 is illustrated as a computer model. In other embodiments, atlas 724 and patient anatomical region 726 may be any combination of CT images and/or computer models. As shown in FIG. 43, atlas 724 is a reference anatomical region of a reference anatomy. Atlas 724 is beneficial to use in programming stimulation therapy because the location of specific structures is know and readily identifiable. However, atlas 724 does not represent the actual anatomy of patient 12 surrounding implanted lead 14. Patient anatomical region 726 represents the actual anatomy of patient 12, but a clinician may not be able to easily identify the specific location of structures that should be subject to electrical stimulation.

To fit atlas 724 to patient anatomical region 726, programmer 19 may essentially map the locations of structures of the atlas to the actual locations of the tissue of the patient anatomical region. This fitting may be completed by identifying specific markers common to all anatomies and fitting the remaining atlas 724 to the coordinates of patient anatomical region 726. This resulting morphed atlas 728 may allow a clinician to select structures at the specific location in question. One example of how programmer 19 may create morphed atlas 728 is described in U.S. Patent Application No. 2005/0070781 by Dawant et al., entitled, "ELECTROPHYSIOLOGICAL ATLAS AND APPLICATIONS OF SAME" and filed Jul. 1, 2004. FIGS. 44-47 illustrate the use of morphed atlas 728 for programming stimulation therapy.

Morphed atlas 728 may provide some advantages to the clinician over atlas 724 or patient anatomical region 726 alone. For example, the clinician may be able to define a stimulation field on morphed atlas 728 and review that the desire structure resides within the volumetric stimulation field. Alternatively, the clinician may request a particular structure, and morphed atlas 728 may point the clinician directly to the corresponding location of the patient anatomy.

Figure 44:
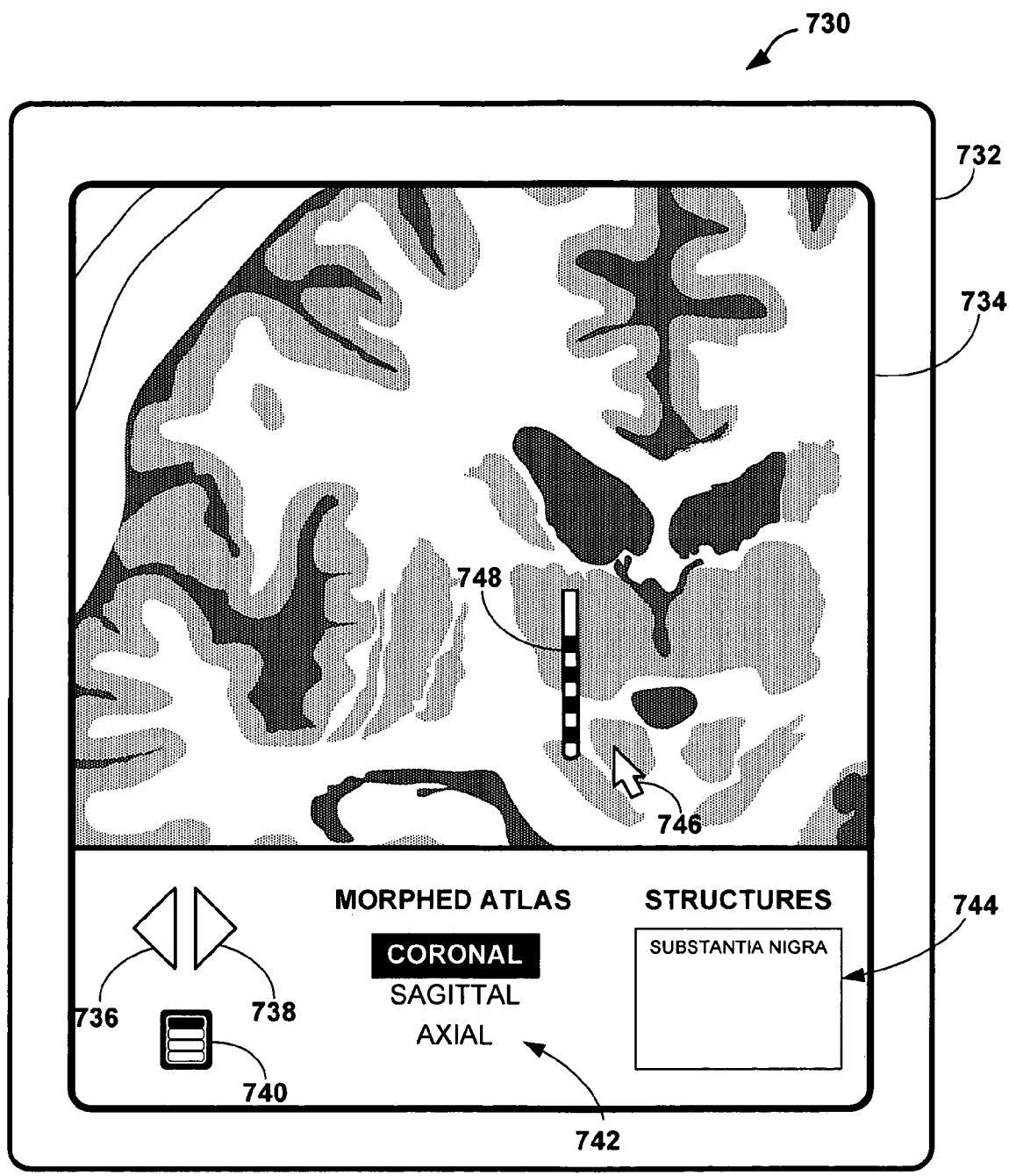
FIG. 44 is an example screen shot of a coronal view of a morphed atlas to aid the user in selecting a structure of the anatomy to stimulate.

FIG. 44 is an example screen shot of a coronal view of a morphed atlas to aid the user in selecting a structure of the anatomy to stimulate. As shown in FIG. 44, user interface 730 presents coronal view 734 of morphed atlas 728 to the clinician via programmer 732. Programmer 732 is an embodiment of programmer 19. User interface 730 also includes previous arrow 736, next arrow 738, menu 740, view indicator 742, and structure box 744. Lead icon 748 represents the location of lead 14 in patient 12. Pointer 746 is used by the clinician, or another user, to select a structure of coronal view 734 of morphed atlas 728 to program stimulation therapy. The clinician may select any structure by pointing to a location of coronal view 734, and the specific structure is then listed in structure box 744.

Other 2D slices of morphed atlas 728 at different depths may be viewed by the clinician via selecting previous arrow 736 or next arrow 738. Programmer 732 generates stimulation parameters based upon the one or more selected structures from coronal view 734 of morphed atlas 728 and the location of the structures to the location of lead 14 represented by lead icon 748. In some embodiments, generating stimulation parameters may include the use of stimulation templates and creating a stimulation template set according to the selected structures. In any case, the morphed atlas allows the clinician to quickly select the most appropriate structure that needs to be stimulated to treat the condition of patient 12.

Figure 45:
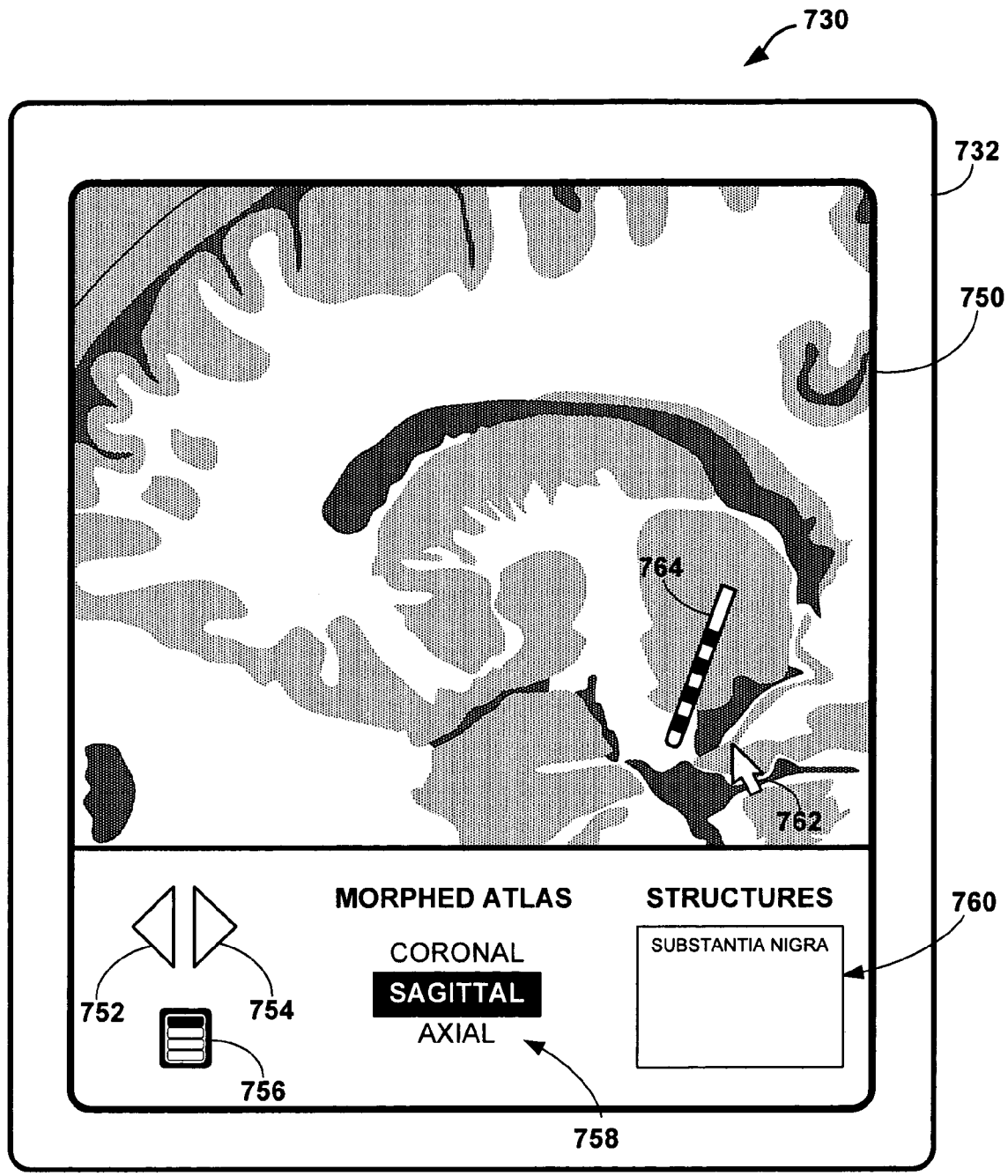
FIG. 45 is an example screen shot of a sagittal view of a morphed atlas to aid the user in selecting a structure of the anatomy to stimulate.

FIG. 45 is an example screen shot of a sagittal view of a morphed atlas to aid the user in selecting a structure of the anatomy to stimulate. As shown in FIG. 45, user interface 730 presents sagittal view 750 of morphed atlas 728 to the clinician via programmer 732. User interface 730 also includes previous arrow 752, next arrow 754, menu 756, view indicator 758, and structure box 760. Lead icon 764 represents the location of lead 14 in patient 12. Pointer 762 is used by the clinician, or another user, to select a structure of sagittal view 750 of morphed atlas 728 to program stimulation therapy. The clinician may select any structure by pointing to a location of sagittal view 750, and the specific structure is then listed in structure box 760. Similar to FIG. 44, the clinician may go to other depths of morphed atlas 728 by using previous arrow 752 and next arrow 754. The clinician may also move lead icon 764 to correctly position the lead icon based on the location of lead 14, if adjustments are necessary.

Figure 46:
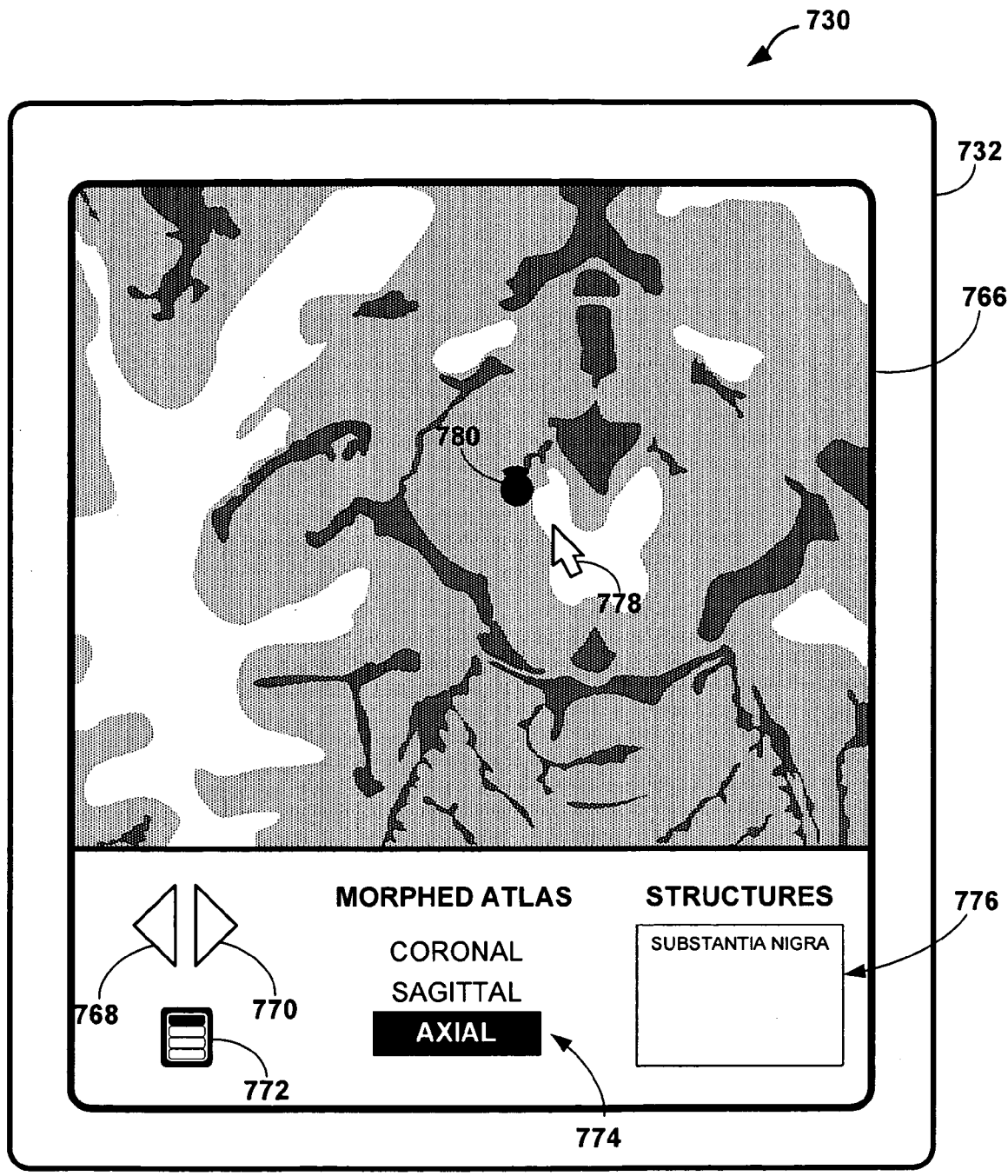
FIG. 46 is an example screen shot of an axial view of a morphed atlas to aid the user in selecting a structure of the anatomy to stimulate.

FIG. 46 is an example screen shot of an axial view of a morphed atlas to aid the user in selecting a structure of the anatomy to stimulate. As shown in FIG. 46, user interface 730 presents axial view 766 of morphed atlas 728 to the clinician via programmer 732. User interface 730 also includes previous arrow 768, next arrow 770, menu 772, view indicator 774, and structure box 776. Lead icon 780 represents the location of lead 14 in patient 12. Pointer 778 is used by the clinician, or another user, to select a structure of axial view 766 of morphed atlas 728 to program stimulation therapy. The clinician may select any structure by pointing to a location of axial view 766, and the specific structure is then listed in structure box 776. Similar to FIG. 44, the clinician may go to other depths of morphed atlas 728 by using previous arrow 768 and next arrow 770. The clinician may also move lead icon 780 to correctly position the lead icon to lead 14, if adjustments are necessary. The clinician may also use view indicator 774 to switch between coronal view 734, sagittal view 750, and axial view 766. Menu 772 may be used to request that programmer 732 generate stimulation parameters to fit the structures that are selected from morphed atlas 728.

Figure 47:
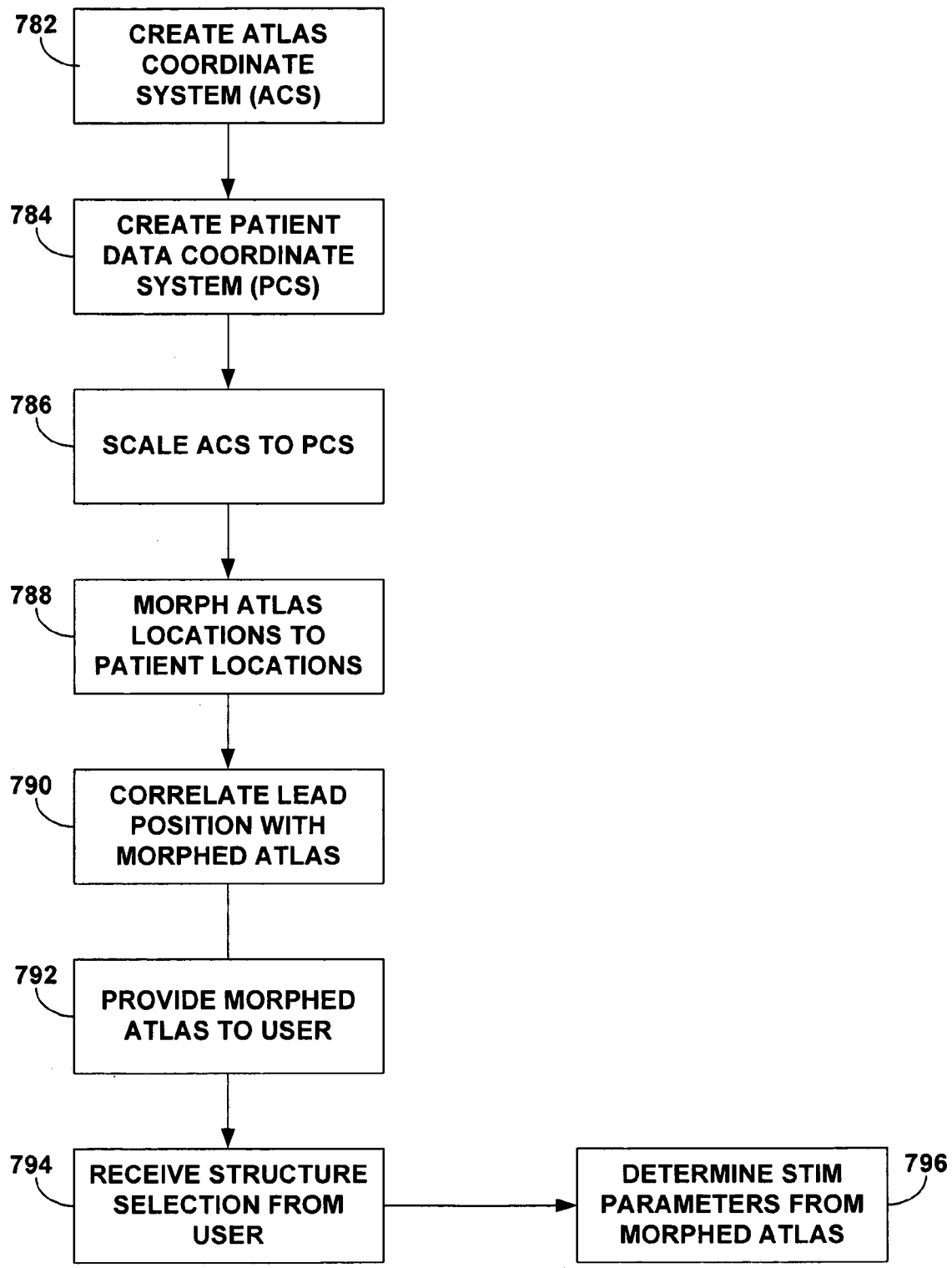
FIG. 47 is a flow diagram illustrating an example technique for creating the morphed atlas and receiving a structure selection from the user.

FIG. 47 is a flow diagram illustrating an example technique for creating the morphed atlas and receiving a structure selection from the user. As shown in FIG. 47, programmer 732 begins by creating an atlas coordinate system (ACS) which includes structures defined within the ACS (782). Next programmer 732 creates a patient data coordinate system (PCS) according to the stored patient anatomy data (784). Programmer 732 scales the sizes of the ACS to the size of the PCS before any other operation takes place (786). Programmer then can fit, or morph, the ACS to the PCS in order to create the morphed atlas 728 (788). In addition, programmer 732 determines the lead 14 location within morphed atlas 728 based on its position in the patient anatomy so that the programmer can generate appropriate stimulation parameters (790). User interface 730 can then present 2D views of morphed atlas 728 as needed to the clinician (792). When prompted by the clinician, user interface 730 receives structure selection from the clinician (794) and generates the appropriate stimulation parameters from the selected structures associated with morphed atlas 728 (796).

In some embodiments, programmer 732 may use stimulation templates in order to generate stimulation parameters for therapy. Alternatively, programmer 732 may use a set of stimulation equations that can handle structure coordinates from the morphed atlas to produce stimulation parameter sets. In other embodiments, morphed atlas 732 may need to be generated by a stand alone workstation with sufficient processing power. Programmer 732 embodied as a hand held computing device may not be capable of generating the morphed atlas in an appropriate time frame. It should be mentioned that other methods of producing the morphed atlas from the original atlas and patient anatomy may be used and remain within the scope of this disclosure.

Figure 48:
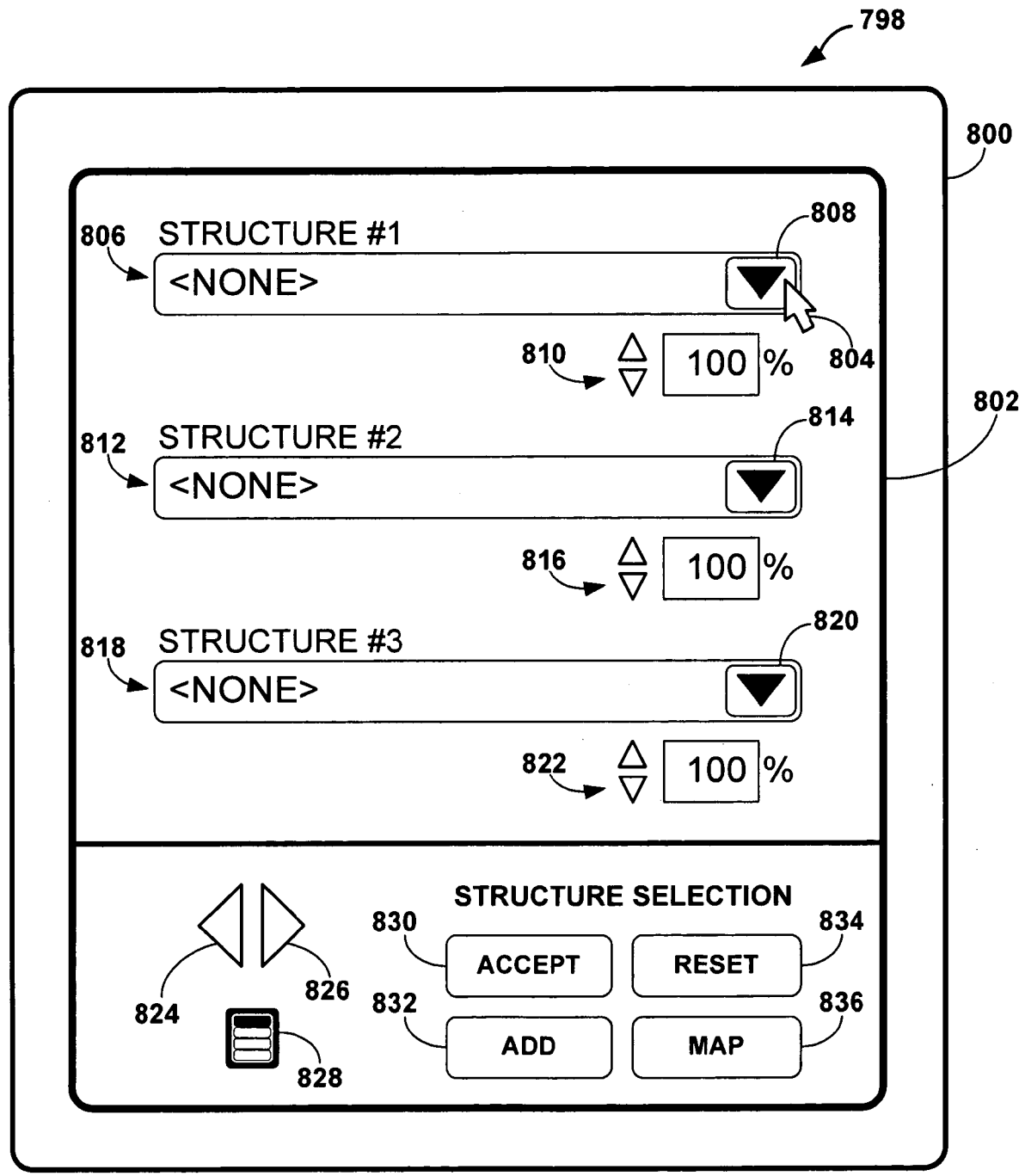
FIG. 48 is an example user interface that allows the user to select structures to stimulate from multiple pull down menus.

FIG. 48 is an example user interface that allows the user to select structures to stimulate from multiple pull down menus. As shown in FIG. 48, the clinician may utilize user interface 798 to select structures that should be stimulated by IMD 20. Alternatively, the clinician may determine "keepout" regions by selection of one or more structures to prevent or avoid electrical stimulation of those selected regions. Programmer 800 may be substantially similar to programmer 19. Programmer 800 displays structure view 802 to a clinician which includes structure menus 806, 812 and 818. Structure view 802 also includes previous arrow 824, next arrow 826, menu 828, accept button 830, add button 832, reset button 834 and map button 836. Structure menus 806, 812 and 818 may be considered "drop-down menus," although other means for selecting structures, such as text boxes that allow the clinician to enter text of the structure to stimulate, may be used in alternative embodiments. User interface 798 is an alternative to providing the clinician with a graphical representation of an atlas as illustrated in user interface 554.

A user, such as the clinician, uses pointer 804 to select arrow 808 to open structure menu 806 in which provides multiple structures by name to the clinician. The clinician can then select one of the structures from structure menu 806 as the first structure that is to be stimulated. The clinician may also define the magnitude of the stimulation therapy to the selected first structure. Power value 810 allows the clinician to set a percentage of the default stimulation for that structure.

For example, if the clinician desires to only stimulate part of the first structure, the clinician may set power value 810 to 50% so that the entire structure is not subject to the electrical stimulation.

The user may also select more structures to be stimulated. The user may select a second structure from structure menu 812 using arrow 808 and a third structure from structure menu 818 using arrow 820. Although illustrated as three, any number of structures may be selected. Similar to the first structure, the clinician may use power values 816 and 822 to specific the stimulation magnitude for each respective structure. User interface 798 may provide more structure menus to the clinician by including a scroll option in structure view 802. The clinician may select add button 832 to add another structure menu. Alternatively, user interface 798 may require the clinician to enter another screen to view additional structure menus. In other embodiments, user interface 798 may only provide structures that are physically capable of being stimulated by lead 14 based upon the lead location and IMD 20 capabilities.

Once the clinician has finished selecting the one or more structures for stimulation, the clinician may select accept button 830. Once accept button 830 is selected, programmer 800 may generate the best stimulation parameters according to the selected structures. If the clinician desires to change the structures, the clinician may select reset button 834 to return each structure menu 806, 812 and 818 to its default setting of "none." In addition, the clinician may desire to visualize the selected structures on the atlas or morphed atlas. Once the clinician selects map button 836, structure view 802 may be replaced by a graphical representation of an atlas similar to any of views 558, 572 or 586 of user interface 554. Alternatively, any of user interfaces 600, 652 or 730 may be used to visualize the structures to the clinician after the selection of map button 836.

Figure 49:
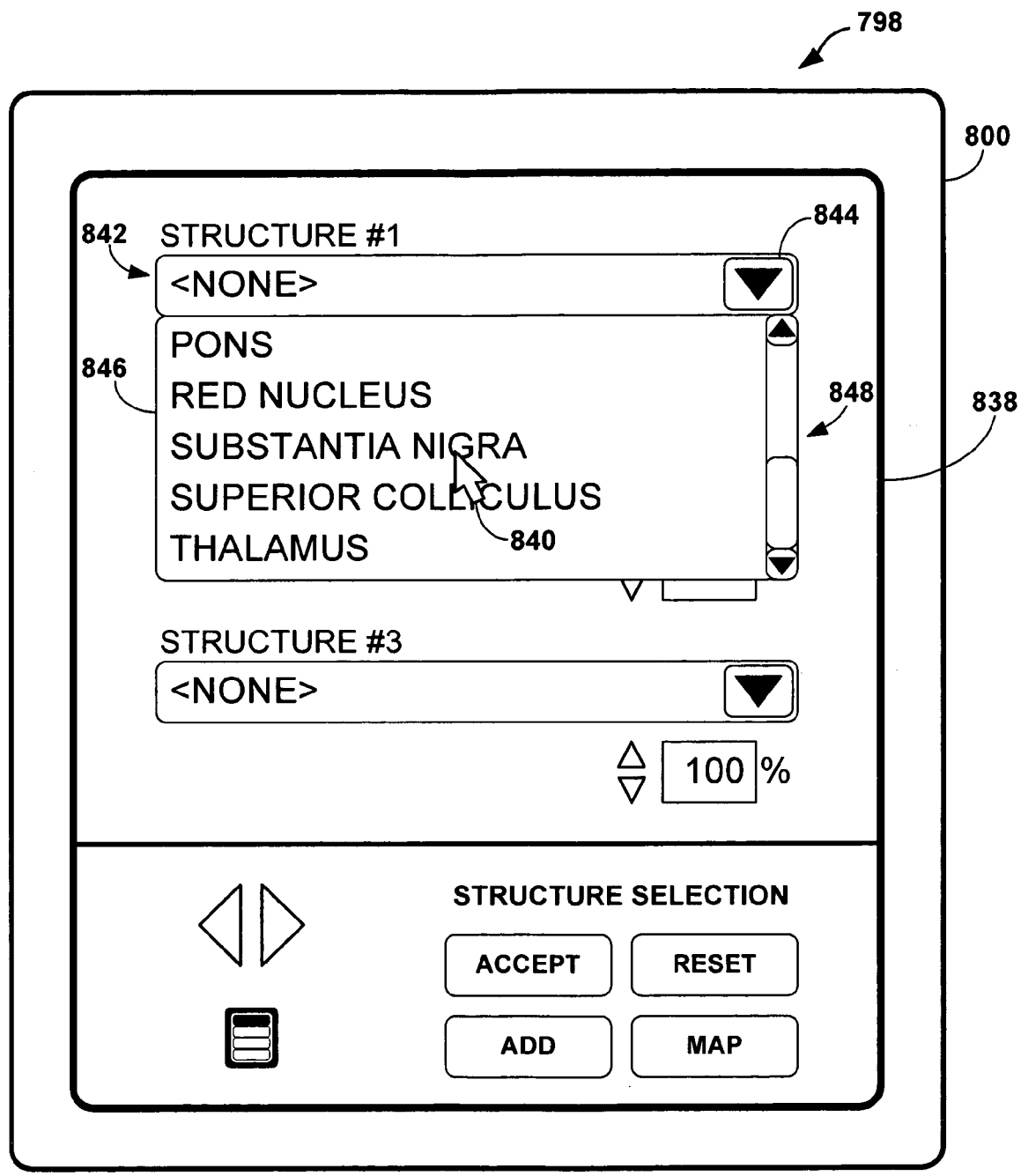
FIG. 49 is an example user interface that shows a pull down menu which contains anatomical structures that the user may select to program the stimulation therapy.

FIG. 49 is an example user interface that shows a pull down menu of FIG. 48 which contains anatomical structures that the user may select to program the stimulation therapy. As shown in FIG. 49, structure view 838 displays that the clinician has selected arrow 844 of structure menu 842 to view the available structures to stimulate in list 846. Scroll bar 848 may be used to view all structures of list 846. Using pointer 840, the clinician is about to select "SUBSTANTIA NIGRA" as the first structure to be stimulated. Once selected, list 846 disappears to allow the clinician to select a second structure if desired. The structures of list 846 are merely exemplary, and may depend upon the anatomical region of interest or allowable stimulated structures of brain 18.

Figure 50:
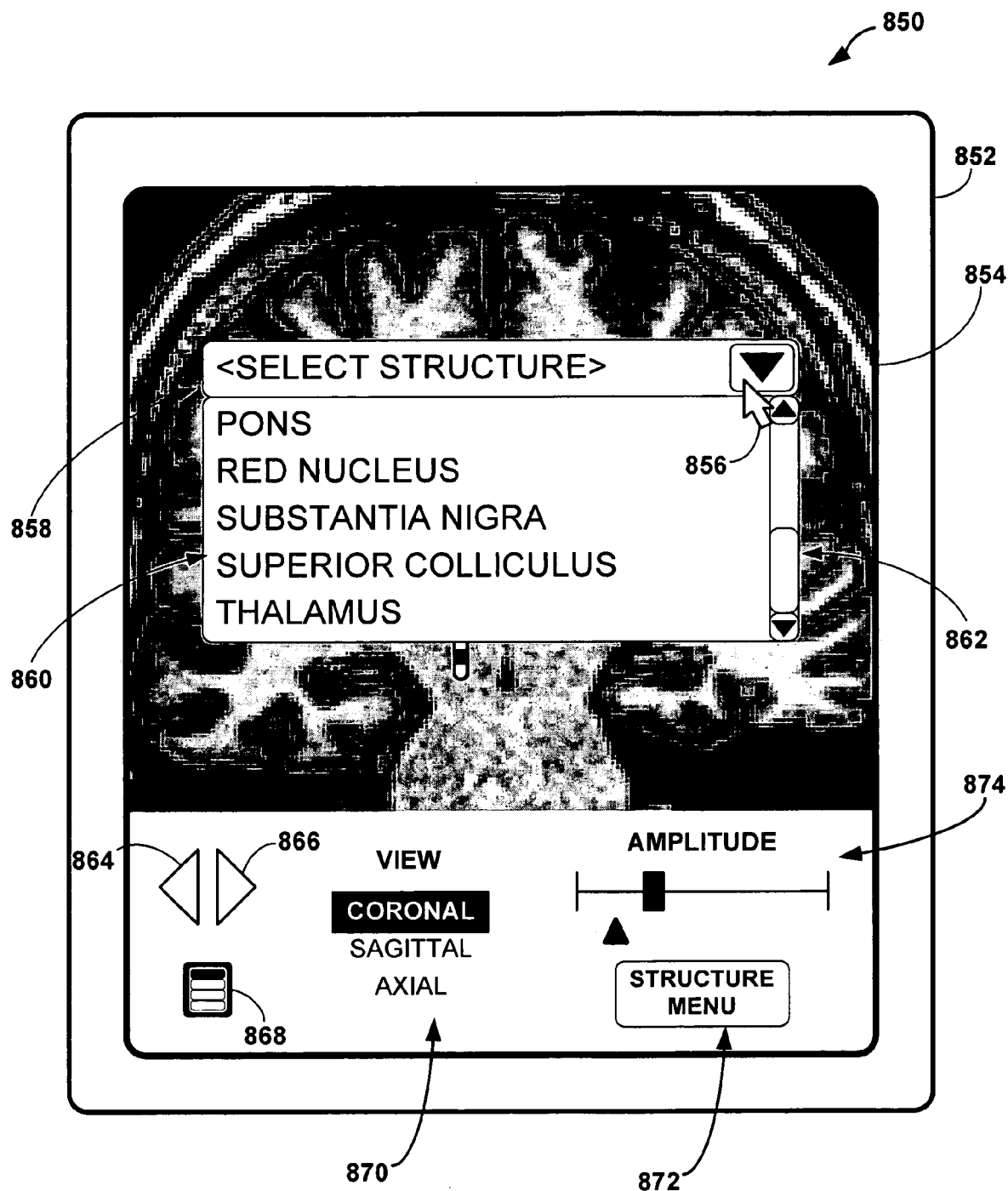
FIG. 50 is an example screen shot of a coronal view of a reference anatomy with a pull down menu which contains anatomical structures that the user may select to program the stimulation therapy.

FIG. 50 is an example illustration of a coronal view of an atlas with structure menu 858 which contains anatomical structures that the user may select to program the stimulation therapy. As shown in FIG. 50, user interface 850 presents structure menu 858 over coronal view 854 of an atlas, similar to FIG. 36, of to the clinician via programmer 852. Programmer 852 is an embodiment of programmer 19. User interface 850 also includes previous arrow 864, next arrow 866, menu 868, view indicator 870, amplitude slide 874, and structure button 872.

Once the clinician selects structure button 872, structure menu 858 may pop up over the atlas to allow the clinician to easily select the structure of interest. Pointer 856 is used by the clinician, or another user, to select arrow 856 and view list 860. Scroll bar 862 may allow the clinician to view all structures within list 860. Once the clinician selects the desired structure from list 860, the selected structure may then be added to the structures for stimulation. In some embodiments, the selected structure may be highlighted, shaded, or colored for easy identification in coronal view 854. Structure menu 858 may be substantially similar to a structure menu 842 of FIG. 49, except that structure menu 858 is displayed over an atlas. In alternative embodiments, user interface 850 may include structure menu 858 over any views of user interfaces 554, 600, 652 or 730.

Figure 51:
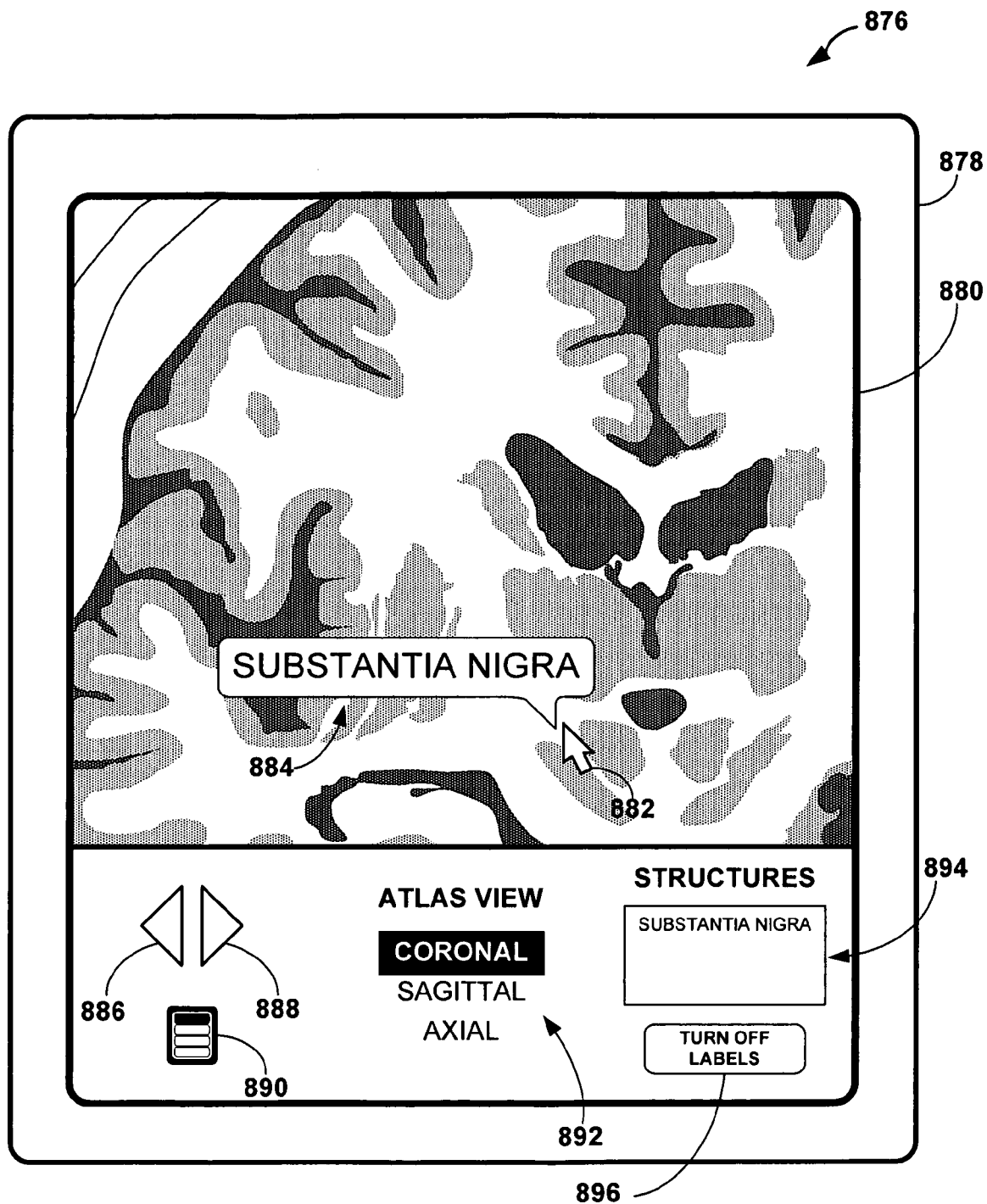
FIG. 51 is an example screen shot of a coronal view of a morphed atlas that indicates which structure the user has pointed to with a pop-up message.

FIG. 51 is an example screen shot of a coronal view of a morphed atlas that indicates which structure the user has pointed to with a pop-up message. As shown in FIG. 51, user interface 876 is an embodiment of any of user interfaces 554, 600, 652 or 730. However, user interface 876 uses morphed atlas 728 of user interface 730 as an example. User interface 876 provides coronal view 880 on programmer 878. Programmer 878 is an embodiment of programmer 19. User interface 876 also presents previous arrow 886, next arrow 888, menu 890, view indicator 892, structure box 894 and labels button 896. As the clinician moves pointer 882 over coronal view 880, pop-up 884 will appear and indicate which structure pointer 882 would select if the clinician selects that area of morphed atlas 728. Pop-up 884 may be turned off by selecting labels button 896.

Figure 52:
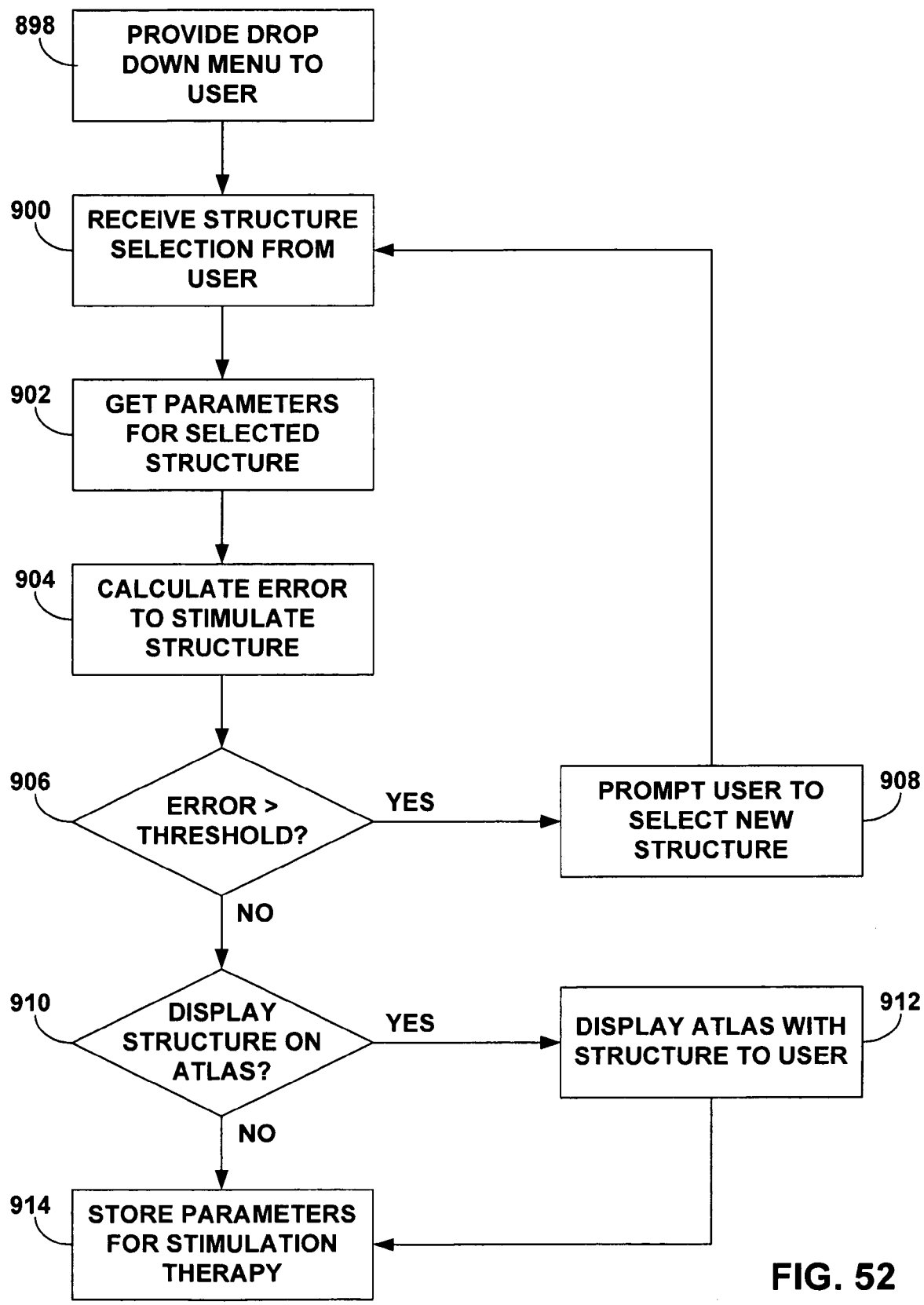
FIG. 52 is flow diagram illustrating an example technique for receiving a structure selection from a user and displaying the structure to the user.

FIG. 52 is flow diagram illustrating an example technique for receiving a structure selection from a user and displaying the structure to the user. The method of FIG. 52 may be used with any of user interfaces 798, 850 or 876; however, the method is described with reference to structure menus of user interface 798. Programmer 800 is used as an example in FIG. 52, but any of programmers 800, 852, or 878 may be used. Programmer 800 provides a structure menu, e.g., a drop down menu, to a clinician (898). User interface 798 next receives one or more structure selections from the clinician (900). Once prompted, programmer 800 generates stimulation parameters for the one or more selected structures (902). Programmer 800 will next calculate an error based upon the stimulation that will be delivered from lead 14 to the selected structures (904). If the error is greater than a predetermined threshold (906), programmer 800 will prompt the clinician to select a new structure that will produce a lesser error (908). Programmer 800 will then proceed to receive new structure selection from the clinician (900). If the error is less than the predetermined threshold (906), user interface 798 will determine if the structure should be displayed on the atlas (910). If the structure is not to be displayed, programmer 800 will store the generated stimulation parameters and transmit the parameters to IMD 20 for therapy (914). If the structure is to be presented on the atlas to the clinician, processor 800 controls user interface 798 will display the atlas and structure to the clinician (912) prior to storing the stimulation parameters and transmitting the parameters to IMD 20.

Figure 53:
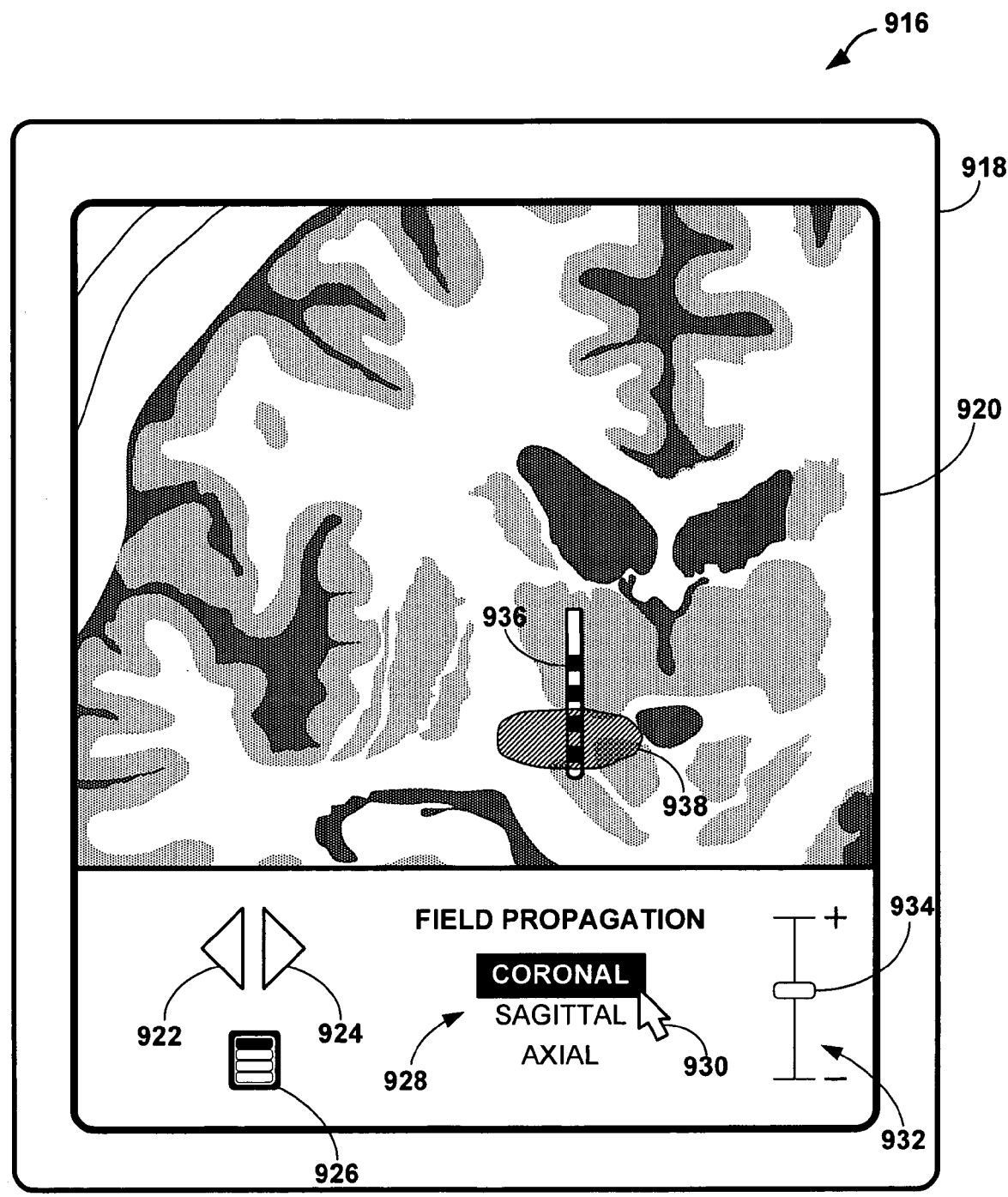
FIG. 53 is an example screen shot of a coronal view of a patient anatomy with an electrical field model of the defined stimulation therapy.

FIGS. 53-57 illustrate an electrical field model that is displayed to a user in orthogonal 2D views to approximate actual stimulation effects from therapy. FIG. 53 is an example screen shot of a coronal view of a patient anatomy with an electrical field model of the defined stimulation therapy. As shown in FIG. 53, programmer 918 controls user interface 916 to display coronal view 920. Programmer 918 may be substantially similar to programmer 19, and coronal view 920 may be a 2D view of any one of an atlas, a morphed atlas, or a patient anatomical region as described herein. User interface 916 also includes previous arrow 922, next arrow 924, menu 926, view indicator 928, and amplitude 932 with slider 934. The clinician interacts with user interface 916 using pointer 930.

Programmer 918 controls user interface 916 to display lead icon 936 and electrical field 938 to illustrate to the clinician what the electrical field of the stimulation therapy would look like according to the stimulation parameters defined by the clinician using any of the programming techniques described herein. Electrical field 938 represents where the electrical current will propagate from lead 14 within brain 18, as tissue variation within brain 18 may change the electrical current propagation from the lead. The variations in electrical field propagation may affect the ability of the therapy to actually treat a desired structure or cause a side-effect.

Electrical field 938 is a 2D slice of the volumetric electrical field model created by programmer 918. Programmer 918 utilizes the patient anatomical region data with electrical field model equations that define current propagation. In this manner, electrical field 938 can be estimated and modeled for the clinician. Accordingly, the clinician may be able to increase or decrease the amplitude of the stimulation parameters with slider 934 and view how the amplitude change would affect the size and shape of electrical field 938. Slider 934 is an analog adjustment mechanism and may also be in the form of an adjustment knob instead of the slider. The clinician may move to other depths of brain 18 by selecting previous arrow 922 or next arrow 924 and continue to view electrical field 938 and the surrounding anatomical region. In some embodiments, user interface 916 may allow the clinician to redefine the stimulation field and generate new stimulation parameters if electrical field 938 is not acceptable for therapy.

Figure 54:
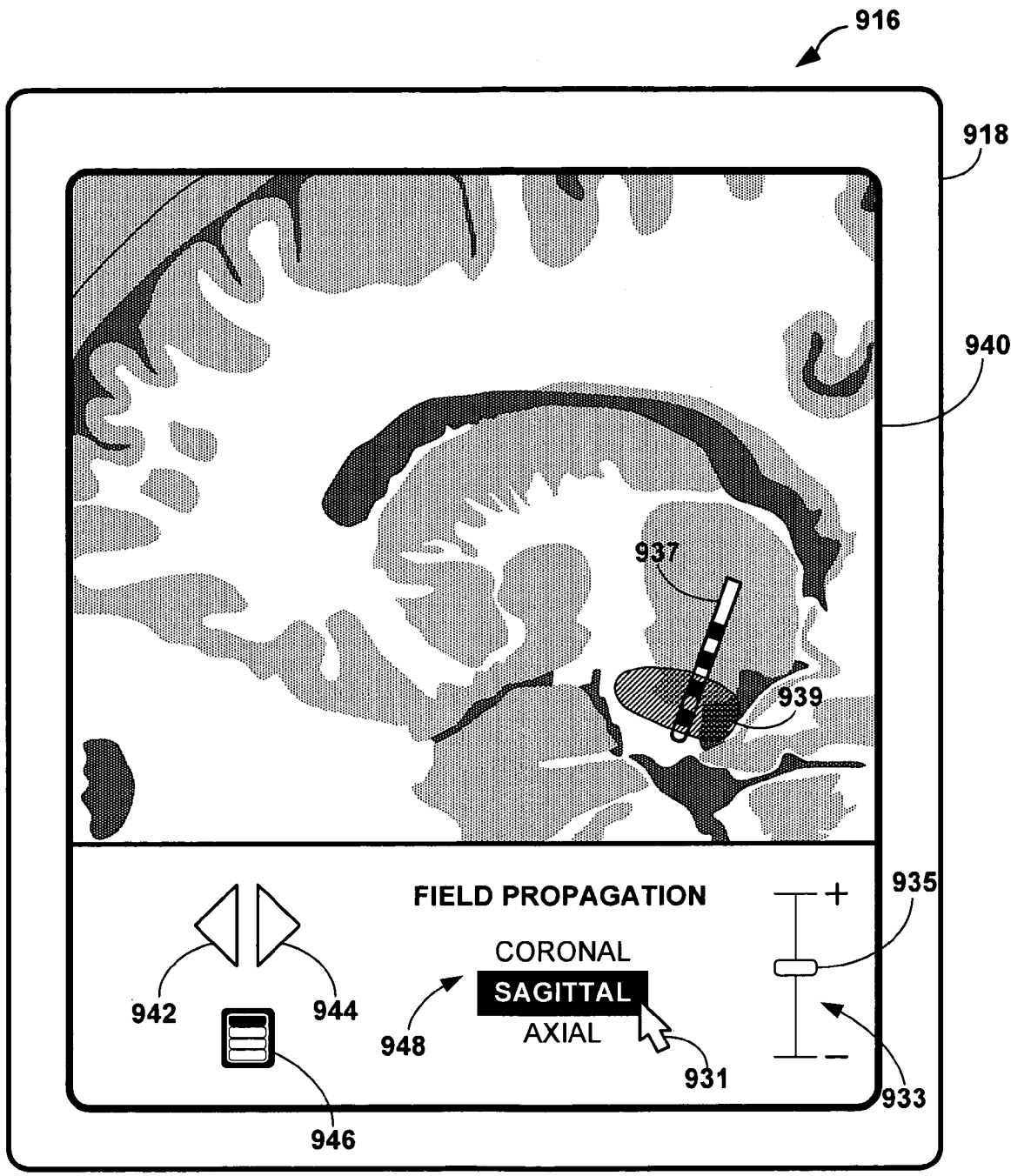
FIG. 54 is an example screen shot of a sagittal view of a patient anatomy with an electrical field model of the defined stimulation therapy.

FIG. 54 is an example screen shot of a sagittal view of a patient anatomy with an electrical field model of the defined stimulation therapy. As shown in FIG. 54, programmer 918 controls user interface 916 to display sagittal view 940 to a clinician. Similar to FIG. 53, sagittal view 940 may be a 2D view of any one of an atlas, a morphed atlas, or a patient anatomical region as described herein. User interface 916 also includes previous arrow 942, next arrow 944, menu 946, view indicator 948, and amplitude 933 with slider 935. The clinician interacts with user interface 916 using pointer 931. Similar to FIG. 53, electrical field 939 provides a model of the actual electrical stimulation around lead icon 937 according to the generated stimulation parameters for therapy. The clinician may move to different depths of sagittal view 940 with previous arrow 942 or next arrow 944 while adjusting the amplitude of electrical field 939 with slider 935. Slider 935 is an analog adjustment mechanism and may also be in the form of an adjustment knob instead of the slider.

Figure 55:
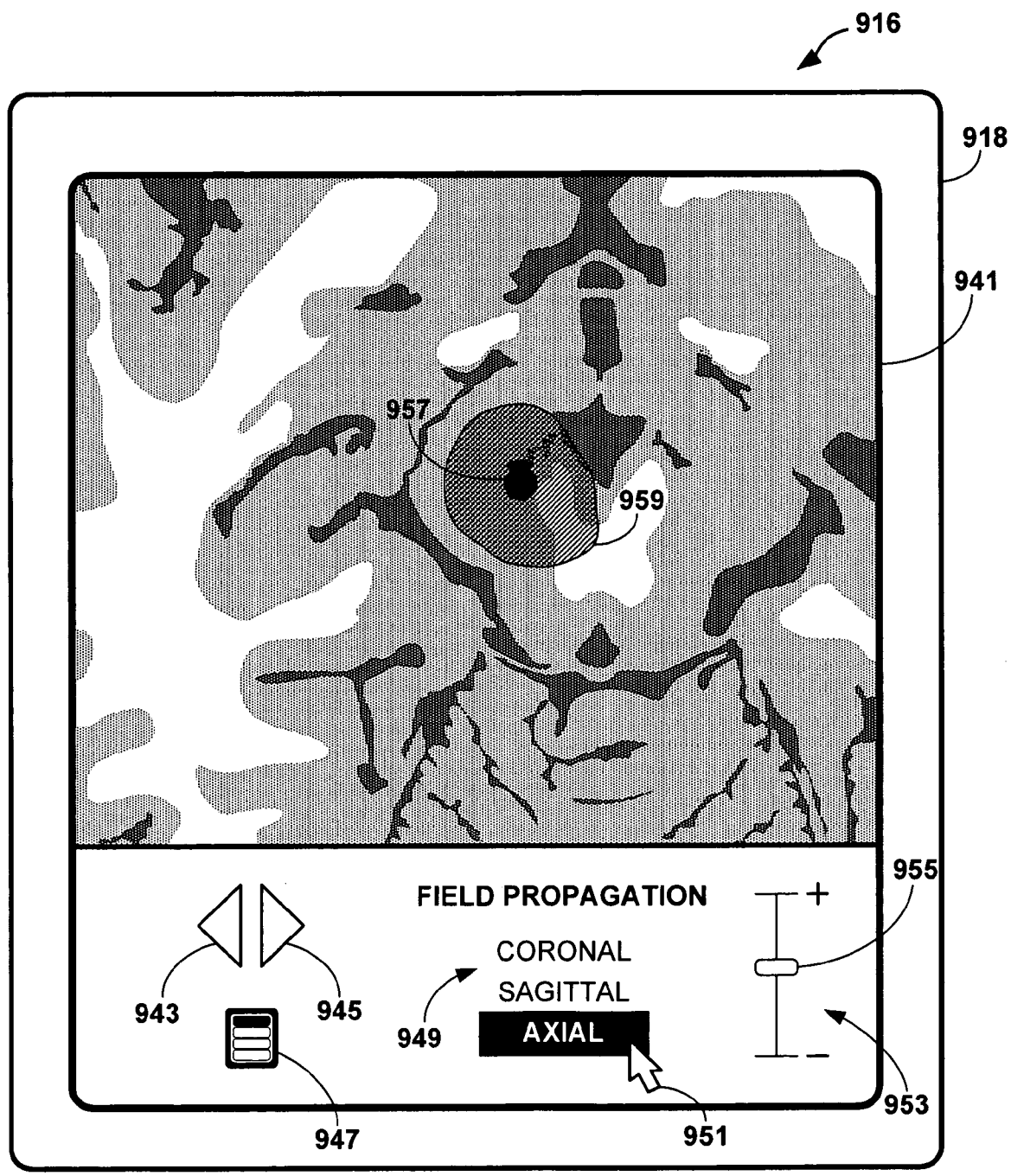
FIG. 55 is an example screen shot of an axial view of a patient anatomy with an electrical field model of the defined stimulation therapy.

FIG. 55 is an example screen shot of an axial view of a patient anatomy with an electrical field model of the defined stimulation therapy. As shown in FIG. 55, user interface 916 displays axial view 941 to a clinician via control from programmer 918. Similar to FIG. 53, axial view 941 may be a 2D view of any one of an atlas, a morphed atlas, or a patient anatomical region as described herein. User interface 916 also includes previous arrow 943, next arrow 945, menu 947, view indicator 949, and amplitude 953 with slider 955. The clinician interacts with user interface 916 using pointer 951. Similar to FIG. 53, electrical field 959 provides a model of the actual electrical stimulation around lead icon 957 according to the generated stimulation parameters for therapy. The clinician may move to different depths of axial view 941 with previous arrow 943 or next arrow 945 while adjusting the amplitude of electrical field 959 with slider 955. Similar to slider 935, slider 955 is an analog adjustment mechanism and may also be in the form of an adjustment knob instead of the slider. When the clinician is finished viewing the electrical field model, the clinician may select menu 947 to either reprogram the stimulation therapy or deliver therapy with the current stimulation parameters.

Figure 56:
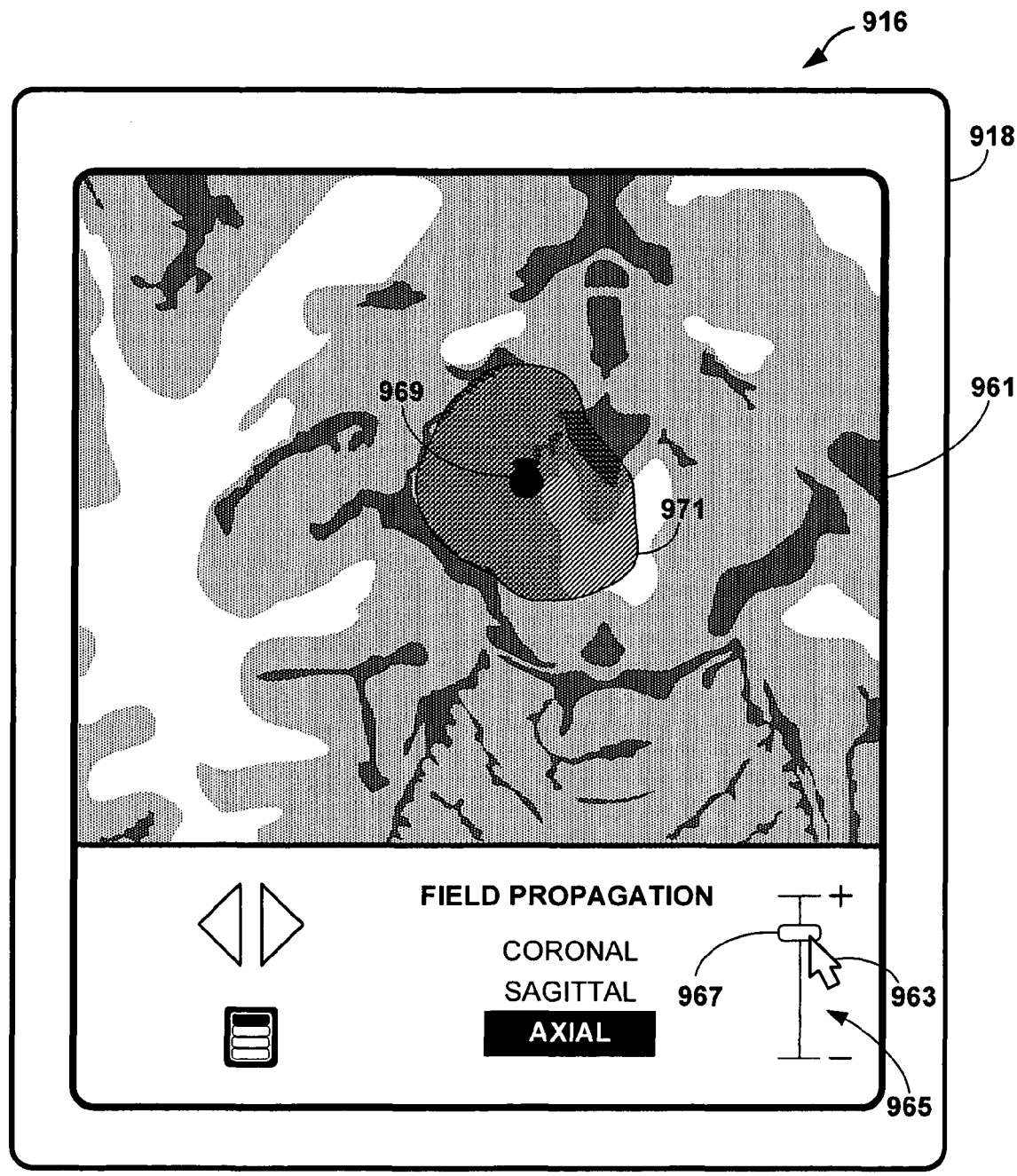
FIG. 56 is an example screen shot of an axial view of a patient anatomy with an electrical field model of the enlarged defined stimulation therapy from FIG. 56.

FIG. 56 is an example screen shot of an axial view of a patient anatomy with an electrical field model of the enlarged defined stimulation therapy from FIG. 55. FIG. 56 includes user interface 916 that displays axial view 961, lead icon 969 and electrical field 971. The clinician has used pointer 963 to move slide 967 towards greater amplitude to increase the size of electrical field 971 as compared to electrical field 959 of FIG. 55. Not only does the size of electrical field 971 increase, but the shape of the electrical field changes as well because of the electrical propagation through the anatomical region. Alternatively, the clinician may grab electrical field 950 to make it bigger, which moves slide 967 towards greater amplitude. It should be noted that increasing the current or voltage amplitude of electrical field 971 will increase power consumption from power source 78 of simulator 20. In some embodiments, user interface 916 may include a power consumption indicator that displays therapy duration with proposed power consumption, rate of power consumption, or some other indicator that the clinician can use to program the stimulation therapy.

Figure 57:
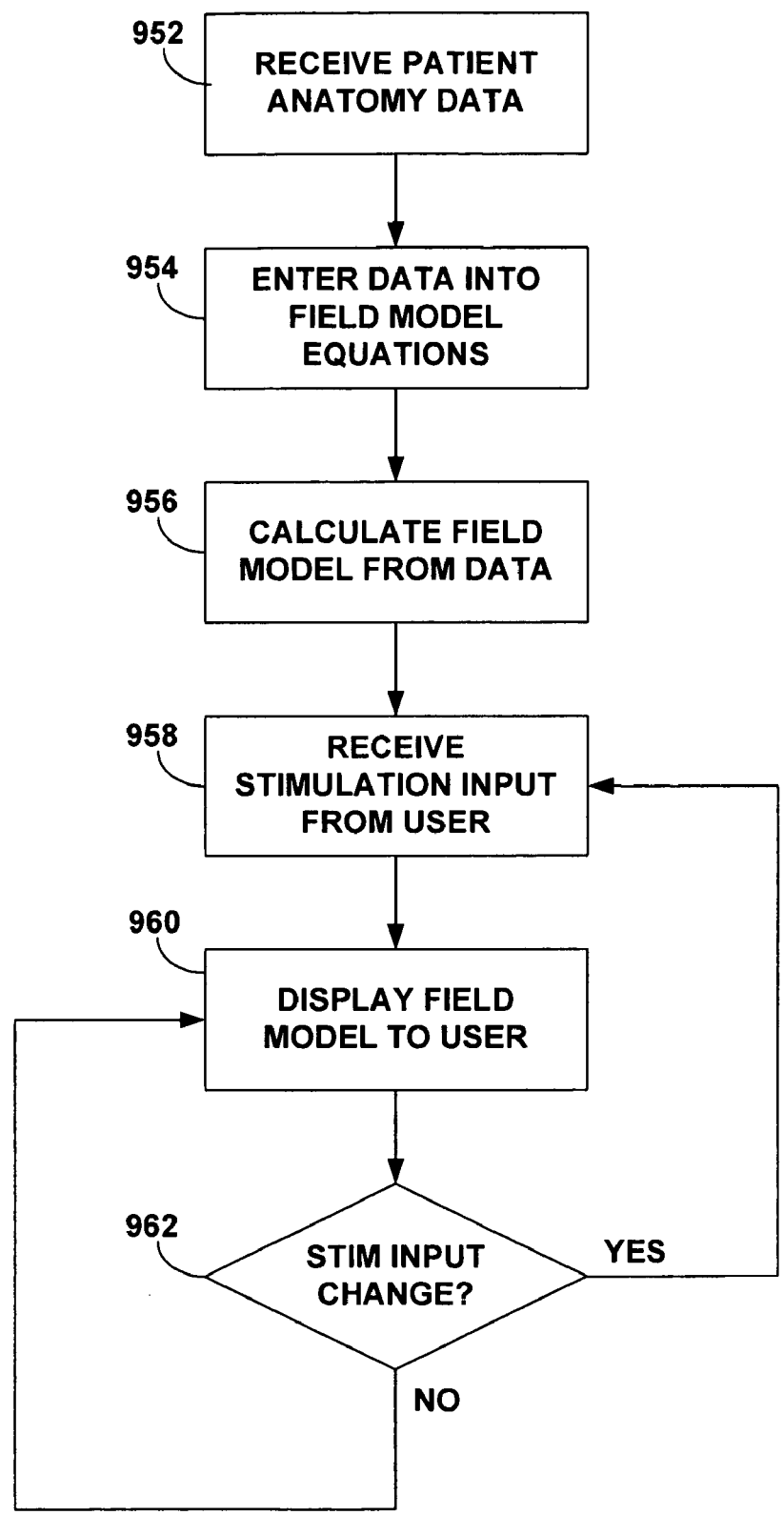
FIG. 57 is a flow diagram illustrating an example technique for calculating and displaying the electrical field model of defined stimulation.

FIG. 57 is a flow diagram illustrating an example technique for calculating and displaying the electrical field model of defined stimulation described with reference to the examples of FIGS. 54-56. As shown in FIG. 57, programmer 918 receives patient anatomy data necessary for creating an electrical field (952). Programmer 918 enters the patient anatomy data in stored electrical field model equations or equation sets to satisfy anatomical variable (954). Programmer 918 next calculates the electrical field model from the data and equations (956). Once user interface 916 receives stimulation input from the clinician defining the stimulation field (958), programmer 918 generates the electrical field that is displayed to the clinician via the user interface (960). If the clinician desires to change the stimulation input (962), user interface 916 receives a change in the stimulation input and programmer 918 makes the corresponding changes (958). If the clinician does not request a stimulation input change (962), user interface 916 continues to display the electrical field to the clinician according to programmer 918 (960).

Figure 58:
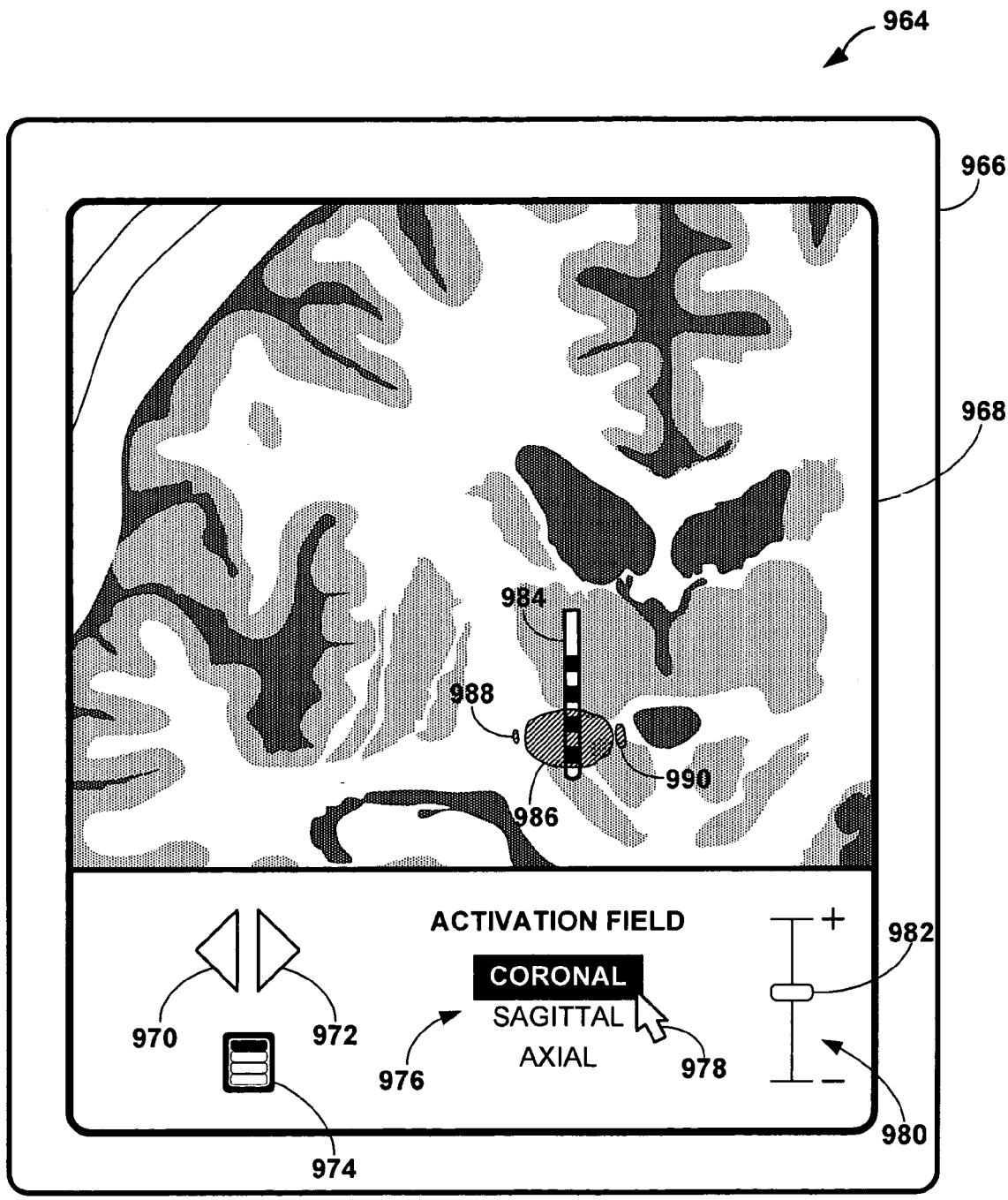
FIG. 58 is an example screen shot of a coronal view of a patient anatomy with an activation field model of the defined stimulation therapy.

FIGS. 58-62 illustrate an activation field model that is presented to a user. FIG. 58 is an example screen shot of a coronal view of a patient anatomy with an activation field model of the defined stimulation therapy. As shown in FIG. 58, user interface 964 includes a programmer that displays coronal view 968 to a clinician. Programmer 966 may be substantially similar to programmer 19, and coronal view 968 may be a 2D view of any one of an atlas, a morphed atlas, or a patient anatomical region as described herein. Coronal view 968 also includes previous arrow 970, next arrow 972, menu 947, view indicator 976, and amplitude 980 with slider 982. The clinician interacts with programmer 966 using pointer 978.

Programmer 966 displays lead icon 984 and activation fields 986, 988 and 990 on coronal view 968 to illustrate to the clinician which neurons in the anatomical region will be activated by the produced electrical field. An activation field model is generated by applying a neuron model to a generated electrical field model. The neuron model indicates the voltage or current amplitude that is required for the tissue within the anatomical region to be stimulated. Since some tissue may be covered by an electrical field of voltage too small to activate the neurons in that tissue, this tissue is not actually affected by the electrical field. The activation field model may accurately indicate which tissues will be treated by the electrical field. As shown in coronal view 968, the activation field model is not continuous. Due to some tissue not activated by the electrical field, the activation field model is broken into activation fields 986, 988 and 990.

Activation fields 986, 988 and 990 are 2D slices of the volumetric activation field model created by programmer 966. Programmer 966 utilizes the patient anatomical region data with electrical field model equations to define an electrical field model. A neuron model is applied to the electrical field model to create the activation field model shown in FIG. 58. Accordingly, the clinician may be able to increase or decrease the amplitude of the stimulation parameters with slider 982, or analog adjustment mechaniss, in view how the amplitude change would affect the size and shape of activation fields 986, 988 and 990. Changing the amplitude of the stimulation may change the number of activation fields as different numbers of neurons in the tissue are activated. The clinician may move to other depths of brain 18 by selecting previous arrow 970 or next arrow 972 and continue to view 2D slices of the activation field model and the surrounding anatomical region. In some embodiments, programmer 966 may allow the clinician to redefine the stimulation field and generate new stimulation parameters if activation fields 986, 988 and 990 is not acceptable for therapy.

Figure 59:
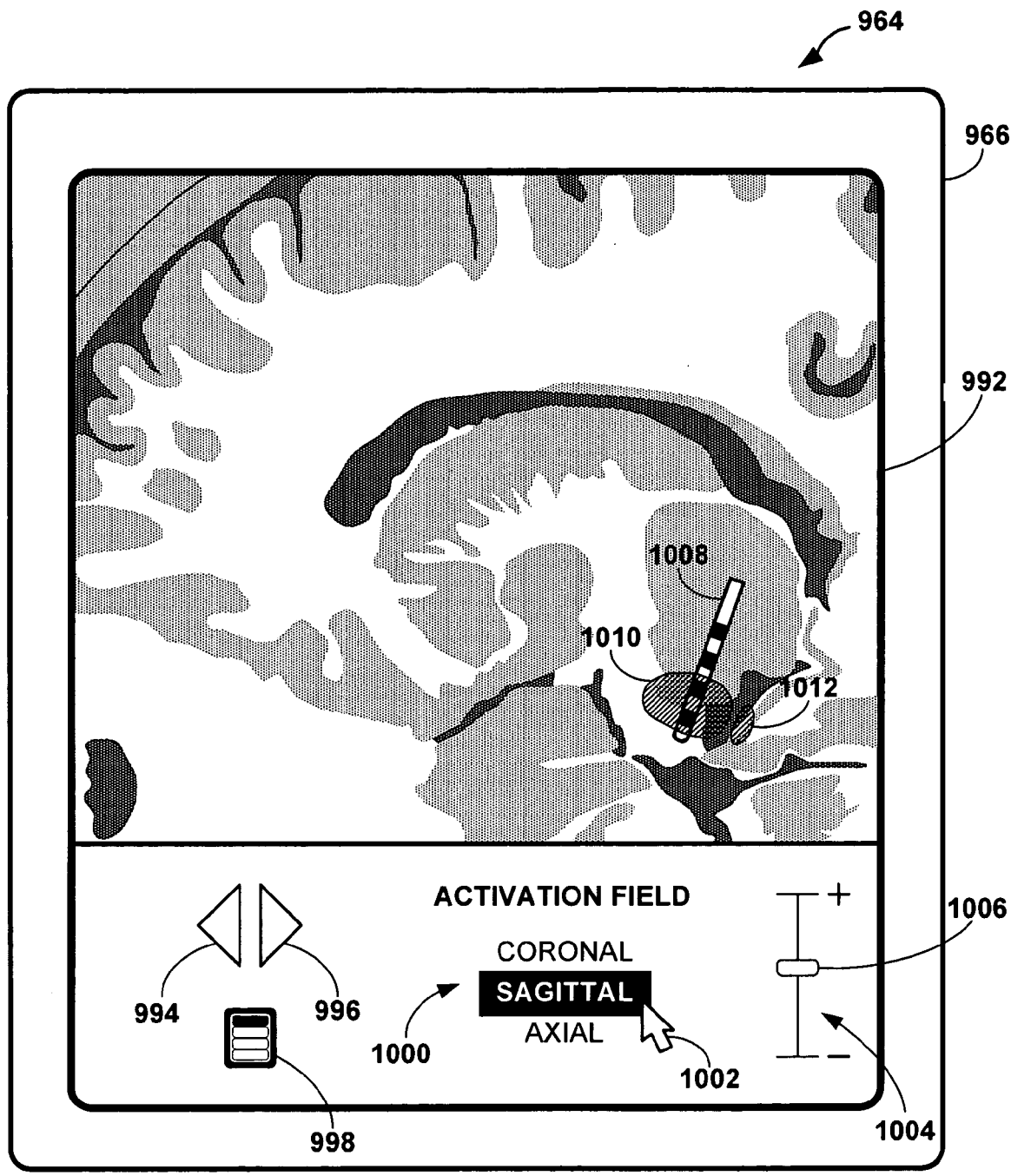
FIG. 59 is an example screen shot of a sagittal view of a patient anatomy with an activation field model of the defined stimulation therapy.

FIG. 59 is an example screen shot of a sagittal view of a patient anatomy with an activation field model of the defined stimulation therapy. As shown in FIG. 59, user interface 964 includes a programmer 966 that displays sagittal view 992 to a clinician. Similar to FIG. 58, sagittal view 992 may be a 2D view of any one of an atlas, a morphed atlas, or a patient anatomical region as described herein. Sagittal view 992 also includes previous arrow 994, next arrow 996, menu 998, view indicator 1000, and amplitude 1004 with slider 1006. The clinician interacts with programmer 966 using pointer 1002. Similar to FIG. 58, activation fields 1010 and 1012 provide a model of the actual neurons that are activated around lead icon 1008 according to the generated stimulation parameters for therapy. The clinician may move to different depths of sagittal view 992 with previous arrow 994 or next arrow 996 while adjusting the amplitude of the activation field model with slider 1006, e.g., an analog adjustment mechanism.

Figure 60:
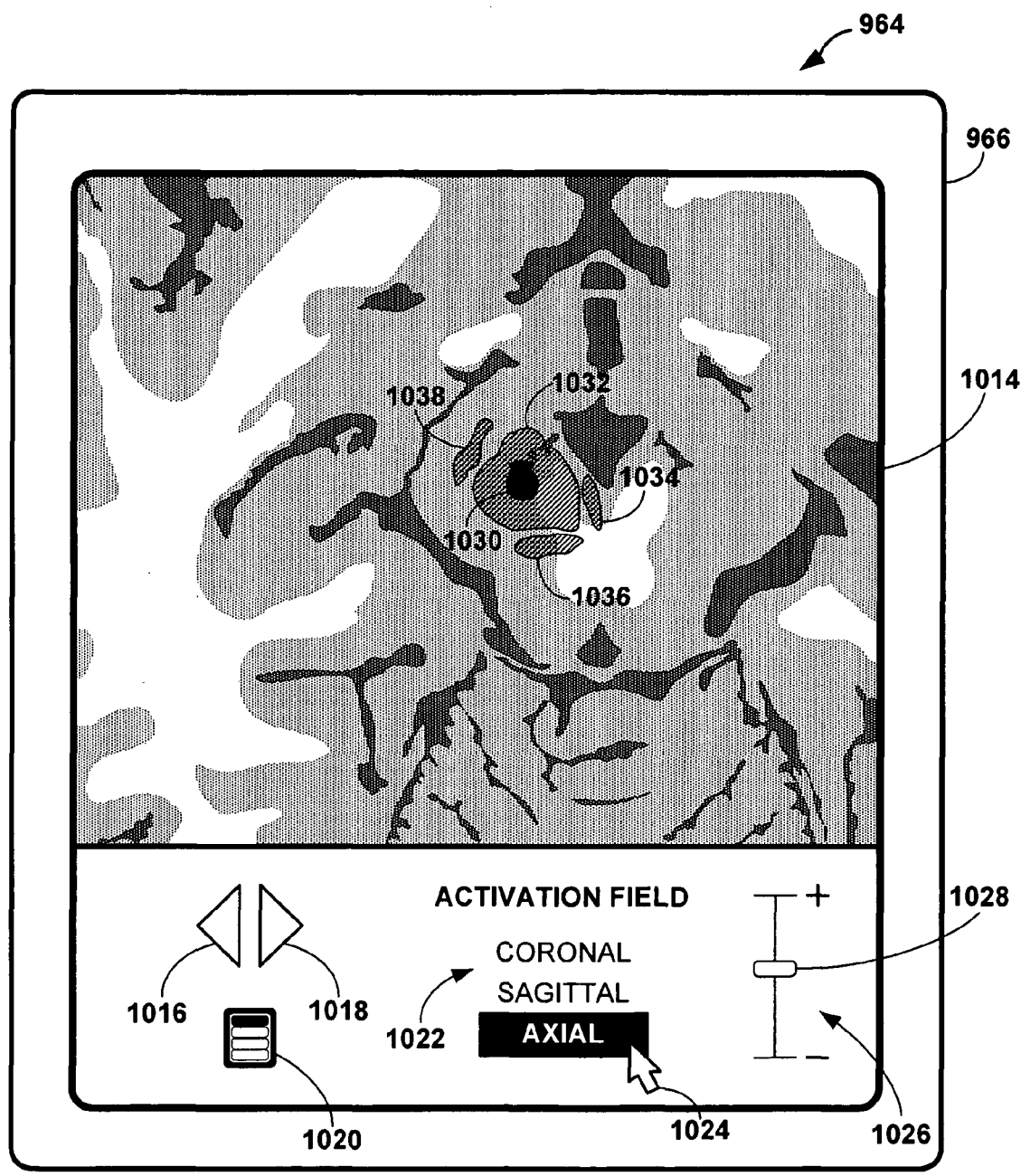
FIG. 60 is an example screen shot of an axial view of a patient anatomy with an activation field model of the defined stimulation therapy.

FIG. 60 is an example screen shot of an axial view of a patient anatomy with an activation field model of the defined stimulation therapy. As shown in FIG. 60, user interface 964 includes programmer 966 that displays axial view 1014 to a clinician. Similar to FIG. 58, axial view 1014 may be a 2D view of any one of an atlas, a morphed atlas, or a patient anatomical region as described herein. Axial view 1014 also includes previous arrow 1016, next arrow 1018, menu 1020, view indicator 1022, and amplitude 1026 with slider 1028. The clinician interacts with user interface 964 using pointer 1024. Similar to FIG. 58, activation fields 1032, 1034, 1036 and 1038 provide a model of the actual neurons that are activated around lead icon 1030 according to the generated stimulation parameters for therapy. The clinician may move to different depths of axial view 1014 with previous arrow 1016 or next arrow 1018 while adjusting the amplitude of the activation field model with slider 1028, e.g., an analog adjustment mechanism. When the clinician is finished viewing the activation field model of user interface 964, the clinician may select menu 1020 to either reprogram the stimulation therapy or deliver therapy with the current stimulation parameters.

Figure 61:
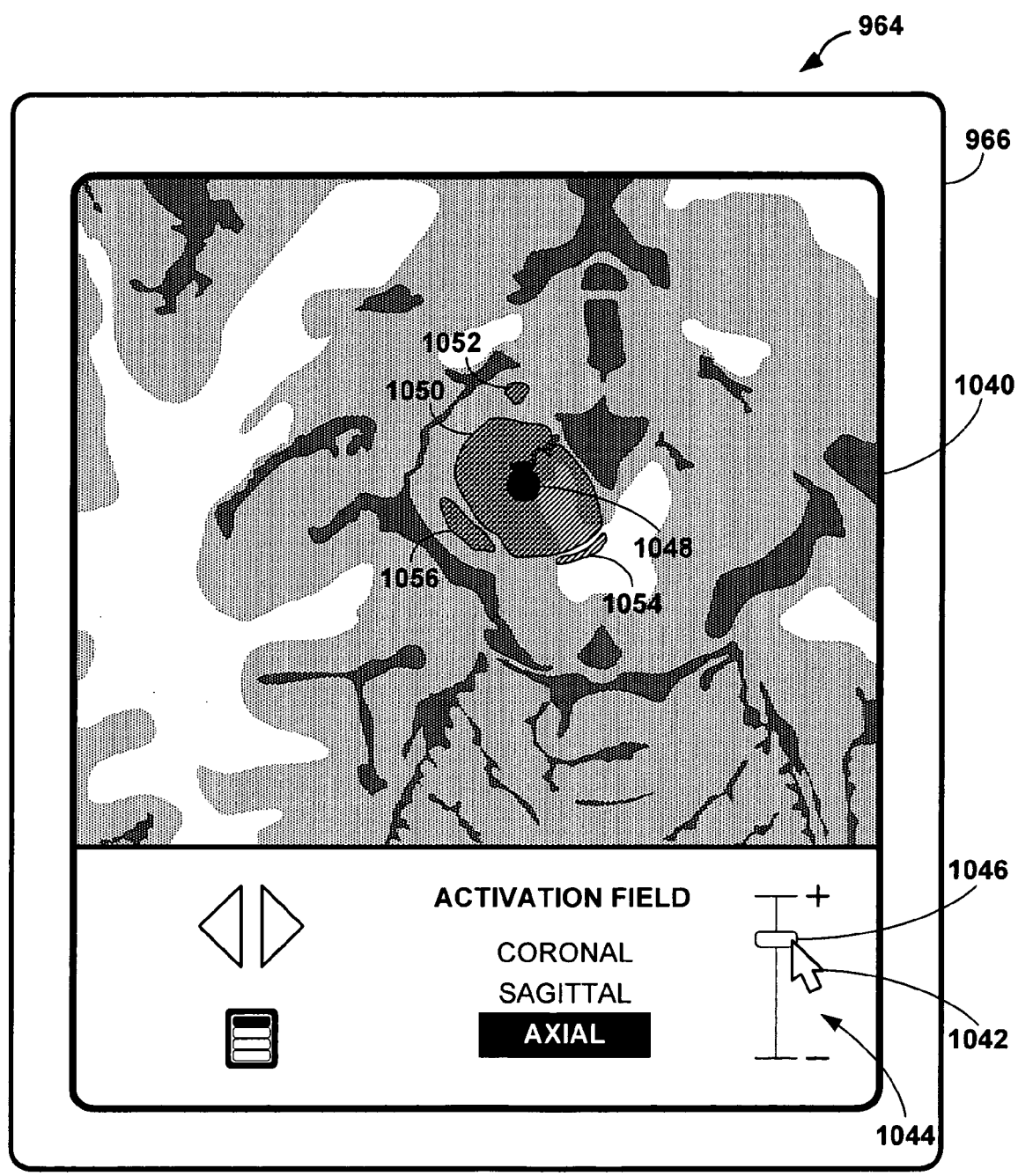
FIG. 61 is an example screen shot of an axial view of a patient anatomy with an enlarged activation field model from increasing the voltage amplitude from FIG. 60.

FIG. 61 is an example screen shot of an axial view of a patient anatomy with an activation field model of the enlarged defined stimulation therapy from FIG. 60. FIG. 61 includes user interface 964 that displays axial view 1040 (similar to axial view 1014) lead icon 1048 and activation fields 1050, 1052, 1054 and 1056 of the full activation field model. The clinician has used pointer 1042 to move slide 1046 towards greater amplitude to increase the size of the activation field model, which is shown by new activation fields 1050, 1052, 1054 and 1056 as compared to electrical fields 1032, 1034, 1036 and 1038 of FIG. 60. Not only does the size of the activation fields increase, but the shape and location of the activation fields change because the increased amplitude of the electrical field changes the tissues that are activated from the stimulation. Alternatively, the clinician may grab any of activation fields 1050-1056 to make it bigger, which moves slide 1046 towards greater amplitude. It should be noted that increasing the current or voltage amplitude of electrical field 971, and the corresponding activation fields, will increase power consumption from power source 78 of simulator 20. In some embodiments, user interface 964 may include a power consumption indicator that displays therapy duration with proposed power consumption, rate of power consumption, or some other indicator that the clinician can use to program the stimulation therapy.

Figure 62:
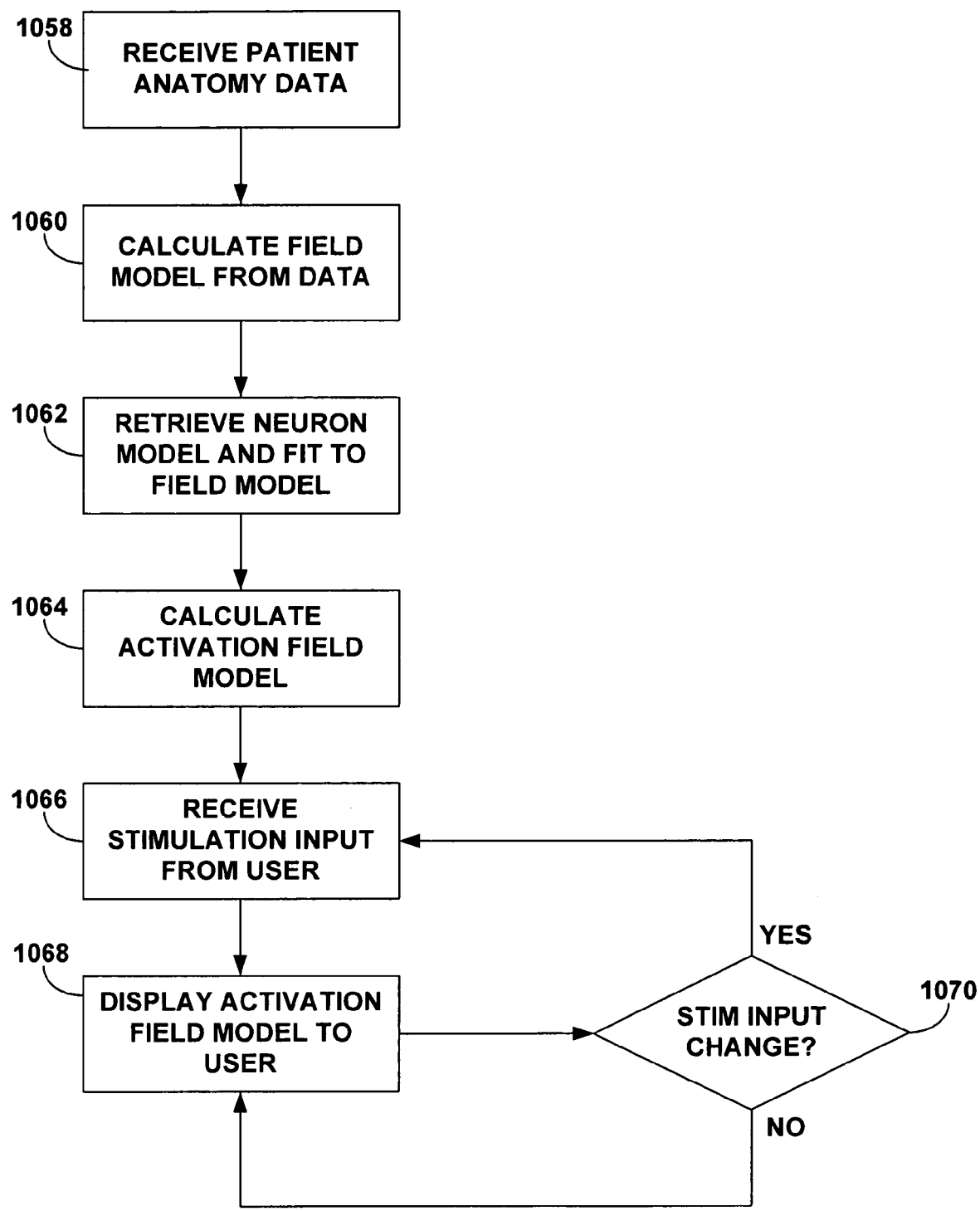
FIG. 62 is a flow diagram illustrating an example technique for calculating and displaying the activation field model of defined stimulation.

FIG. 62 is a flow diagram illustrating an example technique for calculating and displaying the activation field model of defined stimulation. As shown in FIG. 62, programmer 966 receives patient anatomy data through user interface 964 indicative of the anatomy of patient 12 (1058) and the programmer calculates the electrical field model from the patient anatomy data (1060). Programmer 966 then retrieves the neuron model and fits the neuron model to the electrical field (1062). Programmer 966 then calculates the activation field model based upon the electrical field model and neuron model (1064). Programmer 966 is then is able to receive stimulation input through user interface 964 from the clinician defining what structures of the anatomical region should be stimulated (1066). The resulting activation field model is displayed by user interface 964 (1068). If the clinician desires to change the stimulation input (1070), user interface 964 receives stimulation input from the clinician modifying the previous stimulation input (1066). If the stimulation input does not need to be changed (1070), the activation field model continues to be displayed by programmer 966 (1068).

Figure 63:
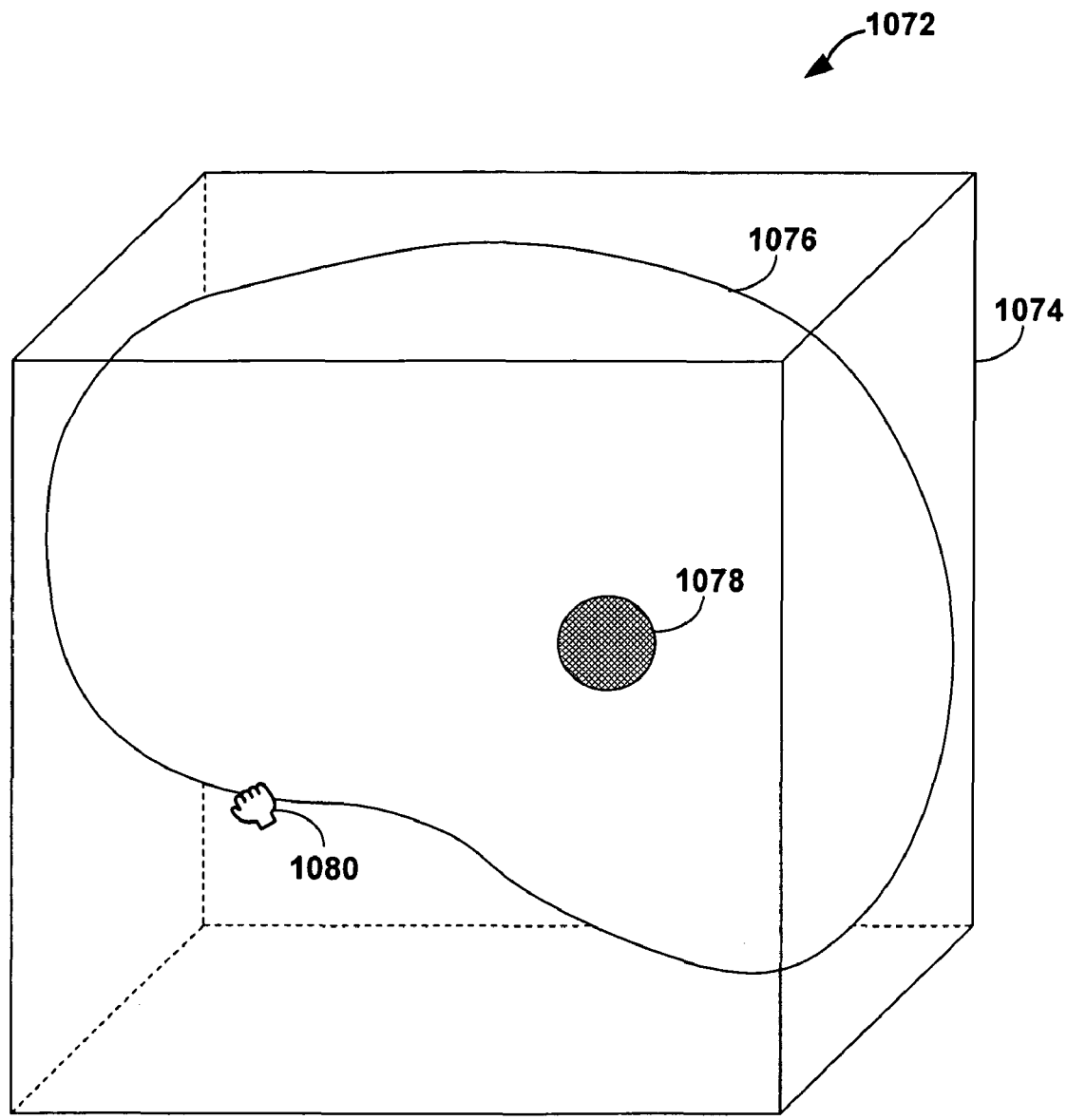
FIG. 63 is a conceptual diagram illustrating a three-dimensional (3D) visualization environment including a 3D brain model for defining a 3D stimulation field.

FIGS. 63-66 are related to an embodiment of the disclosure allowing a user to define a stimulation field in a 3D environment. FIG. 63 is a conceptual diagram illustrating a 3D visualization environment including a 3D brain model for defining a 3D stimulation field. FIG. 63 is a conceptual diagram illustrating a three-dimensional (3D) environment including a 3D brain model for defining a 3D stimulation field. As shown in FIG. 63, user interface 1072 includes 3D view 1074, brain model 1076, stimulation field 1078, and hand 1080. 3D view 1074 is a 3D environment for the clinician to program IMD 20. Brain model 1076 is a 3D anatomical region and stimulation field 1078 is a 3D stimulation field within brain model 1076. Hand 1080 controls the view and aspects of 3D view according to user input from the clinician. Generally, brain model 1076 is stationed showing a sagittal view.

3D view 1074 may be displayed on a hand held programmer, which may include components similar to those illustrated with reference to programmer 19 in FIG. 5, or rendered in a 3D virtual reality space provided by a computing device that shows depth with any type of 3D display. 3D view 1074 can be displayed on a 2D display by using partially transparent surfaces and grey or color shades. A fully interactive 3D view 1074 may allow a clinician to view within brain model 1076 and identify anatomical regions that are targets for stimulation therapy. User interface 1072 may even include a glove or finger device that is the input mechanism for rotating and adjusting 3D view 1074. Brain model 1076 may be generated from imaging data from MRI, CT, or other imaging modality. While shading of brain model 1076 are not shown in FIGS. 63-65, the clinician would see anatomical regions of brain 18.

While a lead icon representing lead 14 is not shown in 3D view 1074, user interface 1072 may incorporate imaging data after lead 14 is implanted to automatically recognize the orientation and location of the lead within patient 12. Alternatively, the clinician may place a lead icon within brain model 1076 based upon stereotactic data or implant coordinates.

User interface 1072 initially displays stimulation field 1078 based upon the location of lead 14. The clinician can adjust and manipulate stimulation field 1078 as desired with hand 1080. The clinician may also use hand 1080 to rotate and spin brain model 1076 in any direction. User interface 1072 also supports zooming in and out and "flying" around 3D view 1074 to see stimulation field 1078 within brain model 1076.

User interface 1072 may include a wand tool that allows the clinician to highlight various ranges in brain model 1076 to be included in stimulation field 1078. The wand tool may automatically select pixels in all three dimensions. In other dimensions, the clinician may grab one of several predefined stimulation field shapes and place the shape within brain model 1076 to become stimulation field 1078. In any case, user interface 1072 may set limits to stimulation field 1078 based upon the characteristics of lead 14 and the capabilities of IMD 20. Patient 12 safety may also govern the size and location of stimulation field 1078.

Figure 64:
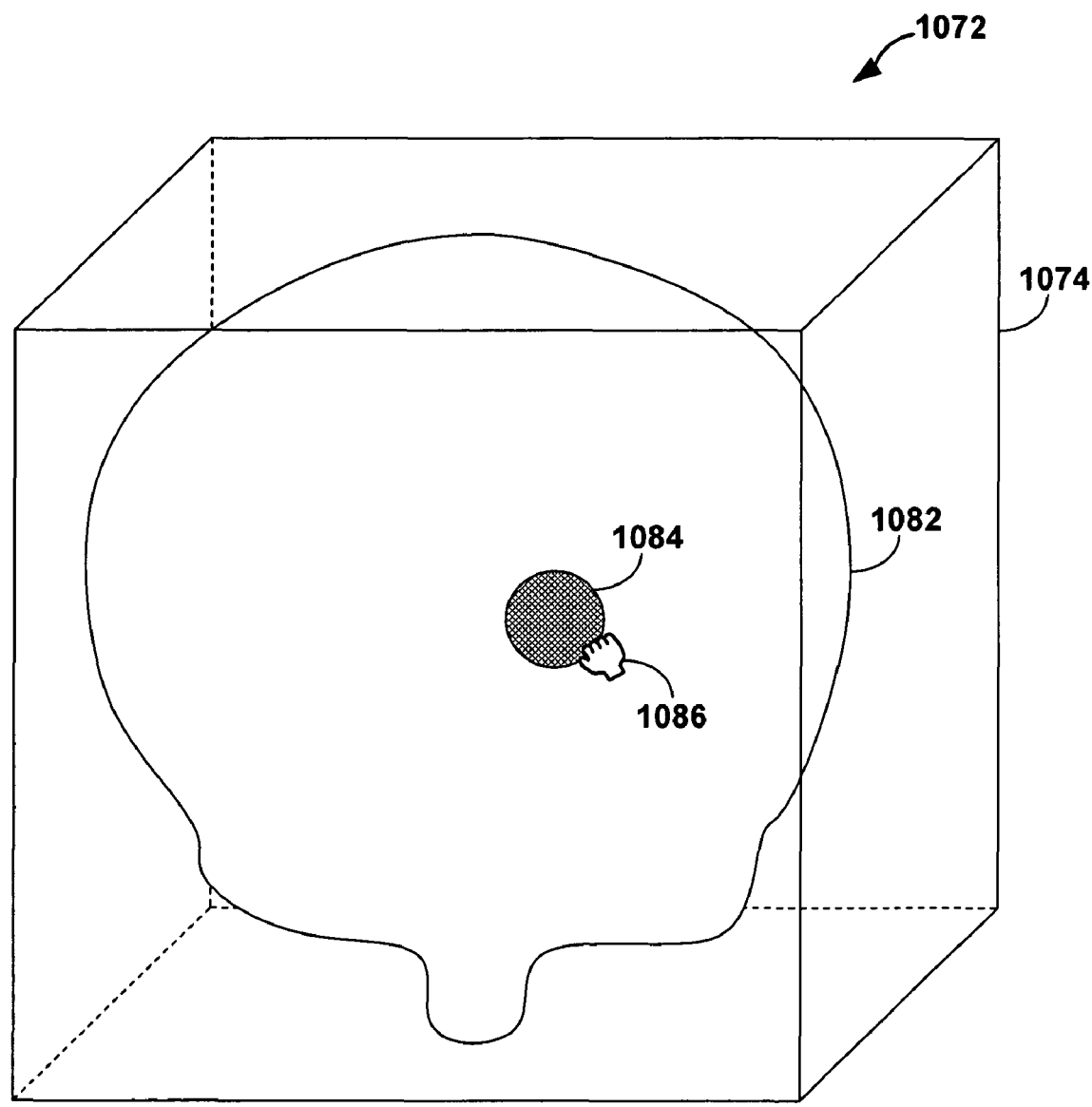
FIG. 64 is a conceptual diagram illustrating a rotated 3D brain model with the currently defined 3D stimulation field.

FIG. 64 is a conceptual diagram illustrating a rotated 3D brain model with the currently defined 3D stimulation field. As shown in FIG. 64, user interface 1072 includes 3D view 1074, brain model 1082, stimulation field 1084 and hand 1086. The clinician has grabbed brain model 1082 with hand 1086 to rotate the brain model to show a coronal view from the front of the brain. 3D view 1074 also shows that stimulation field 1084 is located in the left hemisphere of brain 18. The clinician may move or adjust stimulation field 1084 to cover target anatomical regions and avoid adjacent regions not to be stimulated.

Figure 65:
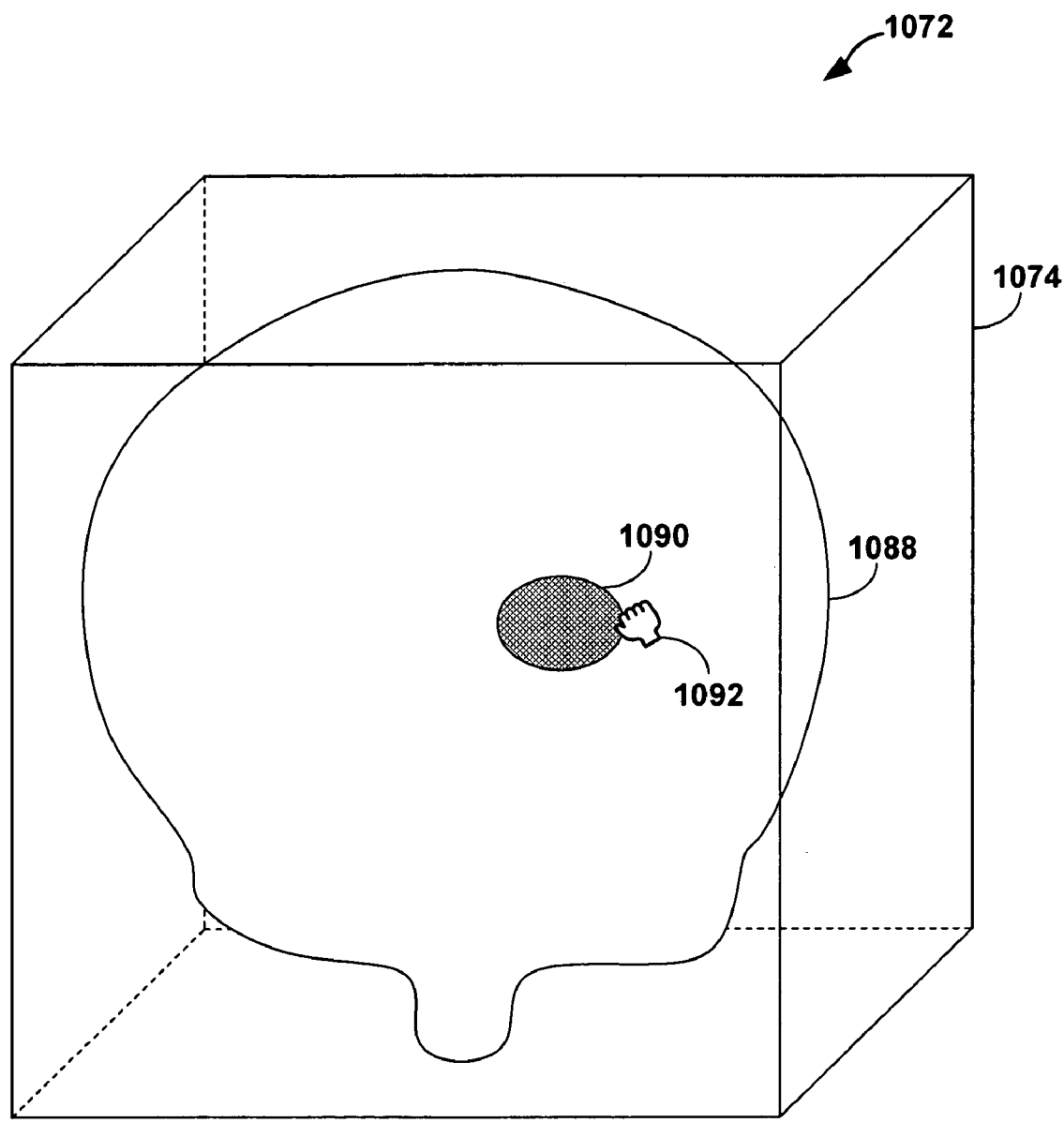
FIG. 65 is a conceptual diagram illustrating a manipulated 3D stimulation field positioned within a 3D brain model.

FIG. 65 is a conceptual diagram illustrating a manipulated 3D stimulation field positioned within a 3D brain model. FIG. 65 is a conceptual diagram illustrating a manipulated 3D stimulation field positioned within 3D brain model 1088. As shown in FIG. 65, the clinician has stretched the shape of stimulation field 1090 with hand 1092. The clinician may continue to stretch and mold the shape of stimulation field 1090 until the stimulation field covers the anatomical regions targeted for electrical stimulation. The clinician may zoom in to have greater fine control over the shape of stimulation field 1090.

The clinician may also use user interface 1072 to add additional stimulation fields, shrink stimulation fields, or split a stimulation field into two stimulation fields. In some embodiments, certain areas of brain 18 may be blocked from stimulation. User interface 1072 may automatically eliminate stimulation from those areas without the clinician needing to match the outline of the blocked areas. Once the clinician is completed with adjusting stimulation field 1088, user interface 1072 may utilize programmer 19 to generate the associated stimulation parameters.

User interface 1072 may be very intuitive and even instructional to clinicians needing to program IMD 20 with a 3D lead such as lead 14. Programming mechanisms similar to this may help a greater number of patients receive the full benefits from stimulation therapy by avoiding some of the less than ideal therapies resulting from manual electrode programming and the lengthy times associated with manual programming.

In some embodiments, user interface 1072 may allow the clinician to locate the correct placement of the lead icon representation of lead 14 within 3D brain model 1088 and continue defining a stimulation field in 2D orthogonal views such as the ones described in user interface 90. Since the central axis of the lead icon may not lie completely within, e.g., be parallel to, the plane of a preset coronal view 92, sagittal view 102, or axial view 102, 3D brain model 1088 may allow the clinician to easily identify an oblique plane (oblique view) that is substantially parallel with the central axis of the lead icon. The clinician may then lock this oblique view and use the oblique view and other orthogonal planes of the oblique view to define a stimulation field, similar to user interface 90. In addition, user interface 1072 may automatically identify an oblique plane that includes the lead icon and allow the clinician to rotate the oblique plane around the lead icon until the clinician creates the desired oblique view. The clinician may then use this oblique view to continue programming using 2D views.

Figure 66:
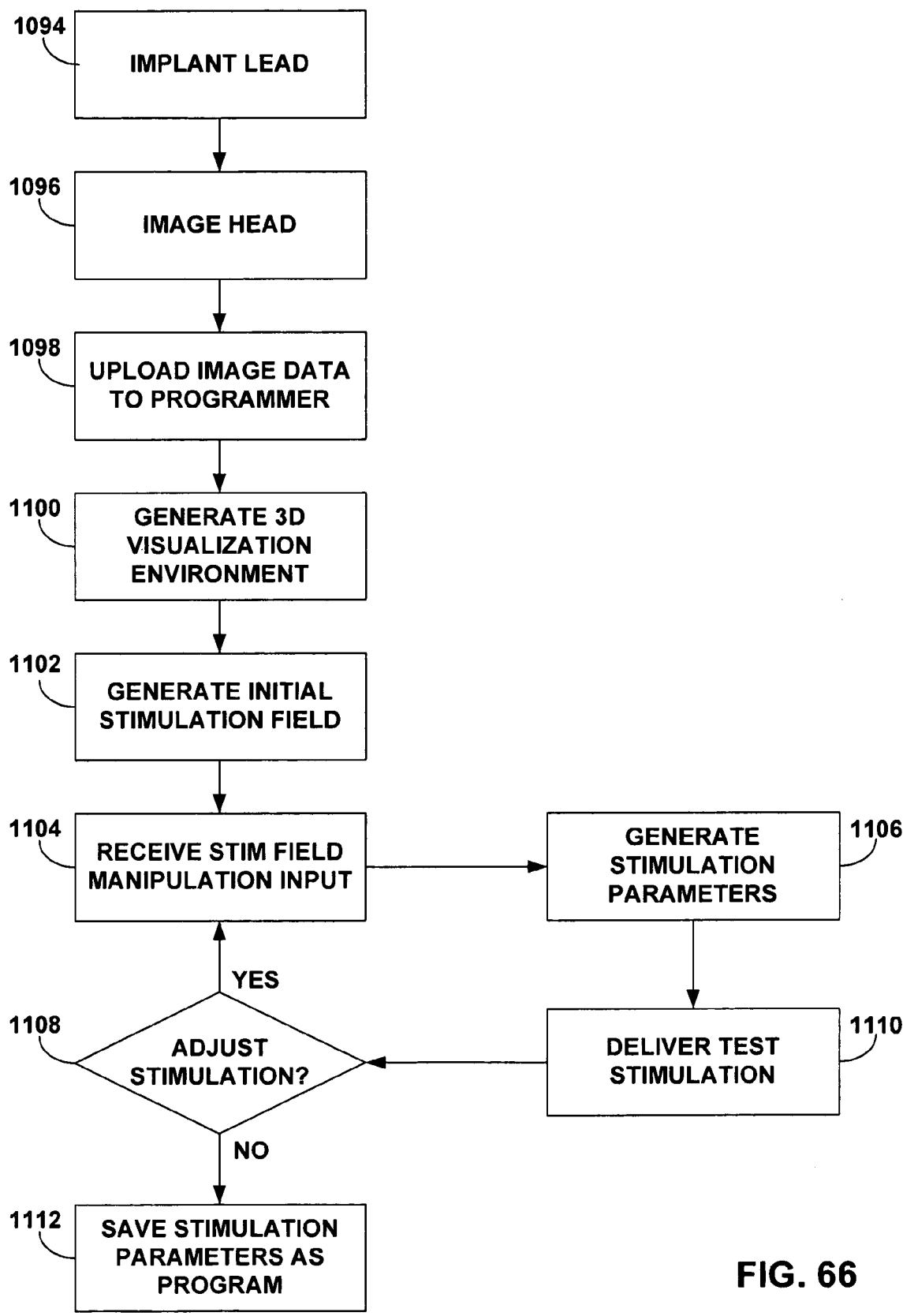
FIG. 66 is a flow diagram illustrating an example technique for defining a 3D stimulation field within a 3D brain model of the patient.

FIG. 66 is a flow diagram illustrating an example technique for defining a 3D stimulation field within a 3D brain model of the patient. FIG. 66 is a flow diagram illustrating an exemplary technique for defining a 3D stimulation field within a 3D brain model of the patient. As shown in FIG. 66, the clinician implants lead 14 according to the technique shown in FIG. 11 (1094). The clinician then images the head of patient 12 to generate the needed data of brain 18 (1096). The clinician uploads the image data to programmer 19 (1098) and the programmer generates the 3D environment (1100). Programmer 19 generates brain model 1076 and the initial stimulation field 1078 (1102).

Programmer 19 receives stimulation field input from a clinician via user interface 1072 to adjust and manipulate stimulation field 1078 (1104). Programmer 19 generates stimulation parameters according to stimulation field 1078 (1106) and IMD 20 delivers test stimulation with the parameters (1110). If the clinician desires to adjust stimulation (1108), programmer 19 again receives stimulation field input (1104). If the stimulation therapy is effective, the clinician saves the stimulation parameters in IMD 20 so that patient 12 can receive therapy with the parameters (1112).

Figure 67:
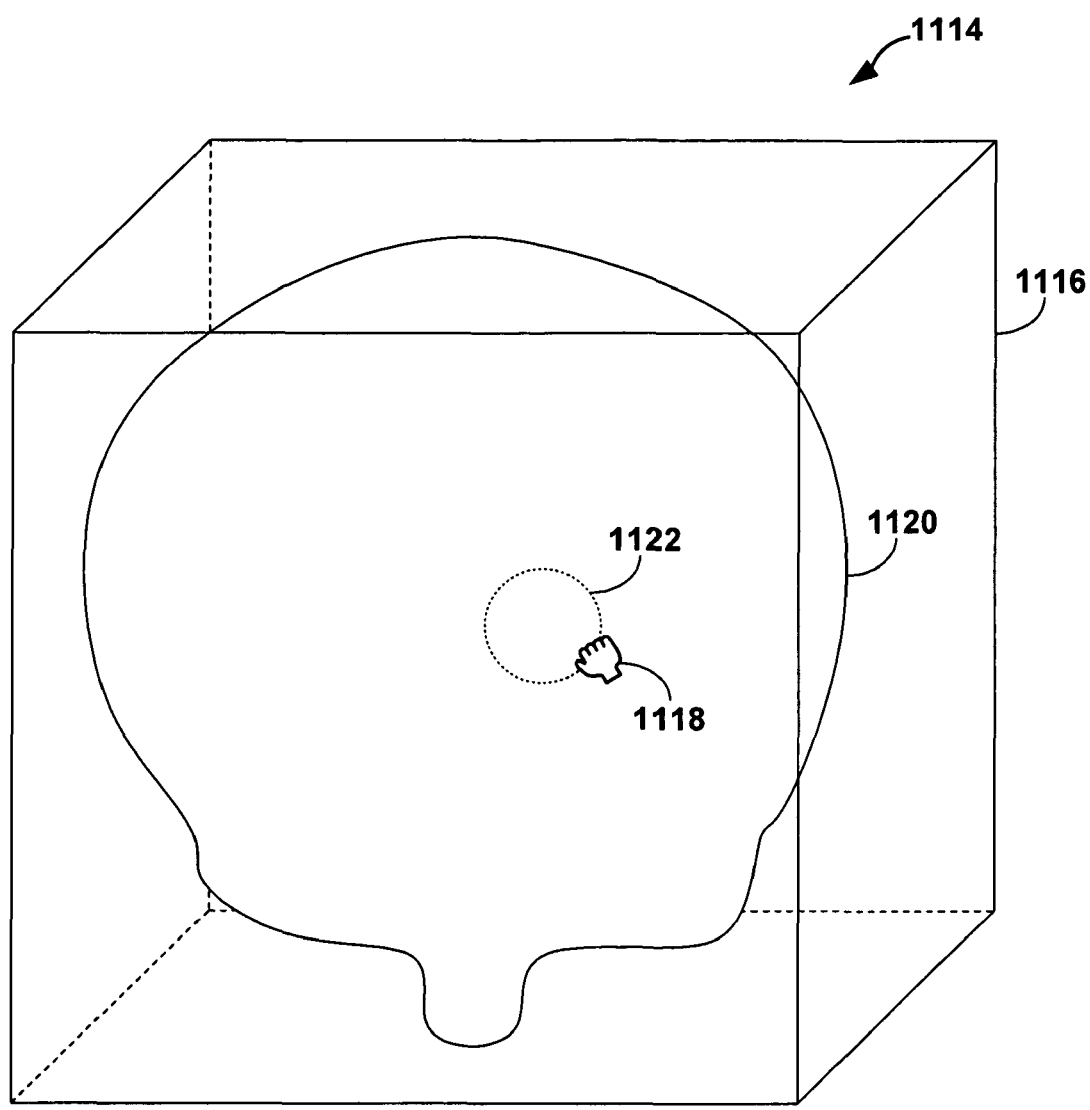
FIG. 67 is a conceptual diagram illustrating a 3D visualization environment including a 3D brain model and defined 3D stimulation field for creating a stimulation template set.

FIGS. 67-70 illustrate a 3D environment for defining a 3D stimulation field with stimulation templates. FIG. 67 is a conceptual diagram illustrating a 3D visualization environment that facilitates programming with a stimulation template set. As shown in FIG. 67, user interface 1114 presents 3D environment 1116 to the clinician which allows the clinician to define 3D stimulation field 1122 within 3D brain model 1120. User interface 1114 may be provided by a programmer substantially similar to programmer 19, or another computing device. User interface 1114 may be similar to user interface 1072 of FIG. 63. However, user interface 1114 is directed to creating a stimulation template set from 3D stimulation field 1122. 3D brain model 1120 is an anatomical region of the patient anatomy and is represented with shading, colors, or some other mechanism of representing the brain 18 in three dimensions to the clinician. The clinician uses hand 1118 to grasp 3D stimulation field 1122 and change the stimulation field shape and size. In some embodiments, user interface 1114 may allow the clinician to split 3D stimulation field 1122 into more than one continuous region. In other embodiments, user interface 1114 may provide a lead icon that represents lead 14 implanted within patient 12.

Figure 68:
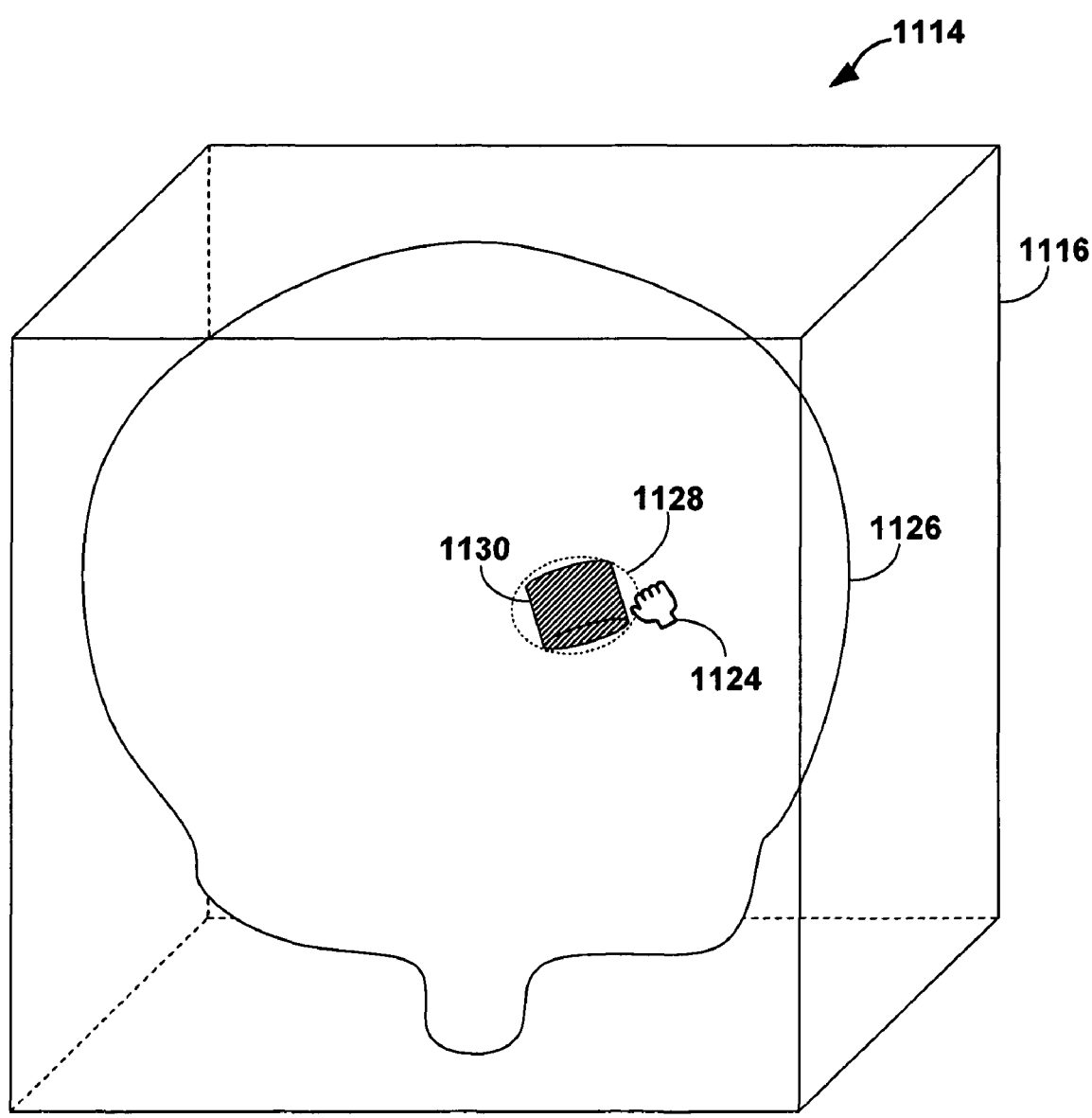
FIG. 68 is a conceptual diagram illustrating a 3D visualization environment including a 3D brain model and the created template set corresponding to the defined 3D stimulation field.

FIG. 68 is a conceptual diagram illustrating a three-dimensional (3D) visualization environment including a 3D brain model and the template set created based on the defined 3D stimulation field. As shown in FIG. 68, user interface 1114 displays 3D brain model 1126 in 3D environment 1116, similar to FIG. 67. Within 3D brain model 1126 is 3D stimulation field 1128 and corresponding stimulation template set 1130. Hand 1124 may still be used to alter the shape, size, and location of 3D stimulation field 1128. User interface 1114 may change stimulation template set 1130 to match and 3D stimulation field 1128 changes, e.g., by adding, removing or replacing stimulation templates from the template sets. The clinician may also use hand 1124 to rotate, zoom in, zoom out, and view 3D brain model 1126 from different angles and perspectives to identify the actual structures of brain 18 that stimulation template set 1130 would affect during therapy.

Stimulation template set 1130 may be created from one or more stimulation templates that relate to each electrode of lead 14. Stimulation template set 1130 may be created in a similar manner as described in FIGS. 28-32. The volumetric stimulation templates that are a best fit to stimulation field 1128 may be combined to create the volumetric stimulation template set 1130. 3D environment 1116 allows the clinician to view the entire stimulation template set 1130 and tissue structures simultaneously to review the suggested stimulation therapy for patient 12.

Figure 69:
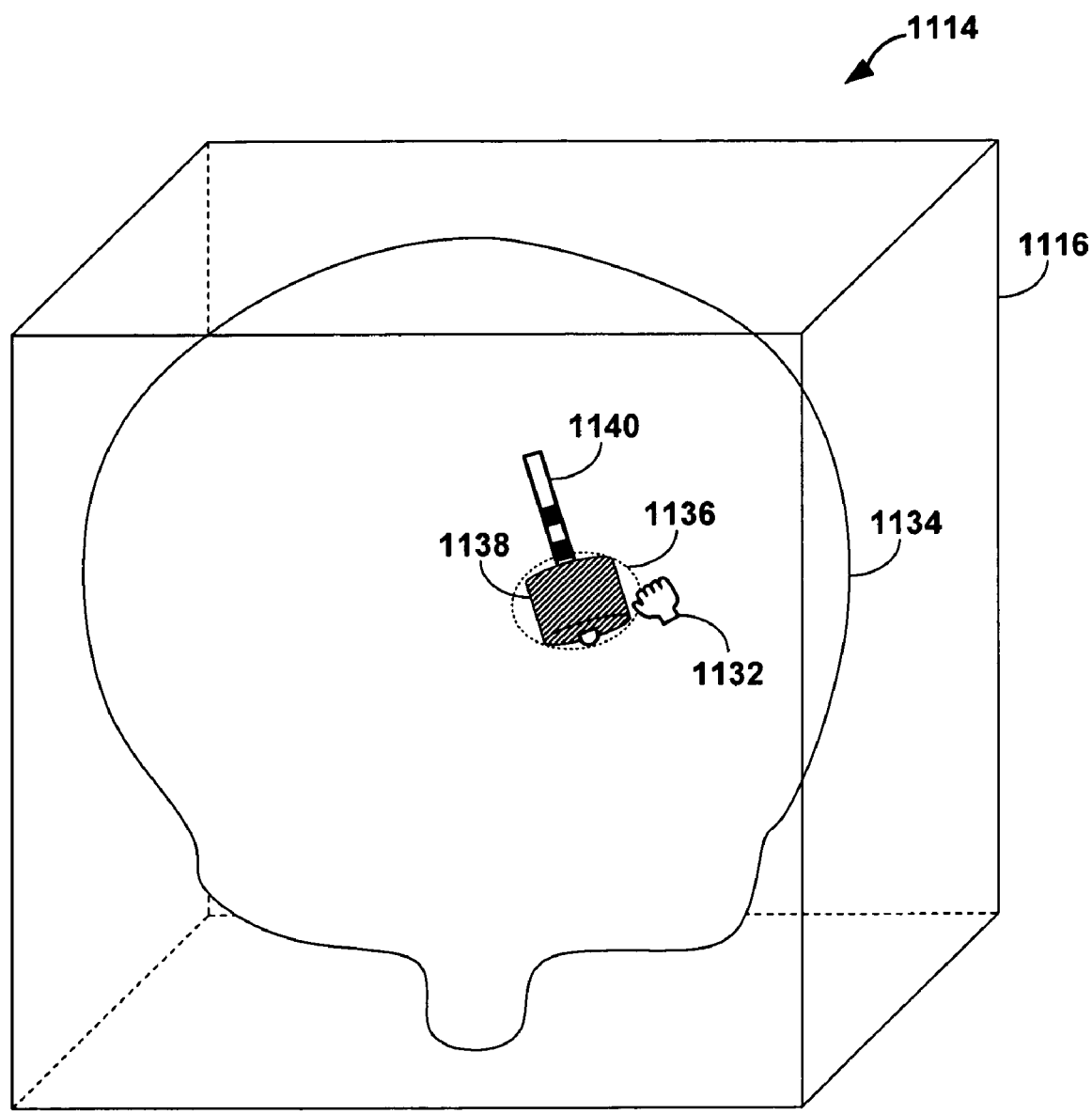
FIG. 69 is a conceptual diagram illustrating a 3D) visualization environment including a 3D brain model, the created template set corresponding to the defined 3D stimulation field, and a lead icon.

FIG. 69 is substantially similar to FIG. 68. User interface 1114 displays 3D brain model 1134 in 3D environment 1116. Within 3D brain model 1134 is 3D stimulation field 1136 and corresponding stimulation template set 1138. Hand 1132 may still be used to alter the shape, size, and location of 3D stimulation field 1128. In addition, lead icon 1140 is provided within 3D brain model 1134 to allow the clinician to view the proposed stimulation template set 1138 in relation to electrodes of lead 14 implanted within patient 12. As shown in FIG. 69, stimulation template set 1138 surrounds lead icon 1140 in a cylindrical type formation. However, any other stimulation template set supported by system 10 may be used to attempt to match 3D stimulation field 1136.

Figure 70:
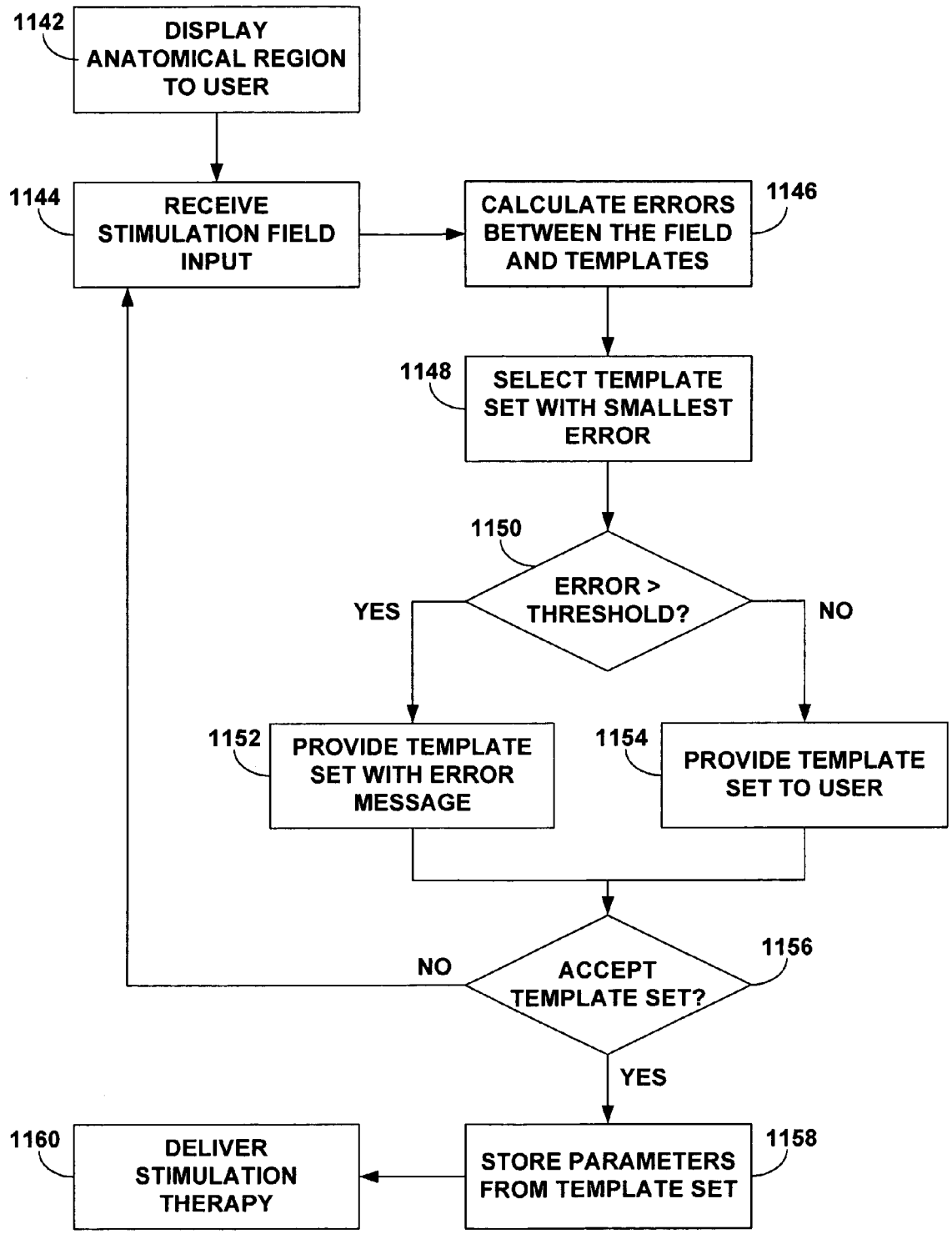
FIG. 70 is a flow diagram illustrating an example technique for creating a template set and displaying the template set in a 3D brain model of the patient.

FIG. 70 is a flow diagram illustrating an example technique for creating a template set and displaying the template set in a 3D brain model of the patient. As shown in FIG. 70, user interface 1114 displays 3D brain model 1126 in 3D environment 1116 (1142). User interface 1114 next receives stimulation field input from the clinician (1144). Processor 80 calculates the error between the stimulation field and the available stimulation templates, e.g., based on a comparison of their volumes (1146). From the error calculations, processor 80 selects the stimulation template set with the smallest error between the templates and the stimulation field (1148). Typically, the template set must remain within the defined stimulation area to prevent stimulation of non-target tissue. However, some embodiments, may allow stimulation template sets that best fit the stimulation area even when a portion of the stimulation template set stimulates tissue outside of the stimulation field.

If the best fit stimulation template set error is greater than a predetermined threshold (1150), user interface 1114 will provide the stimulation template set to the clinician with an error message indicating that the template set exceeds the error threshold (1152). If the best fit stimulation template set error is less than the predetermined threshold (1150), user interface 1114 provides the stimulation template set to the clinician (1154). If the clinician does not accept the created stimulation template set (1156), user interface 1114 will again receive stimulation field input (1144). If the clinician wants to accept the stimulation template set for therapy (1156), programmer 19 stores the stimulation parameters from the stimulation template set (1158). Programmer 19 then delivers the stimulation parameter sets to IMD 20 which delivers the stimulation therapy to patient 12 (1160).

Figure 71:
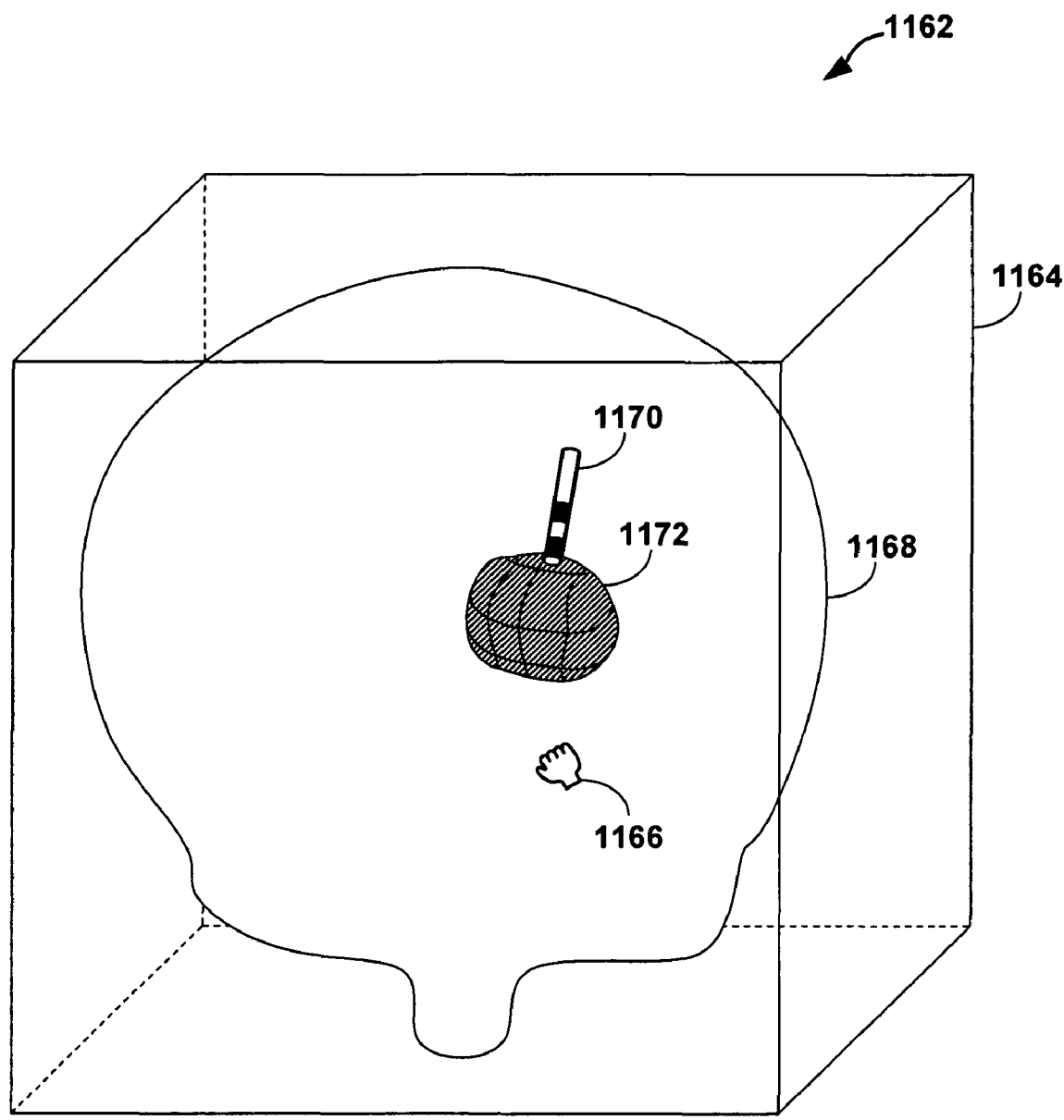
FIG. 71 is a conceptual diagram illustrating a 3D visualization environment including a 3D brain model and 3D electrical field model.
Figure 72:
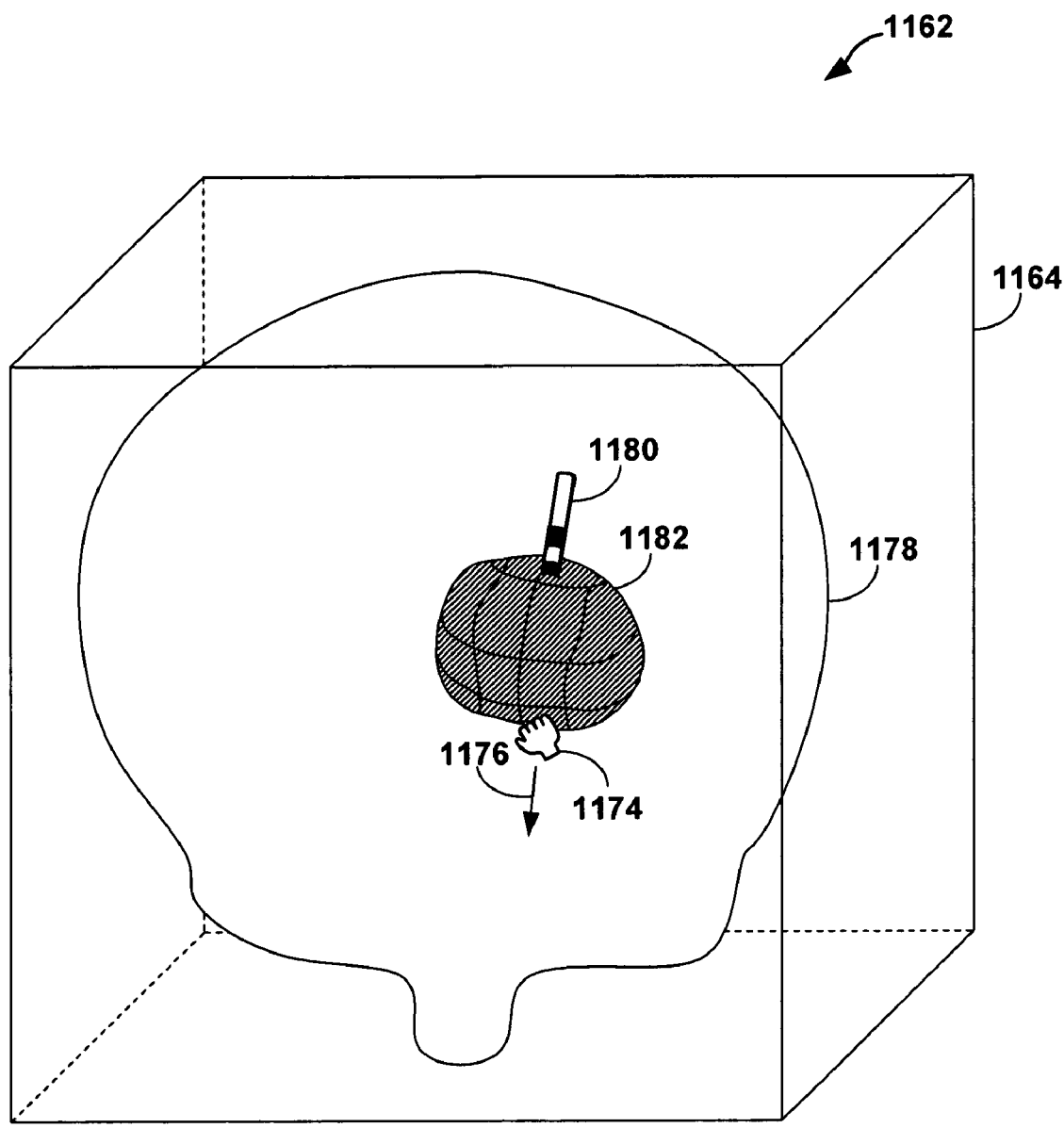
FIG. 72 is a conceptual diagram illustrating a 3D visualization environment including a 3D brain model and enlarged 3D electrical field model as defined by the user.
Figure 73:
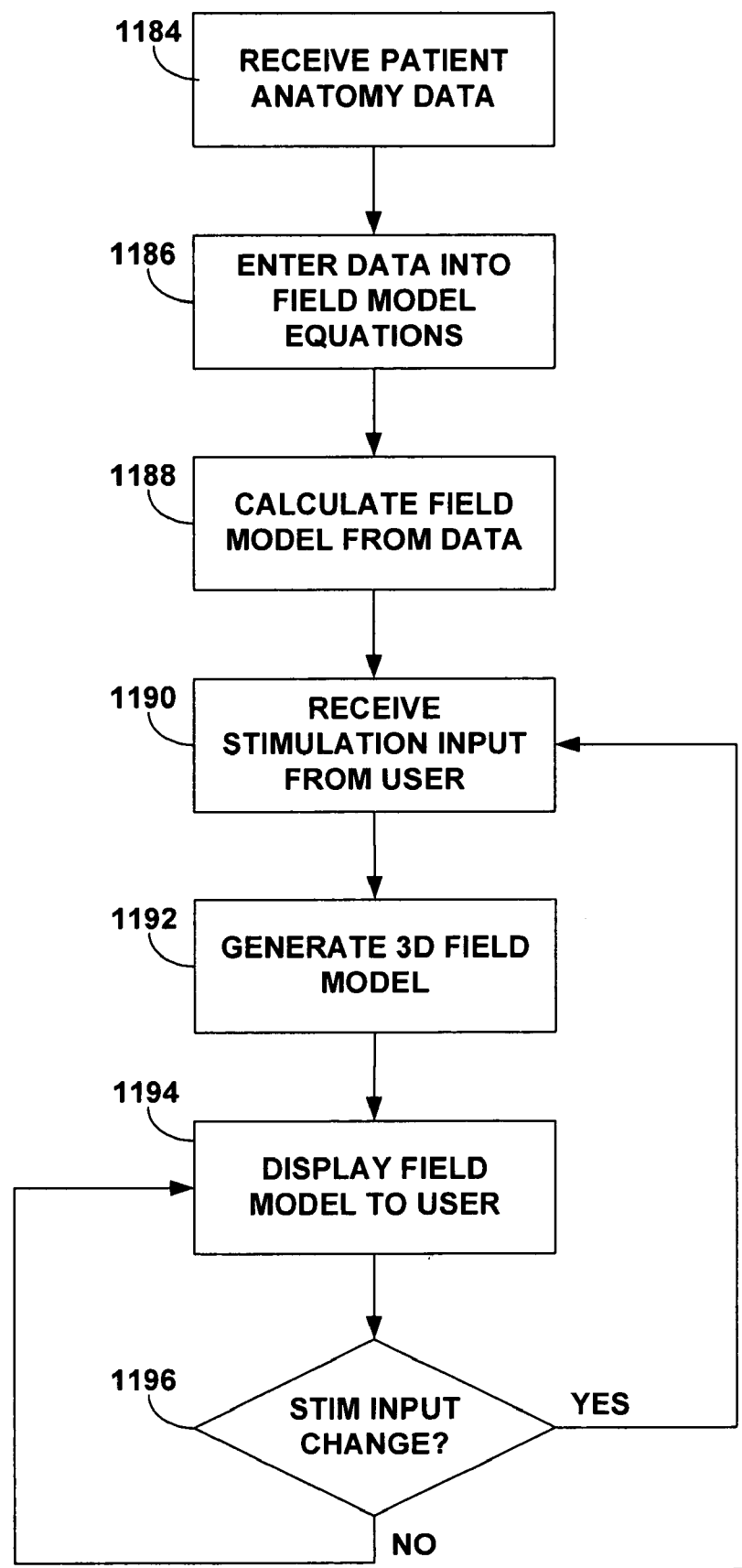
FIG. 73 is a flow diagram illustrating an example technique for calculating an electrical field model and displaying the field model to the user.

FIGS. 71-73 illustrate example electrical field models that show a user which structures of brain 18 will be covered by the electrical field resulting from delivery of stimulation. FIG. 71 is a conceptual diagram illustrating a three-dimensional (3D) visualization environment including a 3D brain model and 3D electrical field model. As shown in FIG. 71, user interface 1162 displays 3D brain model 1168 via 3D environment 1164. 3D environment 1164 is provided to a user through an embodiment of programmer 19. Once the user, or clinician, defines the stimulation field, the appropriate stimulation parameters are generated for therapy. Electrical field model 1172 is generated by a processor, such as processor 80, and is displayed within 3D brain model 1168. Electrical field model 1172 may be the 3D approximation of electrical fields described in FIGS. 53-57. Lead icon 1170 represents the location of lead 14 in brain 18 and is shown within electrical field model 1172. The clinician may user hand 1166 to rotate, zoom in, and zoom out of 3D brain model 1168 to review the proposed stimulation therapy. In some embodiments, the clinician may use hand 1166 to modify electrical field model 1172 size, shape, or location. In this manner, the corresponding stimulation parameters will change accordingly.

FIG. 72 is a conceptual diagram illustrating a three-dimensional (3D) visualization environment including a 3D brain model and enlarged 3D electrical field model as defined by the user. FIG. 72 is similar to FIG. 71. User interface 1162 displays 3D brain model 1178 and lead icon 1180 via 3D environment 1164. Electrical field model 1182 has been increased in size over electrical field model 1172 of FIG. 71. The clinician has used hand 1174 to pull electrical field model 1182 in the direction of arrow 1176 to cause this increase in the electrical field model size. Additionally, hand 1174 may cause electrical stimulation field 1182 to change location or alter its shape as directed by the clinician.

Changes to electrical field model 1182 are essentially caused by hand 1174 forcing changes to the stimulation parameters that define the electrical field model. As electrical field model 1182 increases in size, the shape of the electrical field model changes to reflect the electrical current propagation within the tissue of brain 18 (represented by 3D brain model 1178). Electrical stimulation field 1182 may have limits to the size or location of the field based upon the limitations of system 10.

FIG. 73 is a flow diagram illustrating an example technique for calculating an electrical field model and displaying the field model to the user. The technique is described with reference to programmer 19, which may provide any of the user interfaces described above with reference to FIGS. 71 and 72. As shown in FIG. 73, programmer 19 receives patient anatomy data via user interface 1162 necessary for creating an electrical field (1184). Programmer 19 enters the patient anatomy data in stored electrical field model equations or equation sets to satisfy anatomical variable (1186). Programmer 19 next calculates the electrical field model from the data and equations (1188). Once programmer 19 receives stimulation input from the clinician via user interface 1162 defining the stimulation field (1190), the programmer generates the 3D electrical field model according to the stimulation parameters (1192). The 3D electrical field model may be displayed to the clinician via user interface 1162 (1194). If the clinician desires to change the stimulation input (1196), programmer 19 receives a change in the stimulation input via user interface 1162 (1190). If the clinician does not request a stimulation input change (1196), programmer 19 continues to display the 3D electrical field model to the clinician via user interface 1162 (1194). Programmer 19 may also provide a mechanism to exit the viewing of 3D environment 1164.

Figure 74:
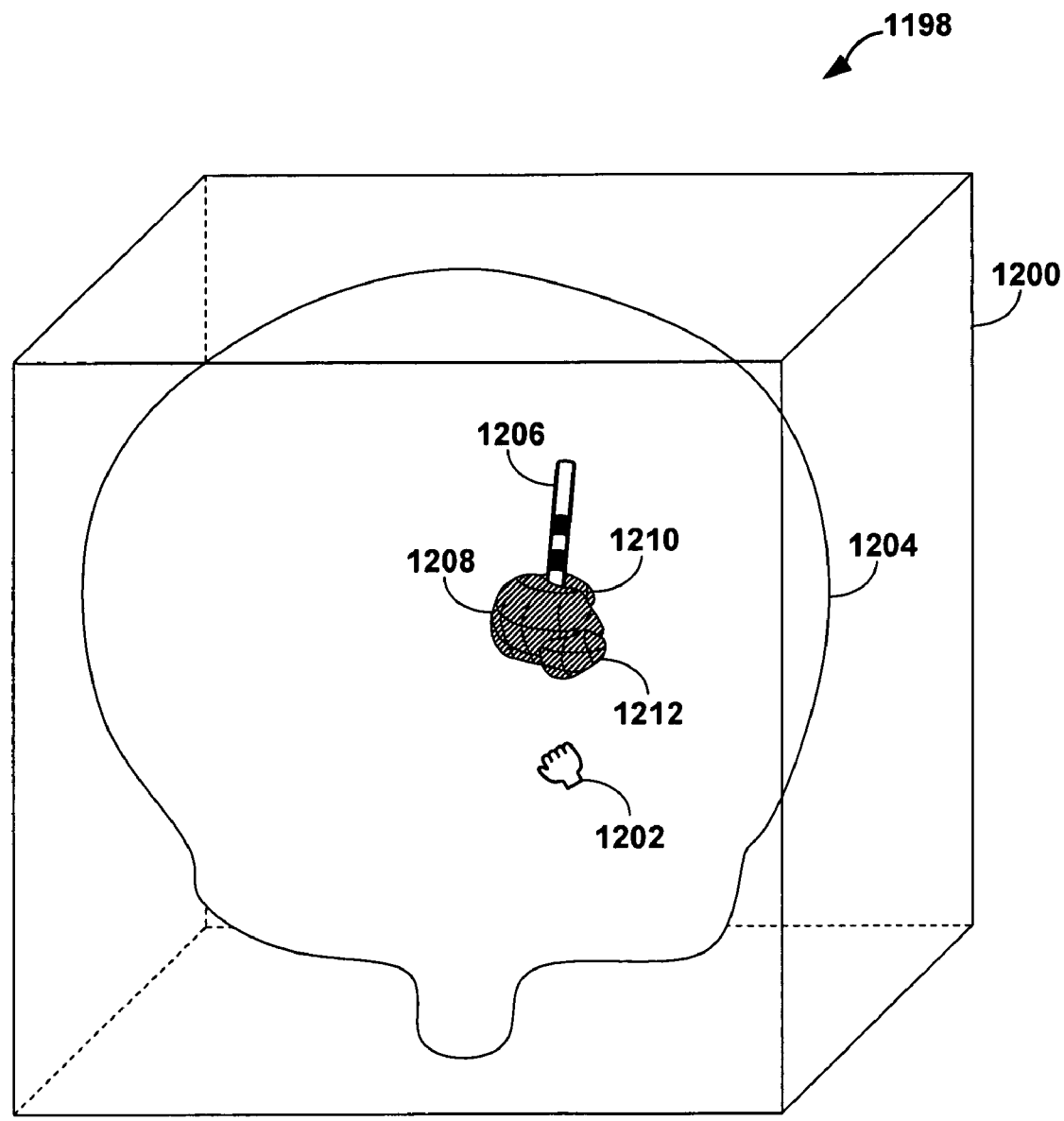
FIG. 74 is a conceptual diagram illustrating a 3D visualization environment including a 3D brain model and 3D activation field model.
Figure 75:
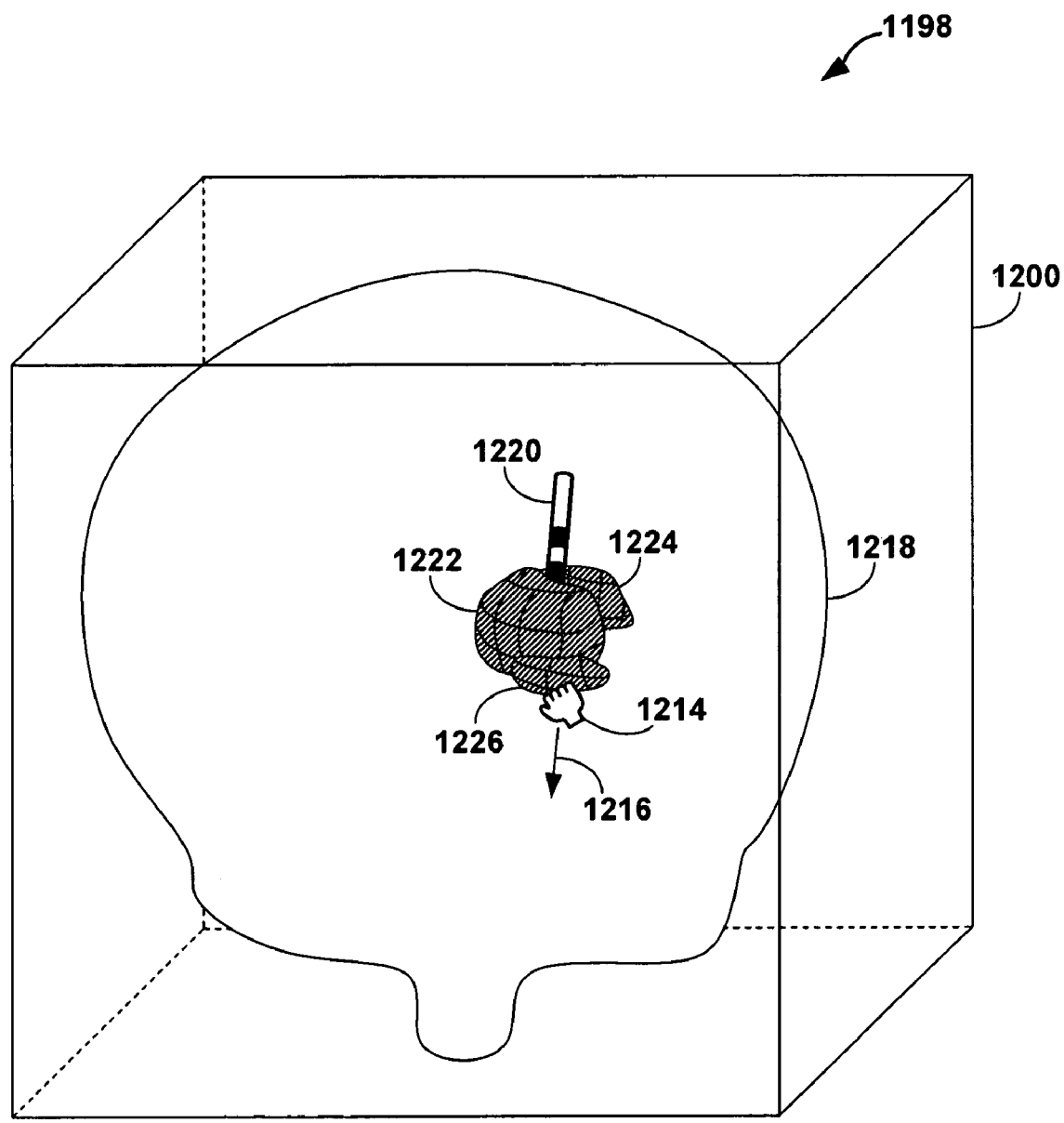
FIG. 75 is a conceptual diagram illustrating a 3D visualization environment including a 3D brain model and enlarged 3D activation field model as defined by the user.
Figure 76:
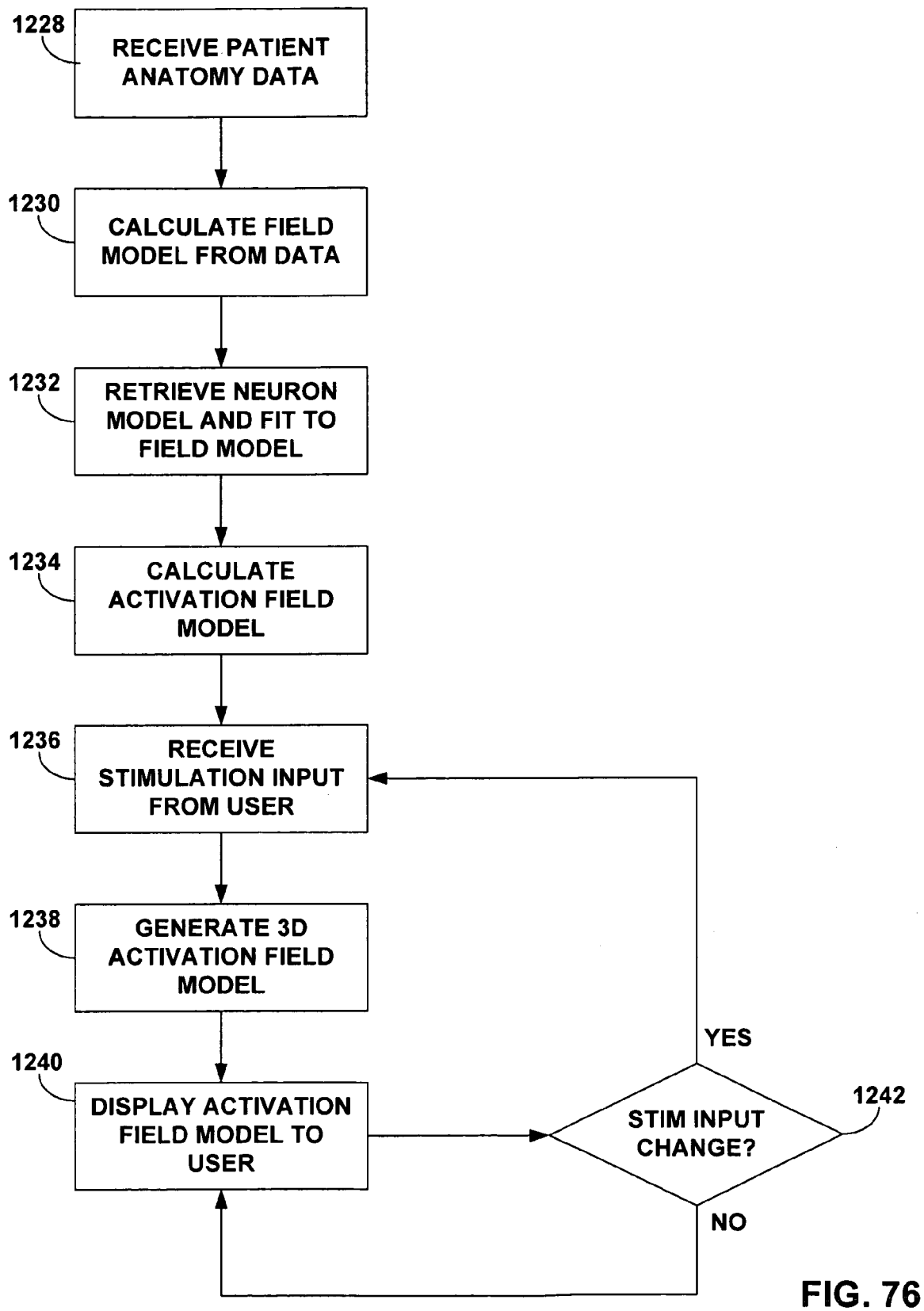
FIG. 76 is a flow diagram illustrating an example technique for calculating an activation field model and displaying the field model to the user.

FIGS. 74-76 illustrate example three-dimensional (3D) activation field models that show a user which neurons of brain 18 tissue will be activated by the produced electrical field during therapy. FIG. 74 is a conceptual diagram illustrating a 3D environment including a 3D brain model and 3D activation field model. As shown in FIG. 74, user interface 1198 displays 3D brain model 1204 via 3D environment 1200. 3D environment 1200 is provided to a user through an embodiment of programmer 19 or other computing device. Once the user, or clinician, defines the stimulation field, the appropriate stimulation parameters are generated for therapy. An electrical field model, such as described in FIGS. 71-73, is applied to a neuron model of brain tissue to generate activation fields 1208, 1210 and 1212 (collectively the activation field model) displayed within 3D brain model 1204. Activation fields 1208, 1210 and 1212 are 3D versions of the activation fields described in FIGS. 58-62. Lead icon 1206 represents the location of lead 14 in brain 18 and is shown within activation fields 1208, 1210 and 1212. The clinician may use hand 1202 to rotate, zoom in, and zoom out of 3D brain model 1204 to review the proposed stimulation therapy. In some embodiments, the clinician may use hand 1202 to modify the activation field model size, shape, or location. In this manner, activation fields 1208, 1210 and 1212 may will change accordingly. While the activation field model is separated into three separate activation fields 1208, 1210 and 1212, the activation field may include one continuous activation field around lead icon 1206 or many smaller separated activation fields caused by pockets of neurons in brain 18 that are not activated by the generated electrical field of the stimulation therapy.

FIG. 75 is a conceptual diagram illustrating a three-dimensional (3D) visualization environment including a 3D brain model and enlarged 3D activation field model as defined by the user. FIG. 75 is similar to FIG. 74. User interface 1198 displays 3D brain model 1218 and lead icon 1220 via 3D environment 1200. Activation fields 1222, 1224 and 1226 have been increased in size over activation fields 1208, 1210 and 1212 of FIG. 74. The clinician has used hand 1214 to pull the activation fields 1222, 1224 and 1226 in the direction of arrow 1216 to cause this increase in the number of activated neurons. Additionally, hand 1214 may be used to move activation fields 1222, 1224 and 1226 or alter their shape as directed by the clinician.

Changes to activation fields 1222, 1224 and 1226 are essentially caused by hand 1214 forcing changes to the stimulation parameters that define the electrical field model, and thus the activation field model. As the activation field model increases in size, the shape of activation fields 1222, 1224 and 1226 change to reflect the actual neurons of brain 18 that would be activated by the electrical field produced by lead 14 (represented by 3D brain model 1220). The activation field model may have limits to the size or location of the field based upon the limitations of system 10.

FIG. 76 is a flow diagram illustrating an example technique for calculating an activation field model and displaying the field model to the user. The technique is described with reference to programmer 19, which may provide any of the user interfaces described above with reference to FIGS. 74 and 75. As shown in FIG. 76, programmer 19 receives patient anatomy data indicative of the anatomy of patient 12 via user interface 1198 (1228) and the programmer calculates the electrical field model from the patient anatomy data (1230). Programmer 19 then retrieves the neuron model and fits the neuron model to the electrical field (1232). Programmer 19 next calculates the activation field model based upon the electrical field model and neuron model (1234). Programmer then is able to receive stimulation input from the clinician via user interface 1198 defining what structures of the anatomical region should be stimulated (1236). Programmer 19 subsequently generates the 3D activation field model (1238) and user interface 1198 displays the activation field model to the clinician (1240). If the clinician desires to change the stimulation input (1242), user interface 1198 receives stimulation input from the clinician modifying the previous stimulation input (1236). If the stimulation input does not need to be changed (1242), the activation field model continues to be displayed by user interface 1198 (1240). The clinician may also be able to leave viewing the activation field model to deliver the stimulation therapy or change aspects of the stimulation parameters.

Although the disclosure may be especially applicable to the simulation of the deep brain, the invention alternatively may be applied more generally to any type of stimulation wherein the parameters of stimulation programs may be automatically generated based upon a defined stimulation field. As examples, cortical brain stimulation, spinal cord stimulation, sacral or pudendal nerve stimulation, or dorsal root stimulation may benefit from the user interface described herein.

Although this disclosure has referred to neurostimulation applications generally, and DBS and SCS applications more particularly, such applications have been described for purposes of illustration and should not be considered limiting of the invention as broadly embodied and described herein. The invention may be more generally applicable to electrical stimulation of tissue, such as nerve tissue or muscle tissue, and may be applicable to a variety of therapy applications including spinal cord stimulation, pelvic floor stimulation, deep brain stimulation, cortical surface stimulation, neuronal ganglion stimulation, gastric stimulation, peripheral nerve stimulation, or subcutaneous stimulation. Such therapy applications may be targeted to a variety of disorders such as chronic pain, peripheral vascular disease, angina, headache, tremor, Parkinson's disease, epilepsy, urinary or fecal incontinence, sexual dysfunction, obesity, or gastroparesis. Also, the invention is not necessarily limited to use with completely implanted neurostimulators, and may also be applicable to external stimulators coupled to implanted leads via a percutaneous port.

In addition, although electrode array geometries having four or eight axial electrode levels and four angular electrode positions have been described, the disclosure may be applicable to a wide variety of electrode array geometries including virtually any number of axial and angular electrode positions. Again, a complex electrode array geometry generally refers to an arrangement of stimulation electrodes at multiple non-planar or non-coaxial positions, in contrast to simple electrode array geometries in which the electrodes share a common plane or a common axis. An example of a simple electrode array geometry is an array of ring electrodes distributed at different axial positions along the length of a lead. Another example of a simple electrode array geometry is a planar array of electrodes on a paddle lead.

An example of a complex electrode array geometry, in accordance with this disclosure, is an array of electrodes positioned at different axial positions along the length of a lead, as well as at different angular positions about the circumference of the lead. In some embodiments, the electrodes in the complex array geometry may appear similar to non-contiguous, arc-like segments of a conventional ring electrode. A lead with a complex electrode array geometry may include multiple rings of electrode segments. Each axially positioned ring is disposed at a different axial position. Each electrode segment within a given ring is disposed at a different angular position. The lead may be cylindrical or have a circular cross-section of varying diameter. Another example of a complex electrode array geometry is an array of electrodes positioned on multiple planes or faces of a lead. As an illustration, arrays of electrodes may be positioned on opposite planes of a paddle lead or multiple faces of a lead having a polygonal cross-section. Also, electrodes positioned at particular axial or angular positions need not be aligned with other electrodes. Rather, in some embodiments, electrodes may be arranged in a staggered or checkerboard-like pattern.

Further, although a single lead may be useful in various stimulation applications, multiple leads may be useful in other applications such as bi-lateral DBS, SCS, or multi-site stimulation for gastric, pelvic or peripheral nerve stimulation. Accordingly, electrode combinations may be formed between electrodes carried by a single lead, electrode combinations formed between electrodes carried by one lead of a pair of leads, or electrode combinations formed between electrodes on different leads, as well as electrodes carried by a stimulator housing, e.g., in a so-called active can configuration.

The techniques described herein may be techniques may be applied to a programming interface or control interface associated with a clinician programmer, a patient programmer, or both. Hence, a clinician may use a clinician programmer in clinic to program and evaluate different electrode combinations and stimulation parameter values. A patient may use a patient programmer during daily use to adjust parameter values, select different electrode combinations, subject to keepout zones and ranges specified by the clinicians. The clinician programmer or patient programmer may be a small, portable, handheld device, similar to a personal digital assistant (PDA). Alternatively, in the case of a clinician programmer, the programmer may be implemented in a general purpose desktop or laptop computer, computer workstation, or dedicated desktop programming unit.

In addition, the programming functionality described in this disclosure may be used to program an implantable stimulator coupled to one or more implantable leads or an external stimulator coupled to one more percutaneous leads. For example, the invention may be used for trial stimulation or chronic stimulation.

The disclosure also contemplates computer-readable media comprising instructions to cause a processor to perform any of the functions described herein. The computer-readable media may take the form of any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Programmer 19 also may contain a more portable removable memory type to enable easy data transfer or offline data analysis.

Various embodiments of the described invention may be implemented using one or more processors that are realized by one or more microprocessors, Application-Specific Integrated Circuits (ASIC), Field-Programmable Gate Arrays (FPGA), or other equivalent integrated or discrete logic circuitry, alone or in any combination.

Many embodiments of the disclosure have been described. Various modifications may be made without departing from the scope of the claims. These and other embodiments are within the scope of the following claims.

The invention claimed is:

1. A method comprising:
receiving a patient anatomy data set that describes at least one characteristic of patient tissue proximate to an electrical stimulation lead implanted within a patient;
receiving user input that defines stimulation parameter values;
generating a stimulation field model that represents where electrical stimulation will propagate from the electrical stimulation lead based upon the patient anatomy data set and stimulation parameter values;
displaying the stimulation field model on a representation of an anatomical region of the patient;
receiving stimulation field input from a user that modifies at least one of the size, shape or location of the stimulation field model relative to the displayed anatomical location; and
determining at least one new stimulation parameter value based on the modification of the stimulation field model.

2. The method of claim 1, wherein generating the stimulation field model comprises applying the patient anatomy data set to a stimulation field equation set.

3. The method of claim 1, wherein displaying the stimulation field model comprises displaying the stimulation field model via one of a two-dimensional display or a three-dimensional environment.

4. The method of claim 1, wherein receiving stimulation field input comprises receiving input that drags at least one of the stimulation field model or a boundary of the stimulation field model relative to the displayed anatomical region.

5. The method of claim 1, wherein displaying the stimulation field model on a representation of an anatomical region comprises displaying the stimulation field model and anatomical region as plurality of different two-dimensional, cross-sectional views, and receiving stimulation field input comprises receiving stimulation field input that modifies a cross-section of the stimulation field model in one or more of the cross-sectional views.

6. The method of claim 5, wherein the views comprise at least one of a coronal view, a sagittal view, an axial view, and an oblique view.

7. The method of claim 1, further comprising:
generating a neuron model that describes at least one characteristic of patient neural tissue proximate to the electrical stimulation lead implanted within the patient;
generating an activation field model that indicates which neural structures of the patient are activated by applying the stimulation field model to the anatomical region of the patient based on the neuron model and the stimulation field model; and
displaying the activation field model over the anatomical region.

8. The method of claim 1, wherein the anatomical region comprises at least one of a spinal cord, a cerebrum, a cerebellum, a brain stem, skeletal muscle, and smooth muscle.

9. The method of claim 8, wherein the structure of the anatomical region is at least one of a substantia nigra, subthalamic nucleus, globus pallidus interna, ventral intermediate, and zona inserta.

10. A system comprising:
a communications module that receives a patient anatomy data set that describes at least one characteristic of patient tissue proximate to an electrical stimulation lead implanted within a patient;
a user interface that receives user input that defines stimulation parameter values; and
a processor that generates a stimulation field model that represents where electrical stimulation will propagate from the electrical stimulation lead based upon the patient anatomy data set and the stimulation parameter values, and displays the stimulation field model on a representation of an anatomical region of the patient via the user interface, wherein the processor receives stimulation field input via the user interface that modifies at least one of the size, shape or location of the stimulation field model relative to the displayed anatomical region, and determines at least one new stimulation parameter value based on the modification of the stimulation field model.

11. The system of claim 10, wherein the processor applies the patient anatomy data set to a stimulation field equation set to generate the stimulation field model.

12. The system of claim 11, wherein the user interface comprises one of a two-dimensional display or a three-dimensional environment to display the stimulation field model on the representation of the anatomical region.

13. The system of claim 12, wherein the processor receives input via the user interface that drags at least one of the stimulation field model or a boundary of the stimulation field model relative to the displayed anatomical location as stimulation field input.

14. The system of claim 13, wherein the user interface displays the three-dimensional stimulation field model and anatomical region as plurality of different two-dimensional, cross-sectional views, and the processor receives stimulation field input via the user interface that modifies a cross-section of the stimulation field model in one or more of the cross-sectional views.

15. The system of claim 12, wherein the views comprise at least one of a coronal view, a sagittal view, an axial view, and an oblique view.

16. The system of claim 10, wherein the processor generates a neuron model that describes at least one characteristic of patient neural tissue proximate to the electrical stimulation lead implanted within the patient, generates an activation field model that indicates which neural structures of the patient are activated by applying the stimulation field model to the anatomical region of the patient based on the neuron model and the stimulation parameter values, and displays the activation field model over the anatomical region.

17. The system of claim 16, further comprising a memory that stores a neuron model equation set, wherein the processor utilizes the patient anatomy data set to generate the neuron model with the neuron model equation set.

18. The system of claim 10, further comprising a programmer for programming an implantable medical device that includes the communications module, the user interface, and the processor.

19. A computer-readable medium comprising instructions that cause a processor to:
receive a patient anatomy data set that describes at least one characteristic of patient tissue proximate to an electrical stimulation lead implanted within a patient;
receive user input that defines stimulation parameter values;
generate a stimulation field model that represents where electrical stimulation will propagate from the electrical stimulation lead based upon the patient anatomy data set and stimulation parameter values;
display the stimulation field model on a representation of an anatomical region of the patient;
receive stimulation field input from a user that modifies at least one of the size, shape or location of the stimulation field model relative to the displayed anatomical location; and
determine at least one new stimulation parameter value based on the modification of the stimulation field model.

20. The computer-readable medium of claim 19, wherein the instructions that cause a processor to receive stimulation field input comprise instructions that cause a processor to receive input that drags at least one of the stimulation field model or a boundary of the stimulation field model relative to the displayed anatomical region.

21. The computer-readable medium of claim 19, wherein the instructions that cause a processor to display the stimulation field model on a representation of an anatomical region comprise instructions that cause a processor to display the three-dimensional stimulation field model and anatomical region as plurality of different two-dimensional, cross-sectional views, and the instructions that cause a processor to receive stimulation field input comprise instructions that cause a processor to receive stimulation field input that modifies a cross-section of the stimulation field model in one or more of the cross-sectional views.

22. The computer-readable medium of claim 19, further comprising instructions that cause a processor to:
generate a neuron model that describes at least one characteristic of patient neural tissue proximate to the electrical stimulation lead implanted within the patient;
generate an activation field model that indicates which neural structures of the patient are activated by applying the stimulation field model to the anatomical region of the patient based on the neuron model and the stimulation field model; and
display the activation field model over the anatomical region.

23. A method comprising:
receiving a patient anatomy data set that describes at least one characteristic of patient neural tissue proximate to an electrical stimulation lead implanted within a patient;
receiving user input that defines stimulation parameter values;
generating an activation field model that indicates which neural structures of the patient are activated based on the patient anatomy data set and stimulation parameter values;
displaying the activation field model over the anatomical region;
receiving user input that modifies at least one of the size, shape or location of the activation field model relative to the displayed anatomical location; and
determining at least one new stimulation parameter value based on the modification of the stimulation field model.

24. The method of claim 23, wherein receiving user input that modifies at least one of the size, shape or location of the activation field model comprises receiving input that drags at least one of the activation field model or a boundary of the activation field model relative to the displayed anatomical region.

25. The method of claim 23, wherein displaying the activation field model on a representation of an anatomical region comprises displaying the activation field model and anatomical region as plurality of different two-dimensional, cross-sectional views, and receiving user input that modifies the activation field comprises receiving user input that modifies a cross-section of the activation field model in one or more of the cross-sectional views.

26. The method of claim 25, wherein the views comprise at least one of a coronal view, a sagittal view, an axial view, and an oblique view.

27. A system comprising:
a communications module that receives a patient anatomy data set that describes at least one characteristic of patient neural tissue proximate to an electrical stimulation lead implanted within a patient;
a user interface that receives user input that defines stimulation parameter values; and a processor that generates an activation field model that indicates which neural structures of the patient are activated based on the patient anatomy data set and the stimulation parameter values, and displays the activation field model on a representation of an anatomical region of the patient via the user interface, wherein the processor receives user input that modifies at least one of the size, shape or location of the activation field model relative to the displayed anatomical location, and determines at least one new stimulation parameter value based on the modification of the activation field model.

28. The system of claim 27, wherein the processor receives input that drags at least one of the activation field model or a boundary of the activation field model relative to the displayed anatomical region via the user interface.

29. The system of claim 27, wherein the user interface displays the activation field model and anatomical region as plurality of different two-dimensional, cross-sectional views, and the processor receives user input that modifies a cross-section of the activation field model in one or more of the cross-sectional views via the user interface.

30. The system of claim 29, wherein the views comprise at least one of a coronal view, a sagittal view, an axial view, and an oblique view.

31. A computer-readable medium comprising instructions that cause a processor to:

receive a patient anatomy data set that describes at least one characteristic of patient neural tissue proximate to an electrical stimulation lead implanted within a patient;

receive user input that defines stimulation parameter values;

generating an activation field model indicates which neural structures of the patient are activated based on the patient anatomy data set and stimulation parameter values;

display the activation field model over the anatomical region;

receive user input that modifies at least one of the size, shape or location of the activation field model relative to the displayed anatomical location; and determine at least one new stimulation parameter value based on modification of the stimulation field model.

32. The computer-readable medium of claim 31, wherein the instructions that cause a processor to receive user input that modifies at least one of the size, shape or location of the activation field model comprise instructions that cause a processor to receive input that drags at least one of the activation field model or a boundary of the activation field model relative to the displayed anatomical region.

33. The computer-readable medium of claim 31, wherein the instructions that cause a processor to display the activation field model on a representation of an anatomical region comprise instructions that cause a processor to display the activation field model and anatomical region as plurality of different two-dimensional, cross-sectional views, and the instructions that cause a processor to receive user input that modifies the activation field comprise instructions that cause a processor to receive user input that modifies a cross-section of the activation field model in one or more of the cross-sectional views.

* * * * *